US008791090B2

(12) United States Patent
Ashikawa et al.

(10) Patent No.: US 8,791,090 B2
(45) Date of Patent: Jul. 29, 2014

(54) PROPHYLACTIC AND/OR THERAPEUTIC AGENT FOR ANEMIA COMPRISING TETRAHYDROQUINOLINE COMPOUND AS ACTIVE INGREDIENT

(75) Inventors: Masanori Ashikawa, Tokyo (JP); Junya Tagashira, Tokyo (JP); Akiyasu Koketsu, Tokyo (JP); Toshiharu Morimoto, Tokyo (JP); Takahiro Kitamura, Shizuoka (JP); Syunji Takemura, Tokyo (JP); Gen Watanabe, Tokyo (JP); Tatsuaki Nishiyama, Tokyo (JP); Satoshi Goda, Tokyo (JP); Masaki Yamabi, Tokyo (JP); Takeshi Doi, Tokyo (JP); Hiroyuki Ishiwata, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 0 days.

(21) Appl. No.: 13/256,549

(22) PCT Filed: Mar. 31, 2010

(86) PCT No.: PCT/JP2010/002355
§ 371 (c)(1),
(2), (4) Date: Sep. 14, 2011

(87) PCT Pub. No.: WO2010/113498
PCT Pub. Date: Oct. 7, 2010

(65) Prior Publication Data
US 2012/0004197 A1 Jan. 5, 2012

(30) Foreign Application Priority Data
Mar. 31, 2009 (JP) ................................. 2009-084368

(51) Int. Cl.
*A01N 57/00* (2006.01)
*A61K 31/385* (2006.01)

(52) U.S. Cl.
USPC .......... 514/84; 514/313; 514/235.2; 514/311; 514/312; 514/253.6; 514/232.5; 544/128; 544/263; 544/121; 544/82; 546/165; 546/153; 546/13; 546/160

(58) Field of Classification Search
USPC ......... 544/128, 263, 121, 82; 514/313, 235.2, 514/311, 312, 253.6, 232.5; 546/165, 153, 546/13, 160
See application file for complete search history.

(56) References Cited

U.S. PATENT DOCUMENTS 7,030,246 B2   4/2006  Bladh et al.
2004/0132724 A1  7/2004  Bladh et al.

FOREIGN PATENT DOCUMENTS

| JP | 11-171774 A | 6/1999 |
|---|---|---|
| JP | 2002-053557 A | 2/2002 |
| JP | 2002053557 A * | 2/2002 |
| JP | 2002-506810 A | 3/2002 |
| JP | 2002-275159 A | 9/2002 |
| JP | 2006-137763 A | 6/2006 |
| WO | 01/76629 A1 | 10/2001 |
| WO | 02/079165 A1 | 10/2002 |
| WO | WO 02079165 A1 * | 10/2002 |
| WO | 03/053997 A2 | 7/2003 |
| WO | 03/105849 A1 | 12/2003 |
| WO | 2004/032848 A2 | 4/2004 |
| WO | 2004/035543 A1 | 4/2004 |
| WO | 2004/052863 A1 | 6/2004 |
| WO | 2005/007094 A2 | 1/2005 |
| WO | 2005/011696 A1 | 2/2005 |
| WO | 2005/100321 A1 | 10/2005 |
| WO | 2007/038571 A2 | 4/2007 |
| WO | 2009/016812 A1 | 2/2009 |
| WO | 2009/041072 A1 | 4/2009 |

OTHER PUBLICATIONS

Notification of Transmittal of Copies of Translation of the International Preliminary Report on Patentability (Form PCT/IB/338) of International Application No. PCT/JP2010/002355 mailed Nov. 24, 2011 with Forms PCT/IB/326, PCT/IB/373 and PCT/ISA/237.
Brines, Michael et al., "Erythropoietin Crosses the Blood-Brain Barrier to Protect Against Experimental Brain Injury," Proceedings of the National Academy of Sciences, Sep. 2000, p. 10526-10531, vol. 97.
Calapai, Gioacchino et al., "Erythropoietin Protects Against Brain Ischemic Injury by Inhibition of Nitric Oxide Formation," European Journal of Pharmacology, 2000, p. 349-256.
Celik, Murat et al., "Erythropoietin Prevents Motor Neuron Apoptosis and Neurological Disability in Experimental Spinal Cord Ischemic Injury," Proceedings of the National Academy of Sciences, Feb. 2002, p. 2258-2263, vol. 99.
Danna, Robert et al., "Erythropoietin Therapy for the Anemia Associated with AIDS and AIDS Therapy and Cancer," 1990, p. 301-324.
Eschbach, Joseph et al., "Correction of the Anemia of End-Stage Renal Disease with Recombinant Human Erythropoietin," The New England Journal of Medicine, Jan. 1987, p. 73-78, vol. 316.
Eschbach, Joseph et al., "Recombinant Human Erythropoietin in Anemic Patients with End-Stage Renal Disease," Annals of Internal Medicine, Dec. 1989, p. 992-1000, vol. 111.

(Continued)

*Primary Examiner* — Wu-Cheng Winston Shen
*Assistant Examiner* — Jean Cornet
(74) *Attorney, Agent, or Firm* — Westerman, Hattori, Daniels & Adrian, LLP

(57) ABSTRACT

Disclosed is a compound which has a low molecular weight and has an activity of enhancing the production of EPO and/or an activity of enhancing the production of hemoglobin. Specifically disclosed is and EPO production enhancer and/or a hemoglobin production enhancer comprising a 1-acyl-4-(substituted oxy, substituted amino, or substituted thio)-1,2,3,4-tetrahydroquinoline derivative, more specifically a tetrahydroquinoline compound represented by general formula (1) [wherein $R^1$, $R^2$, $R^{2'}$, $R^3$ and $R^{3'}$ independently represent a hydrogen atom, a $C_{1-6}$ alkyl group, or the like; $R^4$, $R^5$, $R^6$, $R^7$, $R^8$, $R^9$ and $R^{10}$ independently represent a hydrogen atom, a halogen atom, a $C_{1-6}$ alkyl group, or the like; A represents $N—R^{11}$, a sulfur atom, or an oxygen atom; $R^{11}$ represents a hydrogen atom, a $C_{1-6}$ alkyl group, or the like; B represents a $C_{6-14}$ aryl group, or a 5- to 10-membered heterocyclic group; and n represents an integer of 0 or 1], a salt of the tetrahydroquinoline compound, or a solvate of the tetrahydroquinoline compound or the salt.

5 Claims, No Drawings

(56) References Cited

OTHER PUBLICATIONS

Fang, Jianmin et al., "HIF-1α-mediated Up-Regulation of Vascular Endothelial Growth Factor, Independent of Basic Fibroblast Growth Factor, Is Important in the Switch to the Angiogenic Phenotype During Early Tumorigenesis," Cancer Research, Aug. 2001, p. 5731-5735, vol. 61.

La Ferla, Katia et al., "Inhibition of Erythropoietin Gene Expression Signaling Involves the Transcription Factors GATA-2 and NF-κB," The FASEB Journal, Sep. 2002, p. 1811-1827.

Imagawa, Shigehiko et al., "Negative Regulation of the Eryothropoietin Gene Expression by the GATA Transcription Factors," American Society of Hematology, 1997, p. 1430-1439, vol. 89.

International Search Report of PCT/JP2010/002355, mailing date Apr. 27, 2010.

Jelkmann, Wolfgang, "Molecular Biology of Erythropoietin," Internal Medicine, Aug. 2004, p. 649-659, vol. 43.

Lin, Fu-Kuen et al., "Cloning and Expression of the Human Erythropoietin Gene," Proceedings of the National Academy of Science, Nov. 1985, p. 7580-7584, vol. 82.

Lim, Victoria et al., "Recombinant Human Erythropoietin Treatment in Pre-Dialysis Patients," Annals of Internal Medicine, Jan. 1989, p. 108-114, vol. 110.

Maxwell P.H. et al., "Hypoxia-Inducible Factor-1 Modulates Gene Expression in Solid Tumors and Influences Both Angiogenesis and Tumor Growth," Proceedings of the National Academy of Science, Jul. 1997, p. 8104-8109, vol. 94.

McMahon, F. Gilbert et al., "Pharmacokinetics and Effects of Recombinant Human Erythropoietin After Intravenous and Subcutaneous Injections in Healthy Volunteers," Blood, Nov. 1990, p. 1718-1722, vol. 76.

Sakanaka, Masahiro et al., "In Vivo Evidence that Erythropoietin Protects Neurons from Ischemic Damage," Proceedings of the National Academy of Science, Apr. 1998, p. 4635-4640, vol. 95.

Sirén, Anna-Leena et al., "Erythropoietin Prevents Neuronal Apoptis After Cerebral Ischemia and Metabolic Stress," PNAS, Mar. 2001, p. 4044-4049, vol. 98.

Spivak, Jerry et al., "The In Vivo Metabolism of Recombinant Human Erythropoietin in the Rat," Bloog, Jan. 1989, p. 90-99, vol. 73.

Stead, Richard et al., "Evaluation of the Safety and Pharmacodynamics of Hematide, a Novel Erythropoietic Agent, in a Phase 1, Double-Blind, Placebo-Controlled, Dose-Escalation Study in Healthy Volunteers," Blood, Sep. 2006, p. 1830-1834, vol. 108.

\* cited by examiner

PROPHYLACTIC AND/OR THERAPEUTIC AGENT FOR ANEMIA COMPRISING TETRAHYDROQUINOLINE COMPOUND AS ACTIVE INGREDIENT

TECHNICAL FIELD

The present invention relates to a novel erythropoietin production enhancer and/or a hemoglobin production enhancer. More particularly, the present invention relates to a prophylactic and/or therapeutic agent for a disease attributable to a decrease in erythropoietin production, for example, anemia. The present invention also relates to a novel tetrahydroquinoline compound.

BACKGROUND ART

Erythropoietin (EPO) is a glycoprotein hormone which is involved in the maturation and differentiation from erythroid progenitor cells to mature erythrocytes, and is a monomeric polypeptide composed of 165 naturally occurring amino acids (Non-Patent Document 1).

Human EPO is essential in the proliferation and differentiation of erythrocytes, and is useful for the treatment of blood diseases characterized by decreased production of erythrocytes. From a clinical aspect, EPO is used in the treatment of anemia in chronic renal failure (CRF) patients, autologous blood donation, and anemia of prematurity (Non-Patent Documents 2 to 4), as well as for AIDS patients and cancer patients under chemotherapy (Non-Patent Document 5). Furthermore, EPO has been proved to be effective in chronic anemia.

EPO is produced mainly in the kidney in adults, but is also produced in the astrocytes and neurons of the central nervous system, so that EPO and EPO receptors are expressed in the capillary blood vessels at the encephalo-peripheral boundaries. It has been reported that when EPO is systemically administered, EPO passes through the blood-brain barrier and reduces the loss of neuronal cells responding to cerebral and spinal cord ischemia, mechanical trauma, epilepsy, excitotoxin, and neuroinflammation (Non-Patent Documents 6 to 10).

In the therapy using proteins such as EPO, there are problems such as short plasma half-life due to the susceptibility to degradation by proteases (Non-Patent Documents 11 and 12), and the necessity of multiple intravenous injections in order to maintain the therapeutically effective concentration of the compounds in the circulatory system. Furthermore, subcutaneous injection may replace intravenous injection as a route of administration, and this subcutaneous injection has a slow release effect because absorption from the site of administration is slow. However, the plasma concentration in this case is significantly lower than that obtainable by intravenous injection. Thus, the same number of injections as in the case of intravenous injection must be given in order to obtain an equivalent therapeutic effect, so that this poses a burden to patients. Also, since human serum EPO is a glycoprotein, and since the structures of the sugar chains bonded to the EPO surface are complicated, with a wide and diverse range of glycosylation products being available, human serum EPO molecules exhibit non-uniformity in size. Thus, there is also a problem that human serum EPO cannot be produced with good reproducibility using recombinant human EPO.

Therefore, there is a need for a method and a compound for increasing, not an EPO having low bioavailability in the treatment of diseases attributable to decreased production of EPO, including anemia as described above, but for increasing an endogenous EPO, in the relevant technical field.

On the other hand, it is known that the amount of production of EPO is regulated by the oxygen concentration through intervention of the hypoxia inducible factor (HIF), which is a transcription factor (Non-Patent Document 13). That is, in normoxia, an HIF subunit (HIF-1α) in which a proline residue has been hydroxylated by 2-oxoglutarate dioxygenase enzyme, is decomposed by the ubiquitin-proteasome system, and thus production of EPO is not enhanced. However, in hypoxia, hydroxylation of the proline residue of HIF-1α by 2-oxoglutarate dioxygenase enzyme is suppressed, and as a result, stabilized HIF-1α migrates from the cytoplasm into the nucleus and forms a dimer with HIF-1β. This dimer is bonded to the hypoxia responsible element (HRE) sequence of EPO gene and enhances transcription, and thereby enhances the production of EPO.

Enzyme inhibitors against HIF prolyl hydroxylases such as 2-oxoglutarate dioxygenase enzyme, which utilize such an EPO production mechanism, have been reported as EPO production enhancers (Patent Documents 1 to 4).

However, genes that expressions are regulated by HIF include not only those genes encoding EPO, but also genes encoding the vascular endothelial growth factor (VEGF), and the like. It has been reported that VEGF has angiogenesis promoting activity, and thus may cause exacerbation of malignant tumors through this angiogenesis enhancing function (Non-Patent Documents 14 and 15). Furthermore, anemia is also caused by chemical treatments targeting cancer, and thus, administration of a therapeutic drug for anemia to cancer patients under such chemotherapy may also be contemplated (Non-Patent Document 5). Therefore, a compound having a HIF prolyl hydroxylase enzyme inhibitory activity, which also has a possibility of enhancing the expression of VEGF and the like capable of exacerbating cancer, involves the risk of exacerbating cancer as well.

The production of EPO is regulated by a promoter which is located on the 5'-terminal side of EPO and an enhancer which is located on the 3'-terminal side, and it is contemplated that HIF binds to the HRE sequence in the enhancer, and thereby enhances the production of EPO. In addition, GATA-2, NFκB and the like are also believed to regulate the production of EPO (Non-Patent Documents 16 and 17), and it is thought that enhancing the production of EPO can be achieved as well by mechanisms other than the HIF prolyl hydroxylase enzyme active inhibition. Under such circumstances, it is thought that a compound having an EPO production enhancing activity that is not dependent on the HIF prolyl hydroxylase enzyme active inhibition is useful for the treatment of anemia.

Furthermore, EPO enhances the proliferation and maturation of erythroid progenitor cells as described above, but compounds having an activity of enhancing the maturation and differentiation of erythroid progenitor cells without the intervention of EPO production, are also useful as therapeutic agents for anemia. Compounds having an activity of enhancing the blood cell proliferation enhancing activity EPO possesses or compounds having an inhibitory activity against hematopoietic cell phosphatase that catalyzes dephosphorylation, which is one of important regulatory mechanisms in the signal transduction of EPO, have been reported (Patent Documents 5 to 7); however, it cannot be said that their activities are undoubtedly satisfactory. Furthermore, reports have been made on synthetic peptides and hematides that have effect on EPO receptors (Non-Patent Document 18); however, there is a problem that in order to make the peptides and hematides to show an activity equivalent to that of EPO, high dosage administration is required, and the peptides and hematides cannot be orally administered. A low molecular weight compound having a 2-phenylquinoline skeleton has also been reported (Patent Document 17).

Therefore, an orally administrable, low molecular weight therapeutic agent for anemia which has both an EPO production enhancing activity and a hemoglobin production enhancing activity is considered to be useful for the treatment of anemia in the future.

On the other hand, there have been disclosed compounds having the tetrahydroquinoline skeleton according to the present invention, which are used as a CRTH2 inhibitor that is effective for inflammatory diseases (Patent Documents 8 toll), an eosinophil infiltration suppressant that is effective for inflammatory diseases (Patent Document 12), an upregulator of ecdysone steroid hormone receptor expression that is involved in the growth, ecdisys and development of insects (Patent Document 13), a β-amyloid precursor protein secretion enhancer that is effective for neurodegenerative diseases such as Alzheimer's disease and Parkinson's disease (Patent Document 14), a STAT6 activation suppressant that is effective for atopic dermatitis and the like (Patent Document 15), and apolipoprotein A-I production enhancer that is effective for hyperlipidemia (Patent Document 16). However, there is no description or suggestion that these compounds have an EPO production enhancing activity or a hemoglobin production enhancing activity, and a compound having a tetrahydroquinoline skeleton which is useful as a prophylactic and/or therapeutic agent for anemia is not known at all.

PRIOR ART DOCUMENTS

Patent Documents

Patent Document 1: Japanese Patent Application Laid-Open (JP-A) No, 2006-137763
Patent Document 2: WO 2003/53997
Patent Document 3: WO 2005/11696
Patent Document 4: WO 2007/38571
Patent Document 5: Japanese Translation of PCT Application (JP-T) No. 2000-536365
Patent Document 6: JP-A No. 11-171774
Patent Document 7: JP-A No. 2002-275159
Patent Document 8: WO 2004/32848
Patent Document 9: WO 2004/35543
Patent Document 10: WO 2005/7094
Patent Document 11: WO 2005/100321
Patent Document 12: WO 2004/52863
Patent Document 13: WO 2003/105849
Patent Document 14: WO 2001/76629
Patent Document 15: WO 2002/79165
Patent Document 16: JP-A No. 2002-53557
Patent Document 17: WO 2009/16812

Non Patent-Documents

Non-Patent Document 1: Lin F-K, et al., Proc. Natl. Acad. Sci. USA, 82: 7580-7584 (1985)
Non-Patent Document 2: Eschbach J W, Egrie J C, Downing M R et al., NEJM, 316: 73-78 (1987)
Non-Patent Document 3: Eschbach J W, Abdulhadi M H, Browne J K et al., Ann. Intern. Med., 111: 992 (1989)
Non-Patent Document 4: Lim V S, Degowin R L, Zavala D et al., Ann. Intern. Med., 110: 108-114 (1989)
Non-Patent Document 5: Danna R P, Rudnick S A, Abels R I, Garnick M B, Erythropoietin in Clinical Applications—An International Perspective, New York: Marcel Dekker; pp. 301-324 (1990)
Non-Patent Document 6: Sakanaka M, et al., Proc. Natl. Acad. Sci. USA., 95, 4635-4640 (1998)
Non-Patent Document 7: Celik M, et al., Proc. Natl. Acad. Sci. USA., 99, 2258-2263 (2002)
Non-Patent Document 8: Brines M L, et al., Proc. Natl. Acad. Sci. USA., 97, 10526-10531 (2000)
Non-Patent Document 9: Calapai G, et al., Eur. J. Pharmacol., 401, 349-356 (2000)
Non-Patent Document 10: Siren A-L, et al., Proc. Natl. Acad. Sci. USA., 98, 4044-404 (2001)
Non-Patent Document 11: Spivack J L and Hogans B B, Blood, 73: 90 (1989)
Non-Patent Document 12: McMahon F G, et al., Blood, 76: 1718 (1990)
Non-Patent Document 13: Jelkman W, Internal Medicine, 43, 649-659 (2004)
Non-Patent Document 14: Maxwell P H, et al., Proc. Natl. Acad. Sci. USA., 94, 15, 8104-8109 (1997)
Non-Patent Document 15: Fang J, et al., Cancer Res., 61, 15, 5731-5735 (2001)
Non-Patent Document 16: Imagawa S et al., Blood, 89, 1430-1439 (1997)
Non-Patent Document 17: La Ferla K et al., FASEB J., 16, 1811-1813 (2002)
Non-Patent Document 18: Stead R B, et al., Blood, 108: 1830-1834 (2006)

SUMMARY OF THE INVENTION

Problems to be Solved by the Invention

An objective of the present invention is to provide a low molecular weight compound having an EPO production enhancing activity and/or a hemoglobin production enhancing activity. More particularly, the objective is to provide a medicine useful for the prevention and/or treatment of anemia. Another objective of the present invention is to provide a novel compound which is useful for the prevention and/or treatment of anemia.

Means for Solving the Problems

Under such circumstances as described above, the inventors of the present invention conducted extensive investigations on compounds having an EPO production enhancing activity or hemoglobin production enhancing activity, and as a result, the inventors found that a tetrahydroquinoline compound represented by the following formula (1) enhances EPO production in a test using human hepatic cancer-derived HepG2 cells, and enhances hemoglobin production in a test using K562, which is a human proerythroblast cell line. Thus, the inventors finally completed the present invention.

That is, the present invention relates to an EPO production enhancer containing a 1-acyl-4-(substituted oxy, substituted amino, or substituted thio)-1,2,3,4-tetrahydroquinoline derivative or a salt thereof, or a solvate of the derivative or the salt, as an active ingredient.

More particularly, the present invention is to provide an EPO production enhancer containing, as an active ingredient, a tetrahydroquinoline compound represented by the following formula (1) or a salt thereof, or a solvate of the derivative or the salt:

[Chemical Formula 1]

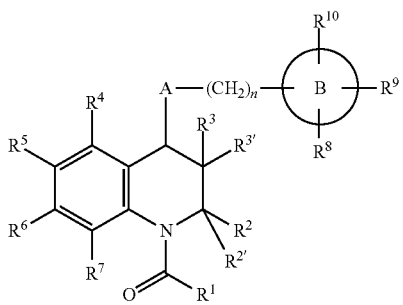

(1)

wherein $R^1$, $R^2$, $R^{2'}$, $R^3$, and $R^{3'}$ independently represent a hydrogen atom, a $C_{1-6}$ alkyl group, a $C_{2-6}$ alkenyl group, a $C_{2-6}$ alkynyl group, a mono($C_{1-6}$ alkyl)amino group, a di($C_{1-6}$ alkyl)amino group, or a $C_{3-6}$ cycloalkyl group;

$R^4$, $R^5$, $R^6$, $R^7$, $R^8$, $R^9$, and $R^{10}$ independently represent a hydrogen atom, a halogen atom, a $C_{1-6}$ alkyl group which may be substituted, a $C_{2-6}$ alkenyl group which may be substituted, a $C_{2-6}$ alkynyl group which may be substituted, a $C_{3-6}$ cycloalkyl group which may be substituted, a $C_{6-14}$ aryl group which may be substituted, a 5- to 10-membered heterocyclic group which may be substituted, a $C_{1-6}$ alkoxy group which may be substituted, a $C_{6-14}$ aryloxy group which may be substituted, an amino group, a mono($C_{1-6}$ alkylcarbonyl) amino group, a mono($C_{1-6}$ alkoxycarbonyl)amino group, a mono($C_{1-6}$ alkyl)amino group which may be substituted, a di($C_{1-6}$ alkyl)amino group which may be substituted, a mono ($C_{6-14}$ aryl)amino group which may be substituted, a $C_{1-6}$ alkylthio group which may be substituted, a $C_{1-6}$ alkylsulfonyl group which may be substituted, a $C_{1-6}$ alkylsulfonylamino group which may be substituted, a $C_{1-6}$ alkylsulfinyl group which may be substituted, a $C_{1-6}$ alkoxycarbonyl group which may be substituted, a $C_{1-6}$ alkanoyl group which may be substituted, a 5- to 7-membered saturated heterocyclic carbonyl group which may be substituted, a hydroxyl group, a nitro group, a carboxyl group, a sulfonic acid group, a boronic acid group, a carbamoyl group which may be substituted, an ester group which may be substituted, or a cyano group, while $R^9$ and $R^{10}$ may be joined together to form a carbocyclic ring or a heterocyclic ring;

A represents N—$R^{11}$, a sulfur atom, or an oxygen atom, wherein $R^{11}$ represents a hydrogen atom or a $C_{1-6}$ alkyl group which may be substituted;

B represents a $C_{6-14}$ aryl group or a 5- to 10-membered heterocyclic group; and n represents an integer of 0 or 1.

Furthermore, the present invention is to provide a hemoglobin production enhancer containing a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, as an active ingredient.

Also, the present invention is to provide a prophylactic and/or therapeutic agent for anemia containing a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, as an active ingredient.

The present invention relates to a use of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, for the manufacture of a preparation for the enhancement of EPO production.

The present invention relates to a use of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, for the manufacture of a preparation for the enhancement of hemoglobin production.

Furthermore, the present invention relates to a 1-acyl-4-(substituted oxy, substituted amino, or substituted thio)-1,2,3,4-tetrahydroquinoline derivative for the use in a preparation for the enhancement of EPO production and/or a preparation for the enhancement of hemoglobin production.

The present invention also relates to a use of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, for the manufacture of a preparation for the prevention and/or treatment of anemia.

Furthermore, the present invention relates to a 1-acyl-4-(substituted oxy, substituted amino, or substituted thio)-1,2,3,4-tetrahydroquinoline derivative for the use in a preparation for the prevention and/or treatment of anemia.

The present invention relates to a method for enhancing FPO production, the method including administering an effective amount of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, to a patient in need of upregulation of EPO production.

The present invention also relates to a method for enhancing hemoglobin production, the method including administering an effective amount of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, to a patient in need of upregulation of hemoglobin expression.

The present invention also relates to a method for preventing and/or treating anemia, the method including administering an effective amount of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, to an anemic patient.

The present invention relates to a method of enhancing EPO production in a cell by bringing the cell into contact with an effective amount of a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt. More particularly, the present invention is to provide a method of enhancing EPO production in a cell by bringing the cell into contact with an effective amount of a tetrahydroquinoline compound represented by the formula (1) or a salt thereof, or a solvate of the compound or the salt. Here, the term "contact" as used herein means addition of the tetrahydroquinoline compound or the like of the present invention to cells through uptake of the compound or the like by cells or through interaction at the cellular surface, so that the compound or the like can regulate cellular functions such as proliferation, differentiation, and secretion of physiologically active substances.

The present invention relates to a pharmaceutical composition for the enhancement of EPO production, containing a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, and a pharmaceutically acceptable carrier.

The present invention also relates to a pharmaceutical composition for the enhancement of hemoglobin production, containing a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, and a pharmaceutically acceptable carrier.

Furthermore, the present invention relates to a pharmaceutical composition for the prevention and/or treatment of anemia, containing a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, and a pharmaceutically acceptable carrier.

The present invention relates to a tetrahydroquinoline compound represented by the following formula (1), or a salt, or a solvate of the compound or the salt:

[Chemical Formula 1]

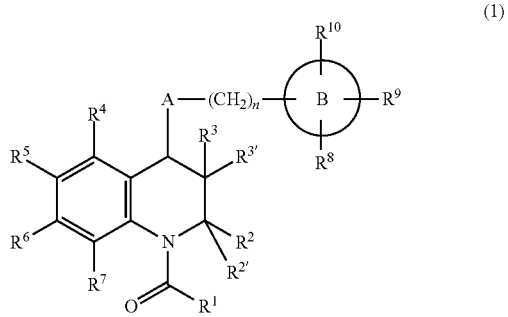

(1)

wherein $R^1$, $R^2$, $R^{2'}$, $R^3$, and $R^{3'}$ independently represent a hydrogen atom, a $C_{1-6}$ alkyl group, a $C_{2-6}$ alkenyl group, a $C_{2-6}$ alkynyl group, a mono($C_{1-6}$ alkyl)amino group, a di($C_{1-6}$ alkyl)amino group, or a $C_{3-6}$ cycloalkyl group;

$R^4$, $R^5$, $R^6$, $R^7$, $R^8$, $R^9$, and $R^{10}$ independently represent a hydrogen atom, a halogen atom, a $C_{1-6}$ alkyl group which may be substituted, a $C_{2-6}$ alkenyl group which may be substituted, a $C_{2-6}$ alkynyl group which may be substituted, a $C_{3-6}$ cycloalkyl group which may be substituted, a $C_{6-14}$ aryl group which may be substituted, a 5- to 10-membered heterocyclic group which may be substituted, a $C_{1-6}$ alkoxy group which may be substituted, a $C_{6-14}$ aryloxy group which may be substituted, an amino group, a mono($C_{1-6}$ alkylcarbonyl)amino group, a mono($C_{1-6}$ alkoxycarbonyl)amino group, a mono($C_{1-6}$ alkyl)amino group which may be substituted, a di($C_{1-6}$ alkyl)amino group which may be substituted, a mono ($C_{6-14}$ aryl)amino group which may be substituted, a $C_{1-6}$ alkylthio group which may be substituted, a $C_{1-6}$ alkylsulfonyl group which may be substituted, a $C_{1-6}$ alkylsulfonylamino group which may be substituted, a $C_{1-6}$ alkylsulfinyl group which may be substituted, a $C_{1-6}$ alkoxycarbonyl group which may be substituted, a $C_{1-6}$ alkanoyl group which may be substituted, a 5- to 7-membered saturated heterocyclic carbonyl group which may be substituted, a hydroxyl group, a nitro group, a carboxyl group, a sulfonic acid group, a boronic acid group, a carbamoyl group which may be substituted, an ester group which may be substituted, or a cyano group, while $R^9$ and $R^{10}$ may be joined together to form a carbocyclic ring or a heterocyclic ring;

A represents N—$R^{11}$, a sulfur atom, or an oxygen atom, wherein $R^{11}$ represents a hydrogen atom or a $C_{1-6}$ alkyl group which may be substituted;

B represents a $C_{6-14}$ aryl group or a 5- to 10-membered heterocyclic group; and n represents an integer of 0 or 1, provided that a combination in which A is —$NR^{11}$; $R^{11}$ is a hydrogen atom; $R^4$, $R^5$, $R^6$, and $R^7$ are each any one of a hydrogen atom, a $C_{1-6}$ alkyl group, or a halogen atom; and $R^8$, $R^9$, and $R^{10}$ are each any one of a hydrogen atom, a halogen atom, a $C_{1-6}$ alkyl group, a $C_{1-6}$ alkoxy group, a $C_{6-14}$ aryloxy group, or a cyano group, is excluded.

Examples of the compound of the present invention include the following compounds.

A family of compounds including:
1-acetyl-8-fluoro-4-[(2-fluorophenyl)amino]-2-methyl-1,2,3,4-tetrahydroquinoline [compound (4)];
1-cyclohexanecarbonyl-6-fluoro-4-[(4-fluorophenyl)amino]-2-methyl-1,2,3,4-tetrahydroquinoline [compound (6)];
1-acetyl-7-cyano-2-methyl-4-phenylamino-1,2,3,4-tetrahydroquinoline [compound (7)];
1-acetyl-6-cyano-2-methyl-4-phenylamino-1,2,3,4-tetrahydroquinoline [compound (14)];
1-acetyl-2-methyl-4-[(4-morpholinophenyl)amino]-1,2,3,4-tetrahydroquinoline [compound (19)];
1-acetyl-4-[(4-N,N-dimethylaminophenyl)amino]-2-methyl-1,2,3,4-tetrahydroquinoline [compound (20)];
1-acetyl-7-bromo-2-methyl-4-phenylamino-1,2,3,4-tetrahydroquinoline [compound (23)];
1-acetyl-4-[(4-hydroxyphenyl)amino]-2-methyl-1,2,3,4-tetrahydroquinoline [compound (24)];
1-acetyl-2-methyl-4-[(1,1'-biphenyl-4-yl)amino]-1,2,3,4-tetrahydroquinoline [compound (25)];
1-acetyl-2-methyl-4-phenoxy-1,2,3,4-tetrahydroquinoline [compound (26)];
1-acetyl-4-(4-fluorophenoxy)-2-methyl-1,2,3,4-tetrahydroquinoline [compound (27)];
1-acetyl-4-(3-fluorophenoxy)-2-methyl-1,2,3,4-tetrahydroquinoline [compound (28)];
1-acetyl-4-(2-fluorophenoxy)-2-methyl-1,2,3,4-tetrahydroquinoline [compound (29)];
1-acetyl-4-(2,4-difluorophenoxy)-2-methyl-1,2,3,4-tetrahydroquinoline [compound (30)];
1-acetyl-4-(3,4-difluorophenoxy)-2-methyl-1,2,3,4-tetrahydroquinoline [compound (31)];
1-acetyl-7-fluoro-2-methyl-4-phenoxy-1,2,3,4-tetrahydroquinoline [compound (32)];
1-acetyl-8-fluoro-2-methyl-4-phenoxy-1,2,3,4-tetrahydroquinoline [compound (33)];
1-acetyl-4-(4-fluorophenoxy)-6-fluoro-2-methyl-1,2,3,4-tetrahydroquinoline [compound (34)];
1-acetyl-6-fluoro-2-methyl-4-phenoxy-1,2,3,4-tetrahydroquinoline [compound (35)];
1-acetyl-2-methyl-4-benzyloxy-1,2,3,4-tetrahydroquinoline [compound (36)];
1-acetyl-4-[(4-fluorophenyl)amino]-2-methyl-6-methoxy-1,2,3,4-tetrahydroquinoline [compound (37)];

1-acetyl-4-[(4-hydroxymethylphenyl)amino]-2-methyl-1,2,3,4-tetrahydroquinoline [compound (38)];

1-acetyl-4-[(4-methanesulfonylamidophenyl)amino]-2-methyl-1,2,3,4-tetrahydroquinoline [compound (39)];

1-acetyl-4-[(4-chlorophenyl)amino]-2-methyl-6-morpholino-1,2,3,4-tetrahydroquinoline [compound (40)];

ethyl 1-acetyl-4-[(4-chlorophenyl)amino]-2-methyl-1,2,3,4-tetrahydroquinoline-6-carboxylate [compound (41)];

1-acetyl-4-[(4-chlorophenyl)amino]-2-methyl-1,2,3,4-tetrahydroquinoline-6-carboxylic acid [compound (42)];

1-acetyl-4-[(4-chlorophenyl)amino]-2-methyl-1,2,3,4-tetrahydroquinoline-6-carboxamide [compound (43)];

1-acetyl-4-[(4-chlorophenyl)amino]-2-methyl-7-morpholino-1,2,3,4-tetrahydroquinoline [compound (44)];

1-acetyl-4-[(4-chlorophenyl)amino]-2-methyl-6-methane sulfonylamino-1,2,3,4-tetrahydroquinoline [compound (45)];

ethyl 1-acetyl-4-(4-fluorophenoxy)-2-methyl-1,2,3,4-tetrahydroquinoline-6-carboxylate [compound (53)];

1-acetyl-4-(4-fluorophenoxy)-2-methyl-1,2,3,4-tetrahydroquinoline-6-carboxamide [compound (54)];

1-acetyl-4-(4-morpholinophenoxy)-2-methyl-1,2,3,4-tetrahydroquinoline [compound (55)];

1-acetyl-7-fluoro-4-(4-fluorophenoxy)-2-methyl-1,2,3,4-tetrahydroquinoline [compound (56)];

1-acetyl-4-(4-hydroxyphenoxy)-2-methyl-1,2,3,4-tetrahydroquinoline [compound (57)];

1-acetyl-7-fluoro-4-[(3-fluorophenyl)amino]-2-methyl-1,2,3,4-tetrahydroquinoline [compound (58)];

1-acetyl-2-ethyl-4-phenylamino-1,2,3,4-tetrahydroquinoline [compound (59)];

1-acetyl-3,3-dimethyl-4-phenylamino-1,2,3,4-tetrahydroquinoline [compound (60)];

1-acetyl-3,3-dimethyl-4-phenylamino-1,2,3,4-tetrahydroquinoline [compound (61)];

1-acetyl-4-(3,5-difluorophenoxy)-2-methyl-1,2,3,4-tetrahydroquinoline [compound (62)];

1-acetyl-8-bromo-4-phenylamino-2-methyl-1,2,3,4-tetrahydroquinoline [compound (63)];

1-acetyl-4-(4-benzyloxyphenoxy)-2-methyl-1,2,3,4-tetrahydroquinoline [compound (64)];

6-fluoro-4-[(4-fluorophenyl)amino]-2-methyl-1-N-methylcarbamoyl-1,2,3,4-tetrahydroquinoline [compound (65)];

1-cyclopentanecarbonyl-6-fluoro-2-methyl-4-[(4-fluorophenyl)amino]-1,2,3,4-tetrahydroquinoline [compound (66)];

1-acetyl-2-methyl-4-(4-nitrophenoxy)-1,2,3,4-tetrahydroquinoline [compound (67)];

1-acetyl-4-(4-aminophenoxy)-2-methyl-1,2,3,4-tetrahydroquinoline [compound (68)];

1-acetyl-4-[(4-methoxymethylphenyl)amino]-2-methyl-1,2,3,4-tetrahydroquinoline [compound (69)];

1-acetyl-4-[(4-ethoxycarbonylmethylphenyl)amino]-2-methyl-1,2,3,4-tetrahydroquinoline [compound (70)];

1-acetyl-4-[(4-carboxymethylphenyl)amino]-2-methyl-1,2,3,4-tetrahydroquinoline [compound (71)];

1-acetyl-2-methyl-4-[(2-morpholinophenyl)amino]-1,2,3,4-tetrahydroquinoline [compound (72)];

1-acetyl-4-[(4-fluoro-3-morpholinophenyl)amino]-2-methyl-1,2,3,4-tetrahydroquinoline [compound (73)];

1-acetyl-2-methyl-4-[(4-piperazinylphenyl)amino]-1,2,3,4-tetrahydroquinoline [compound (76)];

1-acetyl-4-{[4-(4-acetylpiperazinyl)phenyl]amino}-2-methyl-1,2,3,4-tetrahydroquinoline [compound (77)];

1-acetyl-4-{[4-(4-methanesulfonylpiperazinyl)phenyl]amino}-2-methyl-1,2,3,4-tetrahydroquinoline [compound (78)];

1-acetyl-6-[(4-acetyl)piperazino]-4-[(4-chlorophenyl)amino]-2-methyl-1,2,3,4-tetrahydroquinoline [compound (79)];

1-acetyl-6-[(4-methanesulfonyl)piperazino]-4-[(4-chlorophenyl)amino]-2-methyl-1,2,3,4-tetrahydroquinoline [compound (80)];

1-acetyl-4-[(4-chlorophenyl)amino]-6-[(4-isopropyl)piperazino]-2-methyl-1,2,3,4-tetrahydroquinoline [compound (81)];

1-acetyl-4-[(4-chlorophenyl)amino]-6-[(2-hydroxy)ethylamino]-2-methyl-1,2,3,4-tetrahydroquinoline [compound (82)];

1-acetyl-4-[(4-chlorophenyl)amino]-6-[(3,5-dimethyl)morpholino]-2-methyl-1,2,3,4-tetrahydroquinoline [compound (83)];

1-acetyl-4-[(4-chlorophenyl)amino]-6-[(4-isopropylcarbonyl)piperazino]-2-methyl-1,2,3,4-tetrahydroquinoline [compound (84)];

1-acetyl-4-[(4-chlorophenyl)amino]-6-[(4-cyclohexylcarbonyl)piperazino]-2-methyl-1,2,3,4-tetrahydroquinoline [compound (85)];

1-acetyl-6-[(4-benzoyl)piperazino]-2-methyl-4-[(4-chlorophenyl)amino]-1,2,3,4-tetrahydroquinoline [compound (86)];

1-acetyl-4-[(4-chlorophenyl)amino]-6-[(4-(N,N-diethylaminocarbonyl)piperazino-2-methyl-1,2,3,4-tetrahydroquinoline [compound (87)];

1-acetyl-4-[(4-chlorophenyl)amino]-6-[(4-(isopropylaminocarbonyl)piperazino-2-methyl-1,2,3,4-tetrahydroquinoline [compound (88)];

1-acetyl-4-[(4-carboxymethylphenyl)amino]-6-morpholino-2-methyl-1,2,3,4-tetrahydroquinoline [compound (89)];

1-acetyl-4-[(4-carbamoylmethylphenyl)amino]-2-methyl-6-morpholino-1,2,3,4-tetrahydroquinoline [compound (90)];

1-acetyl-6-(4-acetylpiperazinyl)-4-[(4-carboxymethylphenyl)amino]-2-methyl-1,2,3,4-tetrahydroquinoline [compound (91)];

1-acetyl-2-methyl-4-[(4-morpholinophenyl)amino]-1,2,3,4-tetrahydroquinoline-6-carboxamide [compound (92)];

1-acetyl-4-[(4-chlorophenyl)amino]-6-[(1-morpholino)carbonyl]-2-methyl-1,2,3,4-tetrahydroquinoline [compound (93)];

1-acetyl-6-[(4-acetyl)piperazino]-2-methyl-4-[(4-morpholinophenyl)amino]-1,2,3,4-tetrahydroquinoline [compound (94)];

1-acetyl-6-amino-4-[(4-chlorophenyl)amino]-2-methyl-1,2,3,4-tetrahydroquinoline [compound (95)];

1-acetyl-6-acetylamino-4-[(4-chlorophenyl)amino]-2-methyl-1,2,3,4-tetrahydroquinoline [compound (96)];

1-acetyl-4-[(4-chlorophenyl)amino]-2-methyl-1,2,3,4-tetrahydroquinoline-6-ethylcarbamate [compound (97)];

1-acetyl-6-methanesulfonylamino-2-methyl-4-[(4-morpholinophenyl)amino]-1,2,3,4-tetrahydroquinoline [compound (98)];

1-acetyl-6-methanesulfonylamino-2-methyl-4-[(4-ethoxycarbonylmethylphenyl)amino]-1,2,3,4-tetrahydroquinoline [compound (99)];

1-acetyl-4-[(4-fluorophenyl)amino]-2-methyl-1,2,3,4-tetrahydroquinoline-6-carboxylic acid [compound (100)];

ethyl 1-acetyl-4-[(4-methanesulfonylaminophenyl)amino]-2-methyl-1,2,3,4-tetrahydroquinoline-6-carboxylate [compound (101)];

1-acetyl-4-[(4-methanesulfonylaminophenyl)amino]-2-methyl-1,2,3,4-tetrahydroquinoline-6-carboxamide [compound (102)];

ethyl 1-acetyl-4-[(4-cyanomethylphenyl)amino]-2-methyl-1,2,3,4-tetrahydroquinoline-6-carboxylate [compound (103)];

1-acetyl-4-[(4-cyanomethylphenyl)amino]-2-methyl-1,2,3,4-tetrahydroquinoline-6-carboxamide [compound (104)];

1-acetyl-4-[(4-carboxymethylphenyl)amino]-2-methyl-1,2,3,4-tetrahydroquinoline-6-carboxamide [compound (105)];

1-acetyl-4-[(4-carbamoylmethylphenyl)amino]-2-methyl-1,2,3,4-tetrahydroquinoline-6-carboxamide [compound (106)];

1-acetyl-4-[(4-chlorophenyl)amino]-7-methanesulfonylamino-2-methyl-1,2,3,4-tetrahydroquinoline [compound (107)];

1-acetyl-4-[(4-hydroxy-3-methoxycarbonylphenyl)amino]-2-methyl-1,2,3,4-tetrahydroquinoline [compound (108)];

1-acetyl-4-[(2-carboxyphenyl)amino]-2-methyl-1,2,3,4-tetrahydroquinoline [compound (109)];

1-acetyl-6-[(2,6-dimethyl)morpholino]-4-[(4-methanesulfonylaminophenyl)amino]-2-methyl-1,2,3,4-tetrahydroquinoline [compound (110)];

1-acetyl-6-[(4-isopropylcarbonyl)piperazino]-4-[(4-methanesulfonylaminophenyl)amino]-2-methyl-1,2,3,4-tetrahydroquinoline [compound (111)];

1-acetyl-4-[(4-benzylphenyl)amino]-2-methyl-1,2,3,4-tetrahydroquinoline [compound (112)];

1-acetyl-4-[(4-chlorophenyl)amino]-N,N,2-trimethyl-1,2,3,4-tetrahydroquinoline-6-carboxamide [compound (113)];

1-acetyl-4-[(4-chlorophenyl)amino]-N,2-dimethyl-1,2,3,4-tetrahydroquinoline-6-carboxamide [compound (114)];

1-acetyl-4-[(4-chlorophenyl)amino]-2-methyl-1,2,3,4-tetrahydroquinoline-6-carbohydrazide [compound (115)];

1-acetyl-4-[(4-chlorophenyl)amino]-6-cyano-2-methyl-1,2,3,4-tetrahydroquinoline [compound (117)];

1-acetyl-4-[(4-chlorophenyl)amino]-N-methoxy-2-methyl-1,2,3,4-tetrahydroquinoline-6-carboxamide [compound (118)];

1-acetyl-4-[(4-chlorophenyl)amino]-2-methyl-6-(1H-tetrazol-5-yl)-1,2,3,4-tetrahydroquinoline [compound (119)];

1-acetyl-4-[(4-chlorophenyl)amino]-2-methyl-6-[1,2,4-oxadiazol-5(2H)-on-3-yl]-1,2,3,4-tetrahydroquinoline [compound (120)];

1-acetyl-4-[(4-chlorophenyl)amino]-6-hydroxymethyl-2-methyl-1,2,3,4-tetrahydroquinoline [compound (121)];

1-acetyl-4-[(4-ethoxycarbonylmethylphenyl)amino]-6-fluoro-2-methyl-1,2,3,4-tetrahydroquinoline [compound (122)];

1-acetyl-4-[(4-carboxymethylphenyl)amino]-6-fluoro-2-methyl-1,2,3,4-tetrahydroquinoline [compound (123)];

1-acetyl-4-[(4-carbamoylmethylphenyl)amino]-6-fluoro-2-methyl-1,2,3,4-tetrahydroquinoline [compound (124)];

1-acetyl-4-[4-(N,N-dimethylaminocarbonylmethyl)phenyl amino]-6-fluoro-2-methyl-1,2,3,4-tetrahydroquinoline [compound (125)];

1-acetyl-4-[(4-chlorophenyl)amino]-N-(2-hydroxyethyl)-2-methyl-1,2,3,4-tetrahydroquinoline-6-carboxamide [compound (126)];

4-{1-acetyl-4-[(4-chlorophenyl)amino]-2-methyl-1,2,3,4-tetrahydroquinolin-6-yl}-2-methyl-1H-imidazole [compound (127)];

1-acetyl-4-[(4-chlorophenyl)amino]-N-cyano-2-methyl-1,2,3,4-tetrahydroquinoline-6-carboxamide [compound (128)];

1-acetyl-4-[(4-chlorophenyl)amino]-N-hydroxy-2-methyl-1,2,3,4-tetrahydroquinoline-6-carboxamide [compound (129)];

1-acetyl-4-[(4-chlorophenyl)amino]-2-methyl-N-phenyl-1,2,3,4-tetrahydroquinoline-6-carboxamide [compound (130)];

1-acetyl-4-[(4-chlorophenyl)amino]-2-methyl-N-(3-pyridyl)-1,2,3,4-tetrahydroquinoline-6-carboxamide [compound (131)];

1-acetyl-4-[(4-morpholinophenyl)amino]-N,2-dimethyl-1,2,3,4-tetrahydroquinoline-6-carboxamide [compound (132)];

1-acetyl-4-[(4-morpholinophenyl)amino]-2-methyl-1,2,3,4-tetrahydroquinoline-6-carbohydrazide [compound (133)];

1-acetyl-4-[(4-morpholinophenyl)amino]-2-methyl-6-[1,3,4-oxadiazol-2(3H)-on-5-yl]-1,2,3,4-tetrahydroquinoline [compound (134)];

1-acetyl-4-[(4-morpholinophenyl)amino]-N-methoxy-2-methyl-1,2,3,4-tetrahydroquinoline-6-carboxamide [compound (135)];

1-acetyl-4-[(benzoxazol-5-yl)amino]-2-methyl-1,2,3,4-tetrahydroquinoline [compound (136)];

1-acetyl-6-fluoro-4-[(4-carboxyphenyl)amino]-2-methyl-1,2,3,4-tetrahydroquinoline [compound (137)];

1-acetyl-4-[(4-chlorophenyl)amino]-2-methyl-1,2,3,4-tetrahydroquinolin-6-ylboronic acid [compound (138)];

1-acetyl-2-methyl-4-(4-morpholinophenoxy)-1,2,3,4-tetrahydroquinoline-6-carboxylic acid [compound (139)];

1-acetyl-N,2-dimethyl-4-(4-morpholinophenoxy)-1,2,3,4-tetrahydroquinoline-6-carboxamide [compound (140)];

1-acetyl-4-(4-chlorophenoxy)-2-methyl-1,2,3,4-tetrahydroquinoline-6-carboxylic acid [compound (141)];

1-acetyl-4-(4-chlorophenoxy)-2-methyl-1,2,3,4-tetrahydroquinoline-6-carboxamide [compound (142)];

N-{4-[(1-acetyl-2-methyl-1,2,3,4-tetrahydroquinolin-4-yl)oxy]phenyl}methanesulfonamide [compound (143)];

ethyl 1-acetyl-4-[(4-cyclohexylphenyl)amino]-2-methyl-1,2,3,4-tetrahydroquinoline-6-carboxylate [compound (144)];

1-acetyl-4-[(4-cyclohexylphenyl)amino]-2-methyl-1,2,3,4-tetrahydroquinoline-6-carboxylic acid [compound (145)];

1-acetyl-4-[(4-cyclohexylphenyl)amino]-N,2-dimethyl-1,2,3,4-tetrahydroquinoline-6-carboxamide [compound (146)];

1-acetyl-4-[(4-cyclohexylphenyl)amino]-2-methyl-1,2,3,4-tetrahydroquinoline-6-carboxamide [compound (147)];

tert-butyl 12-{1-acetyl-4-[(4-chlorophenyl)amino]-2-methyl-1,2,3,4-tetrahydroquinoline-6-carboxamido}-4,7,10-trioxadodecanoate [compound (148)];

tert-butyl 12-{1-acetyl-2-methyl-4-[(4-morpholinophenyl)amino]-1,2,3,4-tetrahydroquinoline-6-carboxamido}-4,7,10-trioxadodecanoate [compound (149)];

methyl 4-(4-{1-acetyl-4-[(4-chlorophenyl)amino]-2-methyl-1,2,3,4-tetrahydroquinoline-6-carboxamido}phenyl)butanoate [compound (150)];

methyl 4-(4-{1-acetyl-2-methyl-4-[(4-morpholinophenyl)amino]-1,2,3,4-tetrahydroquinoline-6-carboxamido}phenyl)butanoate [compound (151)];

1-acetyl-4-(4-chlorophenoxy)-2-methyl-6-morpholino-1,2,3,4-tetrahydroquinoline [compound (152)];

ethyl 1-acetyl-2-methyl-4-{[4-(tetrahydro-2H-pyran-4-yl)phenyl]amino}-1,2,3,4-tetrahydroquinoline-6-carboxylate [compound (153)];

1-acetyl-2-methyl-4-{[4-(tetrahydro-2H-pyran-4-yl)phenyl]amino}-1,2,3,4-tetrahydroquinoline-6-carboxylic acid [compound (154)];

1-acetyl-N,2-dimethyl-4-{[4-(tetrahydro-2H-pyran-4-yl)phenyl]amino}-1,2,3,4-tetrahydroquinoline-6-carboxamide [compound (155)];

1-acetyl-2-methyl-4-{[4-(tetrahydro-2H-pyran-4-yl)phenyl]amino}-1,2,3,4-tetrahydroquinoline-6-carboxamide [compound (156)];

methyl 6-{1-acetyl-2-methyl-4-[(4-morpholinophenyl)amino]-1,2,3,4-tetrahydroquinoline-6-carboxamido}hexanoate [compound (157)];

methyl 6-{1-acetyl-4-[(4-chlorophenyl)amino]-2-methyl-1,2,3,4-tetrahydroquinoline-6-carboxamido}hexanoate [compound (158)];

1-acetyl-6-(4-isopropylpiperazin-1-yl)-2-methyl-4-[(4-morpholinophenyl)amino]-1,2,3,4-tetrahydroquinoline [compound (159)];

1-acetyl-2-methyl-6-[4-(methylsulfonyl)piperazin-1-yl]-4-[(4-morpholinophenyl)amino]-1,2,3,4-tetrahydroquinoline [compound (160)];

1-acetyl-2-methyl-6-morpholino-4-[(4-morpholinophenyl)amino]-1,2,3,4-tetrahydroquinoline [compound (161)];

ethyl 1-acetyl-2-methyl-4-{[4-(2-methylthiazol-4-yl)phenyl]amino}-1,2,3,4-tetrahydroquinoline-6-carboxylate [compound (162)];

1-acetyl-2-methyl-4-{[4-(2-methylthiazol-4-yl)phenyl]amino}-1,2,3,4-tetrahydroquinoline-6-carboxylic acid [compound (163)];

1-acetyl-2-methyl-4-{[4-(2-methylthiazol-4-yl)phenyl]amino}-1,2,3,4-tetrahydroquinoline-6-carboxamide [compound (164)];

1-acetyl-N,2-dimethyl-4-{[4-(2-methylthiazol-4-yl)phenyl]amino}-1,2,3,4-tetrahydroquinoline-6-carboxamide [compound (165)];

1-acetyl-N-benzoyl-2-methyl-4-[(4-morpholinophenyl)amino]-1,2,3,4-tetrahydroquinoline-6-carboxamide [compound (166)];

ethyl 1-acetyl-2-methyl-4-{[4-(oxazol-2-yl)phenyl]amino}-1,2,3,4-tetrahydroquinoline-6-carboxylate [compound (167)];

1-acetyl-2-methyl-4-{[4-(oxazol-2-yl)phenyl]amino}-1,2,3,4-tetrahydroquinoline-6-carboxylic acid [compound (168)];

1-acetyl-2-methyl-4-{[4-(oxazol-2-yl)phenyl]amino}-1,2,3,4-tetrahydroquinoline-6-carboxamide [compound (169)];

1-acetyl-N,2-dimethyl-4-([4-(oxazol-2-yl)phenyl]amino]-1,2,3,4-tetrahydroquinoline-6-carboxamide [compound (170)];

ethyl 1-acetyl-2-methyl-4-{[4-(1,2,3-thiadiazol-5-yl)phenyl]amino}-1,2,3,4-tetrahydroquinoline-6-carboxylate [compound (171)];

1-acetyl-2-methyl-4-{[4-(1,2,3-thiadiazol-5-yl)phenyl]amino}-1,2,3,4-tetrahydroquinoline-6-carboxylic acid [compound (172)];

1-acetyl-2-methyl-4-{[4-(1,2,3-thiadiazol-5-yl)phenyl]amino}-1,2,3,4-tetrahydroquinoline-6-carboxamide [compound (173)];

1-acetyl-N,2-dimethyl-4-{[4-(1,2,3-thiadiazol-5-yl)phenyl]amino}-1,2,3,4-tetrahydroquinoline-6-carboxamide [compound (174)];

N,1-diacetyl-2-methyl-4-[(4-morpholinophenyl)amino]-1,2,3,4-tetrahydroquinoline-6-carboxamide [compound (175)];

1-acetyl-N-isopropyl-2-methyl-4-[(4-morpholinophenyl)amino]-1,2,3,4-tetrahydroquinoline-6-carboxamide [compound (176)];

1-acetyl-2-methyl-4-[(4-morpholinophenyl)amino]-N-(pyridin-2-yl)-1,2,3,4-tetrahydroquinoline-6-carboxamide [compound (177)];

1-acetyl-N-cyclohexyl-2-methyl-4-[(4-morpholinophenyl)amino]-1,2,3,4-tetrahydroquinoline-6-carboxamide [compound (178)];

1-acetyl-2-methyl-4-[(3-morpholinophenyl)amino]-1,2,3,4-tetrahydroquinoline-6-carboxylic acid [compound (179)];

1-acetyl-N,2-dimethyl-4-[(3-morpholinophenyl)amino]-1,2,3,4-tetrahydroquinoline-6-carboxamide [compound (180)]; and 1-acetyl-2-methyl-4-[(3-morpholinophenyl)amino]-1,2,3,4-tetrahydroquinoline-6-carboxamide [compound (181)].

Furthermore, the present invention relates to a tetrahydroquinoline compound represented by formula (1) in which A represents an oxygen atom, or a salt thereof, or a solvate of the compound or the salt:

[Chemical Formula 1]

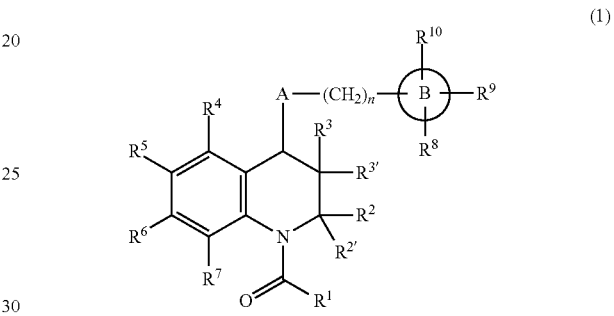

(1)

wherein $R^1$, $R^2$, $R^{2'}$, $R^3$, and $R^{3'}$ independently represent a hydrogen atom, a $C_{1-6}$ alkyl group, a $C_{2-6}$ alkenyl group, a $C_{2-6}$ alkynyl group, a mono($C_{1-6}$ alkyl)amino group, a di($C_{1-6}$ alkyl)amino group, or a $C_{3-6}$ cycloalkyl group;

$R^4$, $R^5$, $R^6$, $R^7$, $R^8$, $R^9$, and $R^{10}$ independently represent a hydrogen atom, a halogen atom, a $C_{1-6}$ alkyl group which may be substituted, a $C_{2-6}$ alkenyl group which may be substituted, a $C_{2-6}$ alkynyl group which may be substituted, a $C_{3-6}$ cycloalkyl group which may be substituted, a $C_{6-14}$ aryl group which may be substituted, a 5- to 10-membered heterocyclic group which may be substituted, a $C_{1-6}$ alkoxy group which may be substituted, a $C_{6-14}$ aryloxy group which may be substituted, an amino group, a mono($C_{1-6}$ alkylcarbonyl)amino group, a mono($C_{1-6}$ alkoxycarbonyl)amino group, a mono($C_{1-6}$ alkyl)amino group which may be substituted, a di($C_{1-6}$ alkyl)amino group which may be substituted, a mono($C_{6-14}$ aryl)amino group which may be substituted, a $C_{1-6}$ alkylthio group which may be substituted, a $C_{1-6}$ alkylsulfonyl group which may be substituted, a $C_{1-6}$ alkylsulfonylamino group which may be substituted, a $C_{1-6}$ alkylsulfinyl group which may be substituted, a $C_{1-6}$ alkoxycarbonyl group which may be substituted, a $C_{1-6}$ alkanoyl group which may be substituted, a 5- to 7-membered saturated heterocyclic carbonyl group which may be substituted, a hydroxyl group, a nitro group, a carboxyl group, a sulfonic acid group, a boronic acid group, a carbamoyl group which may be substituted, an ester group which may be substituted, or a cyano group, while $R^9$ and $R^{10}$ may be joined together to form a carbocyclic ring or a heterocyclic ring;

A represents an oxygen atom;

$R^{11}$ represents a hydrogen atom, or a $C_{1-6}$ alkyl group which may be substituted;

B represents a $C_{6-14}$ aryl group or a 5- to 10-membered heterocyclic group; and n represents an integer of 0 or 1.

Preferred examples of the compound of the present invention include the following group of compounds.

A family of compounds including:

1-acetyl-2-methyl-4-phenoxy-1,2,3,4-tetrahydroquinoline [compound (26)];

1-acetyl-4-(4-fluorophenoxy)-2-methyl-1,2,3,4-tetrahydroquinoline [compound (27)];

1-acetyl-4-(3-fluorophenoxy)-2-methyl-1,2,3,4-tetrahydroquinoline [compound (28)];

1-acetyl-4-(2-fluorophenoxy)-2-methyl-1,2,3,4-tetrahydroquinoline [compound (29)];

1-acetyl-4-(2,4-difluorophenoxy)-2-methyl-1,2,3,4-tetrahydroquinoline [compound (30)];

1-acetyl-4-(3,4-difluorophenoxy)-2-methyl-1,2,3,4-tetrahydroquinoline [compound (31)];

1-acetyl-7-fluoro-2-methyl-4-phenoxy-1,2,3,4-tetrahydroquinoline [compound (32)];

1-acetyl-8-fluoro-2-methyl-4-phenoxy-1,2,3,4-tetrahydroquinoline [compound (33)];

1-acetyl-4-(4-fluorophenoxy)-6-fluoro-2-methyl-1,2,3,4-tetrahydroquinoline [compound (34)];

1-acetyl-6-fluoro-2-methyl-4-phenoxy-1,2,3,4-tetrahydroquinoline [compound (35)];

1-acetyl-2-methyl-4-benzyloxy-1,2,3,4-tetrahydroquinoline [compound (36)];

ethyl 1-acetyl-4-(4-fluorophenoxy)-2-methyl-1,2,3,4-tetrahydroquinoline-6-carboxylate [compound (53)];

1-acetyl-4-(4-fluorophenoxy)-2-methyl-1,2,3,4-tetrahydroquinoline-6-carboxamide [compound (54)];

1-acetyl-4-(4-morpholinophenoxy)-2-methyl-1,2,3,4-tetrahydroquinoline [compound (55)];

1-acetyl-7-fluoro-4-(4-fluorophenoxy)-2-methyl-1,2,3,4-tetrahydroquinoline [compound (56)];

1-acetyl-4-(4-hydroxyphenoxy)-2-methyl-1,2,3,4-tetrahydroquinoline [compound (57)];

1-acetyl-4-(3,5-difluorophenoxy)-2-methyl-1,2,3,4-tetrahydroquinoline [compound (62)];

1-acetyl-4-(4-benzyloxyphenoxy)-2-methyl-1,2,3,4-tetrahydroquinoline [compound (64)];

1-acetyl-2-methyl-4-(4-nitrophenoxy)-1,2,3,4'-tetrahydroquinoline [compound (67)];

1-acetyl-4-(4-aminophenoxy)-2-methyl-1,2,3,4-tetrahydroquinoline [compound (68)];

1-acetyl-2-methyl-4-(4-morpholinophenoxy)-1,2,3,4-tetrahydroquinoline-6-carboxylic acid [compound (139)];

1-acetyl-N,2-dimethyl-4-(4-morpholinophenoxy)-1,2,3,4-tetrahydroquinoline-6-carboxamide [compound (140)];

1-acetyl-4-(4-chlorophenoxy)-2-methyl-1,2,3,4-tetrahydroquinoline-6-carboxylic acid [compound (141)];

1-acetyl-4-(4-chlorophenoxy)-2-methyl-1,2,3,4-tetrahydroquinoline-6-carboxamide [compound (142)];

N-{4-[(1-acetyl-2-methyl-1,2,3,4-tetrahydroquinolin-4-yl)oxy]phenyl}methanesulfonamide [compound (143)]; and 1-acetyl-4-(4-chlorophenoxy)-2-methyl-6-morpholino-1,2,3,4-tetrahydroquinoline [compound (152)].

The present invention also relates to a pharmaceutical composition containing the tetrahydroquinoline compound of the present invention or a salt thereof, or a solvate of the compound or the salt, and a pharmaceutically acceptable carrier.

Furthermore, the present invention relates to a tetrahydroquinoline compound selected from the following group of compounds, or a salt thereof, or a solvate of the compound or the salt.

A family of compounds including:

1-acetyl-8-fluoro-4-[(2-fluorophenyl)amino]-2-methyl-1,2,3,4-tetrahydroquinoline [compound (4)];

1-cyclohexanecarbonyl-6-fluoro-4-[(4-fluorophenyl)amino]-2-methyl-1,2,3,4-tetrahydroquinoline [compound (6)];

1-acetyl-7-cyano-2-methyl-4-phenylamino-1,2,3,4-tetrahydroquinoline [compound (7)];

1-acetyl-6-cyano-2-methyl-4-phenylamino-1,2,3,4-tetrahydroquinoline [compound (14)];

1-acetyl-4-[(4-isopropoxyphenyl)amino]-2-methyl-1,2,3,4-tetrahydroquinoline [compound (18)];

1-acetyl-2-methyl-4-[(4-morpholinophenyl)amino]-1,2,3,4-tetrahydroquinoline [compound (19)];

1-acetyl-4-[(4-N,N-dimethylaminophenyl)amino]-2-methyl-1,2,3,4-tetrahydroquinoline [compound (20)];

1-acetyl-7-bromo-2-methyl-4-phenylamino-1,2,3,4-tetrahydroquinoline [compound (23)];

1-acetyl-4-[(4-hydroxyphenyl)amino]-2-methyl-1,2,3,4-tetrahydroquinoline [compound (24)];

1-acetyl-2-methyl-4-[(1,1'-biphenyl-4-yl)amino]-1,2,3,4-tetrahydroquinoline [compound (25)];

1-acetyl-2-methyl-4-phenoxy-1,2,3,4-tetrahydroquinoline [compound (26)];

1-acetyl-4-(4-fluorophenoxy)-2-methyl-1,2,3,4-tetrahydroquinoline [compound (27)];

1-acetyl-4-(3-fluorophenoxy)-2-methyl-1,2,3,4-tetrahydroquinoline [compound (28)];

1-acetyl-4-(2-fluorophenoxy)-2-methyl-1,2,3,4-tetrahydroquinoline [compound (29)];

1-acetyl-4-(2,4-difluorophenoxy)-2-methyl-1,2,3,4-tetrahydroquinoline [compound (30)];

1-acetyl-4-(3,4-difluorophenoxy)-2-methyl-1,2,3,4-tetrahydroquinoline [compound (31)];

1-acetyl-7-fluoro-2-methyl-4-phenoxy-1,2,3,4-tetrahydroquinoline [compound (32)];

1-acetyl-8-fluoro-2-methyl-4-phenoxy-1,2,3,4-tetrahydroquinoline [compound (33)];

1-acetyl-4-(4-fluorophenoxy)-6-fluoro-2-methyl-1,2,3,4-tetrahydroquinoline [compound (34)];

1-acetyl-6-fluoro-2-methyl-4-phenoxy-1,2,3,4-tetrahydroquinoline [compound (35)];

1-acetyl-2-methyl-4-benzyloxy-1,2,3,4-tetrahydroquinoline [compound (36)];

1-acetyl-4-[(4-fluorophenyl)amino]-2-methyl-6-methoxy-1,2,3,4-tetrahydroquinoline [compound (37)];

1-acetyl-4-[(4-hydroxymethylphenyl)amino]-2-methyl-1,2,3,4-tetrahydroquinoline [compound (38)];

1-acetyl-4-[(4-methanesulfonylamidophenyl)amino]-2-methyl-1,2,3,4-tetrahydroquinoline [compound (39)];

1-acetyl-4-[(4-chlorophenyl)amino]-2-methyl-6-morpholino-1,2,3,4-tetrahydroquinoline [compound (40)];

ethyl 1-acetyl-4-[(4-chlorophenyl)amino]-2-methyl-1,2,3,4-tetrahydroquinoline-6-carboxylate [compound (41)];

1-acetyl-4-[(4-chlorophenyl)amino]-2-methyl-1,2,3,4-tetrahydroquinoline-6-carboxylic acid [compound (42)];

1-acetyl-4-[(4-chlorophenyl)amino]-2-methyl-1,2,3,4-tetrahydroquinoline-6-carboxamide [compound (43)];

1-acetyl-4-[(4-chlorophenyl)amino]-2-methyl-7-morpholino-1,2,3,4-tetrahydroquinoline [compound (44)];

1-acetyl-4-[(4-chlorophenyl)amino]-2-methyl-6-methanesulfonylamino-1,2,3,4-tetrahydroquinoline [compound (45)];

ethyl 1-acetyl-4-(4-fluorophenoxy)-2-methyl-1,2,3,4-tetrahydroquinoline-6-carboxylate [compound (53)];

1-acetyl-4-(4-fluorophenoxy)-2-methyl-1,2,3,4-tetrahydroquinoline-6-carboxamide [compound (54)];

1-acetyl-4-(4-morpholinophenoxy)-2-methyl-1,2,3,4-tetrahydroquinoline [compound (5.5)];

1-acetyl-7-fluoro-4-(4-fluorophenoxy)-2-methyl-1,2,3,4-tetrahydroquinoline [compound (56)];

1-acetyl-4-(4-hydroxyphenoxy)-2-methyl-1,2,3,4-tetrahydroquinoline [compound (57)];

1-acetyl-7-fluoro-4-[(3-fluorophenyl)amino]-2-methyl-1,2,3,4-tetrahydroquinoline [compound (58)];

1-acetyl-2-ethyl-4-phenylamino-1,2,3,4-tetrahydroquinoline [compound (59)];

1-acetyl-3,3-dimethyl-4-phenylamino-1,2,3,4-tetrahydroquinoline [compound (60)];

1-acetyl-3,3-dimethyl-4-phenylamino-1,2,3,4-tetrahydroquinoline [compound (61)];

1-acetyl-4-(3,5-difluorophenoxy)-2-methyl-1,2,3,4-tetrahydroquinoline [compound (62)];

1-acetyl-8-bromo-4-phenylamino-2-methyl-1,2,3,4-tetra hydroquinoline [compound (63)];

1-acetyl-4-(4-benzyloxyphenoxy)-2-methyl-1,2,3,4-tetrahydroquinoline [compound (64)];

6-fluoro-4-[(4-fluorophenyl)amino]-2-methyl-1-N-methylcarbamoyl-1,2,3,4-tetrahydroquinoline [compound (65)];

1-cyclopentanecarbonyl-6-fluoro-2-methyl-4-[(4-fluoro phenyl)amino]-1,2,3,4-tetrahydroquinoline [compound (66)];

1-acetyl-2-methyl-4-(4-nitrophenoxy)-1,2,3,4-tetrahydroquinoline [compound (67)];

1-acetyl-4-(4-aminophenoxy)-2-methyl-1,2,3,4-tetrahydroquinoline [compound (68)];

1-acetyl-4-[(4-methoxymethylphenyl)amino]-2-methyl-1,2,3,4-tetrahydroquinoline [compound (69)];

1-acetyl-4-[(4-ethoxycarbonylmethylphenyl)amino]-2-methyl-1,2,3,4-tetrahydroquinoline [compound (70)];

1-acetyl-4-[(4-carboxymethylphenyl)amino]-2-methyl-1,2,3,4-tetrahydroquinoline [compound (71)];

1-acetyl-2-methyl-4-[(2-morpholinophenyl)amino]-1,2,3,4-tetrahydroquinoline [compound (72)];

1-acetyl-4-[(4-fluoro-3-morpholinophenyl)amino]-2-methyl-1,2,3,4-tetrahydroquinoline [compound (73)];

1-acetyl-6-bromo-4-[(4-chlorophenyl)amino]-2-methyl-1,2,3,4-tetrahydroquinoline [compound (74)];

1-acetyl-2-methyl-4-[(4-piperazinylphenyl)amino]-1,2,3,4-tetrahydroquinoline [compound (76)];

1-acetyl-4-{[4-(4-acetylpiperazinyl)phenyl]amino}-2-methyl-1,2,3,4-tetrahydroquinoline [compound (77)];

1-acetyl-4-{[4-(4-methanesulfonylpiperazinyl)phenyl]amino}-2-methyl-1,2,3,4-tetrahydroquinoline [compound (78)];

1-acetyl-6-[(4-acetyl)piperazino]-4-[(4-chlorophenyl)amino]-2-methyl-1,2,3,4-tetrahydroquinoline [compound (79)];

1-acetyl-6-[(4-methanesulfonyl)piperazino]-4-[(4-chlorophenyl)amino]-2-methyl-1,2,3,4-tetrahydroquinoline [compound (80)];

1-acetyl-4-[(4-chlorophenyl)amino]-6-[(4-isopropyl)piperazino]-2-methyl-1,2,3,4-tetrahydroquinoline [compound (81)]:

1-acetyl-4-[(4-chlorophenyl)amino]-6-[(2-hydroxy)ethylamino]-2-methyl-1,2,3,4-tetrahydroquinoline [compound (82)];

1-acetyl-4-[(4-chlorophenyl)amino]-6-[(3,5-dimethyl)morpholino]-2-methyl-1,2,3,4-tetrahydroquinoline [compound (83)];

1-acetyl-4-[(4-chlorophenyl)amino]-6-[(4-isopropylcarbonyl)piperazino]-2-methyl-1,2,3,4-tetrahydroquinoline [compound (84)];

1-acetyl-4-[(4-chlorophenyl)amino]-6-[(4-cyclohexylcarbonyl)piperazino]-2-methyl-1,2,3,4-tetrahydroquinoline [compound (85)];

1-acetyl-6-[(4-benzoyl)piperazino]-2-methyl-4-[(4-chlorophenyl)amino]-1,2,3,4-tetrahydroquinoline [compound (86)];

1-acetyl-4-[(4-chlorophenyl)amino]-6-[4-(N,N-diethylaminocarbonyl)piperazino-2-methyl-1,2,3,4-tetrahydroquinoline [compound (87)];

1-acetyl-4-[(4-chlorophenyl)amino]-6-[4-(isopropylaminocarbonyl)piperazino-2-methyl-1,2,3,4-tetrahydroquinoline [compound (88)];

1-acetyl-4-[(4-carboxymethylphenyl)amino]-6-morpholino-2-methyl-1,2,3,4-tetrahydroquinoline [compound (89)];

1-acetyl-4-[(4-carbamoylmethylphenyl)amino]-2-methyl-6-morpholino-1,2,3,4-tetrahydroquinoline [compound (90)];

1-acetyl-6-(4-acetylpiperazinyl)-4-[(4-carboxymethylphenyl)amino]-2-methyl-1,2,3,4-tetrahydroquinoline [compound (91)];

1-acetyl-2-methyl-4-[(4-morpholinophenyl)amino]-1,2,3,4-tetrahydroquinoline-6-carboxamide [compound (92)];

1-acetyl-4-[(4-chlorophenyl)amino]-6-[(1-morpholino)carbonyl]-2-methyl-1,2,3,4-tetrahydroquinoline [compound (93)];

1-acetyl-6-[(4-acetyl)piperazino]-2-methyl-4-[(4-morpholinophenyl)amino]-1,2,3,4-tetrahydroquinoline [compound (94)];

1-acetyl-6-amino-4-[(4-chlorophenyl)amino]-2-methyl-1,2,3,4-tetrahydroquinoline [compound (95)];

1-acetyl-6-acetylamino-4-[(4-chlorophenyl)amino]-2-methyl-1,2,3,4-tetrahydroquinoline [compound (96)];

1-acetyl-4-[(4-chlorophenyl)amino]-2-methyl-1,2,3,4-tetrahydroquinoline-6-ethylcarbamate [compound (97)];

1-acetyl-6-methanesulfonylamino-2-methyl-4-[(4-morpholinophenyl)amino]-1,2,3,4-tetrahydroquinoline [compound (98)];

1-acetyl-6-methanesulfonylamino-2-methyl-4-[(4-ethoxy carbonylmethylphenyl)amino]-1,2,3,4-tetrahydroquinoline [compound (99)];

1-acetyl-4-[(4-fluorophenyl)amino]-2-methyl-1,2,3,4-tetrahydroquinoline-6-carboxylic acid [compound (100)];

ethyl 1-acetyl-4-[(4-methanesulfonylaminophenyl)amino]-2-methyl-1,2,3,4-tetrahydroquinoline-6-carboxylate [compound (101)];

1-acetyl-4-[(4-methanesulfonylaminophenyl)amino]-2-methyl-1,2,3,4-tetrahydroquinoline-6-carboxamide [compound (102)];

ethyl 1-acetyl-4-[(4-cyanomethylphenyl)amino]-2-methyl-1,2,3,4-tetrahydroquinoline-6-carboxylate [compound (103)];

1-acetyl-4-[(4-cyanomethylphenyl)amino]-2-methyl-1,2,3,4-tetrahydroquinoline-6-carboxamide [compound (104)];

1-acetyl-4-[(4-carboxymethylphenyl)amino]-2-methyl-1,2,3,4-tetrahydroquinoline-6-carboxamide [compound (105)];

1-acetyl-4-[(4-carbamoylmethylphenyl)amino]-2-methyl-1,2,3,4-tetrahydroquinoline-6-carboxamide [compound (106)];

1-acetyl-4-[(4-chlorophenyl)amino]-7-methanesulfonylamino-2-methyl-1,2,3,4-tetrahydroquinoline [compound (107)];

1-acetyl-4-[(4-hydroxy-3-methoxycarbonylphenyl) amino]-2-methyl-1,2,3,4-tetrahydroquinoline [compound (108)];

1-acetyl-4-[(2-carboxyphenyl)amino]-2-methyl-1,2,3,4-tetrahydroquinoline [compound (109)];

1-acetyl-6-[(2,6-dimethyl)morpholino]-4-[(4-methanesulfonylaminophenyl)amino]-2-methyl-1,2,3,4-tetrahydroquinoline [compound (110)];

1-acetyl-6-[(4-isopropylcarbonyl)piperazino]-4-[(4-methanesulfonylaminophenyl)amino]-2-methyl-1,2,3,4-tetrahydro quinoline [compound (111)];

1-acetyl-4-[(4-benzylphenyl)amino]-2-methyl-1,2,3,4-tetrahydroquinoline [compound (112)];

1-acetyl-4-[(4-chlorophenyl)amino]-N,N,2-trimethyl-1,2,3,4-tetrahydroquinoline-6-carboxamide [compound (113)];

1-acetyl-4-[(4-chlorophenyl)amino]-N,2-dimethyl-1,2,3,4-tetrahydroquinoline-6-carboxamide [compound (114)];

1-acetyl-4-[(4-chlorophenyl)amino]-2-methyl-1,2,3,4-tetrahydroquinoline-6-carbohydrazide [compound (115)];

1-acetyl-4-[(4-chlorophenyl)amino]-6-cyano-2-methyl-1,2,3,4-tetrahydroquinoline [compound (117)];

1-acetyl-4-[(4-chlorophenyl)amino]-N-methoxy-2-methyl-1,2,3,4-tetrahydroquinoline-6-carboxamide [compound (118)];

1-acetyl-4-[(4-chlorophenyl)amino]-2-methyl-6-(1H-tetrazol-5-yl)-1,2,3,4-tetrahydroquinoline [compound (119)];

1-acetyl-4-[(4-chlorophenyl)amino]-2-methyl-6-[1,2,4-oxadiazol-5(2H)-on-3-yl]-1,2,3,4-tetrahydroquinoline [compound (120)];

1-acetyl-4-[(4-chlorophenyl)amino]-6-hydroxymethyl-2-methyl-1,2,3,4-tetrahydroquinoline [compound (121)];

1-acetyl-4-[(4-ethoxycarbonylmethylphenyl)amino]-6-fluoro-2-methyl-1,2,3,4-tetrahydroquinoline [compound (122));

1-acetyl-4-[(4-carboxymethylphenyl)amino]-6-fluoro-2-methyl-1,2,3,4-tetrahydroquinoline [compound (123)];

1-acetyl-4-[(4-carbamoylmethylphenyl)amino]-6-fluoro-2-methyl-1,2,3,4-tetrahydroquinoline [compound (124)];

1-acetyl-4-[(4-(N,N-dimethylaminocarbonylmethyl)phenyl amino]-6-fluoro-2-methyl-1,2,3,4-tetrahydroquinoline [compound (125)];

1-acetyl-4-[(4-chlorophenyl)amino]-N-(2-hydroxyethyl)-2-methyl-1,2,3,4-tetrahydroquinoline-6-carboxamide [compound (126)];

4-{1-acetyl-4-[(4-chlorophenyl)amino]-2-methyl-1,2,3,4-tetrahydroquinoline-6-yl}-2-methyl-1H-imidazole [compound (127)];

1-acetyl-4-[(4-chlorophenyl)amino]-N-cyano-2-methyl-1,2,3,4-tetrahydroquinoline-6-carboxamide [compound (128)];

1-acetyl-4-[(4-chlorophenyl)amino]-N-hydroxy-2-methyl-1,2,3,4-tetrahydroquinoline-6-carboxamide [compound (129)];

1-acetyl-4-[(4-chlorophenyl)amino]-2-methyl-N-phenyl-1,2,3,4-tetrahydroquinoline-6-carboxamide [compound (130)];

1-acetyl-4-[(4-chlorophenyl)amino]-2-methyl-N-(3-pyridyl)-1,2,3,4-tetrahydroquinoline-6-carboxamide [compound (131)];

1-acetyl-4-[(4-morpholinophenyl)amino]-N,2-dimethyl-1,2,3,4-tetrahydroquinoline-6-carboxamide [compound (132)];

1-acetyl-4-[(4-morpholinophenyl)amino]-2-methyl-1,2,3,4-tetrahydroquinoline-6-carbohydrazide [compound (133)];

1-acetyl-4-[(4-morpholinophenyl)amino]-2-methyl-6-[1,3,4-oxadiazol-2(3H)-on-5-yl]-1,2,3,4-tetrahydroquinoline [compound (134)];

1-acetyl-4-[(4-morpholinophenyl)amino]-N-methoxy-2-methyl-1,2,3,4-tetrahydroquinoline-6-carboxamide [compound (135)];

1-acetyl-4-[(benzoxazol-5-yl)amino]-2-methyl-1,2,3,4-tetrahydroquinoline [compound (136)];

1-acetyl-6-fluoro-4-[(4-carboxyphenyl)amino]-2-methyl-1,2,3,4-tetrahydroquinoline [compound (137)];

1-acetyl-4-[(4-chlorophenyl)amino]-2-methyl-1,2,3,4-tetrahydroquinolin-6-ylboronic acid [compound (138)];

1-acetyl-2-methyl-4-(4-morpholinophenoxy)-1,2,3,4-tetrahydroquinoline-6-carboxylic acid [compound (139)];

1-acetyl-N,2-dimethyl-4-(4-morpholinophenoxy)-1,2,3,4-tetrahydroquinoline-6-carboxamide [compound (140)];

1-acetyl-4-(4-chlorophenoxy)-2-methyl-1,2,3,4-tetrahydroquinoline-6-carboxylic acid [compound (141)];

1-acetyl-4-(4-chlorophenoxy)-2-methyl-1,2,3,4-tetrahydroquinoline-6-carboxamide [compound (142)];

N-{4-[(1-acetyl-2-methyl-1,2,3,4-tetrahydroquinolin-4-yl)oxy]phenyl}methanesulfonamide [compound (143)];

ethyl 1-acetyl-4-[(4-cyclohexylphenyl)amino]-2-methyl-1,2,3,4-tetrahydroquinoline-6-carboxylate [compound (144)];

1-acetyl-4-[(4-cyclohexylphenyl)amino]-2-methyl-1,2,3,4-tetrahydroquinoline-6-carboxylic acid [compound (145)];

1-acetyl-4-[(4-cyclohexylphenyl)amino]-N,2-dimethyl-1,2,3,4-tetrahydroquinoline-6-carboxamide [compound (146)];

1-acetyl-4-[(4-cyclohexylphenyl)amino]-2-methyl-1,2,3,4-tetrahydroquinoline-6-carboxamide [compound (147)];

tert-butyl 12-{1-acetyl-4-[(4-chlorophenyl)amino]-2-methyl-1,2,3,4-tetrahydroquinoline-6-carboxamido}-4,7,10-trioxadodecanoate [compound (148)];

tert-butyl 12-{1-acetyl-2-methyl-4-[(4-morpholinophenyl)amino]-1,2,3,4-tetrahydroquinoline-6-carboxamido}-4,7,10-trioxadodecanoate [compound (149)];

methyl 4-(4-{1-acetyl-4-[(4-chlorophenyl)amino]-2-methyl-1,2,3,4-tetrahydroquinoline-6-carboxamido}phenyl)butanoate [compound (150)];

methyl 4-(4-{1-acetyl-2-methyl-4-[(4-morpholinophenyl)amino]-1,2,3,4-tetrahydroquinoline-6-carboxamido}phenyl)butanoate [compound (151)];

1-acetyl-4-(4-chlorophenoxy)-2-methyl-6-morpholino-1,2,3,4-tetrahydroquinoline [compound (152)];

ethyl 1-acetyl-2-methyl-4-{[4-(tetrahydro-2H-pyran-4-yl)phenyl]amino}-1,2,3,4-tetrahydroquinoline-6-carboxylate [compound (153)];

1-acetyl-2-methyl-4-{[4-(tetrahydro-2H-pyran-4-yl)phenyl]amino}-1,2,3,4-tetrahydroquinoline-6-carboxylic acid [compound (154)];

1-acetyl-N,2-dimethyl-4-{[4-(tetrahydro-2H-pyran-4-yl)phenyl]amino}-1,2,3,4-tetrahydroquinoline-6-carboxamide [compound (155)];

1-acetyl-2-methyl-4-{[4-(tetrahydro-2H-pyran-4-yl)phenyl]amino}-1,2,3,4-tetrahydroquinoline-6-carboxamide [compound (156)];

methyl 6-{1-acetyl-2-methyl-4-[(4-morpholinophenyl)amino]-1,2,3,4-tetrahydroquinoline-6-carboxamido}hexanoate [compound (157)];

methyl 6-{1-acetyl-4-[(4-chlorophenyl)amino]-2-methyl-1,2,3,4-tetrahydroquinoline-6-carboxamido}hexanoate [compound (158)];

1-acetyl-6-(4-isopropylpiperazin-1-yl)-2-methyl-4-[(4-morpholinophenyl)amino]-1,2,3,4-tetrahydroquinoline [compound (159)];

1-acetyl-2-methyl-6-[4-(methylsulfonyl)piperazin-1-yl]-4-[(4-morpholinophenyl)amino]-1,2,3,4-tetrahydroquinoline [compound (160)];

1-acetyl-2-methyl-6-morpholino-4-[(4-morpholinophenyl)amino]-1,2,3,4-tetrahydroquinoline [compound (161)];

ethyl 1-acetyl-2-methyl-4-{[4-(2-methylthiazol-4-yl)phenyl]amino}-1,2,3,4-tetrahydroquinoline-6-carboxylate [compound (162)];

1-acetyl-2-methyl-4-{[4-(2-methylthiazol-4-yl)phenyl]amino}-1,2,3,4-tetrahydroquinoline-6-carboxylic acid [compound (163)];

1-acetyl-2-methyl-4-{[4-(2-methylthiazol-4-yl)phenyl]amino}-1,2,3,4-tetrahydroquinoline-6-carboxamide [compound (164)];

1-acetyl-N,2-dimethyl-4-{[4-(2-methylthiazol-4-yl)phenyl]amino}-1,2,3,4-tetrahydroquinoline-6-carboxamide [compound (165)];

1-acetyl-N-benzoyl-2-methyl-4-[(4-morpholinophenyl)amino]-1,2,3,4-tetrahydroquinoline-6-carboxamide [compound (166)];

ethyl 1-acetyl-2-methyl-4-{[4-(oxazol-2-yl)phenyl]amino}-1,2,3,4-tetrahydroquinoline-6-carboxylate [compound (167)];

1-acetyl-2-methyl-4-{[4-(oxazol-2-yl)phenyl]amino}-1,2,3,4-tetrahydroquinoline-6-carboxylic acid [compound (168)];

1-acetyl-2-methyl-4-{[4-(oxazol-2-yl)phenyl]amino}-1,2,3,4-tetrahydroquinoline-6-carboxamide [compound (169)];

1-acetyl-N,2-dimethyl-4-{[4-(oxazol-2-yl)phenyl]amino}-1,2,3,4-tetrahydroquinoline-6-carboxamide [compound (170)];

ethyl 1-acetyl-2-methyl-4-{[4-(1,2,3-thiadiazol-5-yl)phenyl]amino}-1,2,3,4-tetrahydroquinoline-6-carboxylate [compound (171)];

1-acetyl-2-methyl-4-{[4-(1,2,3-thiadiazol-5-yl)phenyl]amino}-1,2,3,4-tetrahydroquinoline-6-carboxylic acid [compound (172)];

1-acetyl-2-methyl-4-{[4-(1,2,3-thiadiazol-5-yl)phenyl]amino}-1,2,3,4-tetrahydroquinoline-6-carboxamide [compound (173)];

1-acetyl-N,2-dimethyl-4-{[4-(1,2,3-thiadiazol-5-yl)phenyl]amino}-1,2,3,4-tetrahydroquinoline-6-carboxamide [compound (174)];

N,1-diacetyl-2-methyl-4-[(4-morpholinophenyl)amino]-1,2,3,4-tetrahydroquinoline-6-carboxamide [compound (175)];

1-acetyl-N-isopropyl-2-methyl-4-[(4-morpholinophenyl)amino]-1,2,3,4-tetrahydroquinoline-6-carboxamide [compound (176)];

1-acetyl-2-methyl-4-[(4-morpholinophenyl)amino]-N-(pyridin-2-yl)-1,2,3,4-tetrahydroquinoline-6-carboxamide [compound (177)];

1-acetyl-N-cyclohexyl-2-methyl-4-[(4-morpholinophenyl)amino]-1,2,3,4-tetrahydroquinoline-6-carboxamide [compound (178)];

1-acetyl-2-methyl-4-[(3-morpholinophenyl)amino]-1,2,3,4-tetrahydroquinoline-6-carboxylic acid [compound (179)];

1-acetyl-N,2-dimethyl-4-[(3-morpholinophenyl)amino]-1,2,3,4-tetrahydroquinoline-6-carboxamide [compound (180)]; and 1-acetyl-2-methyl-4-[(3-morpholinophenyl)amino]-1,2,3,4-tetrahydroquinoline-6-carboxamide [compound (181)].

Furthermore, the present invention relates to a pharmaceutical composition containing one kind or two or more kinds of compounds among the tetrahydroquinoline compounds selected from the group of compounds described above, or salts thereof, or solvates of the compounds or the salts, and a pharmaceutically acceptable carrier thereof. The present invention also relates to a pharmaceutical composition which is a pharmaceutical composition for the enhancement of EPO production, a pharmaceutical composition for the promotion of hemoglobin production, or a pharmaceutical composition for the prevention and/or treatment of anemia.

Moreover, the present invention relates to a 1-acyl-4-(substituted oxy, substituted amino, or substituted thio)-1,2,3,4-tetrahydroquinoline derivative, more particularly, the tetrahydroquinoline compound represented by the formula (1), or a salt thereof, or a solvate of the compound or the salt, as an EPO production enhancer, a hemoglobin production enhancer, and/or a prophylactic/therapeutic agent for anemia.

Effects of the Invention

The present invention was made by finding that a 1-acyl-4-(substituted oxy, substituted amino, or substituted thio)-1,2,3,4-tetrahydroquinoline derivative, more particularly, the tetrahydroquinoline compound represented by the formula (1) of the present invention, or a salt thereof, or a solvate of the compound or the salt has an excellent EPO production enhancing activity and/or a hemoglobin production enhancing activity. Thus, the present invention is useful as a pharmaceutical composition for the prevention and/or treatment of diseases in which the symptoms are ameliorated by enhancing EPO production and/or by enhancing hemoglobin production (for example, anemia such as anemia in chronic renal failure patients, autologous blood donation, anemia of premature, anemia of AIDS patients and cancer patients under chemotherapy, chronic anemia, iron-deficiency anemia, aplastic anemia, hemolytic anemia, and megaloblastic anemia). Furthermore, the present invention provides a prophylactic and/or therapeutic agent for anemia containing, as an active ingredient, an orally administrable, low molecular weight compound having an EPO production enhancing activity and/or hemoglobin production enhancing activity.

MODES FOR CARRYING OUT THE INVENTION

Hereinafter, the present invention will be described in detail.

The definitions for the terms used in the present invention are as follows.

The "1-acyl-4-(substituted oxy, substituted amino, or substituted thio)-1,2,3,4-tetrahydroquinoline derivative" according to the present invention is a 1-acyl-4-(substituted oxy, substituted amino, or substituted thio)-1,2,3,4-tetrahydroquinoline or a derivative thereof, in which the nitrogen atom at the 1-position in 1,2,3,4-tetrahydroquinoline is acylated, and a substituent selected from the group consisting of substituted oxy groups such as a phenoxy group, a benzyloxy group, and a heterocyclic oxy group; substituted amino groups such as a phenylamino group, a benzylamino group, and a heterocyclic amino group; and substituted thio groups such as a phenylthio group, a benzylthio group, and a heterocyclic thio group, is bonded to the 4-position. Examples of the acyl group that is bonded to the 1-position include an alkylcarbonyl group, a cycloalkylcarbonyl group, or an aminocarbonyl group. Therefore, the "1-acyl-4-(substituted oxy, substituted amino, or substituted thio)-1,2,3,4-tetrahydroquinoline" of the present invention may be more specifically "1-(alkylcarbonyl, cycloalkylcarbonyl, or aminocarbonyl)-4-(phenoxy, benzyloxy, phenylamino, benzylamino, phenylthio, benzylthio, heterocyclic oxy, heterocyclic amino, or heterocyclic thio)-1,2,3,4-tetrahydroquinoline."

The derivative of the present invention is a collective name for the compound I-acyl-4-(substituted oxy, substituted amino, or substituted thio)-1,2,3,4-tetrahydroquinoline, in which two hydrogen atoms at the 2-position; two hydrogen atoms at the 3-position; the cyclic hydrogen atoms in the phenoxy group, benzyloxy group, phenylamino group, benzylamino group, phenylthio group, benzylthio group, heterocyclic oxy group, heterocyclic amino group or heterocyclic thio group, or the hydrogen atoms of the amino group at the 4-position; and the hydrogen atoms at the 5-position, 6-position, 7-position, and 8-position of the tetrahydroquinoline ring, are each substituted by an atom other than hydrogen atom, or by a substituent (atomic group). Examples of such atom or substituent include a halogen atom, a $C_{1-6}$ alkyl group, a $C_{2-6}$ alkenyl group, a $C_{2-6}$ alkynyl group, a $C_{3-6}$ cycloalkyl group, a $C_{6-14}$ aryl group, a $C_{7-10}$ arylalkyl group, a 5- to 10-membered heterocyclic group, a $C_{1-6}$ alkoxy group, a $C_{6-14}$ aryloxy group, a $C_{7-18}$ arylalkoxy group, an amino group, a mono($C_{1-6}$ alkylcarbonyl)amino group, a mono($C_{1-6}$ alkoxycarbonyl)amino group, a mono($C_{1-6}$ alkyl)amino group, a di($C_{1-6}$ alkyl)amino group, a mono($C_{6-14}$ aryl) amino group, a mono($C_{7-18}$ arylalkyl)amino group, a $C_{1-6}$ alkylthio group, a $C_{1-6}$ alkylsulfonyl group, a $C_{1-6}$ alkylsulfonylamino group, a $C_{1-6}$ alkylsulfinyl group, a $C_{1-6}$ alkanoyl group, a 5- to 7-membered saturated heterocyclic carbonyl group, a hydroxyl group, a nitro group, a nitrile group, a sulfonic acid group, a boronic acid group, a carboxyl group, a carbamoyl group, and an ester group. These substituents may be further substituted with other substituents.

Preferred examples of the 1,2,3,4-tetrahydroquinoline derivative of the present invention include 1-acyl-2-alkyl-4-(substituted oxy, substituted amino, or substituted thio)-1,2,3,4-tetrahydroquinoline or derivatives thereof, in which an alkyl group, preferably an alkyl group having 1 to 6 carbon atoms, and more preferably an alkyl group having 1 to 4 carbon atoms, is bonded to the carbon atom at the 2-position, and more preferably, bonded in the cis-configuration. The number of such substituents that can be present in the carbon atom at the 2-position may be one or two, but it is preferable that one substituent be present. Furthermore, preferred examples of the substituent for the carbon atom at the 3-position include a hydrogen atom or an alkyl group, but a hydrogen atom is more preferable The "halogen atom" of the present invention means a halogeno group, and specific examples include a fluorine atom, a chlorine atom, a bromine atom, or an iodine atom.

The "alkyl group" of the present invention may be linear or branched. Therefore, specific examples of the "$C_{1-6}$ alkyl group" include linear or branched alkyl groups having 1 to 6 carbon atoms, such as a methyl group, an ethyl group, an n-propyl group, an isopropyl group, an n-butyl group, an isobutyl group, a sec-butyl group, a test-butyl group, an n-pentyl group, an isopentyl group, a neopentyl group, a 4-methylbutyl group, a 1-ethylpropyl group, an n-hexyl group, an isohexyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, and a 2-ethylbutyl group. A more preferred "alkyl group" is a "$C_{1-4}$ alkyl group."

Specific examples of the "$C_{1-4}$ alkyl group" of the present invention include linear or branched alkyl groups having 1 to 4 carbon atoms, such as a methyl group, an ethyl group, an n-propyl group, an isopropyl group, an n-butyl group, an isobutyl group, a sec-butyl group, and a tert-butyl group.

The alkyl group in the alkylcarbonyl group of the present invention is preferably the alkyl group described above.

The "alkenyl group" of the present invention may be linear or branched. Therefore, specific examples of the "$C_{2-6}$ alkenyl group" include linear or branched alkenyl groups having 2 to 6 carbon atoms, such as a vinyl group, a prop-1-en-1-yl group, an allyl group, an isopropenyl group, a but-1-en-1-yl group, a but-2-en-1-yl group, a but-3-en-1-yl group, a 2-methylprop-2-en-1-yl group, a 1-methylprop-2-en-1-yl group, a pent-1-en-1-yl group, a pent-2-en-1-yl group, a pent-3-en-1-yl group, a pent-4-en-1-yl group, a 3-methylbut-2-en-1-yl group, a 3-methylbut-3-en-1-yl group, a hex-1-en-1-yl group, a hex-2-en-1-yl group, a hex-3-en-1-yl group, a hex-4-en-1-yl group, a hex-5-en-1-yl group, and a 4-methylpent-3-en-1-yl group. The "alkenyl group" is more preferably a "$C_{2-4}$ alkenyl group."

Specific examples of the "$C_{2-4}$ alkenyl group" of the present invention include linear or branched alkenyl groups having 2 to 4 carbon atoms, such as a vinyl group, a prop-1-en-1-yl group, an allyl group, an isopropenyl group, a but-1-en-1-yl group, a but-2-en-1-yl group, a but-3-en-1-yl group, a 2-methylprop-2-en-1-yl group, and a 1-methylprop-2-en-1-yl group.

The "alkynyl group" of the present invention may be linear or branched. Therefore, specific examples of the "$C_{2-6}$ alkynyl group" include linear or branched alkynyl groups having 2 to 6 carbon atoms, such as an ethynyl group, a prop-1-yn-1-yl group, a prop-2-yn-1-yl group, a but-1-yn-1-yl group, a but-3-yn-1-yl group, a 1-methylprop-2-yn-1-yl group, a pent-1-yn-1-yl group, a pent-4-yn-1-yl group, a hex-1-yn-1-yl group, and a hex-5-yn-1-yl group. The "alkynyl group" is more preferably a "$C_{2-4}$ alkynyl group."

Specific examples of the "$C_{2-4}$ alkynyl group" of the present invention include linear or branched alkynyl groups having 2 to 4 carbon atoms, such as an ethynyl group, a prop-1-yn-1-yl group, a prop-2-yn-1-yl group, a but-1-yn-1-yl group, a but-3-yn-1-yl group, and a 1-methylprop-2-yn-1-yl group.

Specific examples of the "$C_{3-6}$ cycloalkyl group" of the present invention include monocyclic cycloalkyl groups having 3 to 6 carbon atoms, such as a cyclopropyl group, a cyclobutyl group, a cyclopentyl group, and a cyclohexyl group.

Furthermore, the cycloalkyl group in the "cycloalkylcarbonyl group" of the present invention is preferably a "$C_{3-6}$ cycloalkyl group" such as described above.

The "aryl group" of the present invention is a monocyclic, polycyclic or fused-ring aromatic hydrocarbon group having 6 to 14 carbon atoms. Therefore, specific examples of the "$C_{6-14}$ aryl group" include monocyclic, polycyclic, or fused-ring aromatic hydrocarbon groups having 6 to 14 carbon atoms, such as a phenyl group, a naphthyl group, an azulenyl group, an anthryl group, an indenyl group, a fluorenyl group, and a phenanthryl group. The "aryl group" is more preferably a "$C_{6-10}$ aryl group."

The "$C_{6-10}$ aryl group" of the present invention is a monocyclic, polycyclic, or fused-ring aromatic hydrocarbon group having 6 to 10 carbon atoms, and specific examples include a phenyl group, a naphthyl group, and an azulenyl group.

The "heterocyclic group" of the present invention means a 5- to 10-membered monocyclic, polycyclic, or fused-ring saturated or unsaturated heterocyclic group containing one to four heteroatoms selected from an oxygen atom, a sulfur atom, and a nitrogen atom. Therefore, specific examples of the "5- to 10-membered heterocyclic group" include a pyrrolidinyl group, an imidazolidinyl group, an imidazolinyl group, a pyrazolidinyl group, a pyrazolinyl group, a piperidyl group, a piperazinyl group, a morpholinyl group, a diazepan-1-yl group, an oxolanyl group, a furyl group, a thienyl group, a pyrrolyl group, an oxazolyl group, an isoxazolyl group, a dihydroisoxazolyl group, a thiazolyl group, an isothiazolyl group, an imidazolyl group, a pyrazolyl group, an oxadiazolyl group, an oxooxadiazolyl group, a thiadiazolyl group, a triazolyl group, a tetrazolyl group, a pyridinyl group, an azepinyl group, an oxazepinyl group, a benzofuranyl group, an isobenzofuranyl group, a benzothienyl group, an indolyl group, an isoindolyl group, an indazolyl group, a benzimidazolyl group, a benzoxazolyl group, a benzisoxazolyl group, a benzothiazolyl group, a benzisothiazolyl group, a benzoxadiazolyl group, a benzothiadiazolyl group, a benzotriazolyl group, a quinolyl group, an isoquinolyl group, a cinnolinyl group, a quinazolinyl group, a quinoxalinyl group, a phthalazinyl group, a naphthyridinyl group, a purinyl group, and a pteridinyl group. The "heterocyclic group" is more preferably a "5- to 7-membered heterocyclic group."

Specific examples of the "5- to 7-membered heterocyclic group" of the present invention include a pyrrolidinyl group, an imidazolidinyl group, a pyrazolidinyl group, a piperidyl group, a piperazinyl group, a morpholinyl group, an oxolanyl group, a furyl group, a thienyl group, a pyrrolyl group, an oxazolyl group, an isoxazolyl group, a dihydroisoxazolyl group, a thiazolyl group, an isothiazolyl group, an imidazolyl group, a pyrazolyl group, an oxadiazolyl group, a thiadiazolyl group, a triazolyl group, a tetrazolyl group, and a pyridinyl group. Particularly preferably, the "5- to 7-membered heterocyclic group" may be a 5- to 7-membered monocyclic "5- to 7-membered heterocyclic group" containing 1 to 4 heteroatoms consisting of an oxygen atom, a nitrogen atom or a sulfur atom, such as a piperidyl group, a piperazinyl group, a morpholinyl group, a tetrazolyl group, an oxadiazolyl group, or an oxolanyl group.

The "alkoxy group" of the present invention may be linear or branched. Therefore, specific examples of the "$C_{1-6}$ alkoxy group" include linear or branched alkoxy groups having 1 to 6 carbon atoms, such as a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a neopentoxy group, a 4-methylbutoxy group, a 1-ethylpropoxy group, an n-hexyloxy group, an isohexyloxy group, a 3-methylpentoxy group, a 2-methylpentoxy group, a 1-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 1-ethylbutoxy group, and a 2-ethylbutoxy group. The "alkoxy group" is more preferably a "$C_{1-4}$ alkoxy group."

Specific examples of the "$C_{1-4}$ alkoxy group" of the present invention include a methoxy group, an ethoxy group, an n-propoxy group, an isopropoxy group, an n-butoxy group, an isobutoxy group, a sec-butoxy group, and a tert-butoxy group.

The "mono(alkylcarbonyl)amino group" of the present invention means a group in which one alkylcarbonyl group that will be described below is bonded to the nitrogen atom of an amino group. Therefore, specific examples of the "$C_{1-6}$ alkylcarbonylamino group" include a formylamino group, an acetylamino group, a propionylamino group, a butyrylamino group, an isobutyrylamino group, a valerylamino group, an isovalerylamino group, and a pivaloylamino group. The "mono(alkylcarbonyl)amino group" is more preferably a "mono($C_{1-4}$ alkylcarbonyl)amino group."

The "mono(alkoxycarbonyl)amino group" of the present invention means a group in which one alkoxycarbonyl group that will be described below is bonded to the nitrogen atom of an amino group. Therefore, specific examples of the "mono($C_{1-6}$ alkoxycarbonyl)amino group" include a methoxycarbonylamino group, an ethoxycarbonylamino group, an n-propoxycarbonylamino group, an isopropoxycarbonylamino group, an n-butoxycarbonylamino group, an isobutoxycarbonylamino group, a sec-butoxycarbonylamino group, a tert-butoxycarbonylamino group, an n-pentoxycarbonylamino group, an isopentoxycarbonylamino group, a neopentoxycarbonylamino group, a 4-methylbutoxycarbonylamino group, a 1-ethylpropoxycarbonylamino group, an n-hexyloxycarbonylamino group, an isohexyloxycarbonylamino group, a 3-methylpentoxycarbonylamino group, a 2-methylpentoxycarbonylamino group, a 1-methylpentoxycarbonylamino group, a 3,3-dimethylbutoxycarbonylamino group, a 2,2-dimethylbutoxycarbonylamino group, a 1,1-dimethylbutoxycarbonylamino group, a 1,2-dimethylbutoxycarbonylamino group, a 1,3-dimethylbutoxycarbonylamino group, a 2,3-dimethylbutoxycarbonylamino group, a 1-ethylbutoxycarbonylamino group, and a 2-ethylbutoxycarbonylamino group. The "mono(alkoxycarbonyl)amino group" is more preferably a "mono($C_{1-4}$ alkoxycarbonyl)amino group."

The "$C_{6-14}$ aryloxy group" of the present invention means a group in which an oxygen atom is bonded to a "$C_{6-14}$ aryl group" described above. Therefore, specific examples of the "$C_{6-14}$ aryloxy group" include a phenyloxy group, a naphthyloxy group, an azulenyloxy group, an anthryloxy group, an indenyloxy group, a fluorenyloxy group, and a phenanthryloxy group. The "$C_{6-14}$ aryloxy group" is more preferably a "$C_{6-10}$ aryloxy group."

Specific examples of the "$C_{6-10}$ aryloxy group" of the present invention include a phenyloxy group, a naphthyloxy group, and an azulenyloxy group.

The "mono(alkyl)amino group" of the present invention means a group in which one alkyl group described above is bonded to the nitrogen atom of an amino group. Therefore, specific examples of the "mono($C_{1-6}$ alkyl)amino group" include a methylamino group, an ethylamino group, an n-propylamino group, an isopropylamino group, an n-butylamino group, a sec-butylamino group, a tert-butylamino group, an n-pentylamino group, an isopentylamino group, a neopentylamino group, a 4-methylbutylamino group, a 1-ethylpropylamino group, an n-hexylamino group, an isohexylamino group, a 3-methylpentylamino group, a 2-methylpentylamino group, a 1-methylpentylamino group, a 3,3-dimethylbutylamino group, a 2,2-dimethylbutylamino group, a 1,1-dimethylbutylamino group, a 1,2-dimethylbutylamino group, a 1,3-dimethylbutylamino group, a 2,3-dimethylbutylamino group, a 1-ethylbutylamino group, and a 2-ethylbutylamino group. The "mono(alkyl)amino group" is more preferably a "mono($C_{1-4}$ alkylamino group."

Specific examples of the "mono($C_{1-4}$ alkyl)amino group" of the present invention include a methylamino group, an ethylamino group, an n-propylamino group, an isopropylamino group, an n-butylamino group, a sec-butylamino group, and a tert-butylamino group.

The "di(alkyl) amino group" of the present invention means a group in which two identical or different alkyl groups described above are bonded to a nitrogen atom. Therefore, specific examples of the "di($C_{1-6}$ alkyl)amino group" include a dimethylamino group, a methylethylamino group, a diethylamino group, a methyl-n-propylamino group, an ethyl-n-propylamino group, a di-n-propylamino group, a methylisopropylamino group, an ethylisopropylamino group, a diisopropylamino group, a methyl-n-butylamino group, an ethyl-n-butylamino group, an n-propyl-n-butylamino group, a di-n-butylamino group, a di-sec-butylamino group, a di-tert-butylamino group, a dipentylamino group, and a dihexylamino group. The "di(alkyl)amino group" is more preferably a "di($C_{1-4}$ alkyl)amino group."

Specific examples of the "di($C_{1-4}$ alkyl)amino group" of the present invention include a dimethylamino group, a methylethylamino group, a diethylamino group, a methyl-n-propylamino group, an ethyl-n-propylamino group, a di-n-propylamino group, a methylisopropylamino group, an ethylisopropylamino group, a diisopropylamino group, a methyl-n-butylamino group, an ethyl-n-butylamino group, an n-propyl-n-butylamino group, a di-n-butylamino group, a di-sec-butylamino group, and a di-tert-butylamino group.

The "mono($C_{6-14}$ aryl)amino group" of the present invention means a group in which one "$C_{6-14}$ aryl group" described above is bonded to the nitrogen atom of an amino group. Therefore, specific examples of the "mono($C_{6-14}$ aryl)amino group" include a phenylamino group, a naphthylamino group, an azulenylamino group, an anthrylamino group, an indenylamino group, a fluorenylamino group, and a phenanthrylamino group. The "mono($C_{6-14}$ aryl)amino group" is more preferably a "mono($C_{6-10}$ aryl)amino group."

Specific examples of the "mono($C_{6-10}$ aryl)amino group" of the present invention include a phenylamino group, a naphthylamino group, and an azulenylamino group.

The "alkylthio group" of the present invention means a group in which one alkyl group described above is bonded to a sulfur atom. Therefore, specific examples of the "$C_{1-6}$ alkylthio group" include a methylthio group, an ethylthio group, an n-propylthio group, an isopropylthio group, an n-butylthio group, an isobutylthio group, a sec-butylthio group, a tert-butylthio group, an n-pentylthio group, an isopentylthio group, a neopentylthio group, a 4-methylbutyl thio group, a 1-ethylpropylthio group, an n-hexylthio group, an isohexylthio group, a 3-methylpentylthio group, a 2-methylpentylthio group, a 1-methylpentylthio group, a 3,3-dimethylbutylthio group, a 2,2-dimethylbutylthio group, a 1,1-dimethylbutylthio group, a 1,2-dimethylbutylthio group, a 1,3-dimethylbutylthio group, a 2,3-dimethylbutylthio group, a 1-ethylbutylthio group, and a 2-ethylbutylthio group. The "alkylthio group" is more preferably a "$C_{1-4}$ alkylthio group."

Specific examples of the "$C_{1-4}$ alkylthio group" of the present invention include a methylthio group, an ethylthio group, an n-propylthio group, an isopropylthio group, an n-butylthio group, an isobutylthio group, a sec-butylthio group, and a tert-butylthio group.

The "alkylsulfonyl group" of the present invention means a sulfonyl ($SO_2$) substituted with an alkyl group described above. Therefore, specific examples of the "$C_{1-6}$ alkylsulfonyl group" include a methylsulfonyl group, an ethylsulfonyl group, an n-propylsulfonyl group, an isopropylsulfonyl group, an n-butylsulfonyl group, an isobutylsulfonyl group, a sec-butylsulfonyl group, a tert-butylsulfonyl group, an n-pentylsulfonyl group, an isopentylsulfonyl group, a neopentylsulfonyl group, a 4-methylbutylsulfonyl group, a 1-ethylpropylsulfonyl group, an n-hexylsulfonyl group, an isohexylsulfonyl group, a 3-methylpentylsulfonyl group, a 2-methylpentylsulfonyl group, a 1-methylpentylsulfonyl group, a 3,3-dimethylbutylsulfonyl group, a 2,2-dimethylbutylsulfonyl group, a 1,1-dimethylbutylsulfonyl group, a 1,2-dimethylbutylsulfonyl group, a 1,3-dimethylbutylsulfonyl group, a 2,3-dimethylbutylsulfonyl group, a 1-ethylbutylsulfonyl group, and a 2-ethylbutylsulfonyl group. The "alkylsulfonyl group" is more preferably a "$C_{1-4}$ alkylsulfonyl group."

Specific examples of the "$C_{1-4}$ alkylsulfonyl group" of the present invention include a methylsulfonyl group, an ethylsulfonyl group, an n-propylsulfonyl group, an isopropylsulfonyl group, an n-butylsulfonyl group, an isobutylsulfonyl group, a sec-butylsulfonyl group, and a tert-butylsulfonyl group.

The "alkylsulfonylamino group" of the present invention means a group in which one "alkylsulfonyl group" described above is bonded to the nitrogen atom of an amino group. Therefore, specific examples of the "$C_{1-6}$ alkylsulfonylamino group" include a methanesulfonylamino group, an ethanesulfonylamino group, a propanesulfonylamino group, an isopropanesulfonylamino group, an n-butanesulfonylamino group, a 2-methylpropanesulfonylamino group, a 1-methylpropanesulfonylamino group, a 1,1-dimethylethylsulfonylamino group, a pentanesulfonylamino group, a 3-methylbutanesulfonylamino group, a 2-methylbutanesulfonylamino group, a 1-methylbutanesulfonylamino group, a 1,1-dimethylpropanesulfonylamino group, a 1,2-dimethylpropanesulfonylamino group, a 2,2-dimethylpropanesulfonylamino group, a 1-ethylpropanesulfonylamino group, a hexanesulfonylamino group, a 1-methylpentanesulfonylamino group, a 2-methylpentanesulfonylamino group, a 3-methylpentanesulfonylamino group, a 4-methylpentanesulfonylamino group, a 1,1-dimethylbutanesulfonylamino group, a 1,2-dimethylbutanesulfonylamino group, a 1,3-dimethylbutanesulfonylamino group, a 2,2-dimethylbutanesulfonylamino group, a 2,3-dimethylbutanesulfonylamino group, a 3,3-dimethylbutanesulfonylamino group, a 1-ethylbutanesulfonylamino group, a 2-ethylbutanesulfonylamino group, and a 3-ethylbutanesulfonylamino group. The "alkylsulfonylamino group" is more preferably a "$C_{1-4}$ alkylsulfonylamino group."

Specific examples of the "$C_{1-4}$ alkylsulfonylamino group" of the present invention include a methanesulfonylamino group, an ethanesulfonylamino group, a propanesulfonylamino group, an isopropanesulfonylamino group, an n-butanesulfonylamino group, a 2-methylpropanesulfonylamino group, a 1-methylpropanesulfonylamino group, and a 1,1-dimelhylethylsulfonylamino group.

The "alkylsulfinyl group" of the present invention means a sulfinyl (SO) substituted with an alkyl group described above. Therefore, specific examples of the "$C_{1-6}$ alkylsulfinyl group" include a methylsulfinyl group, an ethylsulfinyl group, an n-propylsulfinyl group, an isopropylsulfinyl group, an n-butylsulfinyl group, an isobutylsulfinyl group, a sec-butylsulfinyl group, a tert-butylsulfinyl group, an n-pentylsulfinyl group, an isopentylsulfinyl group, a neopentylsulfinyl group, a 4-methylbutylsulfinyl group, a 1-ethylpropylsulfinyl group, an n-hexylsulfinyl group, an isohexylsulfinyl group, a 3-methylpentylsulfinyl group, a 2-methylpentylsulfinyl group, a 1-methylpentylsulfinyl group, a 3,3-dimethylbutylsulfinyl group, a 2,2-dimethylbutylsulfinyl group, a 1,1-dimethylbutylsulfinyl group, a 1,2-dimethylbutylsulfinyl group, a 1,3-dimethylbutylsulfinyl group, a 2,3-dimethylbutylsulfinyl group, a 1-ethylbutylsulfinyl group, and a 2-ethylbutylsulfinyl group. The "alkylsulfinyl group" is more preferably a "$C_{1-4}$ alkylsulfinyl group."

Specific examples of the "$C_{1-4}$ alkylsulfinyl group" of the present invention include a methylsulfinyl group, an ethylsulfinyl group, an n-propylsulfinyl group, an isopropylsulfinyl group, an n-butylsulfinyl group, an isobutylsulfinyl group, a sec-butylsulfinyl group, and a tert-butylsulfinyl group.

The "alkoxycarbonyl group" of the present invention means a group in which an "alkoxy group" described above is bonded to a carbonyl group. Therefore, specific examples of the "$C_{1-6}$ alkoxycarbonyl group" include a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, an n-pentoxycarbonyl group, an isopentoxycarbonyl group, a neopentoxycarbonyl group, a 4-methylbutoxycarbonyl group, a 1-ethylpropoxycarbonyl group, an n-hexyloxycarbonyl group, an isohexyloxycarbonyl group, a 3-methylpentoxycarbonyl group, a 2-methylpentoxycarbonyl group, a 1-methylpentoxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group, a 1-ethylbutoxycarbonyl group, and a 2-ethylbutoxycarbonyl group. The "alkoxycarbonyl group" is more preferably a "$C_{1-4}$ alkoxycarbonyl group."

Specific examples of the "$C_{1-4}$ alkoxycarbonyl group" of the present invention include a methoxycarbonyl group, an ethoxycarbonyl group, an n-propoxycarbonyl group, an iso-propoxycarbonyl group, an n-butoxycarbonyl group, an isobutoxycarbonyl group, a sec-butoxycarbonyl group, and a tert-butoxycarbonyl group.

The "alkanoyl group (alkylcarbonyl group)" of the present invention means a group in which an oxo group is bonded to a hydrogen atom or to the 1-position of a "$C_{1-6}$ alkyl group" described above, and the alkanoyl group may be linear or branched. Therefore, specific examples of the "$C_{1-6}$ alkanoyl group" include a formyl group, an acetyl group, a propionyl group, a butyryl group, an isobutyryl group, a valeryl group, an isovaleryl group, and a pivaloyl group. The "alkanoyl group" is more preferably a "$C_{1-4}$ alkanoyl group."

Specific examples of the "$C_{1-4}$ alkanoyl group" of the present invention include a formyl group, an acetyl group, a propionyl group, a butyryl group, and an isobutyryl group.

The "5- to 7-membered saturated heterocyclic carbonyl group" of the present invention means a group in which a saturated "5- to 7-membered heterocyclic ring" is bonded to a carbonyl group. Specific examples include a pyrrolidinylcarbonyl group, an imidazolidinylcarbonyl group, a pyrazolidinylcarbonyl group, a piperidylcarbonyl group, a piperazinylcarbonyl group, and a morpholinylcarbonyl group.

The "acyl group" of the present invention means a "cycloalkylcarbonyl group" in which an "alkanoyl group (alkylcarbonyl group)" described above or a cyclic alkyl group is bonded through a carbonyl moiety; an "arylcarbonyl group" in which an aryl group is bonded through a carbonyl moiety; and a "heterocyclic carbonyl group" in which a saturated or unsaturated heterocyclic group is bonded through a carbonyl moiety. Specific examples of the "alkanoyl group" include "$C_{1-6}$ alkanoyl groups" such as a formyl group, an acetyl group, a propionyl group, a butyryl group, an isobutyryl group, a valeryl group, an isovaleryl group, and a pivaloyl group. Examples of the "cycloalkylcarbonyl group" include "$C_{3-6}$ cycloalkylcarbonyl groups" such as a cyclopropylcarbonyl group, a cyclobutylcarbonyl group, a cyclopentylcarbonyl group, and a cyclohexylcarbonyl group. Examples of the "arylcarbonyl group" include "$C_{6-10}$ arylcarbonyl group" such as a benzoyl group, a naphthylcarbonyl group, and an azulenylcarbonyl group. Examples of the "heterocyclic carbonyl group" include "5- to 10-membered heterocyclic carbonyl groups" such as a pyrrolidinylcarbonyl group, an imidazolidinylcarbonyl group, an oxazolidinylcarbonyl group, a thiazolidinylcarbonyl group, an oxolanylcarbonyl group, a morpholinylcarbonyl group, a piperazinylcarbonyl group, a piperidinylcarbonyl group, a hexahydro-1H-1,4-diazepinylcarbonyl group, a furoyl group, a thenoyl group, a pyrrolylcarbonyl group, a pyridylcarbonyl group, a pyrazinylcarbonyl group, a pyrimidinylcarbonyl group, a pyridazinylcarbonyl group, an imidazolylcarbonyl group, a pyrazolylcarbonyl group, an oxazolylcarbonyl group, an isoxazolylcarbonyl group, a thiadiazolylcarbonyl group, a 1,2,3-triazolylcarbonyl group, a 1,2,4-triazolylcarbonyl group, a tetrazolylcarbonyl group, a benzofuranylcarbonyl group, an isobenzofuranylcarbonyl group, a benzothiophenylcarbonyl group, an indolylcarbonyl group, an indolinylcarbonyl group, an isoindolylcarbonyl group, an indazolylcarbonyl group, a benzimidazolylcarbonyl group, a benzoxazolylcarbonyl group, a benzisoxazolylcarbonyl group, a benzothiazolylcarbonyl group, a benzisothiazolylcarbonyl group, a benzotriazolylcarbonyl group, a chromenylcarbonyl group, a quinolylcarbonyl group, an isoquinolylcarbonyl group, a 1,2,3,4-tetrahydroquinolylcarbonyl group, a 1,2,3,4-tetrahydroisoquinolylcarbonyl group, cinnolinylcarbonyl group, a quinazolinylcarbonyl group, a quinoxalinylcarbonyl group, a phthalazinylcarbonyl group, and a naphthyridinylcarbonyl group.

The "sulfonic acid group" of the present invention is a group represented by formula: —$SO_3H$, and the "boronic acid group" is a group represented by formula: —B $(OH)_2$. Furthermore, examples of the carbamoyl group which may be substituted include a carbamoyl group (—$CONH_2$), and groups in which one or each of two hydrogen atoms on the nitrogen atom of a carbamoyl group is substituted by a $C_{1-6}$ alkyl group; a $C_{1-6}$ alkoxy group; a $C_{1-6}$ alkyl group substituted with a hydroxyl group, an amino group, an alkoxy group, a cyano group or the like; a $C_{6-10}$ aryl group such as a phenyl group; a heterocyclic group such as a pyridyl group; a group in which two hydrogen atoms bonded to a nitrogen atom are substituted by a $C_{3-6}$ alkylene group (one or two carbon atoms of the alkylene group may be substituted by an oxygen atom or a nitrogen atom), and the alkylene group forms a ring together with the adjacent nitrogen atom; an alkanoyl group; an arylcarbonyl group; a hydroxyl group; an amino group; a $C_{1-6}$ alkyl-substituted amino group; a cyano group; and the like.

Furthermore, examples of the ester group which may be substituted include an ester group (—COOR), and groups in which the R moiety of an ester group is substituted by a $C_{1-6}$ alkyl group substituted with a hydroxyl group, an amino group, an aryl group, a cyano group or the like; a $C_{6-10}$ aryl group; a $C_{7-12}$ arylalkyl group; and the like.

Examples of the "substituent" moiety for the "$C_{1-6}$ alkyl group which may be substituted", "$C_{2-6}$ alkenyl group which may be substituted", "$C_{2-6}$ alkynyl group which may be substituted", "$C_{3-6}$ cyclo alkyl group which may be substituted", "$C_{6-14}$ aryl group which may be substituted", "5- to 10-membered heterocyclic group which may be substituted", "$C_{1-6}$ alkoxy group which may be substituted", "$C_{6-14}$ aryloxy group which may be substituted", "mono($C_{1-6}$ alkyl) amino group which may be substituted", "di($C_{1-6}$ alkyl) amino group which may be substituted", "mono($C_{6-14}$ aryl)amino group which may be substituted", "$C_{1-6}$ alkylthio group which may be substituted", "$C_{1-6}$ alkylsulfonyl group which may be substituted", "mono($C_{1-6}$ alkylsulfonyl)amino group which may be substituted", "$C_{1-6}$ alkylsulfinyl group which may be substituted", "$C_{1-6}$ alkoxycarbonyl group which may be substituted", "$C_{1-6}$ alkanoyl group which may be substituted", "5- to 7-membered saturated heterocyclic carbonyl group which may be substituted", and "carbamoyl group which may be substituted" of the present invention, include a halogen atom; a $C_{1-6}$ alkyl group which may be substituted with a hydroxyl group, an alkoxy group such as a tert-butoxycarbonylethoxyethoxyethoxy group, an alkoxycarbonyl group such as a methoxycarbonyl group, or the like; a $C_{2-6}$ alkenyl group; a $C_{2-6}$ alkynyl group; a $C_{3-6}$ cycloalkyl group; a $C_{6-14}$ aryl group; a $C_{7-18}$ arylalkyl group; a 5- to 10-membered heterocyclic group which may be substituted with a $C_{1-6}$ alkyl group; a $C_{1-6}$ alkoxy group which may be substituted with a methoxy group; a $C_{6-14}$ aryloxy group; a $C_{7-18}$ arylalkoxy group; a mono($C_{1-6}$ alkyl)amino group; a di($C_{1-6}$ alkyl)amino group; a mono($C_{6-14}$ aryl)amino group; a mono ($C_{7-18}$ arylalkyl)amino group; a $C_{1-6}$ alkylthio group; a $C_{1-6}$ alkylsulfonyl group; a mono($C_{1-6}$ alkylsulfonyl)amino group; a $C_{1-6}$ alkylsulfinyl group; a $C_{1-6}$ alkanoyl group; a hydroxyl group; a nitro group; a nitrile group; a carboxyl group; a carbamoyl group; a $C_{1-6}$ alkoxycarbonyl group; a $C_{1-6}$ alkylsulfonylamino group; a cyano group; an amino group; a mono(alkyl)carbamoyl group such as an isopropylcarbamoyl group; a di(alkyl) carbamoyl group such as a dimethylcarbamoyl group or a diethylcarbamoyl group; an alkylcarbonyl group such as an isopropylcarbonyl group; a cycloalkylcarbonyl group such as a cyclopropylcarbonyl group; an arylcarbonyl group such as a phenylcarbonyl group; and a mono($C_{1-6}$ alkanoyl)amino group such as an acetylamino group.

Unless particularly stated, the number of substituents substantially means that the relevant group "may be substituted with one or more substituents," more preferably means that the relevant group "may be substituted with one to five substituents," and even more preferably means that the relevant group "may be substituted with one to three substituents." Therefore, examples of a "$C_{1-6}$ alkyl group which may be substituted" include a $C_{1-6}$ alkyl group which may be substituted with one or two or more substituents such as a halo-$C_{1-6}$ alkyl group.

Examples of the "halo-$C_{1-6}$ alkyl group" of the present invention include a trifluoromethyl group, a 2-fluoroethyl group, a 2-chloroethyl group, a 2-bromoethyl group, a 3-fluoropropyl group, a 3-chloropropyl group, a 4-fluorobutyl group, a 4-chlorobutyl group, a 2,2,2-trifluoroethyl group, a 3,3,3-trifluoropropyl group, a pentafluoroethyl group, and a 2,2,2-trifluoro-1-trifluoromethylethyl group. The "halo-$C_{1-6}$ alkyl group" is more preferably a "halo-$C_{1-4}$ alkyl group."

The "carbocyclic ring" according to the present invention is a saturated or partially saturated, 3- to 7-membered carbocyclic ring formed to include adjacent carbon atoms, and examples thereof include a cyclopropene ring, a cyclobutene ring, a cyclopentene ring, a cyclohexene ring, a cycloheptene ring, a benzene ring, and the like.

The "heterocyclic ring" according to the present invention is an unsaturated or partially saturated 3- to 7-membered heterocyclic ring which is formed to include adjacent carbon atoms, and contains 1 to 4 heteroatoms selected from an oxygen atom, a sulfur atom, and a nitrogen atom. Examples thereof include a 1,3-dioxole ring, a 1,4-dioxene ring, a 1,4-dihydropyridine ring, a 1,2,3,4-tetrahydropyrazine ring, a 6,7-dihydro-5H-1,4-dioxepine ring, a furan ring, a thiophene ring, a pyrrole ring, an oxazole ring, a triazole ring, an imidazole ring, a pyrazole ring, a 1,2,3-oxadiazole ring, a 1,2,3-thiadiazole ring, a 1,2,3-triazole ring, a pyridine ring, a pyrimidine ring, a pyridazine ring, a 1H-1,4-diazepine ring, and the like.

In addition to these, those groups that are not defined herein are intended to have the definitions conventionally used.

The "$C_{1-6}$ alkyl group" for $R^1$ in the formula (1) is preferably a "$C_{1-4}$ alkyl group, and more preferred examples include a methyl group and an ethyl group, with a methyl group being particularly preferred.

Preferred examples of the "$C_{3-6}$ cycloalkyl group" for $R^1$ in the formula (1) include a cyclopropyl group, a cyclobutyl group, a cyclopentyl group, and a cyclohexyl group, and more preferred examples include a cyclopropyl group.

The "mono($C_{1-6}$ alkyl)amino group" for $R^1$ in the formula (I) is preferably a "mono($C_{1-4}$ alkyl)amino group," and more preferred examples include a methylamino group.

$R^2$ and $R^{2'}$ in the formula (1) are each preferably a hydrogen atom, or a $C_{1-6}$ alkyl group which may be substituted. The "$C_{1-6}$ alkyl group" is more preferably a "$C_{1-4}$ alkyl group," and particularly preferably a methyl group. When $R^2$ is a $C_{1-6}$ alkyl group, $R^{2'}$ is preferably a hydrogen atom.

$R^3$ and $R^{3'}$ in the formula (1) are each preferably a hydrogen atom.

The "halogen atom" for $R^4$ in the formula (1) is preferably a fluorine atom or a bromine atom.

The "halogen atom" for $R^5$ in the formula (1) is preferably a fluorine atom or a bromine atom.

The "$C_{1-6}$ alkyl group which may be substituted" for $R^5$ in the formula (1) is preferably a "$C_{1-4}$ alkyl group which may be substituted," and is more preferably a methyl group or a hydroxymethyl group.

The "$C_{1-6}$ alkoxy group" for $R^5$ in the formula (1) is preferably a "$C_{1-4}$ alkoxy group," and more preferably a methoxy group.

The "5- to 10-membered heterocyclic group" for $R^5$ in the formula (1) is preferably a "5- to 7-membered heterocyclic group," and more preferred examples include a piperidyl group (a piperidino group, a piperidin-2-yl group, a piperidin-3-yl group, or a piperidin-4-yl group), a piperazinyl group (a piperazino group, or a piperazin-2-yl group), a morpholinyl group (a morpholino group, a morpholin-2-yl group, or a morpholin-3-yl group), a tetrazolyl group, and an oxadiazolyl group. Particularly preferred examples include a piperidino group, a piperazino group, a morpholino group, a tetrazolyl group, and an oxadiazolyl group.

The "$C_{1-6}$ alkoxycarbonyl group" for $R^5$ in the formula (1) is preferably a "$C_{1-4}$ alkoxycarbonyl group," and particularly preferred examples include a methoxycarbonyl group and an ethoxycarbonyl group.

The "$C_{1-6}$ alkylsulfonylamino group" for $R^5$ in the formula (1) is preferably a "$C_{1-4}$ alkylsulfonylamino group," and more preferred examples include a methanesulfonylamino group.

The "mono($C_{1-6}$ alkyl)amino group which may be substituted" for $R^5$ in the formula (1) is preferably a hydroxyethylamino group.

The "mono($C_{1-6}$ alkylcarbonyl)amino group" for $R^5$ in the formula (1) is preferably a "mono($C_{1-4}$ alkylcarbonyl)amino group," and is preferably an acetylamino group.

The "mono($C_{1-6}$ alkoxycarbonyl)amino group" for $R^5$ in the formula (1) is preferably a "mono($C_{1-4}$ alkoxycarbonyl)amino group," and is preferably an ethoxycarbonylamino group.

The "5- to 7-membered saturated heterocyclic carbonyl group" for $R^5$ in the formula (1) is preferably a morpholinocarbonyl group.

Preferred examples of the "carbamoyl group which may be substituted" for $R^5$ in the formula (1) include a mono($C_{1-6}$ alkyl)carbamoyl group, a mono(hydroxyl-$C_{1-6}$ alkyl)carbamoyl group, a mono(substituted-$C_{1-6}$ alkylalkyl)carbamoyl group, a mono($C_{1-6}$ alkoxycarbonylalkyl)carbamoyl group, a mono($C_{3-6}$ cycloalkyl) carbamoyl group, a mono($C_{1-6}$ alkoxy) carbamoyl group, a mono($C_{6-10}$ aryl)carbamoyl group, a mono(5- to 7-membered saturated heterocyclic carbonyl)carbamoyl group, a mono($C_{6-10}$ arylcarbonyl)carbamoyl group, a mono(cyano)carbamoyl group, a mono(hydroxy)carbamoyl group, a mono(amino)carbamoyl group, and a di($C_{1-6}$ alkyl) carbamoyl group, and more preferred examples include a methylcarbamoyl group, an isopropylcarbamoyl group, a mono(2-hydroxyethyl)carbamoyl group, a mono(tert-butoxycarbonylethoxyethoxyethoxymethyl)carbamoyl group, a mono(methoxycarbonylpentyl)carbamoyl group, a mono(cyclohexyl) carbamoyl group, a mono(phenyl) carbonyl group, a mono(pyridinyl)carbonyl group, a mono(benzyl)carbamoyl group, a mono(cyano)carbamoyl group, a mono(hydroxy)carbamoyl group, a mono(amino) carbamoyl group, and a di(methyl) carbamoyl group.

The "halogen atom" for $R^6$ in the formula (1) is preferably a fluorine atom or a bromine atom.

The "$C_{1-6}$ alkoxy group" for $R^6$ in the formula (1) is preferably a "$C_{1-4}$ alkoxy group," and more preferred examples include a methoxy group.

The "5- to 10-membered heterocyclic group" for $R^6$ in the formula (1) is preferably a "5- to 7-membered saturated heterocyclic group," and more preferred examples include a piperidyl group (a piperidino group, a piperidin-2-yl group, a piperidin-3-yl group, or a piperidin-4-yl group), a piperazinyl group (a piperazino group or a piperazin-2-yl group), and a morpholinyl group (a morpholino group, a morpholin-2-yl group, or a morpholin-3-yl group). Particularly preferred examples include a piperidino group, a piperazino group, and a morpholino group.

The "halogen atom" for $R^7$ in the formula (1) is preferably a fluorine atom or a chlorine atom.

The "halogen atom" for $R^8$ to $R^{10}$ in the formula (1) is preferably a fluorine atom or a chlorine atom.

The "$C_{1-6}$ alkyl group" for $R^8$ to $R^{10}$ in the formula (1) is preferably a "$C_{1-4}$ alkyl group," and more preferred examples include a methyl group, an ethyl group, and an isopropyl group. In regard to the "substituent" for the "$C_{1-6}$ alkyl group," it is preferable that the $C_{1-6}$ alkyl group be substituted with one of a hydroxyl group, a $C_{1-6}$ alkoxy group, a carboxy group, a carbamoyl group, a di($C_{1-6}$ alkyl) carbamoyl group, a cyano group, and a $C_{1-6}$ alkoxycarbonyl group, or with one to three halogen atoms (particularly, fluorine atoms).

The "$C_{1-6}$ alkoxy group" for $R^8$ to $R^{10}$ in the formula (1) is preferably a "$C_{1-4}$ alkoxy group," and more preferred examples include a methoxy group, an ethoxy group, and an isopropoxy group.

The "di($C_{1-6}$ alkyl)amino group" for $R^8$ to $R^{10}$ in the formula (1) is preferably a "di($C_{1-4}$ alkyl)amino group," and more preferred examples include a dimethylamino group.

The "$C_{6-14}$ aryl group" for $R^8$ to $R^{10}$ in the formula (1) is preferably a $C_{6-10}$ aryl group, and more preferred examples include a phenyl group.

The "5- to 10-membered heterocyclic group" for $R^8$ to $R^{10}$ in the formula (1) is preferably a "5- to 7-membered saturated heterocyclic group" or a "5- to 6-membered heteroaryl group," and more preferred examples include a piperidyl group (a piperidino group, a piperidin-2-yl group, a piperidin-3-yl group, or a piperidin-4-yl group), a piperazinyl group (a piperazino group, or a piperazin-2-yl group), a morpholinyl group (a morpholino group, a morpholin-2-yl group, or a morpholin-3-yl group), a thiazolyl group (a thiazol-2-yl group), an oxazolyl group (an oxazol-2-yl group), and a thiadiazolyl group (a thiadiazol-5-yl group). Particularly preferred examples include a piperidino group, a piperazino group, a thiazolyl group, an oxazolyl group, and a thiadiazolyl group. The thiazolyl group may further have a substituent such as a $C_{1-6}$ alkyl group.

The "$C_{1-6}$ alkylsulfonylamino group" for $R^8$ to $R^{10}$ in the formula (1) is preferably a "$C_{1-4}$ alkylsulfonylamino group," and more preferred examples include a methanesulfonylamino group.

The "$C_{1-6}$ alkyl group" for $R^{11}$ in the formula (1) is preferably a "$C_{1-4}$ alkyl group," and more preferred examples include a methyl group.

The group for $R^1$ in the formula (1) of the present invention is preferably a $C_{1-6}$ alkyl group, a $C_{1-6}$ alkylamino group, a di-$C_{1-6}$ alkylamino group, or a $C_{3-6}$ cycloalkyl group. The group for $R^2$ in the formula (1) according to the present invention is preferably a hydrogen atom or a $C_{1-6}$ alkyl group. The group for $R^{2'}$ in the formula (1) according to the present invention is preferably a hydrogen atom or a $C_{1-6}$ alkyl group, and is more preferably a hydrogen atom. The group for $R^3$ and the group for $R^{3'}$ in the formula (1) according to the present invention are each independently preferably a hydrogen atom, or a $C_{1-6}$ alkyl group, and more preferably a hydrogen atom. The group for $R^4$ in the formula (1) according to the present invention is preferably a hydrogen atom, a halogen atom, or a $C_{1-6}$ alkyl group which may be substituted, and is more preferably a hydrogen atom.

The group for $R^5$ in the formula (1) according to the present invention is preferably a hydrogen atom, a halogen atom, a $C_{1-6}$ alkyl group which may be substituted, a $C_{2-6}$ alkenyl group which may be substituted, a $C_{2-6}$ alkynyl group which may be substituted, a $C_{3-6}$ cycloalkyl group which may be substituted, a $C_{6-14}$ aryl group which may be substituted, a 5- to 10-membered heterocyclic group which may be substituted, a $C_{1-6}$ alkoxy group which may be substituted, a $C_{6-14}$ aryloxy group which may be substituted, an amino group, a mono($C_{1-6}$ alkylcarbonyl)amino group, a mono($C_{1-6}$ alkoxycarbonyl)amino group, a mono($C_{1-6}$ alkyl)amino group which may be substituted, a di($C_{1-6}$ alkyl)amino group which may be substituted, a mono($C_{6-14}$ aryl)amino group which may be substituted, a $C_{1-6}$ alkylthio group which may be substituted, a $C_{1-6}$ alkylsulfonyl group which may be substituted, a $C_{1-6}$ alkylsulfonylamino group which may be substituted, a $C_{1-6}$ alkylsulfinyl group which may be substituted, a $C_{1-6}$ alkoxycarbonyl group which may be substituted, a $C_{1-6}$ alkanoyl group which may be substituted, a 5- to 7-membered saturated heterocyclic carbonyl group which may be substituted, a hydroxyl group, a nitro group, a carboxyl group, a sulfonic acid group, a boronic acid group, a carbamoyl group which may be substituted, an ester group which may be substituted, or a cyano group.

The group for $R^6$ and the group for $R^7$ in the formula (1) according to the present invention are each independently preferably a hydrogen atom, a halogen atom, a $C_{1-6}$ alkoxy group, or a $C_{1-6}$ alkylsulfonylamino group which may be substituted, and more preferably a hydrogen atom, or a halogen atom.

The group for $R^8$ in the formula (1) according to the present invention is preferably a hydrogen atom, a halogen atom, a $C_{1-6}$ alkyl group which may be substituted, a $C_{3-6}$ cycloalkyl group which may be substituted, a 5- to 10-membered heterocyclic group which may be substituted, a $C_{1-6}$ alkoxy group which may be substituted, a $C_{6-14}$ aryloxy group which may be substituted, an amino group, a $C_{1-6}$ alkylsulfonylamino group which may be substituted, a hydroxyl group, or a cyano group. These groups for $R^8$ are preferably bonded to the 4-position on the benzene ring, but the present invention is not intended to be limited thereto.

The group for $R^9$ and the group for $R^{10}$ in the formula (1) according to the present invention are each independently preferably a hydrogen atom, a halogen atom, a $C_{1-6}$ alkyl group which may be substituted, or a hydroxyl group, and more preferably a hydrogen atom, a halogen atom, or a hydroxyl group. These groups for $R^9$ and groups for $R^{10}$ may be bonded to any position on the benzene ring.

In a tetrahydroquinoline compound having an oxygen atom for A in the formula (1), preferably, the group for $R^1$ may be a $C_{1-6}$ alkyl group; the group for $R^2$ may be a $C_{1-6}$ alkyl group; the group for $R^{2'}$ may be a hydrogen atom; the group for $R^3$ and the group for may be each a hydrogen atom; the group for $R^4$ may be a hydrogen atom; the group for $R^5$ may be a hydrogen atom, a halogen atom, a $C_{1-6}$ alkoxycarbonyl group, a carbamoyl group, a mono($C_{1-6}$ alkyl)carbamoyl group, a carboxyl group, or a morpholino group; the group for $R^6$ may be a hydrogen atom or a halogen atom; the group for $R^7$ may be a hydrogen atom or a halogen atom; the group for R⁸, the group for R⁹, and the group for R¹⁰ may be each independently a hydrogen atom, a halogen atom, a hydroxyl group, an amino group, a nitro group, or a morpholino group; and n may be an integer of 0 or 1.

The ring B in the formula (1) of the present invention is preferably a $C_{6-14}$ aryl group or a 5- to 10-membered heterocyclic group, and more preferably an aryl group such as a phenyl group, benzazoles condensed with a benzene ring, for example, benzimidazole or benzoxazole.

Among the 1,2,3,4-tetrahydroquinoline derivatives of the present invention, and more particularly, the 1,2,3,4-tetrahydroquinoline derivatives represented by the formula (1), when asymmetric centers are present at the 2-position and the 4-position of the quinoline ring, the configuration of the 2-position and the 4-position may be any of the cis-configuration and the trans-configuration, but the cis-configuration is more preferred.

Preferred groups for $R^1$ to $R^{11}$ in the tetrahydroquinoline compound represented by the formula (1) of the present invention may be selected in appropriate combinations of any of the groups for $R^1$ to $R^{11}$ described above.

The 1,2,3,4-tetrahydroquinoline derivatives of the present invention, more particularly, the tetrahydroquinoline compound represented by the formula (1), may have optical isomers, and the present invention includes mixtures of all possible optical isomers, racemates and the like.

The 1,2,3,4-tetrahydroquinoline derivatives of the present invention, more particularly, the tetrahydroquinoline compound represented by the formula (1), salts thereof, or solvates of the compound or the salts, include the 1,2,3,4-tetrahydroquinoline derivatives of the present invention, more particularly, the tetrahydroquinoline compound represented by the formula (1) as well as pharmaceutically acceptable salts thereof, various hydrates or solvates thereof, substances having crystalline polymorphism, and substances serving as prodrugs of those foregoing substances.

Specific examples of the pharmaceutically acceptable salts of the 1,2,3,4-tetrahydroquinoline derivatives of the present invention, more particularly, the tetrahydroquinoline compound represented by the formula (1), in the case of handling the compounds as basic compounds, include acid addition salts with inorganic acids (for example, hydrochloric acid, hydrobromic acid, hydroiodic acid, sulfuric acid, nitric acid, and phosphoric acid), and organic acids (for example, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, and glutamic acid); and in the case of handling the compound as acidic compounds, include inorganic salts (for example, sodium salts, potassium salts, lithium salts, barium salts, calcium salts, and magnesium salts), or organic salts (for example, pyridinium salts, picolinium salts, and triethylammonium salts).

Examples of the solvates of the 1,2,3,4-tetrahydroquinoline derivatives of the present invention, more particularly, the tetrahydroquinoline compound represented by the formula (1) and pharmaceutically acceptable salts thereof, include hydrates and various solvates (for example, solvates with alcohols such as ethanol).

Specific examples of the compound of the present invention include the compounds, pharmaceutically acceptable salts thereof, or solvates of the compounds and the salts, presented in the following Table 1 to Table 24.

TABLE 1

| Compound No. | Structural formula | Name |
|---|---|---|
| 1 | | 1-Acetyl-2-methyl-4-phenylamino-1,2,3,4-tetrahydroquinoline |
| 2 | | 1-Acetyl-2,6-dimethyl-4-[(4-methylphenyl)amino]-1,2,3,4-tetrahydroquinoline |
| 3 | | 2-Methyl-4-phenylamino-1-propionyl-1,2,3,4-tetrahydroquinolione |
| 4 | | 1-Acetyl-8-fluoro-4-[(2-fluorophenyl)amino]-2-methyl-1,2,3,4-tetrahydroquinoline |
| 5 | | 1-Acetyl-6-fluoro-4-[(4-fluorophenyl)amino]-2-methyl-1,2,3,4-tetrahydroquinoline |

TABLE 1-continued

| Compound No. | Structural formula | Name |
|---|---|---|
| 6 | | 1-Cyclohexanecarbonyl-6-fluoro-4-[(4-fluorophenyl)amino]-2-methyl-1,2,3,4-tetrahydroquinoline |
| 7 | | 1-Acetyl-7-cyano-2-methyl-4-phenylamino-1,2,3,4-tetrahydroquinoline |
| 8 | | 1-Acetyl-4-[(4-chlorophenyl)amino]-2-methyl-1,2,3,4-tetrahydroquinoline |

TABLE 2

| Compound No. | Structural formula | Name |
|---|---|---|
| 9 | | 1-Acetyl-4-[(4-cyanophenyl)amino]-2-methyl-1,2,3,4-tetrahydroquinoline |

TABLE 2-continued

| Compound No. | Structural formula | Name |
|---|---|---|
| 10 | | 1-Acetyl-4-[(4-methoxyphenyl)amino]-2-methyl-1,2,3,4-tetrahydroquinoline |
| 11 | | 1-Acetyl-4-[(3-methoxyphenyl)amino]-2-methyl-1,2,3,4-tetrahydroquinoline |
| 12 | | 1-Acetyl-4-[(2-methoxyphenyl)amino]-2-methyl-1,2,3,4-tetrahydroquinoline |
| 13 | | 1-Acetyl-6-bromo-2-methyl-4-phenylamino-1,2,3,4-tetrahydroquinoline |
| 14 | | 1-Acetyl-6-cyano-2-methyl-4-phenylamino-1,2,3,4-tetrahydroquinoline |

TABLE 2-continued

| Compound No. | Structural formula | Name |
|---|---|---|
| 15 | | 1-Acetyl-4-[(4-fluorophenyl)amino]-2-methyl-1,2,3,4-tetrahydroquinoline |
| 16 | | 1-Acetyl-4-[(3-fluorophenyl)amino]-2-methyl-1,2,3,4-tetrahydroquinoline |
| 17 | | 1-Acetyl-4-[(4-phenoxyphenyl)amino]-2-methyl-1,2,3,4-tetrahydroquinoline |

TABLE 3

| Compound No. | Structural formula | Name |
|---|---|---|
| 18 | | 1-Acetyl-4-[(4-isopropoxyphenyl)amino]-2-methyl-1,2,3,4-tetrahydroquinoline |
| 19 | | 1-Acetyl-2-methyl-4-[(4-morpholinophenyl)amino]-1,2,3,4-tetrahydroquinoline |
| 20 | | 1-Acetyl-4-[(4-N,N-dimethylaminophenyl)amino]-2-methyl-1,2,3,4-tetrahydroquinoline |
| 21 | | 1-Acetyl-4-[(4-isopropylphenyl)amino]-2-methyl-1,2,3,4-tetrahydroquinoline |
| 22 | | 1-Acetyl-4-[(2-fluorophenyl)amino]-2-methyl-1,2,3,4-tetrahydroquinoline |

TABLE 3-continued

| Compound No. | Structural formula | Name |
|---|---|---|
| 23 | | 1-Acetyl-7-bromo-2-methyl-4-phenyl-amino-1,2,3,4-tetrahydroquinoline |
| 24 | | 1-Acetyl-4-[(4-hydroxyphenyl)amino]-2-methyl-1,2,3,4-tetrahydroquinoline |
| 25 | | 1-Acetyl-2-methyl-4-[(1,1'-biphenyl-4-yl)amino]-1,2,3,4-tetrahydroquinoline |
| 26 | | 1-Acetyl-2-methyl-4-phenoxy-1,2,3,4-tetrahydroquinoline |

TABLE 4

| Compound No. | Structural formula | Name |
|---|---|---|
| 27 | | 1-Acetyl-4-(4-fluorophenoxy)-2-methyl-1,2,3,4-tetrahydroquinoline |
| 28 | | 1-Acetyl-4-(3-fluorophenoxy)-2-methyl-1,2,3,4-tetrahydroquinoline |

TABLE 4-continued

| Compound No. | Structural formula | Name |
|---|---|---|
| 29 | | 1-Acetyl-4-(2-fluorophenoxy)-2-methyl-1,2,3,4-tetrahydroquinoline |
| 30 | | 1-Acetyl-4-(2,4-difluorophenoxy)-2-methyl-1,2,3,4-tetrahydroquinoline |
| 31 | | 1-Acetyl-4-(3,4-difluorophenoxy)-2-methyl-1,2,3,4-tetrahydroquinoline |
| 32 | | 1-Acetyl-7-fluoro-2-methyl-4-phenoxy-1,2,3,4-tetrahydroquinoline |
| 33 | | 1-Acetyl-8-fluoro-2-methyl-4-phenoxy-1,2,3,4-tetrahydroquinoline |

TABLE 4-continued

| Compound No. | Structural formula | Name |
|---|---|---|
| 34 | | 1-Acetyl-4-(4-fluorophenoxy)-6-fluoro-2-methyl-1,2,3,4-tetrahydroquinoline |

TABLE 5

| Compound No. | Structural formula | Name |
|---|---|---|
| 35 | | 1-Acetyl-6-fluoro-2-methyl-4-phenoxy-1,2,3,4-tetrahydroquinoline |
| 36 | | 1-Acetyl-2-methyl-4-benzyloxy-1,2,3,4-tetrahydroquinoline |
| 37 | | 1-Acetyl-4-[(4-fluorophenyl)amino]-2-methyl-6-methoxy-1,2,3,4-tetrahydroquinoline |

TABLE 5-continued

| Compound No. | Structural formula | Name |
| --- | --- | --- |
| 38 | | 1-Acetyl-4-[(4-hydroxymethylphenyl)amino]-2-methyl-1,2,3,4-tetrahydroquinoline |
| 39 | Ms = MeSO$_2$ | 1-Acetyl-4-[(4-methanesulfonylamidophenyl)amino]-2-methyl-1,2,3,4-tetrahydroquinoline |
| 40 | | 1-Acetyl-4-[(4-chlorophenyl)amino]-2-methyl-6-morpholino-1,2,3,4-tetrahydroquinoline |
| 41 | | Ethyl 1-Acetyl-4-[(4-chlorophenyl)amino]-2-methyl-1,2,3,4-tetrahydroquinoline-6-carboxylate |

TABLE 5-continued

| Compound No. | Structural formula | Name |
|---|---|---|
| 42 | 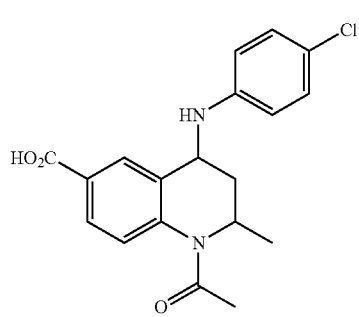 [SMILES: CC(=O)N1c2ccc(C(=O)O)cc2C(Nc2ccc(Cl)cc2)CC1C] | 1-Acetyl-4-[(4-chlorophenyl)amino]-2-methyl-1,2,3,4-tetrahydroquinoline-6-carboxylic acid |

TABLE 6

| Compound No. | Structural formula | Name |
|---|---|---|
| 43 | 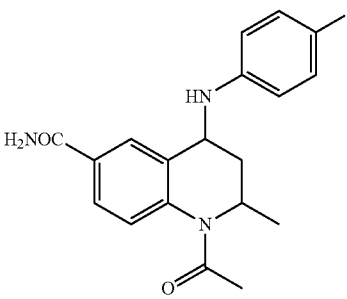 | 1-Acetyl-4-[(4-chlorophenyl)amino]-2-methyl-1,2,3,4-tetrahydroquinoline-6-carboxamide |
| 44 | 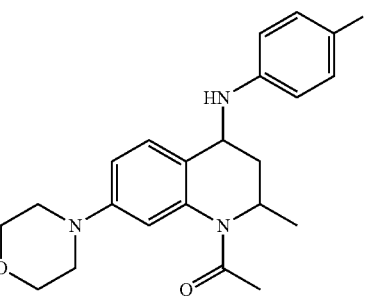 | 1-Acetyl-4-[(4-chlorophenyl)amino]-2-methyl-7-morpholino-1,2,3,4-tetrahydroquinoline |
| 45 | 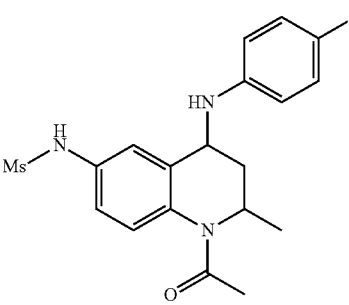 | 1-Acetyl-4-[(4-chlorophenyl)amino]-2-methyl-6-methanesulfonylamino-1,2,3,4-tetrahydroquinoline |

Ms = MeSO$_2$

TABLE 6-continued

| Compound No. | Structural formula | Name |
|---|---|---|
| 46 | | 1-Acetyl-4-(N-methyl-N-phenylamino)-2-methyl-1,2,3,4-tetrahydroquinoline |
| 47 | | 1-Cyclopropanecarbonyl-2-methyl-4-phenylamino-1,2,3,4-tetrahydroquinoline |
| 48 | | 1-Acetyl-2-methyl-7-methoxy-4-phenylamino-1,2,3,4-tetrahydroquinoline |
| 49 | | 1-Acetyl-4-[(2-methylphenyl)amino]-2-methyl-1,2,3,4-tetrahydroquinoline |
| 50 | | 1-Acetyl-4-[(3-methylphenyl)amino]-2-methyl-1,2,3,4-tetrahydroquinoline |

TABLE 6-continued

| Compound No. | Structural formula | Name |
| --- | --- | --- |
| 51 | | 1-Acetyl-4-[(4-methylphenyl)amino]-2-methyl-1,2,3,4-tetrahydroquinoline |

TABLE 7

| Compound No. | Structural formula | Name |
| --- | --- | --- |
| 52 | | 1-Acetyl-2-methyl-4-[(4-trifluoromethylphenyl)amino]-1,2,3,4-tetrahydroquinoline |
| 53 | | Ethyl 1-acetyl-4-(4-fluorophenoxy)-2-methyl-1,2,3,4-tetrahydroquinoline-6-carboxylate |
| 54 | | 1-Acetyl-4-(4-fluorophenoxy)-2-methyl-1,2,3,4-tetrahydroquinoline-6-carboxamide |

TABLE 7-continued

| Compound No. | Structural formula | Name |
| --- | --- | --- |
| 55 | | 1-Acetyl-4-(4-morpholinophenoxy)-2-methyl-1,2,3,4-tetrahydroquinoline |
| 56 | | 1-Acetyl-7-fluoro-4-(4-fluorophenoxy)-2-methyl-1,2,3,4-tetrahydroquinoline |
| 57 | | 1-Acetyl-4-(4-hydroxyphenoxy)-2-methyl-1,2,3,4-tetrahydroquinoline |
| 58 | | 1-Acetyl-7-fluoro-4-[(3-fluorophenyl)amino]-2-methyl-1,2,3,4-tetrahydroquinoline |

TABLE 7-continued

| Compound No. | Structural formula | Name |
|---|---|---|
| 59 | | 1-Acetyl-2-ethyl-4-phenylamino-1,2,3,4-tetrahydroquinoline |

TABLE 8

| Compound No. | Structural formula | Name |
|---|---|---|
| 60 | | 1-Acetyl-3,3-dimethyl-4-phenylamino-1,2,3,4-tetrahydroquinoline |
| 61 | | 1-Acetyl-4-phenylamino-8-methoxy-2-methyl-1,2,3,4-tetrahydroquinoline |
| 62 | | 1-Acetyl-4-(3,5-difluorophenoxy)-2-methyl-1,2,3,4-tetrahydroquinoline |

TABLE 8-continued

| Compound No. | Structural formula | Name |
| --- | --- | --- |
| 63 | | 1-Acetyl-8-bromo-4-phenylamino-2-methyl-1,2,3,4-tetrahydroquinoline |
| 64 | | 1-Acetyl-4-(4-benzyloxyphenoxy)-2-methyl-1,2,3,4-tetrahydroquinoline |
| 65 | | 6-Fluoro-4-[(4-fluorophenyl)amino]-2-methyl-1-N-methylcarbamoyl-1,2,3,4-tetrahydroquinoline |
| 66 | | 1-Cyclopentanecarbonyl-6-fluoro-2-methyl-4-[{4-fluorophenyl)amino]-1,2,3,4-tetrahydroquinoline |

TABLE 8-continued

| Compound No. | Structural formula | Name |
| --- | --- | --- |
| 67 | | 1-Acetyl-2-methyl-4-(4-nitrophenoxy)-1,2,3,4-tetrahydroquinoline |

TABLE 9

| Compound No. | Structural formula | Name |
| --- | --- | --- |
| 68 | | 1-Acetyl-4-(4-aminophenoxy)-2-methyl-1,2,3,4-tetrahydroquinoline |
| 69 | | 1-Acetyl-4-[(4-methoxymethylphenyl)amino]-2-methyl-1,2,3,4-tetrahydroquinoline |
| 70 | | 1-Acetyl-4-[(4-ethoxycarbonylmethylphenyl)amino]-2-methyl-1,2,3,4-tetrahydroquinoline |

TABLE 9-continued

| Compound No. | Structural formula | Name |
|---|---|---|
| 71 | | 1-Acetyl-4-[(4-carboxymethylphenyl)amino]-2-methyl-1,2,3,4-tetrahydroquinoline |
| 72 | | 1-Acetyl-2-methyl-4-[(2-morpholinophenyl)amino]-1,2,3,4-tetrahydroquinoline |
| 73 | | 1-Acetyl-4-[(4-fluoro-3-morpholinophenyl)amino]-2-methyl-1,2,3,4-tetrahydroquinoline |
| 74 | | 1-Acetyl-6-bromo-4-[(4-chlorophenyl)amino]-2-methyl-1,2,3,4-tetrahydroquinoline |

TABLE 10

| Compound No. | Structural formula | Name |
| --- | --- | --- |
| 75 | | 1-Acetyl-4-[(4-carbamoylmethyl-phenyl)amino]-2-methyl-1,2,3,4-tetrahydroquinoline |
| 76 | | 1-Acetyl-2-methyl-4-[(4-piperazinyl-phenyl)amino]-1,2,3,4-tetrahydroquinoline |
| 77 | | 1-Acetyl-4-{[4-(4-acetylpiperazinyl)phenyl]amino}-2-methyl-1,2,3,4-tetrahydroquinoline |
| 78 | | 1-Acetyl-4-{[4-(4-methanesulfonyl-piperazinyl)phenyl]amino}-2-methyl-1,2,3,4-tetrahydroquinoline |

TABLE 10-continued

| Compound No. | Structural formula | Name |
|---|---|---|
| 79 | | 1-Acetyl-6-[(4-acetyl)piperazino]-4-[(4-chlorophenyl)amino]-2-methyl-1,2,3,4-tetrahydroquinoline |
| 80 | | 1-Acetyl-6-[(4-methanesulfonyl)piperazino]-4-[(4-chlorophenyl)amino]-2-methyl-1,2,3,4-tetrahydroquinoline |
| 81 | | 1-Acetyl-4-[(4-chlorophenyl)amino]-6-[(4-isopropyl)piperazino]-2-methyl-1,2,3,4-tetrahydroquinoline |

TABLE 11

| Compound No. | Structural formula | Name |
|---|---|---|
| 82 | | 1-Acetyl-4-[(4-chlorophenyl)amino]-6-[(2-hydroxy)ethylamino]-2-methyl-1,2,3,4-tetrahydroquinoline |

TABLE 11-continued

| Compound No. | Structural formula | Name |
|---|---|---|
| 83 | | 1-Acetyl-4-[(4-chlorophenyl)amino]-6-[(3,5-dimethyl)morpholino]-2-methyl-1,2,3,4-tetrahydroquinoline |
| 84 | | 1-Acetyl-4-[(4-chlorophenyl)amino]-6-[(4-isopropylcarbonyl)piperazino]-2-methyl-1,2,3,4-tetrahydroquinoline |
| 85 | | 1-Acetyl-4-[(4-chlorophenyl)amino]-6-[(4-cyclohexylcarbonyl)piperazino]-2-methyl-1,2,3,4-tetrahydroquinoline |
| 86 | | 1-Acetyl-6-[(4-benzoyl)piperazino]-2-methyl-4-[(4-chlorophenyl)amino]-1,2,3,4-tetrahydroquinoline |
| 87 | | 1-Acetyl-4-[(4-chlorophenyl)amino]-6-[(4-(N,N-diethylaminocarbonyl)piperazino]-2-methyl-1,2,3,4-tetrahydroquinoline |

TABLE 11-continued

| Compound No. | Structural formula | Name |
|---|---|---|
| 88 | | 1-Acetyl-4-[(4-chlorophenyl)amino]-6-[(4-(isopropylaminocarbonyl)piperazino]-2-methyl-1,2,3,4-tetrahydroquinoline |

TABLE 12

| Compound No. | Structural formula | Name |
|---|---|---|
| 89 | | 1-Acetyl-4-[(4-carboxymethylphenyl)amino]-6-morpholino-2-methyl-1,2,3,4-tetrahydroquinoline |
| 90 | | 1-Acetyl-4-[(4-carbamoylmethylphenyl)amino]-2-methyl-6-morpholino-1,2,3,4-tetrahydroquinoline |
| 91 | | 1-Acetyl-6-(4-acetylpiperazinyl)-4-[(4-carboxymethylphenyl)amino]-2-methyl-1,2,3,4-tetrahydroquinoline |

TABLE 12-continued

| Compound No. | Structural formula | Name |
|---|---|---|
| 92 | | 1-Acetyl-2-methyl-4-[(4-morpholino-phenyl)amino]-1,2,3,4-tetrahydroquinoline-6-carboxamide |
| 93 | | 1-Acetyl-4-[(4-chlorophenyl)amino]-2-methyl-6-[(1-morpholino)carbonyl]-1,2,3,4-tetrahydroquinoline |
| 94 | | 1-Acetyl-6-[(4-acetyl)piperazino]-2-methyl-4-[(4-morpholinophenyl)amino]-1,2,3,4-tetrahydroquinoline |
| 95 | | 1-Acetyl-6-amino-4-[(4-chlorophenyl)amino]-2-methyl-1,2,3,4-tetrahydroquinoline |

TABLE 13

| Compound No. | Structural formula | Name |
|---|---|---|
| 96 | 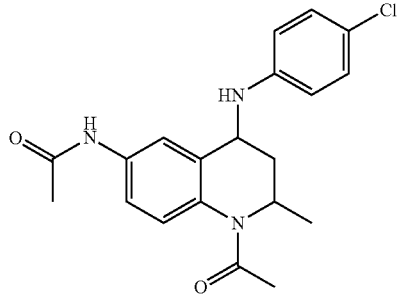 [SMILES: CC(=O)Nc1ccc2c(c1)C(Nc1ccc(Cl)cc1)CC(C)N2C(C)=O] | 1-Acetyl-6-acetylamino-4-[(4-chlorophenyl)amino]-2-methyl-1,2,3,4-tetrahydroquinoline |
| 97 | 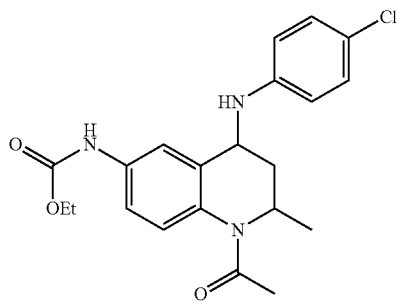 [SMILES: CCOC(=O)Nc1ccc2c(c1)C(Nc1ccc(Cl)cc1)CC(C)N2C(C)=O] | 1-Acetyl-4-[(4-chlorophenyl)amino]-2-methyl-1,2,3,4-tetrahydroquinoline-6-ethyl carbamate |
| 98 | 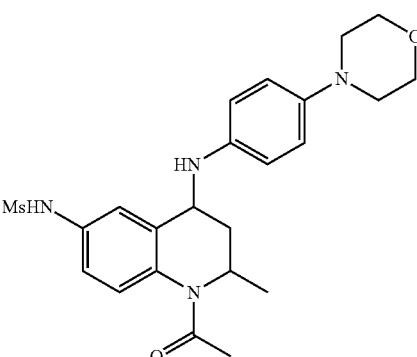 | 1-Acetyl-6-methanesulfonylamino-2-methyl-4-[(4-morpholinophenyl)amino]-1,2,3,4-tetrahydroquinoline |
| 99 | 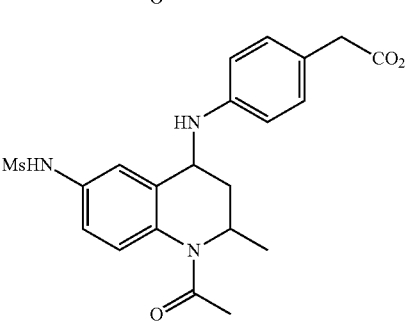 | 1-Acetyl-6-methanesulfonylamino-2-methyl-4-[(4-ethoxycarbonyl-methylphenyl)amino]-1,2,3,4-tetrahydroquinoline |
| 100 | 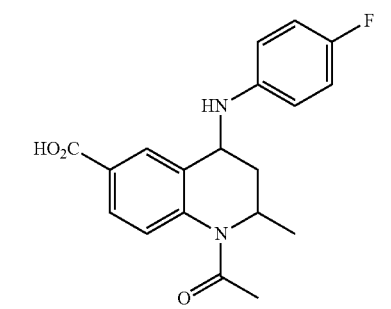 [SMILES: CC(=O)N1c2ccc(C(=O)O)cc2C(Nc2ccc(F)cc2)CC1C] | 1-Acetyl-4-[(4-fluorophenyl)amino]-2-methyl-1,2,3,4-tetrahydroquinoline-6-carboxylic acid |

TABLE 13-continued

| Compound No. | Structural formula | Name |
|---|---|---|
| 101 | | Ethyl 1-Acetyl-4-[(4-methanesulfonyl-aminophenyl)amino]-2-methyl-1,2,3,4-tetrahydroquinoline-6-carboxylate |
| 102 | | 1-Acetyl-4-[(4-methanesulfonyl-aminophenyl)amino]-2-methyl-1,2,3,4-tetrahydroquinoline-6-carboxamide |

TABLE 14

| Compound No. | Structural formula | Name |
|---|---|---|
| 103 | | Ethyl 1-Acetyl-4-[(4-cyanomethylphenyl)amino]-2-methyl-1,2,3,4-tetrahydroquinoline-6-carboxylate |
| 104 | | 1-Acetyl-4-[(4-cyanomethylphenyl)amino]-2-methyl-1,2,3,4-tetrahydroquinoline-6-carboxamide |

TABLE 14-continued

| Compound No. | Structural formula | Name |
|---|---|---|
| 105 | | 1-Acetyl-4-[(4-carboxymethylphenyl)amino]-2-methyl-1,2,3,4-tetrahydroquinoline-6-carboxamide |
| 106 | | 1-Acetyl-4-[(4-carbamoylmethylphenyl)amino]-2-methyl-1,2,3,4-tetrahydroquinoline-6-carboxamide |
| 107 | | 1-Acetyl-4-((4-chlorophenyl)amino]-7-methanesulfonylamino-2-methyl-1,2,3,4-tetrahydroquinoline |
| 108 | | 1-Acetyl-4-[(4-hydroxy-3-methoxycarbonylphenyl)amino]-2-methyl-1,2,3,4-tetrahydroquinoline |
| 109 | | 1-Acetyl-4-[(2-carboxyphenyl)amino]-2-methyl-1,2,3,4-tetrahydroquinoline |

TABLE 15

| Compound No. | Structural formula | Name |
|---|---|---|
| 110 | | 1-Acetyl-6-[(2,6-dimethyl)morpholino]-4-[(4-methanesulfonylaminophenyl)amino]-2-methyl-1,2,3,4-tetrahydroquinoline |
| 111 | | 1-Acetyl-6-[(4-isopropylcarbonyl)piperazino]-4-[(4-methanesulfonyl-aminophenyl)amino]-2-methyl-1,2,3,4-tetrahydroquinoline |
| 112 | | 1-Acetyl-4-[(4-benzylphenyl)amino]-2-methyl-1,2,3,4-tetrahydroquinoline |
| 113 | | 1-Acetyl-4-[(4-chlorophenyl)amino]-N,N,2-trimethyl-1,2,3,4-tetrahydroquinoline-6-carboxamide |
| 114 | | 1-Acetyl-4-[(4-chlorophenyl)amino]-N,2-dimethyl-1,2,3,4-tetrahydroquinoline-6-carboxamide |

TABLE 15-continued

| Compound No. | Structural formula | Name |
|---|---|---|
| 115 | | 1-Acetyl-4-[(4-chlorophenyl)amino]-2-methyl-1,2,3,4-tetrahydroquinoline-6-carbohydrazide |
| 116 | | 1-Acetyl-4-[(4-chlorophenyl)amino]-2-methyl-6-[1,3,4-oxadiazol-2(3H)-on-5-yl]-1,2,3,4-tetrahydroquinoline |
| 117 | | 1-Acetyl-4-[(4-chlorophenyl)amino]-6-cyano-2-methyl-1,2,3,4-tetrahydroquinoline |

TABLE 16

| Compound No. | Structural formula | Name |
|---|---|---|
| 118 | | 1-Acetyl-4-[(4-chlorophenyl)amino]-N-methoxy-2-methyl-1,2,3,4-tetrahydroquinoline-6-carboxamide |

TABLE 16-continued

| Compound No. | Structural formula | Name |
|---|---|---|
| 119 | | 1-Acetyl-4-[(4-chlorophenyl)amino]-2-methyl-6-(1H-tetrazol-5-yl)-1,2,3,4-tetrahydroquinoline |
| 120 | | 1-Acetyl-4-[(4-chlorophenyl)amino]-2-methyl-6-[1,2,4-oxadiazol-5(2H)-on-3-yl]-1,2,3,4-tetrahydroquinoline |
| 121 | | 1-Acetyl-4-[(4-chlorophenyl)amino]-6-hydroxymethyl-2-methyl-1,2,3,4-tetrahydroquinoline |
| 122 | | 1-Acetyl-4-[(4-ethoxycarbonylmethylphenyl)amino]-6-fluoro-2-methyl-1,2,3,4-tetrahydroquinoline |
| 123 | | 1-Acetyl-4-[(4-carboxymethylphenyl)amino]-6-fluoro-2-methyl-1,2,3,4-tetrahydroquinoline |

TABLE 16-continued

| Compound No. | Structural formula | Name |
|---|---|---|
| 124 | | 1-Acetyl-4-[(4-carbamoylmethylphenyl)amino]-6-fluoro-2-methyl-1,2,3,4-tetrahydroquinoline |
| 125 | | 1-Acetyl-4-[4-(N,N-dimethylaminocarbonylmethyl)phenylamino]-6-fluoro-2-methyl-1,2,3,4-tetrahydroquinoline |

TABLE 17

| Compound No. | Structural formula | Name |
|---|---|---|
| 126 | | 1-Acetyl-4-[(4-chlorophenyl)amino]-N-(2-hydroxyethyl)-2-methyl-1,2,3,4-tetrahydroquinoline-6-carboxamide |
| 127 | | 4-{1-Acetyl-4-[(4-chlorophenyl)amino]-2-methyl-1,2,3,4-tetrahydroquinolin-6-yl}-2-methyl-1H-imidazole |

TABLE 17-continued

| Compound No. | Structural formula | Name |
|---|---|---|
| 128 | | 1-Acetyl-4-[(4-chlorophenyl)amino]-N-cyano-2-methyl-1,2,3,4-tetrahydroquinoline-6-carboxamide |
| 129 | | 1-Acetyl-4-[(4-chlorophenyl)amino]-N-hydroxy-2-methyl-1,2,3,4-tetrahydroquinoline-6-carboxamide |
| 130 | | 1-Acetyl-4-[(4-chlorophenyl)amino]-2-methyl-N-phenyl-1,2,3,4-tetrahydroquinoline-6-carboxamide |
| 131 | | 1-Acetyl-4-[(4-chlorophenyl)amino]-2-methyl-N-(3-pyridyl)-1,2,3,4-tetrahydroquinoline-6-carboxamide |
| 132 | | 1-Acetyl-4-[(4-morpholinophenyl)amino]-N,2-dimethyl-1,2,3,4-tetrahydroquinoline-6-carboxamide |

TABLE 17-continued

| Compound No. | Structural formula | Name |
|---|---|---|
| 133 | | 1-Acetyl-4-[(4-morpholinophenyl)amino]-2-methyl-1,2,3,4-tetra-hydroquinoline-6-carbohydrazide |

TABLE 18

| Compound No. | Structural formula | Name |
|---|---|---|
| 134 | | 1-Acetyl-4-[(4-morpholinophenyl)amino]-2-methyl-6-[1,3,4-oxadiazol-2(3H)-on-5-yl]-1,2,3,4-tetrahydroquinoline |
| 135 | | 1-Acetyl-4-[(4-morpholinophenyl)amino]-N-methoxy-2-methyl-1,2,3,4-tetrahydroquinoline-6-carboxamide |

TABLE 18-continued

| Compound No. | Structural formula | Name |
|---|---|---|
| 136 | | 1-Acetyl-4-[(benzoxazol-5-yl)amino]-2-methyl-1,2,3,4-tetrahydroquinoline |
| 137 | | 1-Acetyl-6-fluoro-4-[(4-carboxyphenyl)amino]-2-methyl-1,2,3,4-tetrahydroquinoline |
| 138 | | 1-Acetyl-4-[(4-chlorophenyl)amino]-2-methyl-1,2,3,4-tetrahydroquinolin-6-ylboronic acid |
| 139 | | 1-Acetyl-2-methyl-4-(4-morpholinophenoxy)-1,2,3,4-tetrahydroquinoline-6-carboxylic acid |

TABLE 18-continued

| Compound No. | Structural formula | Name |
|---|---|---|
| 140 | | 1-Acetyl-N,2-dimethyl-4-(4-morpholinophenoxy)-1,2,3,4-tetrahydroquinoline-6-carboxamide |

TABLE 19

| Compound No. | Structural formula | Name |
|---|---|---|
| 141 | | 1-Acetyl-4-(4-chlorophenoxy)-2-methyl-1,2,3,4-tetrahydroquinoline-6-carboxylic acid |
| 142 | | 1-Acetyl-4-(4-chlorophenoxy)-2-methyl-1,2,3,4-tetrahydroquinoline-6-carboxamide |
| 143 | | N-{4-[(1-acetyl-2-methyl-1,2,3,4-tetrahydroquinolin-4-yl)oxy]phenyl}methanesulfonamide |

TABLE 19-continued

| Compound No. | Structural formula | Name |
|---|---|---|
| 144 | | Ethyl 1-Acetyl-4-[(4-cyclohexylphenyl)amino]-2-methyl-1,2,3,4-tetrahydroquinoline-6-carboxylate |
| 145 | | 1-Acetyl-4-[(4-cyclohexylphenyl)amino]-2-methyl-1,2,3,4-tetrahydroquinoline-6-carboxylic acid |
| 146 | | 1-Acetyl-4-[(4-cyclohexylphenyl)amino]-N,2-dimethyl-1,2,3,4-tetrahydroquinoline-6-carboxamide |
| 147 | | 1-Acetyl-4-[(4-cyclohexylphenyl)amino]-2-methyl-1,2,3,4-tetrahydroquinoline-6-carboxamide |

TABLE 20

| Compound No. | Structural formula | Name |
|---|---|---|
| 148 | | Tert-butyl 12-{1-Acetyl-4-[(4-chlorophenyl)amino]-2-methyl-1,2,3,4-tetrahydroquinoline-6-carboxamido}-4,7,10-trioxadodecanoate |
| 149 | | Tert-butyl 12-{1-Acetyl-2-methyl-4-[(4-morpholinophenyl)amino]-1,2,3,4-tetrahydroquinoline-6-carboxamido}-4,7,10-trioxadodecanoate |
| 150 | | Methyl 4-{4-{1-Acetyl-4-[(4-chlorophenyl)amino]-2-methyl-1,2,3,4-tetrahydroquinoline-6-carboxamido}phenyl}butanoate |
| 151 | | Methyl 4-(4-{1-Acetyl-2-methyl-4-[(4-morpholinophenyl)amino]-1,2,3,4-tetrahydroquinoline-6-carboxamido}phenyl)butanoate |
| 152 | | 1-Acetyl-4-(4-chlorophenoxy)-2-methyl-6-morpholino-1,2,3,4-tetrahydroquinoline |

TABLE 20-continued

| Compound No. | Structural formula | Name |
|---|---|---|
| 153 | | Ethyl 1-acetyl-2-methyl-4-{[4-(tetrahydro-2H-pyran-4-yl)phenyl]amino}-1,2,3,4-tetrahydro-quinoline-6-carboxylate |
| 154 | | 1-Acetyl-2-methyl-4-{[4-(tetrahydro-2H-pyran-4-yl)phenyl]amino}-1,2,3,4-tetrahydro-quinoline-6-carboxylic acid |

TABLE 21

| Compound No. | Structural formula | Name |
|---|---|---|
| 155 | | 1-Acetyl-N,2-dimethyl-4-{[4-(tetrahydro-2H-pyran-4-yl)phenyl]amino}-1,2,3,4-tetrahydroquinoline-6-carboxamide |

TABLE 21-continued

| Compound No. | Structural formula | Name |
|---|---|---|
| 156 | | 1-Acetyl-2-methyl-4-{[4-(tetrahydro-2H-pyran-4-yl)phenyl]amino}-1,2,3,4-tetrahydroquinoline-6-carboxamide |
| 157 | | Methyl 6-{1-Acetyl-2-methyl-4-[(4-morpholinophenyl)amino]-1,2,3,4-tetrahydroquinoline-6-carboxamido}hexanoate |
| 158 | | Methyl 6-{1-acetyl-4-[(4-chlorophenyl)amino]-2-methyl-1,2,3,4-tetrahydroquinoline-6-carboxamido}hexanoate |
| 159 | | 1-Acetyl-6-(4-isopropyl-piperazin-1-yl)-2-methyl-4-[(4-morpholinophenyl)amino]-1,2,3,4-tetrahydroquinoline |

TABLE 21-continued

| Compound No. | Structural formula | Name |
|---|---|---|
| 160 | | 1-Acetyl-2-methyl-6-[4-(methylsulfonyl)piperazin-1-yl]-4-[(4-morpholinophenyl)amino]-1,2,3,4-tetrahydroquinoline |
| 161 | | 1-Acetyl-2-methyl-6-morpholino-4-[(4-morpholinophenyl)amino]-1,2,3,4-tetrahydroquinoline |

TABLE 22

| Compound No. | Structural formula | Name |
|---|---|---|
| 162 | | Ethyl 1-Acetyl-2-methyl-4-{[4-(2-methylthiazol-4-yl)phenyl]amino}-1,2,3,4-tetrahydroquinoline-6-carboxylate |

TABLE 22-continued

| Compound No. | Structural formula | Name |
|---|---|---|
| 163 | | 1-Acetyl-2-methyl-4-{[4-(2-methylthiazol-4-yl)phenyl]amino}-1,2,3,4-tetrahydroquinoline-6-carboxylic acid |
| 164 | | 1-Acetyl-2-methyl-4-{[4-(2-methylthiazol-4-yl)phenyl]amino}-1,2,3,4-tetrahydroquinoline-6-carboxamide |
| 165 | | 1-Acetyl-N,2-dimethyl-4-{[4-(2-methylthiazol-4-yl)phenyl]amino}-1,2,3,4-tetrahydroquinoline-6-carboxamide |
| 166 | | 1-Acetyl-N-benzoyl-2-methyl-4-[(4-morpholinophenyl)amino]-1,2,3,4-tetrahydroquinoline-6-carboxamide |

TABLE 22-continued

| Compound No. | Structural formula | Name |
|---|---|---|
| 167 | | Ethyl 1-Acetyl-2-methyl-4-{[4-(oxazol-2-yl)phenyl]amino}-1,2,3,4-tetrahydroquinoline-6-carboxylate |
| 168 | | 1-Acetyl-2-methyl-4-{[4-(oxazol-2-yl)phenyl]amino}-1,2,3,4-tetrahydroquinoline-6-carboxylic acid |

TABLE 23

| Compound No. | Structural formula | Name |
|---|---|---|
| 169 | | 1-Acetyl-2-methyl-4-{[4-(oxazol-2-yl)phenyl]amino}-1,2,3,4-tetrahydroquinoline-6-carboxamide |
| 170 | | 1-Acetyl-N,2-dimethyl-4-{[4-(oxazol-2-yl)phenyl]amino}-1,2,3,4-tetrahydroquinoline-6-carboxamide |

TABLE 23-continued

| Compound No. | Structural formula | Name |
|---|---|---|
| 171 | | Ethyl 1-Acetyl-2-methyl-4-{[4-(1,2,3-thiadiazol-5-yl)phenyl]amino}-1,2,3,4-tetrahydroquinoline-6-carboxylate |
| 172 | | 1-Acetyl-2-methyl-4-{[4-(1,2,3-thiadiazol-5-yl)phenyl]amino}-1,2,3,4-tetrahydroquinoline-6-carboxylic acid |
| 173 | | 1-Acetyl-2-methyl-4-{[4-(1,2,3-thiadiazol-5-yl)phenyl]amino}-1,2,3,4-tetrahydroquinoline-6-carboxamide |
| 174 | | 1-Acetyl-N,2-dimethyl-4-{[4-(1,2,3-thiadiazol-5-yl)phenyl]amino}-1,2,3,4-tetrahydroquinoline-6-carboxamide |

TABLE 23-continued
| Compound No. | Structural formula | Name |
|---|---|---|
| 175 | 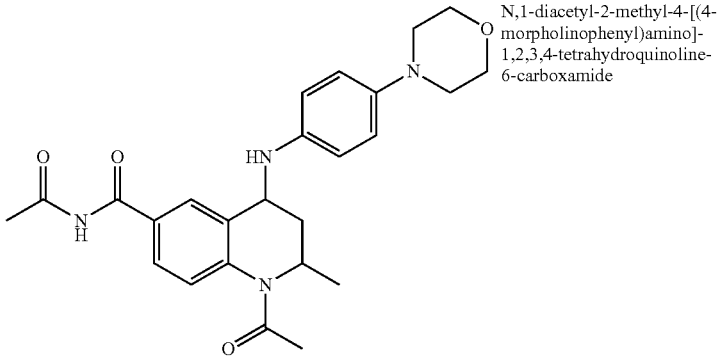 | N,1-diacetyl-2-methyl-4-[(4-morpholinophenyl)amino]-1,2,3,4-tetrahydroquinoline-6-carboxamide |
TABLE 24
| Compound No. | Structural formula | Name |
|---|---|---|
| 176 | 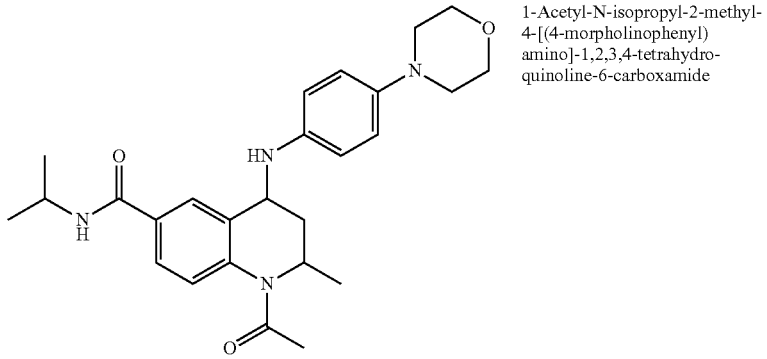 | 1-Acetyl-N-isopropyl-2-methyl-4-[(4-morpholinophenyl)amino]-1,2,3,4-tetrahydroquinoline-6-carboxamide |
| 177 | 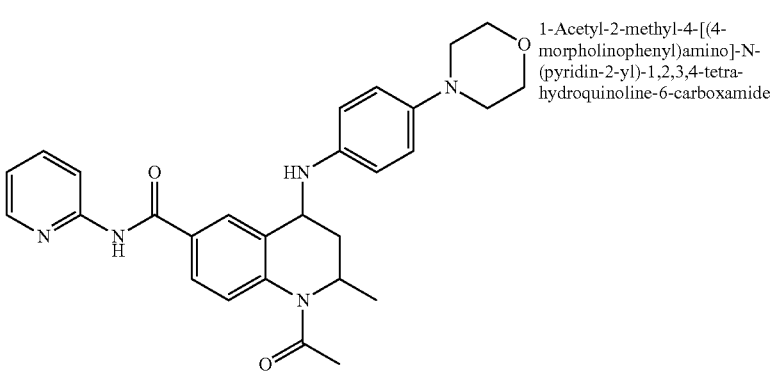 | 1-Acetyl-2-methyl-4-[(4-morpholinophenyl)amino]-N-(pyridin-2-yl)-1,2,3,4-tetrahydroquinoline-6-carboxamide |

TABLE 24-continued

| Compound No. | Structural formula | Name |
|---|---|---|
| 178 | | 1-Acetyl-N-cyclohexyl-2-methyl-4-[(4-morpholinophenyl)amino]-1,2,3,4-tetrahydroquinoline-6-carboxamide |
| 179 | | 1-Acetyl-2-methyl-4-[(3-morpholinophenyl)amino]-1,2,3,4-tetrahydroquinoline-6-carboxylic acid |
| 180 | | 1-Acetyl-N,2-dimethyl-4-[(3-morpholinophenyl)amino]-1,2,3,4-tetrahydroquinoline-6-carboxamide |
| 181 | | 1-Acetyl-2-methyl-4-[(3-morpholinophenyl)amino]-1,2,3,4-tetrahydroquinoline-6-carboxamide |

Compounds 1, 2, and 3 are available from ChemBridge Corp., and compound 47 is available from Princeton BioMolecular Research, Inc. Furthermore, compounds 5, 8, 9, 10, 11, 12, 15, 16, 17, 21, 46, 48, 49, 50, 51, and 52 can be produced according to the methods described in known document (Patent Document 16), and compounds 13 and 75 can be produced according to the methods described in known document (Patent Document 15).

The tetrahydroquinoline compound represented by the formula (1) of the present invention can be produced by known methods. For example, the tetrahydroquinoline compound can be produced by methods described below or methods equivalent thereto.

[Production Method 1] Method for Producing Compound in which A in Formula (1) is NH and N-alkyl 1-1.

Compound [D] of the present invention can be produced by a method represented by the following reaction scheme.

(Step 2) The compound [D] can be synthesized by allowing compound [C] to react in a solvent in the presence of a reducing agent under cooling or heating, for a time period of 5 minutes to 40 hours (preferably, 1 to 18 hours). Examples of a method for reduction include contact reduction using hydrogen gas and using a metal catalyst such as palladium carbon, palladium black, palladium hydroxide, platinum oxide, or Raney nickel; or a method of using sodium borohydride, sodium cyanoborohydride, sodium triacetoxyborohydride, zinc borohydride, borane, aluminum hydride, diisobutylaluminum hydride, sodium-alcohol, or the like. Examples of the solvent include organic solvents such as methanol, ethanol, N,N-dimethylformamide, diethyl ether, 1,4-dioxane, tetrahydrofuran, acetic acid, and ethyl acetate; water; or solvent mixtures thereof, and these solvents can be used singly or in combination.

Furthermore, in addition to the method of carrying out the step 1 and the step 2 in sequence as described above, the

[Chemical Formula 2]

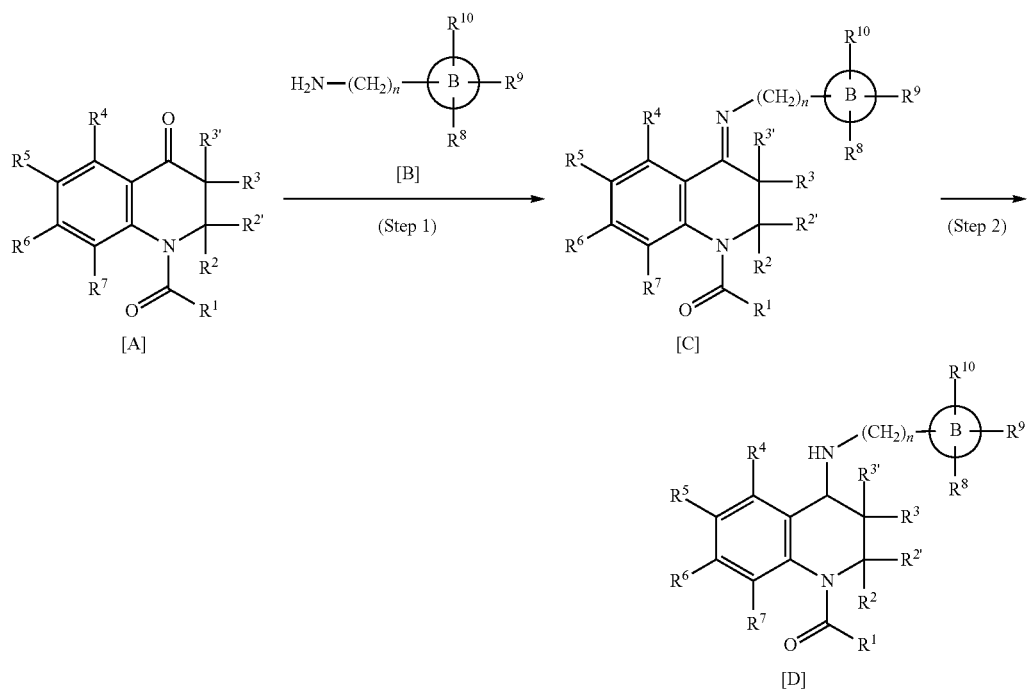

wherein ring B, $R^1$, $R^2$, $R^{2'}$, $R^3$, $R^{3'}$, $R^4$, $R^5$, $R^6$, $R^7$, $R^8$, $R^9$, and $R^{10}$ respectively have the same definitions as described above.

The compound [D] can be produced from 4-oxo-1,2,3,4-tetrahydroquinoline represented by formula [A] by a reductive amination method. The method for introducing an amino group according to a reductive amination method can be found in reference documents, for example, Comprehensive Organic Synthesis, Vol. 8, p. 21 (1991).

(Step 1) Compound [C] can be produced by allowing compound [A] and compound [B] to react in a solvent in the presence of an acid under cooling or heating, for a time period of 5 minutes to 40 hours (preferably, 1 to 18 hours). Examples of the acid include titanium tetrachloride, p-toluenesulfonic acid, and trifluoroacetic acid. Examples of the solvent include organic solvents such as toluene, dichloromethane, benzene and tetrahydrofuran, and these solvents can be used singly or in combination.

compound [D] can also be produced from the compound [A] by a method of carrying out the step 1 and the step 2 simultaneously in a same system.

A compound in which A is an N-alkyl can be produced from the compound [D] using known methods, for example, reductive amination reactions (Borch reaction [J. Amer. Chem. Soc., 2897 (1971)], Leuckart-Wallach reaction [Org. React., 301 (1949)], and Eshweiler-Clarke reaction [J. Amer. Chem. Soc., 4571 (1933)]), or an alkylation reaction of an amino group.

1-2.

The 4-oxo-1,2,3,4-tetrahydroquinoline derivative [A] that is used in the production of the compound [D] of the present invention can be produced, when $R^{3'}$ is a hydrogen atom, according to the following production method with reference to a known procedure, for example, a procedure disclosed in WO 2002/53557.

[Chemical Formula 3]

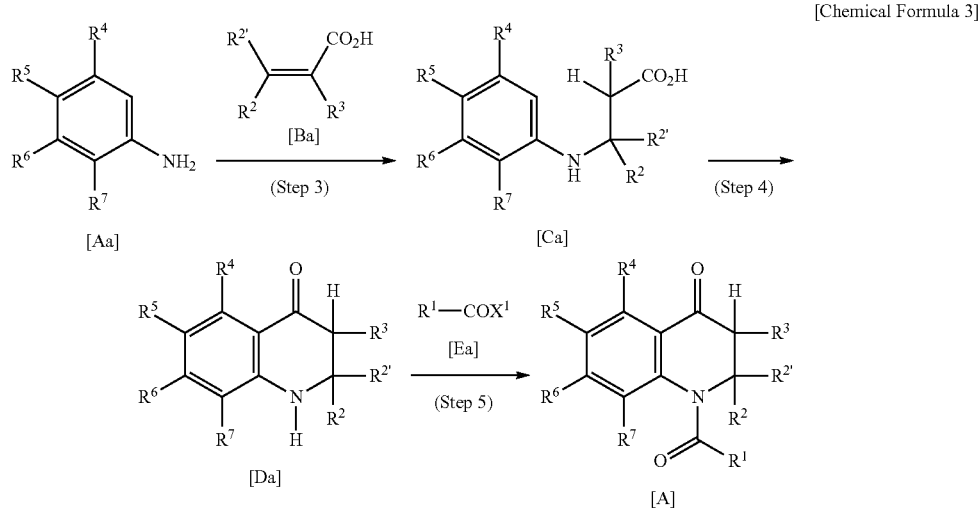

wherein $R^1$, $R^2$, $R^{2'}$, $R^3$, $R^{3'}$, $R^4$, $R^5$, $R^6$, and $R^7$ have the same definitions as described above; and X' represents a leaving group.

(Step 3) Compound [Ca] can be produced by allowing compound [Aa] and compound [Ba] in a solvent under heating for a time period of 5 minutes to 40 hours (preferably, 1 to 18 hours). Examples of the solvent include organic solvents such as toluene, benzene, ethyl acetate, methyl isobutyl ketone, and methyl tert-butyl ether, and these solvents can be used singly or in combination.

(Step 4) Compound [Da] (wherein $R^{3'}$ is a hydrogen atom) can be produced by allowing compound [Ca] in the presence of an acid such as polyphosphoric acid under heating for a time period of 5 minutes to 40 hours (preferably, 1 to 18 hours). Examples of the solvent include organic solvents such as toluene and benzene, and these solvents can be used singly or in combination.

(Step 5) Compound [A] (wherein $R^{3'}$ is a hydrogen atom) can be produced by allowing compound [Da] (wherein $R^{3'}$ is a hydrogen atom) and compound [Ea] to react in a solvent in the presence or absence of a base, under cooling or heating for a time period of 5 minutes to 90 hours (preferably, 1 to 18 hours). Examples of the base include pyridine, triethylamine, N,N-diisopropylethylamine, N-methylmorpholine, N-methylpiperidine, and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide; and water, and these solvents can be used singly or in combination. Here, $X^1$ in the compound [Ea] represents an atom or a functional group which functions as a leaving group, and examples thereof include a halogen atom such as chlorine or bromine; and an acyl group such as a pivaloyl group.

1-3.

The 4-oxo-1,2,3,4-tetrahydroquinoline derivative [A] used in the production of the compound [C] of the present invention can be produced according to a known procedure, for example, the following method disclosed in WO 2002/79165.

[Chemical Formula 4]

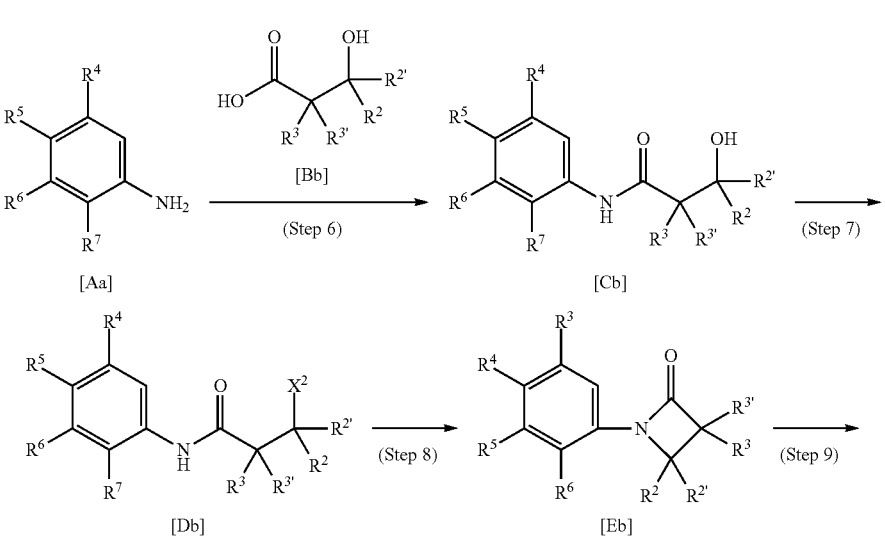

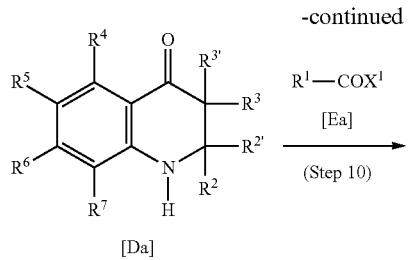 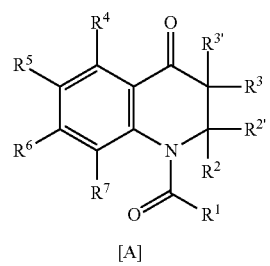

wherein $R^1$, $R^2$, $R^{2'}$, $R^3$, $R^{3'}$, $R^4$, $R^5$, $R^6$, and $R^7$ respectively have the same definitions as described above; and $X^1$ and $X^2$ each represent a leaving group.

(Step 6) compound [Cb] is obtained by allowing compound [Aa] to react with an equal amount or an excess amount of compound [Bb] in a solvent in the presence or absence of a base under cooling or heating, for a time period of 5 minutes to 40 hours (preferably, 1 to 18 hours). At this time, 1,3-dicyclohexylcarbodiimide (DCC), 1-ethyl-3-(3-dimethylaminopropyl)carbodiimide hydrochloride (WSC), oxalyl chloride, thionyl chloride, or the like can be used as a reaction reagent. Examples of the base include organic bases such as pyridine, triethylamine, and N,N-diisopropylethylamine; and inorganic bases such as potassium carbonate, sodium carbonate, potassium hydroxide, sodium hydroxide, and lithium hydroxide. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide; and water, and these solvents can be used singly or in combination.

(Step 7) Compound [Db] can be produced by allowing compound [Cb] and an alkylsulfonyl halide, an arylsulfonyl halide, an alkylsulfonic acid anhydride, an arylsulfonic acid anhydride, or the like to react in a solvent in the presence of a base, under cooling or heating for a time period of 5 minutes to 40 hours (preferably, 5 minutes to 18 hours). Examples of the alkylsulfonyl halide include methanesulfonyl chloride, and trifluoromethanesulfonyl chloride, and examples of the arylsulfonyl halide include toluenesulfonyl chloride. Examples of the alkylsulfonic acid anhydride include methanesulfonic acid anhydride and trifluoromethanesulfonic acid anhydride, and examples of the arylsulfonic acid anhydride include toluenesulfonic acid anhydride. Examples of the base include pyridine, triethylamine, N,N-diisopropylethylamine, N-methylmorpholine, N-methylpiperidine, and picoline. Furthermore, examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide; and water, and these solvents can be used singly or in combination.

(Step 8) Compound [Eb] can be produced by allowing compound [Db] to react in the presence of a base under cooling or heating for a time period of 5 minutes to 40 hours (preferably, 1 to 18 hours). Examples of the base include sodium hydride, potassium hydride, sodium hydroxide, potassium hydroxide, and lithium hydroxide, and the base is preferably sodium hydroxide. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide, and these solvents can be used singly or in combination. The solvent is preferably N,N-dimethylformamide.

(Step 9) Compound [Da] can be produced by allowing compound [Eb] to react in a solvent in the presence of trifluoromethanesulfone or the like, under cooling or heating for a time period of 5 minutes to 40 hours (preferably, 1 to 18 hours). Examples of the solvent include organic solvents such as toluene, dichloromethane, benzene, and tetrahydrofuran, and these solvents can be used singly or in combination.

(Step 10) Compound [A] can be produced from compound [Da] by the method described in (Step 5) of production method 1-2.

1-4.

Furthermore, in regard to the 4-oxo-1,2,3,4-tetrahydroquinoline derivative [A], a compound in which $R^{2'}$ and $R^{3'}$ are each a hydrogen atom, and $R^2$ is —$CH^2$—$R^{3'''}$, can be produced according to a known procedure, for example, the following method disclosed in Journal of the Chemical Society, Perkin Transactions 1: Organic and Bio-Organic Chemistry, Vol. 59, p. 9-13 (1994).

[Chemical Formula 5]

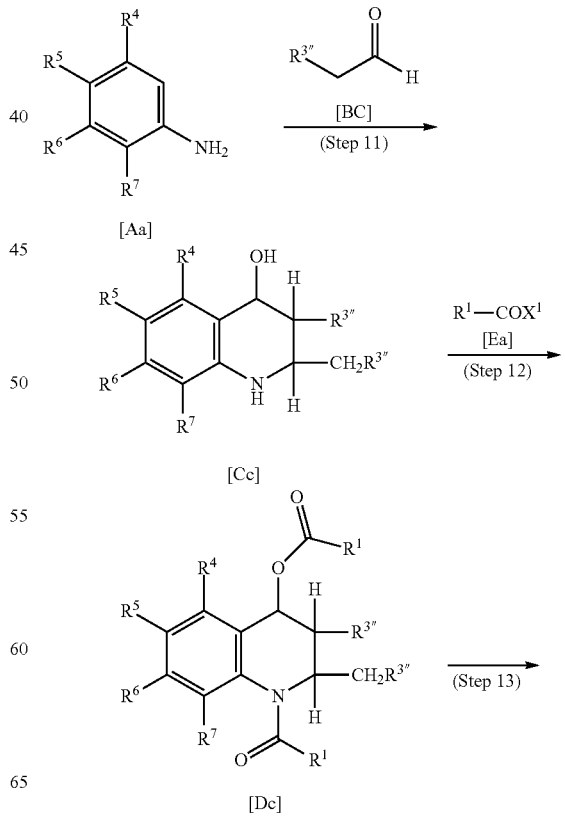

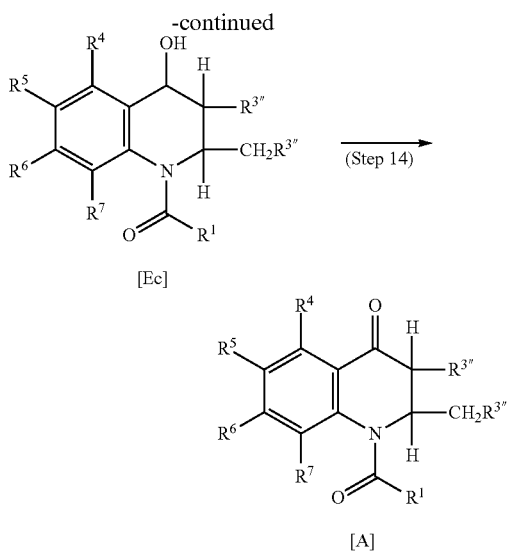

wherein $R^1$, $R^4$, $R^5$, $R^6$, and $R^7$ respectively have the same definitions as described above; $R^{3''}$ represents a hydrogen atom, an alkyl group, a cycloalkyl group, or a 5- to 10-membered heterocyclic group; and $X^1$ represents a leaving group.

(Step 11) Compound [Cc] can be produced by allowing compound [Aa] and compound [Bc] (2 to 10 equivalents, and preferably 3 to 4 equivalents) in a solvent in the presence of an acid, under cooling or heating for a time period of 5 minutes to 40 hours (preferably, 1 to 18 hours). Examples of the acid include inorganic acids such as hydrochloric acid, hydrobromic acid, sulfuric acid, phosphoric acid, and nitric acid; and organic acids such as acetic acid, oxalic acid, citric acid, tartaric acid, maleic acid, and benzoic acid. Examples of the solvent include organic solvents such as dichloromethane, chloroform, toluene, diethyl ether, tetrahydrofuran, 1,4-dioxane, diisopropyl ether, dimethoxymethane, hexane, ethyl acetate, methyl tert-butyl ether, and N,N-dimethylformamide; and water, and these solvents can be used singly or in combination.

(Step 12) Compound [Dc] can be produced by allowing compound [Cc] and compound [Ea] to react in a solvent in the presence or absence of a base, under cooling or heating for a time period of 5 minutes to 40 hours (preferably, 1 to 18 hours). Examples of the base include pyridine, triethylamine, N,N-diisopropylethylamine, N-methylmorpholine, N-methylpiperidine, and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tort-butyl ether, and N,N-dimethylformamide; water; and solvent mixtures thereof, and these solvents can be used singly or in combination. Here, $X^1$ in the compound [Ea] represents an atom or a functional group which functions as a leaving group, and examples thereof include a halogen atom such as fluorine, chlorine or bromine, or an acyl group such as a pivalyl group.

(Step 13) Compound [Ed] can be produced from compound [Dc] by hydrolysis using hydroxide ions or by alcoholysis using an alkoxide. At this time, examples of the base that can be used include potassium carbonate, sodium carbonate, potassium hydroxide, sodium hydroxide, and lithium hydroxide. Examples of the solvent include water, or organic solvents such as methanol, ethanol, isopropyl alcohol, tetrahydrofuran, 1,4-dioxane, and dimethoxyethane, and these solvents can be used singly or in combination with water. The reaction temperature and the reaction time are such that under cooling or heating, a time period of 5 minutes to 40 hours (preferably, 1 to 18 hours) can be applied.

(Step 14) Compound [A] (compound in which $R^{2'}$ and $R^{3'}$ are hydrogen atoms, and $R^2$ is —$CH_2$—$R^{3''}$) is obtained by allowing compound [Ed] and an oxidizing agent to react in a solvent, under cooling or heating for a time period of 5 minutes to 40 hours (preferably, 1 to 18 hours). Examples of the oxidizing agent include dimethyl sulfoxide-oxalyl chloride (or acetic anhydride, trifluoroacetic anhydride, DCC, or the like)-triethylamine, hydrogen peroxide, tetraisopropylammonium perruthenate, manganese dioxide, pyridinium chlorochromate (PCC), pyridinium dichromate (PDC), potassium dichromate, and potassium permanganate. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide; water; and solvent mixtures thereof, and these solvents can be used singly or in combination.

1-5.

Furthermore, compound [D] of the present invention, particularly a tetrahydroquinoline compound in which $R^{2'}$ and $R^{3'}$ are hydrogen atoms; $R^2$ is —$CH_2$—$R^{3''}$; and n is 0, can be produced by a duplex reaction of compound [Aa] according to a known procedure, for example, the following method disclosed in JP-A No. 2002-53557.

[Chemical Formula 6]

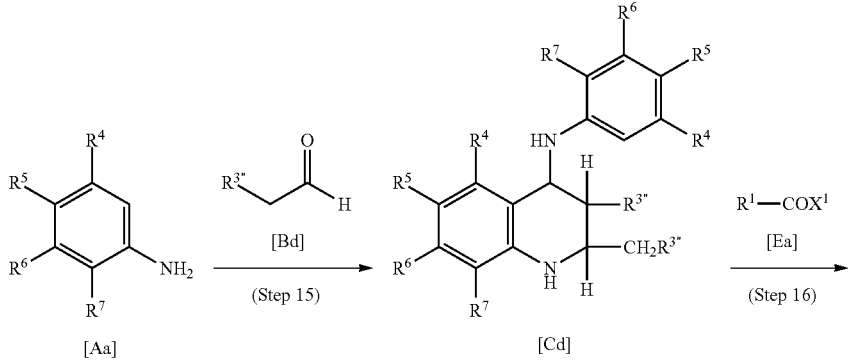

-continued

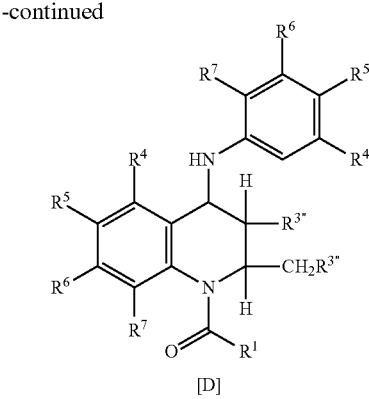

[D]

wherein $R^1$, $R^4$, $R^5$, $R^6$, and $R^7$ respectively have the same definitions as described above; $R^{3''}$ represents a hydrogen atom, an alkyl group, a cycloalkyl group, or a 5- to 10-membered heterocyclic group; and $X^1$ represents a leaving group.

(Step 15) Compound [Cd] can be produced by allowing compound [Aa] and compound [Bd] to react in a solvent in the presence of benzotriazole, under cooling or heating for a time period of 5 minutes to 4 days (preferably, 1 hour to 3 days).

(Step 16) Compound [D] can be produced by allowing compound [Cd] and compound [Ea] to react in a solvent in the presence or absence of a base, under cooling or heating for a time period of 5 minutes to 40 hours (preferably, 1 to 18 hours). Examples of the base include pyridine, triethylamine, N,N-diisopropylethylamine, N-methylmorpholine, N-methylpiperidine, and picoline. Examples of the solvent include organic solvents such as dichloromethane, chloroform, toluene, diethyl ether, tetrahydrofuran, 1,4-dioxane, diisopropyl ether, dimethoxyethane, hexane, ethyl acetate, methyl tert-butyl ether, and N,N-dimethylformamide; water; and solvent mixtures thereof, and these solvents can be used singly or in combination. Here, $X^1$ in the compound [Ea] represents an atom or a functional group which functions as a leaving group, and examples thereof include a halogen atom such as fluorine, chlorine, or bromine; or an acyl group such as a pivaloyl group.

[Production Method 2] Method for Producing Compound in Which A in Formula (1) is Oxygen Atom 2-1.

Compound [G] of the present invention can be produced from 4-hydroxy-1,2,3,4-tetrahydroquinoline represented by formula [F].

[Chemical Formula 7]

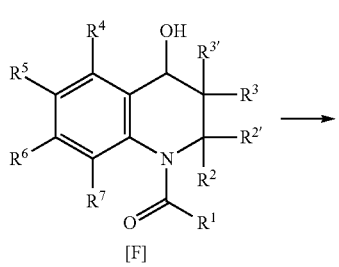

[F]

→

-continued

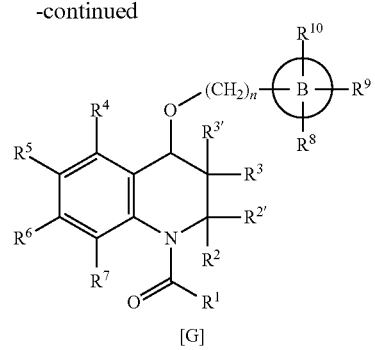

[G]

wherein ring B, $R^1$, $R^4$, $R^5$, $R^6$, and $R^7$ have the same definitions as described above; $R^{3'}$ represents an alkyl group, a cycloalkyl group, or a 5- to 10-membered heterocyclic group; and $X^1$ represents a leaving group.

When n is 0, the compound [G] of the present invention can be produced from 4-hydroxy-1,2,3,4-tetrahydroquinoline represented by formula [F] by a Mitsunobu reaction or a radical substitution reaction.

2-1-1. Mitsunobu Reaction

Compound [G] can be produced by a Mitsunobu reaction between compound [F] and a phenol compound represented by formula: ArOH (Reference Document: Organic Reactions, 42, 335-395 (1992); or Synthesis, 1-28 (1981)). Specifically, when compound [A] and 0.5 to 5 equivalents (preferably, 1 to 1.5 equivalents) of ArOH are allowed to react in a solvent in the co-presence of 0.5 to 5 equivalents (preferably, 1 to 1.5 equivalents) of an azodicarboxylic acid derivative and triallylphosphine or trialkylphosphine, under cooling or heating for a time period of 5 minutes to 40 hours (preferably, 1 to 18 hours), compound [B] can be obtained. Preferred examples of the azodicarboxylic acid include dimethyl azodicarboxylate, diethyl azodicarboxylate, diisopropyl azodicarboxylate, and 1,1-azodicarbonyldipiperidine. Examples of the phosphine compound include triphenylphosphine, and tributylphosphine. Examples of the solvent include organic solvents such as dichloromethane, chloroform, toluene, ether, tetrahydrofuran, 1,4-dioxane, diisopropyl ether, dimethoxyethane, hexane, ethyl acetate, methyl tert-butyl ether, and N,N-dimethylformamide, and these solvents can be used singly or in combination.

2-1-2. Radical Substitution Reaction

Compound [G] can be synthesized by a radical substitution reaction between compound [F] and an aryl radical source (Reference Document: Chemical Reviews, 89, 1487-1501

(1989)). Specifically, the compound [G] is obtained by allowing compound [F] and 1 to 10 equivalents (preferably, 1 to 2 equivalents) of an aryl radical source such as tri(aryl)bismuth diacetate to react in a solvent or without solvent, in the presence of a metal salt such as copper acetate, under cooling or heating for a time period of 5 minutes to 40 hours (preferably, 1 to 18 hours). Examples of the solvent include tetrahydrofuran, dioxane, chloroform, and dichloromethane, and these solvents can be used singly or in combination.

2-1-3.

When n is 1, compound [G] of the present invention can be produced by an alkylation reaction of 4-hydroxy-1,2,3,4-tetrahydroquinoline represented by formula [F]. Specifically, the compound [G] is obtained by allowing compound [F], 1 to 10 equivalents (preferably, 1 to 2 equivalents) of a base, and 1 to 10 equivalents (preferably, 1 to 2 equivalents) of an alkylating agent in a solvent, under cooling or heating for a time period of 5 minutes to 40 hours (preferably, 1 to 18 hours). Examples of the base include sodium hydride; alkyllithiums such as n-butyllithium; Grignard's reagents such as phenylmagnesium bromide; and amide bases such as lithium N,N-diisopropylamide and potassium hexamethyldisilazide. Examples of the solvent include tetrahydrofuran, 1,4-dioxane, and dimethoxyethane, and these solvents can be used singly or in combination.

2-2.

Here, 4-hydroxy-1,2,3,4-tetrahydroquinoline represented by formula [F] in which $R^3$ is a hydrogen atom, can be produced according to a known procedure, for example, the following method disclosed in WO 2002/053557.

[Chemical Formula 8]

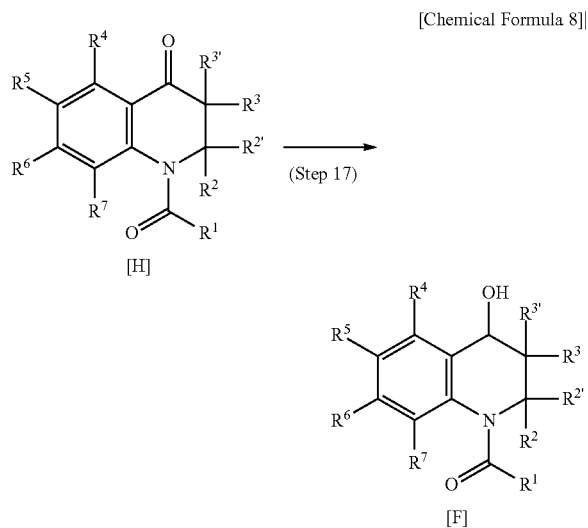

(Step 17) Compound [F] can be synthesized by allowing compound [H] to react in a solvent in the presence of a reducing agent, under cooling or heating for a time period of 5 minutes to 40 hours (preferably, 1 to 18 hours). Examples of a method for reduction include contact reduction using hydrogen gas and using a metal catalyst such as palladium carbon, palladium black, palladium hydroxide, platinum oxide, or Raney nickel; and a method of using sodium borohydride, sodium cyanoborohydride, sodium triacetoxyborohydride, zinc borohydride, borane, aluminum hydride, diisobutylaluminum hydride, sodium-alcohol, or the like. Examples of the solvent include organic solvents such as methanol, ethanol, N,N-dimethylformamide, diethyl ether, 1,4-dioxane, tetrahydrofuran, acetic acid, and ethyl acetate; and water, and these solvents can be used singly or in appropriate combination.

Furthermore, for the purpose of avoiding side reactions, the target compounds can be produced by having the substituents of the respective compounds protected with appropriate protective groups, and performing deprotection after completion of the reaction steps. In regard to the conditions for the protection and deprotection of substituents, those methods generally used (for example, methods described in Protective Groups in Organic Synthesis, Third Edition, John Wiley & Sons, Inc.) can be carried out.

The intermediates and target products obtained by the various reactions described above can be isolated and purified as necessary, by subjecting the compounds to those purification methods that are routinely used in organic synthetic chemistry, for example, filtration, extraction, washing, drying, concentration, recrystallization, and various chromatographic techniques. Furthermore, the intermediates can be supplied to the subsequent reactions without any particular purification of the compounds.

Furthermore, various isomers can be isolated by routine methods, using the differences in the physicochemical properties between the isomers. For instance, a racemic mixture can be derived into optically pure isomers by, for example, a method of performing optical resolution by deriving the racemic mixture into a diastereomer salt with a common optically active acid such as tartaric acid, or by a general method for racemic resolution such as a method using optically active column chromatography. Also, a diastereomer mixture can be divided by, for example, fractional crystallization or various chromatographic techniques. Optically active compounds can also be produced by using appropriate optically active raw materials.

The EPO production enhancer, hemoglobin production enhancer, or therapeutic agent for anemia of the present invention contains a 1-acyl-4-(substituted oxy, substituted amino, or substituted thio)-1,2,3,4-tetrahydroquinoline derivative, more particularly, a tetrahydroquinoline compound represented by the formula (1), a salt thereof, or a solvate of the compound or the salt as an active ingredient, and the agents can be used as pharmaceutical compositions. In that case, the compound of the present invention may be used singly, but usually, the compound is used as a mixture with a pharmaceutically acceptable carrier and/or a diluent.

The route of administration is not particularly limited, and can be appropriately selected in accordance with the purpose of treatment. For example, any of oral preparations, injectable preparations, suppositories, inhalants, and the like may be used. Pharmaceutical composition appropriate for these dosage forms can be prepared by using known formulation methods.

In the case of preparing an oral solid preparation, a pharmaceutically acceptable excipient, and if necessary, a binder, a disintegrant, a lubricating agent, a coloring agent, a flavoring agent, an odor improving agent, and the like are added to a 1-acyl-4-(substituted oxy, substituted amino, or substituted thio)-1,2,3,4-tetrahydroquinoline derivative, more particularly, a compound represented by the formula (1), and then tablets, coated tablets, granules, powders, capsules, and the like can be prepared from the mixture by using conventional methods. Additives may be those agents generally used in the pertinent art. Examples of the excipient include lactose, sucrose, sodium chloride, glucose; starch, calcium carbonate, kaolin, microcrystalline cellulose, and silicic acid. Examples of the binder include water, ethanol, propanol, simple syrup, a glucose solution, a starch solution, a gelatin solution, carboxymethyl cellulose, hydroxypropyl cellulose, hydroxypropyl starch, methyl cellulose, ethyl cellulose, shellac, calcium phosphate, and polyvinyl pyrrolidone. Examples of the disintegrant include dried starch, sodium alginate, powdered agar, sodium hydrogen carbonate, calcium carbonate, sodium lauryl sulfate, stearic acid monoglyceride, and lactose. Examples of the lubricating agent include purified talc, stearic acid salts, borax, and polyethylene glycol. Examples of the flavoring agent include sucrose, orange peel, citric acid, and tartaric acid.

In the case of preparing an oral liquid preparation, a flavoring agent, a buffering agent, a stabilizing agent, an odor improving agent, and the like are added to a 1-acyl-4-(substituted oxy, substituted amino, or substituted thio)-1,2,3,4-tetrahydroquinoline derivative, more particularly, a compound represented by the formula (1), and an internal liquid medicine, a syrup, an elixir, and the like can be prepared from the mixture using conventional methods. Examples of the flavoring agent include those mentioned above, and examples of the buffering agent include sodium citrate. Examples of the stabilizing agent include tragacanth, gum arabic, and gelatin.

In the case of preparing an injectable preparation, a pH adjusting agent, a buffering agent, a stabilizing agent, an isotonic agent, a local anesthetic, and the like are added to a 1-acyl-4-(substituted oxy, substituted amino, or substituted thio)-1,2,3,4-tetrahydroquinoline derivative, more particularly, a compound represented by the formula (1), and subcutaneous, intramuscular, and intravenous injectable preparations can be prepared from the mixture using conventional methods. Examples of the pH adjusting agent and the buffering agent include sodium citrate, sodium acetate, and sodium phosphate. Examples of the stabilizing agent include sodium pyrosulfite, EDTA, thioglycolic acid, and thiolactic acid. Examples of the local anesthetic include procaine hydrochloride, and lidocaine hydrochloride. Examples of the isotonic agent include sodium chloride, and glucose.

In the case of preparing a suppository, known carriers for suppositories, for example, polyethylene glycol, lanolin, cacao fats, fatty acid triglycerides, and the like, and if necessary, surfactants (for example, Tween (registered trademark)) and the like are added to a 1-acyl-4-(substituted oxy, substituted amino, or substituted thio)-1,2,3,4-tetrahydroquinoline derivative, more particularly, a compound represented by the formula (1), and then suppositories can be prepared from the mixture using conventional methods.

In addition to the preparations described above, any appropriate preferable preparations can be prepared using conventional methods.

The dosage of the 1-acyl-4-(substituted oxy, substituted amino, or substituted thio)-1,2,3,4-tetrahydroquinoline derivative of the present invention, more particularly, the compound represented by the formula (1), may vary with the age, body weight, symptoms, dosage form, frequency of administration, and the like, but typically, it is preferable to orally administer or parenterally administer 1 mg to 1000 mg per day in terms of the compound represented by the formula (1), once or in several divided portions, for an adult.

Next, the present invention will be described more specifically by way of Examples and Test Examples, but the present invention is not intended to be limited to these Examples.

EXAMPLE 1

Production of cis-1-acetyl-8-fluoro-4-[(2-fluorophenyl)amino]-2-methyl-1,2,3,4-tetrahydroquinoline (Compound 4)

[Step 1] 1 g of 2-fluoroaniline, 484 mg of acetaldehyde, and 238 mg of benzotriazole were dissolved in ethanol, and the solution was stirred for 14 hours at room temperature. After completion of the reaction, the reaction product was concentrated under reduced pressure, and the resulting residue was purified by using silica gel chromatography (diethyl ether:hexane=1:5). Thus, 163 mg (13%) of 8-fluoro-4-[(2-fluorophenyl)amino]-2-methyl-1,2,3,4-tetrahydroquinoline was obtained as a yellow oily substance.

[Step 2] 60 mg of cis-8-fluoro-4-[(2-fluorophenyl)amino]-2-methyl-1,2,3,4-tetrahydroquinoline was dissolved in 0.5 mL of pyridine and 2 mL of dichloromethane, and 16 mg of acetyl chloride was added to the solution under ice cooling. The resulting mixture was stirred for 2 hour under ice cooling. After completion of the reaction, water was added to the reaction liquid, the mixture was extracted with chloroform, and then the organic layer was washed with a saturated solution of sodium hydrogen carbonate and saturated brine. The washed organic layer was dehydrated over anhydrous sodium sulfate, and then was concentrated under reduced pressure. The resulting residue was purified by using silica gel chromatography (chloroform), and thus 48 mg (70%) of the title compound was obtained as a colorless oily substance.

$^1$H-NMR (400 MHz, CDCl$_3$) δ: 1.16 (3H, d, J=6.6 Hz), 1.25-1.33 (1H, m), 2.11 (3H, s), 2.68 (1H, ddd, J=4.0, 8.4, 12.4 Hz), 4.10 (1H, brs), 4.19-4.21 (1H, m), 4.98 (1H, brs), 6.58-6.72 (2H, m), 6.82-6.86 (1H, m), 7.01-7.07 (1H, m), 6.91-7.11 (2H, m), 7.17-7.22 (1H, m).

EXAMPLE 2

Production of cis-1-acetyl-4-[(2-fluorophenyl)amino]-2-methyl-1,2,3,4-tetrahydroquinoline (Compound 22)

[Step 1] 50 mg of 1-acetyl-4-oxo-2-methyl-1,2,3,4-tetrahydroquinoline and 83 mg of 2-fluoroaniline were dissolved in 2 mL of toluene, and 125 µL of titanium tetrachloride (1.0 M dichloromethane solution) was added to the solution under ice cooling. The resulting mixture was stirred for one hour under ice cooling, and then was stirred for 3 hours at 80° C. After completion of the reaction, the reaction liquid was filtered through Celite and was concentrated under reduced pressure. The resulting residue was purified by using silica gel chromatography (diethyl ether:hexane=2:1), and thus 60 mg (81%) of 1-acetyl-2-methyl-4-[(2-fluorophenyl)imino]-1,2,3,4-tetrahydroquinoline was obtained as a yellow oily substance.

[Step 2] 60 mg of 1-acetyl-2-methyl-4-[(2-fluorophenyl)imino]-1,2,3,4-tetrahydroquinoline and 28 mg of sodium cyanoborohydride were dissolved in 2 mL of methanol, and the solution was stirred for 18 hours at 50° C. After completion of the reaction, 1 N hydrochloric acid was added to the reaction liquid, and the mixture was stirred for 30 minutes. The reaction liquid was neutralized with a saturated aqueous solution of sodium hydrogen carbonate, and then was extracted with chloroform. The organic layer was washed with a saturated solution of sodium hydrogen carbonate and saturated brine, dehydrated over anhydrous sodium sulfate, and then concentrated under reduced pressure. The resulting residue was purified by using silica gel chromatography (diethyl ether:hexane=2:1), and thus 53 mg (88%) of the title compound was obtained as a colorless oily substance.

$^1$H-NMR (400 MHz, CDCl$_3$) δ: 1.17 (3H, d, J=6.4 Hz), 1.28-1.37 (1H, m), 2.19 (3H, s), 2.68 (1H, ddd, J=4.1, 8.5, 12.4 Hz), 4.09 (1H, brs), 4.23 (1H, dd, J=4.2, 11.5 Hz), 4.92 (1H, brs), 6.61-6.71 (2H, m), 6.91-6.98 (1H, m), 7.01-7.07 (1H, m), 7.14-7.23 (2H, m), 7.45 (2H, d, J=3.8 Hz).

EXAMPLE 3

Production of cis-1-acetyl-7-bromo-2-methyl-4-phenylamino-1,2,3,4-tetrahydroquinoline (Compound 23)

[Step 1] The production process was carried out in the same manner as in the [Step 2] of Example 1, using 48 my of 7-bromo-4-oxo-2-methyl-1,2,3,4-tetrahydroquinoline, and thus 56 mg (100%) of 1-acetyl-7-bromo-4-oxo-2-methyl-1,2,3,4-tetrahydroquinoline was obtained.

[Step 2] The production process was carried out in the same manner as in Example 2, using 23 mg of 1-acetyl-7-bromo-4-oxo-2-methyl-1,2,3,4-tetrahydroquinoline, and thus 12 mg (60%) of the title compound was obtained as a yellow oily substance.

$^1$H-NMR (400 MHz, CDCl$_3$) δ: 1.17 (3H, d, J=6.3 Hz), 1.28 (1H, m), 2.22 (3H, s), 2.65 (1H, ddd, J=4.4, 8.4, 12.4 Hz), 3.80 (1H, m), 4.11 (1H, m), 4.86 (1H, m), 6.61 (2H, d, J=8.5 Hz), 6.77 (1H, dd, J=7.3, 7.3 Hz), 7.16-7.2 (5H, m).

EXAMPLE 4

Production of 1-acetyl-6-cyano-2-methyl-4-phenylamino-1,2,3,4-tetrahydroquinoline (Compound 14)

100 mg (0.278 mmol) of 1-acetyl-6-bromo-2-methyl-4-phenylamino-1,2,3,4-tetrahydroquinoline), 36 mg (0.31 mmol) of zinc cyanide, and 18 mg (0.015 mmol) of tetrakis(triphenylphosphine)palladium (0) were added to 1.5 mL of DMF, and the mixture was stirred for 2 hours at 120° C. under an argon atmosphere. After completion of the reaction, water was added to the reaction liquid, and the mixture was extracted with ethyl acetate. The organic layer was washed with saturated brine, dehydrated over anhydrous sodium sulfate, and then concentrated under reduced pressure. The resulting residue (104 mg) was purified by using silica gel preparatory thin layer chromatography (ether:hexane=5:1), and thus 63 mg (cis:trans=3:1, 74.1%) of the title compound was obtained as a colorless amorphous solid.

$^1$H-NMR (400 MHz, CDCl$_3$) δ: 1.20 (3H, d, J=6.3 Hz), 1.36 (1H, m), 2.23 (3H, s), 2.68 (1H, ddd, J=9.4, 8.5, 12.4 Hz), 3.80 (1H, m), 4.19 (1H, m), 9.82 (1H, m), 6.60-6.79 (3H, m), 7.18-7.28 (3H, m), 7.50-7.68 (2H, m).

EXAMPLE 5

Production of cis-1-acetyl-7-cyano-2-methyl-9-phenylamino-1,2,3,4-tetrahydroquinoline (Compound 7)

The production process was carried out in the same manner as in Example 4, using 12 mg of the cis-1-acetyl-7-bromo-2-methyl-4-phenylamino-1,2,3,4-tetrahydroquinoline (compound 23) obtained in Example 3, and thus 6 mg (60%) of the title compound was obtained as a pale yellow amorphous solid.

$^1$H-NMR (400 MHz, CDCl$_3$) δ: 1.19 (3H, d, J=6.3 Hz), 1.33 (1H, m), 2.23 (3H, s), 2.70 (1H, ddd, J=4.4, 8.3, 12.5 Hz), 3.83 m), 4.21 (1H, m), 4.86 (1H, m), 6.60 (2H, d, J=7.8 Hz), 6.80 (1H, dd, J=7.3, 7.3 Hz), 7.16-7.26 (3H, m), 7.44-7.49 (2H, m).

EXAMPLE 6

Production of cis-1-acetyl-4-[(4-isopropoxyphenyl)amino]-2-methyl-1,2,3,4-tetrahydroquinoline (Compound 18)•hydrochloride A compound was produced in the same manner as in Example 2, using 60 mg of 1-acetyl-4-oxo-2-methyl-1,2,3,4-tetrahydroquinoline and 136 mg of 4-isopropoxyaniline, and the compound was converted to the hydrochloride by a known method. Thus, 53 mg (47%) of the title compound was obtained as a white solid.

$^1$H-NMR (400 MHz, CD$_3$OD) δ: 1.14 (3H, d, J=6.4 Hz), 1.34 (6H, d, J=6.1 Hz), 1.30-1.35 (1H, m), 2.14 (3H, s), 2.55 (1H, ddd, J=3.8, 8.6, 12.3 Hz), 4.61-4.74 (3H, m), 7.10 (2H, d, J=9.0 Hz), 7.41-7.52 (6H, m).

EXAMPLE 7

Production of cis-1-acetyl-2-methyl-4-[(4-morpholinophenyl)amino]-1,2,3,4-tetrahydroquinoline (Compound 19)•hydrochloride A compound was produced in the same manner as in Example 2, using 60 mg of 1-acetyl-4-oxo-2-methyl-1,2,3,4-tetrahydroquinoline and 107 mg of 4-morpholinoaniline, and the compound was converted to the hydrochloride by a known method. Thus, 42 mg (33%) of the title compound was obtained as a white solid.

$^1$H-NMR (400 MHz, CD$_3$OD) δ: 1.14 (3H, d, J=6.4 Hz), 1.29-1.36 (1H, m), 2.18 (3H, s), 2.66 (1H, ddd, J=3.9, 8.6, 12.4 Hz), 3.63-3.66 (4H, m), 4.03-4.07 (4H, m), 4.27 (1H, dd, J=4.2, 12.0 Hz), 6.82 (2H, d, J=9.0 Hz), 7.16-7.22 (2H, m), 7.28-7.35 (2H, m), 7.42 (2H, d, J=9.0 Hz).

EXAMPLE 8

Production of cis-1-acetyl-4-[(4-hydroxyphenyl)amino]-2-methyl-1,2,3,4-tetrahydroquinoline (Compound 24)•hydrochloride

[Step 1] 100 mg of 1-acetyl-4-oxo-2-methyl-1,2,3,4-tetrahydroquinoline and 227 mg of 4-acetoxyaniline were dissolved in 3 mL of toluene, and 250 µL of titanium tetrachloride (1.0 M dichloromethane solution) was added to the solution under ice cooling. The mixture was stirred for one hour under ice cooling, and then was stirred for another one hour at room temperature. After completion of the reaction, the reaction liquid was filtered through Celite and was concentrated under reduced pressure. The resulting residue was purified by using silica gel chromatography (chloroform), and thus 50 mg (30%) of 1-acetyl-2-methyl-4-[(4-acetoxyphenyl)imino]-1,2,3,4-tetrahydroquinoline was obtained as a yellow soup-like substance.

[Step 2] 45 mg of 1-acetyl-2-methyl-4-[(4-acetoxyphenyl)imino]-1,2,3,4-tetrahydroquinoline and 17 mg of sodium cyanoborohydride were dissolved in 2 mL of methanol, and the solution was stirred for 18 hours at 50° C. After completion of the reaction, 1 N hydrochloric acid was added to the reaction liquid, and the mixture was stirred for 30 minutes. The reaction mixture was neutralized with a saturated aqueous solution of sodium hydrogen carbonate, and then was extracted with chloroform. The organic layer was washed with a saturated sodium hydrogen carbonate solution and saturated brine, dehydrated over anhydrous sodium sulfate, and concentrated under reduced pressure. The resulting residue was purified by using silica gel chromatography (diethyl ether). After purification, the resulting product was dissolved in a 4 N hydrochloric acid-ethyl acetate solution, and the solution was concentrated under reduced pressure to obtain the hydrochloride. The hydrochloride was subjected to recrystallization from chloroform-hexane, and thus 18 mg (40%) of the title compound was obtained as a white crystal.

$^1$H-NMR (400 MHz, CD$_3$OD) δ: 1.14 (3H, d, J=6.3 Hz), 1.29-1.37 (1H, m), 2.14 (3H, s), 2.54 (1H, ddd, J=3.9, 8.4, 12.3 Hz), 4.61 (1H, dd, J=3.9, 12.4 Hz), 4.61-4.73 (1H, m), 6.97 (2H, d, J=8.8 Hz), 7.37 (2H, d, J=9.0 Hz), 7.41-7.52 (4H, m).

EXAMPLE 9

Production of cis-1-cyclohexanecarbonyl-6-fluoro-4-[(4-fluorophenyl)amino]-2-methyl-1,2,3,4-tetrahydroquinoline (Compound 6)

88 mg of cis-6-fluoro-4-[(4-fluorophenyl)amino]-2-methyl-1,2,3,4-tetrahydroquinoline was dissolved in 3 mL of dichloromethane, and 117 mg of triethylamine and 168 mg of cyclohexanecarbonyl chloride were added to the solution under ice cooling. The mixture was stirred for 16 hours under ice cooling. After completion of the reaction, a saturated aqueous solution of ammonium chloride was added to the reaction liquid, and the mixture was extracted with dichloromethane. Subsequently, the extraction product was dehydrated over anhydrous magnesium sulfate, and then was concentrated under reduced pressure. The resulting residue was subjected to recrystallization using chloroform, and thus 21 mg (17%) of the title compound was obtained as a colorless flake-shaped crystal.

$^1$H-NMR (400 MHz, CDCl$_3$) δ: 1.09 (3H, d, J=6.4 Hz), 1.14-1.30 (1H, m), 1.39-1.93 (10H, m), 2.63-2.74 (2H, m), 3.69 (1H, brs), 3.98-4.05 (1H, m), 4.93 (1H, brs), 6.51-6.54 (2H, m), 6.88-7.11 (5H, m).

EXAMPLE 10

Production of 1-acetyl-4-[(4-N,N-dimethylaminophenyl)amino]-2-methyl-1,2,3,4-tetrahydroquinoline (Compound 20)·dihydrochloride A compound was produced in the same manner as in Example 2, using 100 mg of 1-acetyl-4-oxo-2-methyl-1,2,3,4-tetrahydroquinoline and 201 mg of N,N-dimethyl-p-phenylenediamine, and the compound was converted to the hydrochloride by a known method. Thus, 55 mg (cis:trans=3:1, 28%) of the title compound was obtained as a white solid.

$^1$H-NMR (400 MHz, CDCl$_3$) δ: 1.16 (3H, d, J=6.4 Hz), 1.24-1.38 (1H, m), 2.20 (3H, s), 2.65 (1H, m), 3.23 (6H, s), 4.14-4.22 (1H, m), 4.06 (1H, m), 6.70 (2H, d, J=8.3 Hz), 7.15-7.25 (3H, m), 7.28-7.38 (1H, m), 7.28-7.38 (2H, m).

EXAMPLE 11

Production of cis-1-acetyl-2-methyl-4-phenoxy-1,2,3,4-tetrahydroquinoline (Compound 26)

100 mg of cis-1-acetyl-4-hydroxy-2-methyl-1,2,3,4-tetrahydroquinoline, 300 mg of triphenylbismuth diacetate, and 9.0 mg of copper acetate were dissolved in 4 mL of dichloromethane, and the solution was stirred for 3 hours at room temperature. Water was added to the reaction liquid, and the mixture was extracted with chloroform. Subsequently, the organic layer was washed with saturated brine, dehydrated over anhydrous sodium sulfate, and then concentrated under reduced pressure. The resulting residue was purified by using silica gel chromatography (ethyl acetate:hexane=1:1), and thus 56 mg (yield 49%) of the title compound was obtained as a white solid.

$^1$H-NMR (400 MHz, CDCl$_3$) δ: 1.18 (3H, d, J=6.4 Hz), 1.53 (1H, m), 2.19 (3H, s), 2.76 (1H, ddd, J=4.6, 8.2, 12.8 Hz), 4.89 (1H, brs), 5.07 (1H, dd, J=4.4, 10.8 Hz), 6.98-7.03 (3H, m), 7.17 (1H, s br), 7.23 (1H, d, J=6.0 Hz), 7.30-7.34 (3H, m), 7.45 (1H, d, J=7.6 Hz).

EXAMPLE 12

Production of cis-1-acetyl-4-(4-fluorophenoxy)-2-methyl-1,2,3,4-tetrahydroquinoline (Compound 27)

50 mg of trans-1-acetyl-4-hydroxy-2-methyl-1,2,3,4-tetrahydroquinoline, 112 mg of 4-fluorophenol, 126 mg of 1,1-azodicarbonyldipiperidine, and 125 mg of tributylphosphine were dissolved in 2 mL of toluene, and the solution was stirred for 2 hours at 50° C. The reaction liquid was filtered to remove any insoluble materials, and then the filtrate was concentrated under reduced pressure. The resulting residue was purified by using silica gel chromatography (diethyl ether), and thus 26 mg (yield 36%) of the title compound was obtained as a colorless oily substance.

$^1$H-NMR (400 MHz, CDCl$_3$) δ: 1.18 (3H, d, J=6.4 Hz), 1.53 (1H, m), 2.19 (3H, s), 2.73 (1H, ddd, J=4.6, 8.3, 12.8 Hz), 4.88 (1H, brs), 4.98 (1H, dd, J=4.7, 10.8 Hz), 6.93 (2H, dd, J=4.4, 9.3 Hz), 7.01 (2H, t, J=8.5 Hz), 7.16-7.29 (2H, m), 7.33 (1H, t, J=7.6 Hz), 7.44 (1H, d, J=7.1 Hz).

EXAMPLE 13

Production of cis-1-acetyl-4-(3-fluorophenoxy)-2-methyl-1,2,3,4-tetrahydroquinoline (Compound 28)

A compound was produced in the same manner as in Example 12, using 100 mg of trans-1-acetyl-4-hydroxy-2-methyl-1,2,3,4-tetrahydroquinoline and 112 mg of 3-fluoroaniline, and thus 70 mg (47%) of the title compound was obtained as a colorless oily substance.

$^1$H-NMR (400 MHz, CDCl$_3$) δ: 1.18 (3H, d, J=6.4 Hz), 1.54 (1H, m), 2.20 (3H, s), 2.75 (1H, ddd, J=4.6, 8.2, 12.8 Hz), 4.90 (1H, brs), 5.05 (1H, dd, J=4.6, 10.8 Hz), 6.71 (2H, d, J=8.3 Hz), 6.77 (1H, d, J=9.0 Hz), 7.19 (1H, s), 7.23-7.28 (2H, m), 7.33 (1H, t, J=8.1 Hz), 7.40 (1H, d, J=7.1 Hz).

EXAMPLE 14

Production of cis-1-acetyl-4-(2-fluorophenoxy)-2-methyl-1,2,3,4-tetrahydroquinoline (Compound 29)

A compound was produced in the same manner as in Example 12, using 100 mg of trans-1-acetyl-4-hydroxy-2-methyl-1,2,3,4-tetrahydroquinoline and 112 mg of 2-fluoroaniline, and thus 77 mg (53%) of the title compound was obtained as a colorless oily substance.

$^1$H-NMR (400 MHz, CDCl$_3$) δ: 1.19 (3H, d, J=6.4 Hz), 1.64 (1H, m), 2.18 (3H, s), 2.76 (1H, ddd, J=4.7, 8.1, 12.6 Hz), 4.88 (1H, brs), 5.06 (1H, dd, J=4.8, 10.6 Hz), 6.96-7.09 (3H, m), 7.12-7.16 (2H, m), 7.28 (1H, d, J=7.6 Hz), 7.33 (1H, t, J=7.1 Hz), 7.58 (1H, d, J=7.6 Hz).

EXAMPLE 15

Production of cis-1-acetyl-4-(2,4-difluorophenoxy)-2-methyl-1,2,3,4-tetra hydroquinoline (Compound 30)

A compound was produced in the same manner as in Example 12, using 60 mg of trans-1-acetyl-4-hydroxy-2-methyl-1,2,3,4-tetrahydroquinoline and 112 mg of 2,4-fluoroaniline, and thus 55 mg (59%) of the title compound was obtained as a colorless oily substance.

$^1$H-NMR (400 MHz, CDCl$_3$) δ: 1.19 (3H, d, J=6.4 Hz), 1.61 (1H, m), 2.17 (3H, s), 2.71 (1H, ddd, J=4.8, 8.1, 12.9 Hz), 4.86 (1H, brs), 4.98 (1H, dd, J=4.5, 10.4 Hz), 6.78-6.84 (1H, m), 6.89-6.95 (1H, m), 6.98-7.03 (1H, m), 7.13 (1H, m), 7.28-7.36 (1H, m), 7.58 (1H, d, J=7.2 Hz).

EXAMPLE 16

Production of cis-1-acetyl-4-(3,4-difluorophenoxy)-2-methyl-1,2,3,4-tetrahydroquinoline (Compound 31)

A compound was produced in the same manner as in Example 12, using 60 mg of trans-1-acetyl-4-hydroxy-2-methyl-1,2,3,4-tetrahydroquinoline and 112 mg of 3,4-difluoroaniline, and thus 59 mg (64%) of the title compound was obtained as a colorless oily substance.

$^1$H-NMR (400 MHz, CDCl$_3$) δ: 1.19 (3H, d, J=6.4 Hz), 1.61 (1H, m), 2.19 (3H, s), 2.73 (1H, ddd, J=4.6, 8.4, 12.8 Hz), 4.89 (1H, brs), 4.97 (1H, dd, J=4.6, 10.6 Hz), 6.67-6.70 (1H, m), 6.79-6.84 (1H, m), 7.10 (1H, dd, J=9.2 18.9 Hz), 7.17-7.21 (1H, m), 7.23-7.29 (2H, m), 7.30-7.35 (1H, m), 7.38 (1H, d, J=7.3 Hz).

EXAMPLE 17

Production of cis-1-acetyl-7-fluoro-2-methyl-4-phenoxy-1,2,3,4-tetrahydroquinoline (Compound 32)

(Step 1) 1.1 g of 3-fluoroaniline and 12 g of acetaldehyde were dissolved in 20 mL of 1 N hydrochloric acid, and the solution was stirred for 1.5 hours at 0° C. A 4N aqueous solution of sodium hydroxide was added to the reaction liquid, and the mixture was extracted with chloroform. Subsequently, the extraction product was dehydrated over anhydrous sodium sulfate, and then was concentrated under reduced pressure. The resulting residue was purified by using silica gel chromatography (ethyl acetate:hexane=1:5), and thus 860 mg (yield 47%) of 7-fluoro-4-hydroxy-2-methyl-1,2,3,4-tetrahydroquinoline was obtained as a brown oily substance.

(Step 2) 860 mg of 7-fluoro-4-hydroxy-2-methyl-1,2,3,4-tetrahydroquinoline as a brown oily substance was dissolved in 0.5 mL of pyridine and 10 mL of dichloromethane, and 16 mg of acetyl chloride was added to the solution under ice cooling. The mixture was stirred for 1.5 hours. After completion of the reaction, water was added to the reaction liquid, and the mixture was extracted with chloroform. Subsequently, the organic layer was dehydrated over anhydrous sodium sulfate, and then was concentrated under reduced pressure. The resulting residue was purified by using silica gel chromatography (ethyl acetate:hexane=1:2), and thus 1.9 g (100%) of 1-acetyl-7-fluoro-4-acetoxy-2-methyl-1,2,3,4-tetrahydroquinoline was obtained as an oily substance.

(Step 3) 1.4 g of 1-acetyl-7-fluoro-4-acetoxy-2-methyl-1,2,3,4-tetrahydroquinoline was dissolved in 10 mL of ethanol, and 10 mL of a 1 N aqueous solution of sodium hydroxide was added to the solution. The mixture was stirred for 1.5 hours. After completion of the reaction, water was added to the reaction liquid, and the mixture was extracted with chloroform. Subsequently, the organic layer was dehydrated over anhydrous sodium sulfate, and then was concentrated under reduced pressure. The resulting residue was purified by using silica gel chromatography (ethyl acetate:hexane=1:1), and thus 400 mg (34%) of trans-1-acetyl-7-fluoro-4-hydroxy-2-methyl-1,2,3,4-tetrahydroquinoline was obtained as a white solid.

(Step 4) A compound was produced in the same manner as in Example 2, using 100 mg of trans-1-acetyl-7-fluoro-4-hydroxy-2-methyl-1,2,3,4-tetrahydroquinoline and 84 mg of phenol, and thus 35 mg (26%) of the title compound was obtained as a white solid.

$^1$H-NMR (400 MHz, CDCl$_3$) δ: 1.20 (3H, d, J=6.2 Hz), 1.60 (1H, m), 2.23 (3H, s), 2.71 (1H, ddd, J=5.1, 7.8, 13.0 Hz), 4.84 (1H, brs), 5.05 (1H, dd, J=4.6, 9.8 Hz), 6.92-7.04 (5H, m), 7.32 (1H, dd, J=7.6, 8.8 Hz), 7.41 (1H, dd, J=6.4, 8.1 Hz).

EXAMPLE 18

Production of cis-1-acetyl-8-fluoro-2-methyl-4-phenoxy-1,2,3,4-tetrahydro quinoline (Compound 33)

Cis-1-acetyl-8-fluoro-4-hydroxy-2-methyl-1,2,3,4-tetrahydroquinoline was obtained in the same manner as in Example 17, using 2-fluoroaniline. A compound was produced in the same manner as in Example 1, using 100 mg of cis-1-acetyl-8-fluoro-4-hydroxy-2-methyl-1,2,3,4-tetrahydro quinoline, and thus 52 mg (39%) of the title compound was obtained as a white solid.

$^1$H-NMR (400 MHz, CDCl$_3$) δ: 1.17 (3H, d, J=6.3 Hz), 1.45 (1H, m), 2.10 (3H, s), 2.81 (1H, ddd, J=4.6, 8.6, 13.0 Hz), 4.93 (1H, m), 5.04 (1H, dd, J=4.4, 11.5 Hz), 6.95-7.04 (3H, m), 7.11 (1H, m), 7.20-7.28 (2H, m), 7.32 (2H, dd, J=7.6, 8.6 Hz).

EXAMPLE 19

Production of cis-1-acetyl-4-(4-fluorophenoxy)-6-fluoro-2-methyl-1,2,3,4-tetrahydroquinoline (Compound 34)

Trans-1-acetyl-6-fluoro-4-hydroxy-2-methyl-1,2,3,4-tetrahydroquinoline was obtained in the same manner as in Example 17, using 4-fluoroaniline. A compound was produced in the same manner as in Example 17, using 60 mg of trans-1-acetyl-6-fluoro-4-hydroxy-2-methyl-1,2,3,4-tetrahydroquinoline and 112 mg of 4-fluorophenol, and thus 58 mg (61%) of the title compound was obtained as a colorless oily substance.

$^1$H-NMR (400 MHz, CDCl$_3$) δ: 1.17 (3H, d, J=6.4 Hz), 1.46 (1H, m), 2.16 (3H, s), 2.74 (1H, ddd, J=4.8, 8.2, 12.9 Hz), 4.88 (1H, brs), 4.94 (1H, dd, J=4.6, 10.7 Hz), 6.91-6.95 (2H, m), 6.99-7.04 (3H, m), 7.12 (1H, m), 7.19 (1H, d, J=9.6 Hz).

EXAMPLE 20

Production of cis-1-acetyl-6-fluoro-2-methyl-4-phenoxy-1,2,3,4-tetrahydroquinoline (Compound 35)

A compound was produced in the same manner as in Example 12, using 39 mg of cis-1-acetyl-6-fluoro-4-hydroxy-2-methyl-1,2,3,4-tetrahydro quinoline and phenol, and thus 33 mg (63%) of the title compound was obtained as a white solid.

$^1$H-NMR (400 MHz, CDCl$_3$) δ: 1.18 (3H, d, J=6.4 Hz), 1.53 (1H, m), 2.17 (3H, s), 2.77 (1H, ddd, J=4.6, 8.3, 12.5 Hz), 4.88 (1H, brs), 5.02 (1H, dd, J=4.7, 10.6 Hz), 6.97-7.04 (4H, m), 7.13 (1H, s), 7.21 (1H, dd, J=2.0, 8.8 Hz), 7.33 (2H, t, J=8.1 Hz).

EXAMPLE 21

Production of cis-1-acetyl-2-methyl-4-benzyloxy-1,2,3,4-tetrahydroquinoline (Compound 36)

20 mg of cis-1-acetyl-4-hydroxy-2-methyl-1,2,3,4-tetrahydroquinoline was dissolved in 2 mL of tetrahydrofuran, and 3 mg of sodium hydride was added to the solution under ice cooling. The mixture was stirred for 30 minutes under ice cooling. 15 μL of benzyl bromide was further added to the solution, and the resulting mixture was stirred for one whole day. Water was added to the reaction liquid, and the mixture was extracted with ethyl acetate. Subsequently, the organic layer was washed with saturated brine, dehydrated over anhydrous sodium sulfate, and then concentrated under reduced pressure. The resulting residue was purified by using silica gel Chromatography (ethyl acetate:hexane=1:2), and thus 9 mg (yield 31%) of the title compound was obtained as a yellow solid.

$^1$H-NMR (400 MHz, CDCl$_3$) δ: 1.14 (3H, d, J=6.3 Hz), 1.26-1.35 (1H, m), 2.12 (3H, s), 2.81 (1H, ddd, J=4.5, 8.3, 12.6 Hz), 4.31 (1H, dd, J=4.8, 11.2 Hz), 4.73 (1H, brs), 4.77 (2H, dd, J=12.0, 19.6 Hz), 7.10 (1H, brs), 7.26-7.34 (2H, m), 7.37-7.44 (4H, m), 7.58-7.61 (1H, m).

EXAMPLE 22

Production of 1-acetyl-4-[(4-fluorophenyl)amino]-2-methyl-6-methoxy-1,2,3,4-tetrahydroquinoline (Compound 37)

70 mg of 1-acetyl-6-methoxy-4-oxo-2-methyl-1,2,3,4-tetrahydroquinoline was subjected to reactions and treatments in the same manner as in Example 2, and thus 59 mg (60%) of the title compound was obtained as a yellow oily substance (cis:trans=3:1).

$^1$H-NMR (400 MHz, CDCl$_3$) δ: 1.13 (2.5H, d, J=6.4 Hz), 1.16 (0.5H, d, J=6.6 Hz), 1.19-1.28 (1H, m), 2.13 (0.5H, s), 2.15 (2.5H, s), 2.44-2.53 (0.17H, m), 2.62 (0.83H, ddd, J=4.2, 8.6, 12.3 Hz), 3.66-3.69 (1H, m), 3.75 (2.5H, s), 3.80 (0.5H, s), 4.06-4.14 (0.83H, m), 4.44-4.49 (0.17H, m), 4.91 (1H, brs), 6.56-6.59 (2H, m), 6.78-6.93 (4.17H, m), 7.02-7.07 (0.83H, m).

EXAMPLE 23

Production of 1-acetyl-4-[(4-hydroxymethylphenyl) amino]-2-methyl-1,2,3,4-tetrahydroquinoline (Compound 38)

[Step 1] 610 mg of 1-acetyl-4-oxo-2-methyl-1,2,3,4-tetrahydroquinoline and 3.25 g of 4-aminobenzyl (tert-butyldiphenylsilyl)ether were dissolved in 15 mL of toluene, and 3 mL of titanium tetrachloride (1.0M dichloromethane solution) was added to the solution under ice cooling. The mixture was stirred for one hour under ice cooling, and then was stirred for another 3 hours at 80° C. After completion of the reaction, the reaction liquid was filtered through Celite and was concentrated under reduced pressure. The resulting residue was purified by using silica gel chromatography (diethyl ether:hexane=2:1), and thus 1.5 g (91%) of 1-acetyl-2-methyl-4-[(4-tert-butyldiphenylsilyloxymethylphenyl)imino]-1,2,3,4-tetrahydroquinoline was obtained as a yellow oily substance.

[Step 2] 715 mg of 1-acetyl-2-methyl-4-[(4-tert-butyldiphenylsilyloxymethylphenyl)imino]-1,2,3,4-tetrahydroquinoline, 74 mg of sodium borohydride, and 488 mg of cerium trichloride heptahydrate were dissolved in 8 mL of methanol, and the solution was stirred for 2 hours at 50° C. After completion of the reaction, 1 N hydrochloric acid was added to the reaction liquid, and the mixture was stirred for 30 minutes. The reaction liquid was neutralized with a saturated aqueous solution of sodium hydrogen carbonate, and then was extracted with chloroform. The organic layer was washed with a saturated solution of sodium hydrogen carbonate and saturated brine, dehydrated with anhydrous sodium sulfate, and then concentrated under reduced pressure. The resulting residue was purified by using silica gel chromatography (hexane:ethyl acetate 1:1), and thus 615 mg (85%) of 1-acetyl-4-[(4-tert-butyldiphenylsilyloxymethylphenyl)amino]-2-methyl-1,2,3,4-tetrahydroquinoline was obtained as a yellow oily substance (cis:trans=3:1).

[Step 3] 615 mg of 1-acetyl-4-[(4-tert-butyldiphenylsilyloxymethylphenyl)amino]-2-methyl-1,2,3,4-tetrahydroquinoline was dissolved in 2 mL of tetrahydrofuran, and 2.8 mL of tetrabutylammonium fluoride (1.0M tetrahydrofuran solution) was added to the solution. The mixture was stirred for 3 hours at room temperature. After completion of the reaction, the reaction liquid was extracted with ethyl acetate. The organic layer was washed with a saturated sodium hydrogen carbonate solution and saturated brine, dehydrated over anhydrous sodium sulfate, and then concentrated under reduced pressure. The resulting residue was purified by using silica gel chromatography (developing solvent: ether only), and thus 264 mg (79%) of 1-acetyl-4-[(4-hydroxymethylphenyl)amino]-2-methyl-1,2,3,4-tetrahydroquinoline was obtained as a yellow oily substance (cis:trans=3:1).

$^1$H-NMR (400 MHz, CDCl$_3$) δ: 1.16 (2.25H, d, J=6.4 Hz), 1.19 (0.75H, d, J=6.4 Hz), 1.23-1.28 (1H, m), 2.16 (0.75H, s), 2.19 (2.25H, s), 2.52 (0.25H, ddd, J=5.2, 7.6, 13.4 Hz), 2.65 (0.75H, ddd, J=4.3, 8.7, 12.2 Hz), 3.89-3.91 (1H, m), 4.18-4.25 (0.75H, m), 4.54-4.60 (2.25H, m), 4.91 (1H, brs), 6.62-6.65 (2H, m), 7.14-7.22 (4H, m), 7.26-7.30 (1.75H, m), 7.40 (0.25H, dd, J=1.5, 7.8 Hz).

EXAMPLE 24

Production of cis-4-[(4-methanesulfonylaminophenyl) amino]-2-methyl-1,2,3, 4-tetrahydroquinoline (Compound 39)

Reactions and treatments were carried out in the same manner as in Example 2, and thus 20 mg (53%) of the title compound was obtained as a white solid.

$^1$H-NMR (400 MHz, CDCl$_3$) δ: 1.17 (3H, d, J=6.4 Hz), 1.28-1.37 (1H, m), 2.19 (3H, s), 2.66 (1H, ddd, J=4.1, 8.5, 12.4 Hz), 2.95 (3H, s), 3.91 (1H, d, J=7.6 Hz), 4.18 (1H, dd, J=4.5, 12.5 Hz), 4.92 (1H, brs), 6.02 (1H, s), 6.61 (2H, d, J=8.8 Hz), 7.11 (2H, d, J=8.5 Hz), 7.14-7.31 (4H, m).

EXAMPLE 25

Production of 1-acetyl-4-[(4-chlorophenyl)amino]-2-methyl-6-morpholino-1, 2,3,4-tetrahydroquinoline (Compound 40)•hydrochloride A compound was produced in the same manner as in Example 2, and the compound was converted to the hydrochloride by a known method. The hydrochloride was subjected to recrystallization from chloroform-ether, and thus 19 mg (cis:trans=10:1, 23%) of the title compound was obtained as a brown solid.

$^1$H-NMR (400 MHz, CDCl$_3$) δ: 1.12-1.26 (3.3H, m), 1.56-1.75 (1.1H, m), 2.14 (0.3H, s), 2.16 (3H, s), 2.40-2.50 (0.1H, m), 2.60 (1H, ddd, J=4.2, 8.3, 12.5 Hz), 3.00-3.26 (4.4H, m), 3.72-3.95 (4.4H, m), 4.08-4.17 (1H, m), 4.44-4.52 (0.1H, m), 4.82-4.96 (1.1H, brs), 6.78-6.90 (3.3H, m), 7.01-7.28 (2.2H, m).

EXAMPLE 26

Production of ethyl cis-1-acetyl-4-[(4-chlorophenyl) amino]-2-methyl-1,2,3,4-tetrahydroquinoline-6-carboxylate (Compound 41)

Reactions and treatments were carried out in the same manner as in Example 2, and thus 13 mg (72%) of the title compound was obtained as a colorless oily substance.

$^1$H-NMR (400 MHz, CDCl$_3$) δ: 1.17 (3H, d, J=6.3 Hz), 1.23-1.33 (1H, m), 1.35 (3H, t, J=7.1 Hz), 2.21 (3H, s), 2.68 (1H, ddd, J=4.1, 8.5, 12.4 Hz), 3.86 (1H, d, J=7.8 Hz), 4.15-

4.25 (1H, m), 4.30-4.40 (2H, m), 4.80-4.91 (1H, m), 6.55-6.62 (2H, m), 7.10-7.18 (2H, m), 7.22 (1H, d, J=8.1 Hz), 7.95-8.01 (2H, m).

EXAMPLE 27

Production of 1-acetyl-4-[(4-chlorophenyl)amino]-2-methyl-1,2,3,4-tetrahydroquinoline-6-carboxylic acid (Compound 42)

Compound 41 was hydrolyzed by a known method, and thus 17 mg (61%) of the title compound was obtained as a white solid (cis:trans=10:1).

$^1$H-NMR (400 MHz, CDCl$_3$) δ: 1.19 (3H, d, J=6.3 Hz), 1.23-1.33 (1H, m), 2.23 (3H, s), 2.69 (1H, ddd, J=4.2, 8.5, 12.4 Hz), 4.21 (1H, dd, J=4.2, 12.0 Hz), 4.80-4.92 (1H, m), 6.55-6.62 (2H, m), 7.10-7.28 (3H, m), 7.98-8.07 (2H, m).

EXAMPLE 28

Production of 1-acetyl-4-[(4-chlorophenyl)amino]-2-methyl-1,2,3,4-tetrahydroquinoline-6-carboxamide (Compound 43)

Compound 42 was amidated by a known method, and thus 30 mg (50%) of the title compound was obtained as a white solid (cis:trans=3:1).

$^1$H-NMR (400 MHz, CDCl$_3$) δ: 1.12-1.38 (4H, m), 1.91 (0.25H, m), 2.21 (3H, s), 2.41 (0.25H, m), 2.68 (0.75H, ddd, J=4.1, 8.5, 12.4 Hz), 3.87 (1H, d, J=7.1 Hz), 4.17 (0.75H, m), 4.63 (0.25H, brs), 4.86 (1H, m), 5.63 (1H, brs), 5.97 (1H, brs), 6.54-6.61 (3H, m), 7.10-7.40 (3H, m), 7.66-7.94 (1H, m).

EXAMPLE 29

Production of 1-acetyl-4-[(4-chlorophenyl)amino]-2-methyl-7-morpholino-1,2,3,4-tetrahydroquinoline (Compound 44)

The bromine atom of compound 74 was replaced by a morpholino group by a known method, and thus 31 mg (cis:trans=5:1, 61%) of the title compound was obtained as a yellow solid.

$^1$H-NMR (400 MHz, CDCl$_3$) δ: 1.15-1.20 (3.6H, m), 1.63-1.79 (1.2H, m), 2.18 (3H, s), 2.21 (0.6H, s), 2.38-2.48 (0.2H, m), 2.60 (1H, ddd, J=4.4, 8.0, 12.4 Hz), 3.09-3.23 (4.8H, m), 3.62-3.90 (5.5H, m), 4.08-4.16 (1H, m), 4.46-4.53 (0.2H, m), 4.80-4.96 (1.2H, brs), 6.54-6.57 (2.4H, m), 6.60-6.73 (2.4H, m), 7.05-7.16 (3.6H, m).

EXAMPLE 30

Production of cis-4-[(4-chlorophenyl)amino]-2-methyl-6-methanesulfonylamino-1,2,3,4-tetrahydroquinoline (Compound 45)

Reactions and treatments were carried out in the same manner as in Example 2, and thus 46 mg (56%) of the title compound was obtained as a white solid.

$^1$H-NMR (400 MHz, CDCl$_3$) δ: 1.16 (3H, d, J=6.1 Hz), 1.25-1.33 (1H, m), 2.19 (3H, s), 2.66 (1H, ddd, J=4.2, 8.5, 12.5 Hz), 2.96 (3H, s), 3.82-3.84 (1H, m), 4.13 (1H, dd, J=5.4, 13.7 Hz), 4.89 (1H, brs), 6.33 (1H, s), 6.55 (2H, d, J=8.8 Hz), 7.00 (1H, s), 7.16 (2H, d, J=8.8 Hz), 7.10-7.21 (4H, m).

EXAMPLE 31

Production of ethyl cis-1-acetyl-4-(4-fluorophenoxy)-2-methyl-1,2,3,4-tetrahydroquinoline-6-carboxylate (Compound 53)

Reactions and treatments were carried out in the same manner as in Example 12, and thus 150 mg (90%) of the title compound was obtained as a colorless oily substance.

$^1$H-NMR (400 MHz, CDCl$_1$) δ: 1.20 (3H, d, J=6.3 Hz), 1.37 (3H, t, J=7.0 Hz), 1.50-1.63 (1H, m), 2.21 (3H, s), 2.71 (1H, m), 4.33-4.43 (2H, m), 4.75-4.90 (1H, m), 4.98-5.07 (1H, m), 6.90-7.10 (5H, m), 8.00-8.05 (1H, m), 8.17 (1H, m).

EXAMPLE 32

Production of cis-1-acetyl-4-(4-fluorophenoxy)-2-methyl-1,2,3,4-tetrahydroquinoline-6-carboxamide (Compound 54)

Compound 53 was amidated by a known method, and thus 14 mg (19%) of the title compound was obtained as a white solid.

$^1$H-NMR (400 MHz, CDCl$_3$) δ: 1.20 (3H, d, J=6.3 Hz), 1.50-1.63 (1H, m), 2.21 (3H, s), 2.73 (1H, ddd, J=4.6, 8.0, 12.7 Hz), 4.74-4.88 (1H, m), 5.03 (1H, dd, J=4.7, 10.2 Hz), 5.91 (1H, brs), 6.11 (1H, brs), 6.80-7.08 (4H, m), 7.20-7.40 (1H, m), 7.80-7.86 (1H, m), 7.91 (1H, m).

EXAMPLE 33

Production of 1-acetyl-4-(4-morpholinophenoxy)-2-methyl-1,2,3,4-tetrahydroquinoline (Compound 55)

A morpholine ring was constructed by a known method using compound 68, and thus 27 mg (cis:trans=3:1, 73%) of the title compound was obtained as a pale brown oily substance.

$^1$H-NMR (400 MHz, CDCl$_3$) δ: 1.15-1.80 (4H, m), 1.40-1.64 (1.3H, m), 2.12 (1H, s), 2.18 (3H, s), 2.68-2.82 (1.3H, m), 2.98-3.25 (5.3H, m), 3.75-4.00 (5.3H, m), 4.80-5.18 (2.3H, m), 5.20 (0.3H, dd, 3.68, 3.54 Hz), 6.70-7.55 (10.6H, m).

EXAMPLE 34

Production of cis-1-acetyl-7-fluoro-4-(4-fluorophenoxy)-2-methyl-1,2,3,4-tetrahydroquinoline (Compound 56)

Reactions and treatments were carried out in the same manner as in Example 12, and thus 60 mg (42%) of the title compound was obtained as a white solid.

$^1$H-NMR (400 MHz, CDCl$_3$) δ: 1.19 (3H, d, J=6.3 Hz), 1.50-1.70 (1H, m), 2.22 (3H, s), 2.68 (1H, m), 4.83 (1H, brs), 4.53 (1H, dd, J=4.4, 9.3 Hz), 6.88-7.04 (6H, m), 7.34-7.45 (1H, m).

EXAMPLE 35

Production of cis-1-acetyl-4-(4-hydroxyphenoxy)-2-methyl-1,2,3,4-tetrahydroquinoline (Compound 57)

Compound 64 was treated, and thus 66 mg (86%) of the title compound was obtained as a colorless oily substance.

$^1$H-NMR (400 MHz, CDCl$_3$) δ: 1.18 (3H, d, J=6.4 Hz), 1.40-1.60 (1H, m), 2.18 (3H, s), 2.72 (1H, ddd, J=4.6, 8.3, 12.7 Hz), 4.86 (1H, brs), 4.90-5.00 (2H, m), 6.75-6.82 (2H, m), 6.85-6.90 (2H, m), 7.10-7.35 (3H, m), 7.49 (1H, d, J=7.3 Hz).

EXAMPLE 36

Production of cis-1-acetyl-7-fluoro-4-[(3-fluorophenyl)amino]-2-methyl-1,2,3,4-tetrahydroquinoline (Compound 58)

Reactions and treatments were carried out in the same manner as in Example 1, and thus 80 mg (87%) of the title compound was obtained as a white solid.

$^1$H-NMR (400 MHz, CDCl$_3$) δ: 1.17 (3H, d, J=6.3 Hz), 1.23-1.35 (1H, m), 2.22 (3H, s), 2.65 (1H, ddd, J=4.7, 8.7, 12.7 Hz), 3.93 (1H, brs), 4.06-4.18 (1H, m), 4.80-4.96 (1H, m), 6.30 (1H, dt, J=2.2, 11.2 Hz), 6.40 (1H, dd, J=2.2, 8.1 Hz), 6.44 (1H, dt, J=2.4, 8.4 Hz), 6.85-6.95 (2H, m), 7.09-7.16 (1H, m), 7.20-7.27 (1H, m).

EXAMPLE 37

Production of 1-acetyl-2-ethyl-4-phenylamino-1,2,3,4-tetrahydroquinoline (Compound 59)

Reactions and treatments were carried out in the same manner as in Example 2, and thus 36 mg (79%) of the title compound was obtained as a white solid (cis:trans=5:1).

$^1$H-NMR (400 MHz, CDCl$_3$) δ: 0.83-0.92 (3H, m), 1.25-1.65 (3H, m), 1.82-1.96 (0.15H, brs), 2.14-2.19 (3H, s), 2.37-2.47 (0.15H, m), 2.65 (0.85H, ddd, J=4.6, 8.8, 12.2 Hz), 3.84 (1H, brs), 4.22 (0.85H, d, J=10.0 Hz), 4.62 (0.15H, t, J=5.1 Hz), 4.85 (1H, brs), 6.62-6.78 (3H, m), 7.12-7.44 (6H, m).

EXAMPLE 38

Production of cis-1-acetyl-3,3-dimethyl-4-phenylamino-1,2,3,4-tetrahydroquinoline (Compound 60)

Reactions and treatments were carried out in the same manner as in Example 2, and thus 31 mg (70%) of the title compound was obtained as a white solid.

$^1$H-NMR (400 MHz, CDCl$_3$) δ: 0.91 (3H, s), 1.12 (3H, s), 2.32 (3H, s), 3.63 (1H, d, J=13.6 Hz), 3.71 (1H, brs), 3.77 (1H, d, J=8.8 Hz), 4.30 (1H, d, J=8.8 Hz), 6.62-6.76 (3H, m), 7.05-7.35 (6H, m).

EXAMPLE 39

Production of 1-acetyl-4-phenylamino-8-methoxy-2-methyl-1,2,3,4-tetrahydroquinoline (Compound 61)

Reactions and treatments were carried out in the same manner as in Example 2, and thus 145 mg (85%) of the title compound was obtained as a yellow oily substance (cis:trans=3:1).

$^1$H-NMR (400 MHz, CDCl$_3$) δ: 1.05-1.25 (4H, m), 1.93 (1H, s), 2.02 (2H, s), 2.60-2.72 (1H, m), 3.78-3.88 (4H, m), 4.17 (0.75H, m), 4.52 (0.25H, m), 4.94-5.06 (1H, m), 6.58-6.78 (2H, m), 6.86-7.01 (2H, m), 7.10-7.24 (4H, m).

EXAMPLE 40

Production of cis-1-acetyl-4-(3,5-difluorophenoxy)-2-methyl-1,2,3,4-tetrahydroquinoline (Compound 62)

Reactions and treatments were carried out in the same manner as in Example 12, and thus 58 mg (61%) of the title compound was obtained as a white solid.

$^1$H-NMR (400 MHz, CDCl$_3$) δ: 1.19 (3H, d, J=6.6 Hz), 1.56-1.60 (1H, m), 2.20 (3H, s), 2.74 (1H, ddd, J=4.7, 8.2, 12.7 Hz), 4.90 (1H, brs), 5.02 (1H, dd, J=5.0, 10.6 Hz), 6.67-6.70 (1H, m), 6.79-6.84 (1H, m), 7.10 (1H, dd, J=9.2, 18.9 Hz), 7.17-7.21 (1H, m), 7.23-7.29 (2H, m), 7.30-7.35 (1H, m), 7.38 (1H, d, J=7.3 Hz).

EXAMPLE 41

Production of 1-acetyl-8-bromo-4-phenylamino-2-methyl-1,2,3,4-tetrahydroquinoline (Compound 63)

Reactions and treatments were carried out in the same manner as in Example 2, and thus 215 mg (70%) of the title compound was obtained as a pale brown amorphous substance (cis:trans=3:1).

$^1$H-NMR (400 MHz, CDCl$_3$) δ: 1.13-1.22 (3.75H, m), 1.48-1.55 (0.25H, m), 1.93 (1H, s), 2.10 (2H, s), 2.62-2.74 (1H, m), 3.85 (1H, m), 4.10 (0.75H, m), 4.49 (0.25H, brs), 5.08-5.22 (1H, m), 6.58-6.80 (3H, m), 7.10-7.30 (4H, m), 7.38-7.42 (0.25H, m), 7.52-7.60 (0.75H, m).

EXAMPLE 42

Production of cis-1-acetyl-4-(4-benzyloxyphenoxy)-2-methyl-1,2,3,4-tetrahydroquinoline (Compound 64)

Reactions and treatments were carried out in the same manner as in Example 12, and thus 200 mg (71%) of the title compound was obtained as a colorless oily substance.

$^1$H-NMR (400 MHz, CDCl$_3$) δ: 1.17 (3H, d, J=6.6 Hz), 1.40-1.70 (1H, m), 2.18 (3H, s), 2.72 (1H, m), 4.85 (1H, brs), 4.92-4.98 (1H, m), 5.03 (2H, s), 6.29 (4H, s), 7.10-7.50 (9H, m).

EXAMPLE 43

Production of cis-6-fluoro-4-[(4-fluorophenyl)amino]-2-methyl-1-N-methylcarbamoyl-1,2,3,4-tetrahydroquinoline (Compound 65)

41 mg of cis-6-fluoro-4-[(4-fluorophenyl)amino]-2-methyl-1,2,3,4-tetrahydroquinoline was dissolved in 1.5 mL of dichloromethane, and 29 mg of triphosgene was added to the solution under ice cooling. The mixture was stirred for 30 minutes under ice cooling. After completion of the reaction, the reaction mixture was concentrated under reduced pressure, and the resulting residue was dissolved in 1.5 mL of THF. 0.74 mL of THF solution of methylamine was added to the solution under ice cooling, and the mixture was stirred for one hour. After completion of the reaction, the mixture was concentrated under reduced pressure, and the resulting residue was purified by using silica gel chromatography (diethyl ether:hexane=2:1). Thus, 15 mg (30%) of the title compound was obtained as a white solid.

$^1$H-NMR (400 MHz, CDCl$_3$) δ: 1.17 (3H, d, 6.3 Hz), 1.15-1.40 (1H, m), 1.56-1.77 (1H, brs), 2.16 (1H, ddd, 4.4, 8.4, 12.4 Hz), 2.83 (3H, d, 4.6 Hz), 3.62-3.84 (1H, brs), 4.02-4.17 (1H, m), 4.70-4.90 (2H, m), 6.49-6.63 (2H, m), 6.75-7.11 (3H, m), 7.24-7.34 (2H, m).

EXAMPLE 44

Production of cis-1-cyclopentanecarbonyl-6-fluoro-2-methyl-4-[(4-fluorophenyl)amino]-1,2,3,4-tetrahydroquinoline (Compound 66)

A reaction was carried out in the same manner as in Example 9, and the reaction product was subjected to recrystallization from chloroform-hexane. Thus, 20 mg (24%) of the title compound was obtained as a white powder-like crystal.

$^1$H-NMR (400 MHz, CDCl$_3$) δ: 1.10 (3H, d, J=6.3 Hz), 1.14-2.10 (9H, m), 2.66 (1H, ddd, 4.4, 9.3, 14.4 Hz), 3.00-3.10 (1H, m), 3.98-4.10 (1H, m), 4.84-5.02 (1H, brs), 6.57 (2H, m), 6.80-7.19 (5H, m).

EXAMPLE 45

Production of 1-acetyl-2-methyl-4-(4-nitrophenoxy)-1,2,3,4-tetrahydroquinoline (Compound 67)

Reactions and treatments were carried out in the same manner as in Example 12, and thus 90 mg (cis:trans=2:1, 40%) of the title compound was obtained as a yellow solid.

$^1$H-NMR (400 MHz, CDCl$_3$) δ: 1.18-1.21 (4.5H, m), 1.50-1.75 (1.5H, m), 2.07 (1.5H, s), 2.22 (3H, s), 2.74-2.90 (1.5H, m), 4.86-5.60 (1.5H, m), 5.19 (1H, dd, 4.6, 10.6 Hz), 5.44 (0.5H, dd, 3.2, 3.4 Hz), 6.98 (1H, d, 4.9 Hz), 7.06 (2H, d, 7.1 Hz), 7.18-7.41 (6H, m), 8.15 (1H, d, 4.9 Hz), 8.24 (2H, d, 7.1 Hz).

EXAMPLE 46

Production of 1-acetyl-4-(4-aminophenoxy)-2-methyl-1,2,3,4-tetrahydroquinoline (Compound 68)

Compound 67 was reduced by a known method, and thus 121 mg (cis:trans=2:1, 100%) of the title compound was obtained as a pale brown solid.

$^1$H-NMR (400 MHz, CDCl$_3$) δ: 1.09-1.25 (4.5H, m), 1.41-1.65 (1.5H, m), 2.05 (1.5H, s), 2.13 (3H, s), 2.66-2.80 (1.5H, m), 3.00-3.50 (3H, brs), 4.75-5.00 (2.5H, m), 5.13 (0.5H, dd, 3.4, 2.0 Hz), 6.51-6.88 (6H, m), 7.11-7.41 (6H, m).

EXAMPLE 47

Production of 1-acetyl-4-[(4-methoxymethylphenyl)amino]-2-methyl-1,2,3,4-tetrahydroquinoline (Compound 69)

[Step 1] 16 mg of 1-acetyl-4-[(4-hydroxymethylphenyl)amino]-2-methyl-1,2,3,4-tetrahydroquinoline was dissolved in THF, and the solution was cooled to 0° C. 44 mg of sodium hydride and 121 mg of methane iodide were added to the solution, and the resulting mixture was stirred for two days at 40° C. After completion of the reaction, the reaction mixture was concentrated under reduced pressure, and the resulting residue was purified by using silica gel chromatography (developing solvent: ether only). Thus, 5 mg (29%) of the title compound was obtained as a yellow oily substance (cis:trans—4:1).

$^1$H-NMR (400 MHz, CDCl$_3$) δ: 1.16 (2.4H, d, J=6.4 Hz), 1.19 (0.6H, d, J=6.6 Hz), 1.22-1.31 (1H, m), 2.16 (0.6H, s), 2.19 (2.4H, s), 2.52 (0.2H, ddd, J=5.2, 7.2, 13.6 Hz), 2.66 (0.8H, ddd, J=4.2, 8.6, 12.3 Hz), 3.34 (0.6H, s), 3.36 (2.4H, s), 3.88 (1H, brs), 4.18-4.23 (1H, m), 4.31 (0.4H, s), 4.34 (1.6H, s), 4.90 (1H, brs), 6.61-6.64 (2H, m), 7.13-7.20 (4H, m), 7.26-7.30 (1.8H, m), 7.39 (0.2H, d, J=7.6 Hz).

EXAMPLE 48

Production of 1-acetyl-4-[(4-ethoxycarbonylmethylphenyl)amino]-2-methyl-1, 2,3,4-tetrahydroquinoline (Compound 70)

Reactions and treatments were carried out in the same manner as in Example 2, and thus 106 mg (96%) of the title compound was obtained as a yellow oily substance (cis:trans=3:1).

$^1$H-NMR (400 MHz, CDCl$_3$) δ: 1.16 (2.25H, d, J=6.4 Hz), 1.19 (0.75H, d, J=6.4 Hz), 1.23-1.28 (4H, m), 2.17 (0.75H, s), 2.18 (2.25H, s), 2.51 (0.25H, ddd, J=5.6, 7.4, 13.4 Hz), 2.65 (0.75H, ddd, J=4.0, 8.4, 12.1 Hz), 3.48 (0.5H, s), 3.51 (1.5H, s), 3.79-3.81 (1H, m), 4.10-4.26 (3.75H, m), 4.54-4.60 (0.25H, m), 4.91 (1H, brs), 6.58-6.61 (2H, m), 7.05-7.21 (4H, m), 7.28-7.32 (1.75H, m), 7.38 (0.25H, d, J=7.1 Hz).

EXAMPLE 49

Production of 1-acetyl-4-[(4-carboxymethylphenyl)amino]-2-methyl-1,2,3,4-tetrahydroquinoline (Compound 71)

Compound 70 was treated, and thus 70 mg (84%) of the title compound was obtained as a yellow oily substance (cis:trans=4:1).

$^1$H-NMR (400 MHz, CDCl$_3$) δ: 1.16 (2.4H, d, J=6.3 Hz), 1.19 (0.6H, d, J=6.4 Hz), 1.24-1.28 (1H, m), 2.16 (0.6H, s), 2.19 (2.4H, s), 2.51 (0.2H, ddd, J=5.1, 7.3, 13.6 Hz), 2.64 (0.8H, ddd, J=3.2, 9.3, 11.4 Hz), 3.52 (0.4H, s), 3.57 (1.6H, s), 3.79-3.81 (1H, m), 4.20 (0.8H, dd, J=4.2, 12.0 Hz), 4.57 (0.2H, dd, J=4.8, 4.8 Hz), 4.91 (1H, brs), 6.60-6.63 (2H, m), 7.07-7.20 (4H, m), 7.27-7.32 (1.8H, m), 7.38 (0.2H, d, J=7.3 Hz).

EXAMPLE 50

Production of 1-acetyl-2-methyl-4-[(2-morpholinophenyl)amino]-1,2,3,4-tetrahydroquinoline (Compound 72)

Reactions and treatments were carried out in the same manner as in Example 2, and thus 42 mg (23%) of the title compound was obtained as a yellow oily substance (cis:trans=6:1).

$^1$H-NMR (400 MHz, CDCl$_3$) δ: 1.18 (2.6H, d, J=6.4 Hz), 1.22 (0.4H, d, J=6.6 Hz), 1.29-1.38 (1H, m), 2.14 (0.4H, s), 2.19 (2.6H, s), 2.61-2.79 (1H, m), 2.86-2.90 (2H, m), 3.01-3.11 (2H, m), 3.75-3.86 (5H, m), 4.13-4.19 (0.86H, m), 4.55 (0.14H, brs), 4.86-4.99 (1H, m), 6.55 (1H, dd, J=1.2, 8.1 Hz), 6.68-6.81 (1H, m), 6.99-7.03 (1H, m), 7.09 (1H, dd, J=1.2, 7.8 Hz), 7.14-7.32 (4H, m).

EXAMPLE 51

Production of 1-acetyl-4-[(4-fluoro-3-morpholinophenyl)amino]-2-methyl-1,2,3,4-tetrahydroquinoline (Compound 73)

Reactions and treatments were carried out in the same manner as in Example 2, and thus 80 mg (cis:trans=5:1, 43%) of the title compound was obtained as a yellow solid.

$^1$H-NMR (400 MHz, CDCl$_3$) δ: 1.15-1.18 (3.6H, m), 1.39-1.66 (1.2H, m), 2.16 (0.6H, s), 2.18 (3H, s), 2.66-2.64 (1.2H, m), 2.90-3.30 (4.8H, m), 3.60-3.72 (1H, brs), 3.73-3.94 (4.8H, m), 4.10-4.20 (1.2H, brs), 4.46-4.54 (0.2H, brs), 4.65-4.96 (1.2H, brs), 6.16-6.32 (2.4H, m), 6.72-6.89 (1.2H, m), 7.23-7.42 (4.8H, m).

EXAMPLE 52

Production of cis-1-acetyl-2-methyl-4-[(1,1'-biphenyl-4-yl)amino]-1,2,3,4-tetrahydroquinoline (Compound 25)

Reactions and treatments were carried out in the same manner as in Example 2, and thus 32 mg (7%) of the title compound was obtained.

$^1$H-NMR (400 MHz, CDCl$_3$) δ: 1.12-1.18 (2s, 3H), 1.20-1.85 (m, 1H), 2.12-2.20 (2s, 3H), 2.55-2.86 (m, 1H), 3.90 (s, 1H), 4.25-4.65 (m, 1H), 4.85-4.95 (m, 1H), 6.55-7.65 (m, 13H).

EXAMPLE 53

Production of 1-acetyl-6-bromo-4-[(4-chlorophenyl) amino]-2-methyl-1,2,3,4-tetrahydroquinoline (Compound 74)

Reactions and treatments were carried out in the same manner as in Example 2, and thus 1.1 g (66%) of the title compound was obtained as a colorless oily substance (cis:trans=3:1).

$^1$H-NMR (400 MHz, CDCl$_3$) δ: 1.15 (2.25H, d, J=6.4 Hz), 1.20 (0.75H, d, J=6.6 Hz), 1.22-1.34 (0.75H, m), 1.75-1.90 (0.25H, m), 2.16 (0.75H, s), 2.18 (2.25H, s), 2.38-2.47 (0.25H, m), 2.64 (0.75H, ddd, J=4.3, 8.6, 12.6 Hz), 3.76-3.86 (1H, m), 4.07-4.16 (0.75H, m), 4.49-4.55 (0.25H, m), 4.80-4.95 (1H, m), 6.52-6.58 (2H, m), 7.00-7.18 (3H, m), 7.37-7.45 (1.75H, m), 7.54 (0.25H, d, J=2.2 Hz).

EXAMPLE 54

Production of cis-1-acetyl-2-methyl-4-[(4-piperazinylphenyl)amino]-1,2,3, 4-tetrahydroquinoline (Compound 76)

Reactions and treatments were carried out in the same manner as in Example 2, and thus 42 mg (8%) of the title compound was obtained as a colorless oily substance.

$^1$H-NMR (400 MHz, CDCl$_3$) δ: 1.16 (3H, d, J=6.4 Hz), 1.20-1.26 (1H, m), 2.18 (3H, s), 2.64 (1H, ddd, J=4.2, 8.7, 12.5 Hz), 2.90-3.25 (9H, m), 3.50-3.70 (1H, m), 4.10-4.20 (1H, m), 4.80-5.00 (1H, m), 6.61 (2H, d, J=8.8 Hz), 6.86 (2H, d, J=9.0 Hz), 7.04-7.40 (4H, m).

EXAMPLE 55

Production of cis-1-acetyl-4-{[4-(4-acetylpiperazinyl)phenyl]amino}-2-methyl-1,2,3,4-tetrahydroquinoline (Compound 77)

Compound 76 was acetylated by a known method, and thus 7 mg (70%) of the title compound was obtained as a colorless oily substance.

$^1$H-NMR (400 MHz, CDCl$_3$) δ: 1.15 (3H, d, J=6.4 Hz), 1.18-1.34 (1H, m), 2.14 (3H, s), 2.18 (3H, s), 2.64 (1H, ddd, J=3.9, 8.5, 12.3 Hz), 2.90-3.13 (4H, m), 3.50-3.70 (5H, m), 4.10-4.22 (1H, m), 4.83-4.95 (1H, m), 6.62 (2H, d, J=8.5 Hz), 6.80-6.95 (2H, m), 7.10-7.36 (4H, m).

EXAMPLE 56

Production of cis-1-acetyl-4-{[4-(4-methanesulfonylpiperazinyl)phenyl]amino}-2-methyl-1,2,3,4-tetrahydroquinoline (Compound 78)

Compound 76 was mesylated by a known method, and thus 4 mg (33%) of the title compound was obtained as a colorless oily substance.

$^1$H-NMR (400 MHz, CDCl$_3$) δ: 1.15 (3H, d, J=6.4 Hz), 1.18-1.30 (1H, m), 2.18 (3H, s), 2.64 (1H, ddd, J=4.1, 8.5, 12.4 Hz), 2.82 (3H, s), 3.00-3.25 (4H, m), 3.25-3.50 (4H, m), 3.50-3.75 (1H, m), 4.20 (1H, dd, J=4.1, 12.0 Hz), 4.80-5.00 (1H, m), 6.62 (2H, d, J=8.8 Hz), 6.88 (2H, d, J=8.0 Hz), 7.10-7.35 (4H, m).

EXAMPLE 57

Production of cis-1-acetyl-6-[(4-acetyl)piperazino]-4-[(4-chlorophenyl)amino]-2-methyl-1,2,3,4-tetrahydroquinoline (Compound 79)

The bromine atom of compound 74 was replaced by a piperazino group by a known method, and then compound 74 was acetylated. Thus, 8 mg (31%) of the title compound was obtained as a light yellow oily substance.

$^1$H-NMR (400 MHz, CDCl$_3$) δ: 1.14 (3H, d, J=6.4 Hz), 1.20-1.30 (1H, m), 2.12 (3H, s), 2.16 (3H, s), 2.61 (1H, ddd, J=4.3, 8.8, 12.6 Hz), 3.00-3.16 (4H, m), 3.53-3.60 (2H, m), 3.66-3.82 (3H, m), 4.06-4.15 (1H, m), 4.80-5.00 (1H, m), 6.54-6.60 (2H, m), 6.77-6.85 (2H, m), 7.00-7.10 (1H, m), 7.12-7.17 (2H, m).

EXAMPLE 58

Production of 1-acetyl-6-[(4-methanesulfonyl)piperazino]-4-[(4-chlorophenyl)amino]-2-methyl-1,2,3,4-tetrahydroquinoline (Compound 80)

Reactions and treatments were carried out in the same manner as in Example 57, and thus 12 mg (45%) of the title compound was obtained as a light yellow oily substance (cis:trans=3:1).

$^1$H-NMR (400 MHz, CDCl$_3$) δ: 1.14 (2.25H, d, J=6.4 Hz), 1.17 (0.75H, d, J=6.6 Hz), 1.20-1.30 (0.75H, m), 1.67-1.83 (0.25H, m), 2.15 (0.75H, s), 2.16 (2.25H, s), 2.38-2.52 (0.25H, m), 2.62 (0.75H, ddd, J=4.3, 8.8, 12.6 Hz), 2.78-2.85 (3H, m), 3.14-3.42 (8H, m), 3.60-3.90 (1H, m), 4.05-4.15 (0.75H, m), 4.46-4.51 (0.25H, m), 4.80-5.00 (1H, m), 6.53-6.66 (2H, m), 6.75-7.00 (2H, m), 7.00-7.25 (3H, m).

EXAMPLE 59

Production of 1-acetyl-4-[(4-chlorophenyl)amino]-6-[(4-isopropyl)piperazino]-2-methyl-1,2,3,4-tetrahydroquinoline (Compound 81)

Reactions and treatments were carried out in the same manner as in Example 57, and thus 15 mg (51%) of the title compound was obtained as a light yellow oily substance (cis:trans=7:3).

$^1$H-NMR (400 MHz, CDCl$_3$) δ: 1.12-1.30 (10H, m), 2.13 (0.9H, s), 2.15 (2.1H, s), 2.40-2.80 (6H, m), 3.06-3.28 (4H, m), 3.70-3.80 (1H, m), 3.14-3.42 (8H, m), 3.60-3.90 (1H, m), 4.06-4.18 (0.7H, m), 4.44-4.50 (0.3H, m), 4.80-5.00 (1H, m), 6.50-6.70 (2H, m), 6.70-6.95 (2H, m), 6.95-7.20 (3H, m).

EXAMPLE 60

Production of 1-acetyl-4-[(4-chlorophenyl)amino]-6-[(2-hydroxy)ethylamino]-2-methyl-1,2,3,4-tetrahydroquinoline (Compound 82)

Reactions and treatments were carried out in the same manner as in Example 57, and thus 5 mg (56%) of the title compound was obtained as a colorless oily substance (cis:trans=3:1).

$^1$H-NMR (400 MHz, CDCl$_3$) δ: 1.12 (2.25H, d, J=6.4 Hz), 1.15 (0.75H, d, J=6.6 Hz), 1.17-1.24 (1H, m), 2.11 (0.75H, s), 2.14 (2.25H, s), 2.42-2.53 (0.25H, m), 2.58 (0.75H, ddd, J=4.2, 8.7, 12.5 Hz), 3.23 (1.5H, dd, J=1.7, 5.6 Hz), 3.29 (0.5H, t, J=5.3 Hz), 3.72-3.88 (3H, m), 4.05-4.12 (0.75H, m), 4.40-4.45 (0.25H, m), 4.80-4.95 (1H, m), 6.50-6.64 (4H, m), 6.90-6.96 (1H, m), 7.07-7.15 (2H, m).

EXAMPLE 61

Production of 1-acetyl-4-[(4-chlorophenyl)amino]-6-[(cis-3,5-dimethyl)morpholino]-2-methyl-1,2,3,4-tetrahydroquinoline (Compound 83)

The bromine atom of compound 74 was replaced by an amino group by a known method, and 75 mg (69%) of the title compound was obtained as a colorless oily substance (cis:trans=8:3).

¹H-NMR (900 MHz, CDCl₃) δ: 1.10-1.30 (10H, m), 2.14 (0.82H, s), 2.15 (2.18H, s), 2.30-2.50 (2.27H, m), 2.61 (0.73H, ddd, J=4.2, 8.6, 12.5 Hz), 3.27-3.45 (2H, m), 3.70-3.84 (3H, m), 4.10-4.18 (0.73H, m), 9.45-4.52 (0.27H, m), 4.84-4.95 (1H, m), 6.52-6.62 (2H, m), 6.74-6.90 (2H, m), 6.98-7.18 (3H, m).

EXAMPLE 62

Production of 1-acetyl-4-[(4-chlorophenyl)amino]-6-[(4-isopropylcarbonyl)piperazino]-2-methyl-1,2,3,4-tetrahydroquinoline (Compound 84)

Reactions and treatments were carried out in the same manner as in Example 57, and thus 45 mg (42%) of the title compound was obtained as a yellow amorphous substance (cis:trans=8:3).

¹H-NMR (400 MHz, CDCl₃) δ: 1.10-1.18 (9H, m), 1.18-1.37 (0.73H, m), 1.64-1.83 (0.27H, m), 2.14 (1.13H, s), 2.16 (1.87H, s), 2.40-2.50 (0.27H, m), 2.56-2.66 (0.73H, m), 2.74-2.88 (1H, m), 3.00-3.24 (4H, m), 3.58-3.86 (5H, m), 4.05-4.22 (0.73H, m), 4.42-4.61 (0.27H, m), 4.78-5.97 (1H, m), 6.50-6.68 (2H, m), 6.68-6.88 (2H, m), 6.88-7.27 (3H, m).

EXAMPLE 63

Production of 1-acetyl-4-[(4-chlorophenyl)amino]-6-[(4-cyclohexylcarbonyl)piperazino]-2-methyl-1,2,3,4-tetrahydroquinoline (Compound 85)

Reactions and treatments were carried out in the same manner as in Example 57, and thus 57 mg (50%) of the title compound was obtained as a yellow amorphous substance (cis:trans=7:3).

¹H-NMR (400 MHz, CDCl₃) δ: 1.10-1.20 (3H, m), 1.20-1.85 (10.7H, m), 1.90-2.00 (0.3H, m), 2.14 (0.9H, s), 2.16 (2.1H, s), 2.30-2.40 (0.3H, m), 2.40-2.55 (1.3H, m), 2.55-2.66 (0.7H, m), 3.00-3.20 (4H, m), 3.55-3.80 (5H, m), 4.05-4.20 (0.7H, m), 4.46-4.58 (0.3H, m), 4.75-5.00 (1H, m), 6.57 (1.4H, d, J=8.5 Hz), 6.65 (0.6H, d, J=8.3 Hz), 6.70-6.95 (2H, m), 6.95-7.20 (3H, m).

EXAMPLE 64

Production of 1-acetyl-6-[(4-benzoyl)piperazino]-2-methyl-4-[(4-chlorophenyl)amino]-1,2,3,4-tetrahydroquinoline (Compound 86)

Reactions and treatments were carried out in the same manner as in Example 57, and thus 68 mg (55%) of the title compound was obtained as a yellow amorphous substance (cis:trans=3:1).

¹H-NMR (400 MHz, CDCl₃) δ: 1.10-1.30 (3.75H, m), 1.81-1.97 (0.25H, m), 2.14 (0.75H, s), 2.16 (2.25H, s), 2.41-2.50 (0.25H, m), 2.56-2.66 (0.75H, m), 2.90-3.40 (4H, m), 3.40-4.00 (4H, m), 4.05-4.20 (0.75H, m), 4.44-4.58 (0.25H, m), 4.75-5.00 (1H, m), 6.55-6.67 (2H, m), 6.70-6.95 (2H, m), 7.00-7.25 (3H, m), 7.38-7.45 (5H, m).

EXAMPLE 65

Production of 1-acetyl-4-[(4-chlorophenyl)amino]-6-[4-(N,N-diethylaminocarbonyl)piperazino]-2-methyl-1,2,3,4-tetrahydroquinoline (Compound 87)

Reactions and treatments were carried out in the same manner as in Example 57, and thus 56 mg (50%) of the title compound was obtained as a yellow amorphous substance (cis:trans=3:1).

¹H-NMR (400 MHz, CDCl₃) δ: 1.10-1.18 (10H, m), 2.14 (0.75H, s), 2.15 (2.25H, s), 2.40-2.50 (0.25H, m), 2.56-2.66 (0.75H, m), 3.05-3.40 (12H, m), 3.64-3.90 (1H, m), 4.06-4.22 (0.75H, m), 4.44-4.58 (0.25H, m), 4.75-5.00 (1H, m), 6.54-6.68 (2H, m), 6.68-6.98 (2H, m), 7.00-7.25 (3H, m).

EXAMPLE 66

Production of 1-acetyl-4-[(4-chlorophenyl)amino]-6-[4-(isopropylaminocarbonyl)piperazino]-2-methyl-1,2,3,4-tetrahydroquinoline (Compound 88)

Reactions and treatments were carried out in the same manner as in Example 57, and thus 50 mg (46%) of the title compound was obtained as a yellow amorphous substance (cis:trans=7:3).

¹H-NMR (400 MHz, CDCl₃) δ: 1.10-1.30 (9.7H, m), 1.61-1.85 (0.3H, m), 2.14 (0.9H, s), 2.16 (2.1H, s), 2.40-2.50 (0.3H, m), 2.56-2.66 (0.75H, m), 3.00-3.20 (4H, m), 3.40-3.55 (4H, m), 3.65-3.90 (1H, m), 3.94-4.04 (1H, m), 4.05-4.15 (0.75H, m), 4.15-4.30 (1H, m), 4.45-4.58 (0.25H, m), 4.80-5.00 (1H, m), 6.54-6.67 (2H, m), 6.70-6.95 (2H, m), 7.00-7.25 (3H, m).

EXAMPLE 67

Production of 1-acetyl-4-[(4-carboxymethylphenyl) amino]-6-morpholino-2-methyl-1,2,3,4-tetrahydroquinoline (Compound 89)

Reactions and treatments were carried out in the same manner as in Example 57, and thus 27 mg of the title compound was obtained as a yellow amorphous substance (cis:trans=3:1).

¹H-NMR (400 MHz, CDCl₃) δ: 1.10-1.30 (3.75H, m), 1.64-1.81 (0.25H, m), 2.15 (3H, s), 2.40-2.45 (0.25H, m), 2.60 (0.75H, ddd, J=4.4, 8.8, 12.7 Hz), 3.00-3.20 (4H, m), 3.52 (0.75H, s), 3.55 (2.25H, s), 3.81 (2.25H, t, 4.8 Hz), 3.85 (0.75H, t, 4.8 Hz), 4.10-4.20 (0.75H, m), 4.46-4.54 (0.25H, m), 4.80-5.00 (1H, m), 6.55-6.65 (2H, m), 6.75-6.85 (1H, m), 6.85-6.95 (1H, m), 6.95-7.15 (3H, m).

EXAMPLE 68

Production of 1-acetyl-4-[(4-carbamoylmethylphenyl) amino]-2-methyl-6-morpholino-1,2,3,4-tetrahydroquinoline (Compound 90)

Compound 89 was amidated by a known method, and thus 10 mg (56%) of the title compound was obtained as a light brown solid (cis:trans=3:1).

¹H-NMR (400 MHz, CDCl₃) δ: 1.10-1.30 (3.75H, m), 1.64-1.81 (0.25H, m), 2.15 (0.75H, s), 2.16 (2.25H, s), 2.45-2.55 (0.25H, m), 2.62 (0.75H, ddd, J=4.2, 8.5, 12.4 Hz), 3.05-3.20 (4H, m), 3.46 (0.75H, s), 3.49 (2.25H, s), 3.75-3.92 (5H, m), 4.12-4.22 (0.75H, m), 4.50-4.57 (0.25H, m), 4.78-5.00 (1H, m), 5.47 (2H, s), 6.65 (2H, d, J=8.3 Hz), 6.80-6.89 (1H, m), 6.89-6.97 (1H, m), 7.02-7.14 (3H, m).

EXAMPLE 69

Production of cis-1-acetyl-6-(4-acetylpiperazinyl)-4-[(4-carboxymethylphenyl)amino]-2-methyl-1,2,3,4-tetrahydroquinoline (Compound 91)

Reactions and treatments were carried out in the same manner as in Example 57, and thus 37 mg of the title compound was obtained as a yellow amorphous substance.

¹H-NMR (400 MHz, CDCl₃) δ: 1.13 (3H, d, J=6.4 Hz), 1.16-1.27 (1H, m), 2.11 (3H, s), 2.16 (3H, s), 2.63 (1H, ddd, J=4.4, 8.7, 12.6 Hz), 2.88-2.97 (1H, m), 3.00-3.16 (3H, m), 3.44-3.72 (6H, m), 3.72 (1H, dd, J=4.1, 12.0 Hz), 4.82-4.98

(1H, m), 6.56-6.64 (2H, m), 6.74-6.82 (2H, m), 6.98-7.06 (1H, m), 7.13 (2H, d, J=8.5 Hz).

EXAMPLE 70

Production of 1-acetyl-2-methyl-4-[(4-morpholinophenyl)amino]-1,2,3,4-tetrahydroquinoline-6-carboxamide (Compound 92)

Reactions and treatments were carried out in the same manner as in Example 28, and thus 22 mg (44%) of the title compound was obtained as a light yellow amorphous substance (cis:trans=4:1).

$^1$H-NMR (400 MHz, CDCl$_3$) δ: 1.10-1.32 (3.8H, m), 1.82-1.22 (0.2H, m), 2.15 (2.4H, s), 2.21 (0.6H, s), 2.34-2.47 (0.2H, m), 2.60-2.74 (0.8H, m), 2.83-3.20 (4H, m), 3.41-3.80 (1H, m), 3.80-3.90 (4H, m), 4.00-4.27 (0.8H, m), 4.55-4.65 (0.2H, m), 4.74-4.92 (1H, m), 5.67 (1H, brs), 6.02 (1H, brs), 6.63 (2H, brs), 6.82 (2H, brs), 7.23-7.52 (1H, m), 7.68-7.92 (2H, m).

EXAMPLE 71

Production of 1-acetyl-4-[(4-chlorophenyl)amino]-6-[(1-morpholino)carbonyl]2-methyl-1,2,3,4-tetrahydroquinoline (Compound 93)·hydrochloride Compound 42 was amidated by a known method and then was converted to the hydrochloride. Thus, 50 mg (46%) of the title compound was obtained as a light brown powder (cis:trans-3:1).

$^1$H-NMR (400 MHz, CDCl$_3$) δ: 1.07-1.20 (3H, m), 1.27-1.44 (0.75H, m), 1.78-1.92 (0.25H, m), 2.22 (2.25H, s), 2.31 (0.73H, s), 2.47-2.78 (1H, m), 3.10-3.78 (9H, m), 4.10-4.34 (0.75H, m), 4.64-4.71 (0.25H, m), 4.78-4.9.5 (1H, m), 6.65 (1H, brs), 7.00-7.31 (4H, m), 7.31-8.00 (3H, m).

EXAMPLE 72

Production of cis-1-acetyl-6-[(4-acetyl)piperazino]-2-methyl-4-[(4-morpholinophenyl)amino]-1,2,3,4-tetrahydroquinoline (Compound 94)·trihydrochloride Reactions and treatments were carried out in the same manner as in Example 57, and thus 25 mg of the title compound was obtained as a yellow amorphous substance.

$^1$H-NMR (400 MHz, CDCl$_3$) δ: 1.10-1.34 (4H, m), 2.00-2.27 (6H, m), 2.61 (1H, ddd, J=4.1, 8.5, 12.4 Hz), 2.96-3.20 (8H, m), 3.44-3.92 (9H, m), 4.02-4.18 (1H, m), 4.80-4.96 (1H, m), 6.64 (2H, d, J=8.8 Hz), 6.76-6.90 (3H, m), 6.90-7.10 (2H, m).

EXAMPLE 73

Production of 1-acetyl-6-amino-4-[(4-chlorophenyl)amino]-2-methyl-1,2,3,4-tetrahydroquinoline (Compound 95)

The bromine atom of compound 74 was replaced by an amino group by a known method, and thus 55 mg (66%) of the title compound was obtained as a light brown powder (cis:trans=8:3).

$^1$H-NMR (400 MHz, CDCl$_3$) δ: 1.12 (2.18H, d, J=6.4 Hz), 1.15 (0.82H, d, J=6.6 Hz), 1.17-1.30 (1H, m), 2.11 (0.82H, s), 2.14 (2.18H, s), 2.40-2.51 (0.27H, m), 2.58 (0.73H, ddd, J=4.3, 8.7, 12.5 Hz), 3.58-3.92 (3H, m), 4.00-4.14 (0.73H, m), 4.37-4.47 (0.27H, m), 4.78-5.00 (1H, m), 6.51-6.68 (4H, m), 6.81-6.98 (1H, m), 7.08-7.16 (2H, m).

EXAMPLE 74

Production of 1-acetyl-6-acetylamino-4-[(4-chlorophenyl)amino]-2-methyl-1,2,3,4-tetrahydroquinoline (Compound 96)

Compound 95 was acetylated by a known method, and 20 mg (88%) of the title compound was obtained as a yellow amorphous substance (cis:trans=3:1).

$^1$H-NMR (400 MHz, CDCl$_3$) δ: 1.13 (2.25H, d, J=6.3 Hz), 1.17 (0.25H, d, J=6.6 Hz), 1.20-1.30 (1H, m), 2.11 (2.25H, s), 2.13 (0.75H, s), 2.16 (0.75H, s), 2.17 (2.25H, s), 2.38-2.50 (0.25H, m), 2.60 (0.75H, ddd, J=4.1, 8.7, 12.4 Hz), 3.85-3.95 (1H, m), 4.06-4.16 (0.75H, m), 4.45-4.55 (0.25H, m), 4.78-4.96 (1H, m), 6.50-6.57 (2H, m), 6.85-7.44 (3.75H, m), 7.58-7.81 (2H, m), 8.55-8.62 (0.25H, m).

EXAMPLE 75

Production of 1-acetyl-4-[(4-chlorophenyl)amino]-2-methyl-1, 2,3,4-tetrahydroquinoline-6-ethyl carbamate (Compound 97)

Compound 95 was subjected to reactions and treatments according to known methods, and thus 26 mg (76%) of the title compound was obtained as a yellow amorphous substance (cis:trans=3:1).

$^1$H-NMR (400 MHz, CDCl$_3$) δ: 1.14 (2.25H, d, J=6.3 Hz), 1.17 (0.25H, d, J=6.6 Hz), 1.20-1.35 (3.75H, m), 1.68-1.78 (0.25H, m), 2.13 (0.75H, s), 2.17 (2.25H, s), 2.43-2.52 (0.25H, m), 2.62 (0.75H, ddd, J=4.3, 8.6, 12.6 Hz), 3.75-3.90 (1H, m), 4.07-4.27 (2.75H, m), 4.45-4.55 (0.25H, m), 4.78-5.00 (1H, m), 6.50-6.64 (3H, m), 7.04-7.18 (3H, m), 7.44-7.58 (1H, m).

EXAMPLE 76

Production of 1-acetyl-6-methanesulfonylamino-2-methyl-4-[(4-morpholinophenyl)amino]-1,2,3,4-tetrahydroquinoline (Compound 98)

Reactions and treatments were carried out in the same manner as in Example 2, and thus 66 mg (43%) of the title compound was obtained as a yellow amorphous substance (cis:trans=3:1).

$^1$H-NMR (400 MHz, CDCl$_3$) δ: 1.15 (2.25H, d, J=6.4 Hz), 1.19 (0.25H, d, J=6.6 Hz), 1.20-1.30 (0.75H, m), 1.72-1.83 (0.25H, m), 2.18 (3H, s), 2.90-2.52 (0.25H, m), 2.57-2.71 (0.75H, m), 2.96 (2.25H, s), 2.98 (6.75H, s), 2.98-3.19 (4H, m), 3.50-3.72 (1H, m), 3.78-3.92 (4H, m), 4.00-4.20 (0.75H, m), 4.46-4.58 (0.75H, m), 4.72-5.00 (1H, m), 6.50-6.70 (3H, m), 6.70-6.93 (2H, m), 7.04-7.30 (3H, m).

EXAMPLE 77

Production of 1-acetyl-6-methanesulfonylamino-2-methyl-4-[(4-ethoxycarbonylmethylphenyl)amino]-1,2,3,4-tetrahydroquinoline (Compound 99)

Reactions and treatments were carried out in the same manner as in Example 2, and thus 100 mg (21%) of the title compound was obtained as a yellow amorphous substance (cis:trans=3:1).

$^1$H-NMR (400 MHz, CDCl$_3$) δ: 1.00-1.34 (6.75H, m), 2.75-2.88 (0.25H, m), 2.18 (2.25H, s), 2.19 (0.75H, s), 2.41-2.51 (0.25H, m), 2.65 (0.75H, ddd, J=4.2, 8.7, 12.5 Hz), 2.93 (2.25H, s), 2.98 (0.75H, s), 3.48 (0.75H, s), 3.50 (2.25H, s), 3.76-3.96 (1H, m), 4.08-4.20 (2.75H, m), 4.51-4.64 (0.25H, m), 4.72-4.98 (1H, m), 6.47-6.78 (3H, m), 7.00-7.41 (4H, m).

EXAMPLE 78

Production of 1-acetyl-4-[(4-fluorophenyl)amino]-2-methyl-1,2,3,4-tetrahydroquinoline-6-carboxylic acid (Compound 100)

Reactions and treatments were carried out in the same manner as in Example 27, and thus 126 mg (58%) of the title compound was obtained as a white solid (cis:trans=6:1).

$^1$H-NMR (400 MHz, CDCl$_3$) δ: 1.17 (2.6H, d, J=6.4 Hz), 1.22 (0.4H, d, J=6.6 Hz), 1.23-1.31 (1H, m), 2.22 (0.4H, s), 2.23 (2.6H, s), 2.48-2.54 (0.14H, m), 2.64-2.74 (0.86H, m), 4.10-4.28 (2H, m), 4.55-4.64 (0.14H, m), 4.84-4.94 (0.86H, m), 6.55-6.62 (2H, m), 6.82-6.93 (2H, m), 7.24-7.30 (1H, m), 7.99-8.13 (2H, m).

EXAMPLE 79

Production of ethyl 1-acetyl-4-[(4-methanesulfonylaminophenyl)amino]-2-methyl-1,2,3,4-tetrahydroquinoline-6-carboxylate (Compound 101)

Reactions and treatments were carried out in the same manner as in Example 26, and thus 251 mg (79%) of the title compound was obtained as a pale yellow oily substance (cis:trans=6:1).

$^1$H-NMR (400 MHz, CDCl$_3$) δ: 1.18 (2.6H, d, J=6.4 Hz), 1.22 (0.4H, d, J=6.6 Hz), 1.33-1.42 (4H, m), 2.22 (3H, m), 2.44-2.53 (0.14H, m), 2.69 (0.86H, ddd, J=4.2, 8.6, 12.5 Hz), 2.93 (0.4H, s), 2.95 (2.6H, s), 4.20-4.26 (0.86H, m), 4.30-4.40 (2.14H, m), 4.62-4.66 (0.14H, m), 4.83-4.92 (0.86H, m), 6.64 (2H, d, J=8.8 Hz), 7.10-7.16 (2H, m), 7.22-7.25 (1H, m), 7.94-8.06 (2H, m).

EXAMPLE 80

Production of cis-1-acetyl-4-[(4-methanesulfonylaminophenyl)amino]-2-methyl-1,2,3,4-tetrahydroquinoline-6-carboxamide (Compound 102)

Reactions and treatments were carried out in the same manner as in Example 28, and thus 32 mg (35%) of the title compound was obtained as a light yellow oily substance.

$^1$H-NMR (400 MHz, CDCl$_3$) δ: 1.18 (3H, d, J=6.4 Hz), 1.23-1.33 (1H, m), 2.22 (3H, s), 2.69 (1H, ddd, J=4.2, 8.6, 12.6 Hz), 2.95 (3H, s), 3.92-3.96 (1H, m), 4.16-4.24 (1H, m), 4.83-4.94 (1H, m), 5.61 (1H, brs), 5.98 (1H, brs), 6.62 (2H, d, J=8.8 Hz), 7.12 (2H, d, J=8.8 Hz), 7.22-7.26 (1H, m), 7.74-7.79 (2H, m).

EXAMPLE 81

Production of ethyl 1-acetyl-4-[(4-cyanomethylphenyl)amino]-2-methyl-1,2,3,4-tetrahydroquinoline-6-carboxylate (Compound 103)

Reactions and treatments were carried out in the same manner as in Example 2, and thus 250 mg (64%) of the title compound was obtained as a pale yellow oily substance (cis:trans=4:1).

$^1$H-NMR (400 MHz, CDCl$_3$) δ: 1.18 (2.4H, d, J=6.3 Hz), 1.21-1.45 (4.6H, m), 2.21 (0.6H, s), 2.22 (2.9H, s), 2.44-2.54 (0.2H, m), 2.69 (0.8H, ddd, J=4.1, 8.4, 12.5 Hz), 3.61-6.68 (3H, m), 4.26-4.42 (3H, m), 9.61-4.68 (0.2H, m), 4.83-4.94 (0.8H, m), 6.63-6.70 (2H, m), 7.08-7.29 (3H, m), 7.97-8.16 (2H, m).

EXAMPLE 82

Production of 1-acetyl-4-[(4-cyanomethylphenyl)amino]-2-methyl-1,2,3,4-tetrahydroquinoline-6-carboxamide (Compound 104)

Reactions and treatments were carried out in the same manner as in Example 28, and thus 8 mg (80%) of the title compound was obtained as a pale yellow oily substance (cis:trans=5:1).

$^1$H-NMR (400 MHz, CDCl$_3$) δ: 1.17 (2.5H, d, J=6.4 Hz), 1.23-1.36 (1.5H, m), 2.21 (3H, brs), 2.38-2.46 (0.17H, m), 2.68 (0.83H, ddd, J=4.0, 8.4, 12.3 Hz), 3.61 (0.33H, s), 3.64 (1.67H, s), 4.04-4.33 (2H, m), 4.67 (0.17H, brs), 4.85 (0.83H, brs), 5.93 (1H, brs), 6.14 (1H, brs), 6.60-6.68 (2H, m), 7.09-7.14 (2H, m), 7.24-7.26 (1H, m), 7.73-7.80 (2H, m).

EXAMPLE 83

Production of cis-1-acetyl-4-[(4-carboxymethylphenyl)amino]-2-methyl-1,2,3,4-tetrahydroquinoline-6-carboxamide (Compound 105)

Compound 104 was hydrolyzed by a known method, and 14 mg (52%) of the title compound was obtained as a yellowish brown oily substance.

$^1$H-NMR (400 MHz, CDCl$_3$) δ: 1.18-1.35 (4H, m), 2.24 (3H, s), 2.69 (1H, ddd, J=4.1, 8.4, 12.4 Hz), 3.65 (2H, s), 4.22-4.36 (2H, m), 4.83-4.93 (1H, m), 6.64 (2H, d, J=8.4 Hz), 7.14 (2H, d, J=8.4 Hz), 7.23-7.27 (1H, m), 8.03-8.08 (2H, m).

EXAMPLE 84

Production of cis-1-acetyl-4-[(4-carbamoylmethylphenyl)amino]-2-methyl-1, 2,3,4-tetrahydroquinoline-6-carboxamide (Compound 106)

Compound 105 was amidated by a known method, and thus 2.5 mg (25%) of the title compound was obtained as a yellowish brown oily substance.

$^1$H-NMR (400 MHz, CDCl$_3$) δ: 1.18 (3H, d, J=6.4 Hz), 1.24-1.38 (1H, m), 2.22 (3H, s), 2.69 (1H, ddd, J=4.2, 8.4, 12.5 Hz), 3.65 (2H, s), 3.93-3.96 (1H, m), 4.18-4.27 (1H, m), 4.83-4.93 (1H, m), 6.63 (2H, d, J=6.3 Hz), 7.15 (2H, d, J=6.3 Hz), 7.23-7.27 (1H, m), 7.70-7.83 (2H, m).

EXAMPLE 85

Production of 1-acetyl-4-[(4-chlorophenyl)amino]-7-methanesulfonylamino-2-methyl-1,2,3,4-tetrahydroquinoline (Compound 107)•hydrochloride Reactions and treatments were carried out in the same manner as in Example 2, and the product was converted to the hydrochloride by a known method. The hydrochloride was subjected to recrystallization from ethyl acetate. Thus, 15 mg (15%) of the title compound was obtained as a light yellow crystalline powder (cis:trans=6:1).

Melting 105.0° C. to 106.0° C.

$^1$H-NMR (400 MHz, CD$_3$OD) δ: 1.13-1.26 (3.86H, m), 1.85-1.96 (0.14H, m), 2.20 (0.42H, s), 2.25 (2.58H, s), 2.40-2.47 (0.14H, m), 2.72 (0.86H, ddd, J=3.9, 8.3, 14.8 Hz), 2.96-2.98 (3H, m), 4.49-4.52 (0.14H, m), 4.80-4.98 (1H, m), 5.26-5.34 (0.86H, m), 6.84 (0.28H, d, J=8.8 Hz), 7.03 (1.72H, d, J=8.8 Hz), 7.19-7.50 (5H, m).

EXAMPLE 86

Production of 1-acetyl-4-[(4-hydroxy-3-methoxycarbonylphenyl)amino]-2-methyl-1,2,3,4-tetrahydroquinoline (Compound 108)•hydrochloride Reactions and treatments were carried out in the same manner as in Example 2, and the reaction product was converted by the hydrochloride by a known method. Thus, 30 mg (75%) of the title compound was obtained as a white crystalline powder (cis:trans=3:1).

Melting point: 94.0° C. to 96.0° C.

$^1$H-NMR (400 MHz, CDCl$_3$) δ: 1.09-1.28 (3.75H, m), 1.70-1.75 (0.25H, m), 2.16 (0.75H, s), 2.19 (2.25H, s), 2.50-2.59 (0.25H, m), 2.65 (0.75H, ddd, J=4.2, 8.4, 12.4 Hz), 3.46-3.70 (1H, brs), 3.91 (2.75H, s), 3.93 (0.25H, s), 4.18 (0.75H, dd, J=3.9, 11.8 Hz), 4.51 (0.25H, dd, J=4.4, 4.4 Hz), 4.82-4.97 (1H, m), 6.81-7.37 (7H, m), 10.18 (0.25H, s), 10.22 (0.75H, s).

EXAMPLE 87

Production of cis-1-acetyl-4-[(2-carboxyphenyl)amino]-2-methyl-1,2,3,4-tetrahydroquinoline (Compound 109)

Reactions and treatments were carried out in the same manner as in Example 2, and thus 7 mg (28%) of the title compound was obtained as a white solid.

Melting point: 122.0° C. to 122.7° C.

$^1$H-NMR (400 MHz, CDCl$_3$) δ: 1.19 (3H, dd, 6.4 Hz), 1.37-1.51 (1H, m), 2.22 (1H, s), 2.73 (1H, ddd, J=4.4, 8.3, 12.4 Hz), 4.24-4.40 (1H, brs), 4.86-5.04 (1H, brs), 6.61-6.71 (2H, m), 7.17-7.53 (4H, m), 8.00-8.25 (2H, m).

EXAMPLE 88

Production of 1-acetyl-6-[cis(2,6-dimethyl)morpholino]-4-[(4-methanesulfonylaminophenyl)amino]-2-methyl-1,2,3,4-tetrahydroquinoline (Compound 110)•dihydrochloride Reactions and treatments were carried out in the same manner as in Example 61, and the reaction product was converted to the hydrochloride by a known method. The hydrochloride was washed with ethyl acetate, and thus 56 mg (45%) of the title compound was obtained as a reddish brown solid (cis:trans=10:1).

Melting point: 141.5° C. to 143.2° C.

$^1$H-NMR (400 MHz, CD$_3$OD) δ: 1.13-1.35 (9.91H, m), 1.65-1.71 (0.09H, brs), 2.21-2.24 (3H, m), 2.53-2.75 (1H, m), 2.89 (0.91H, s), 3.00 (0.09H, s), 3.12-3.63 (4H, m), 3.94-4.02 (2H, m), 4.26-4.34 (0.91H, brs), 4.83-4.93 (1.09H, m), 6.78-6.81 (2H, m), 7.12-7.14 (2H, m), 7.28-7.56 (3H, m).

EXAMPLE 89

Production of 1-acetyl-6-[(4-isopropylcarbonyl)piperazino]-4-[(4-methanesulfonylaminophenyl)amino]-2-methyl-1,2,3,4-tetrahydroquinoline (Compound 111)

Reactions and treatments were carried out in the same manner as in Example 62, and thus 8 mg (67%) of the title compound was obtained as a light yellow amorphous substance (cis:trans=10:1).

$^1$H-NMR (400 MHz, CDCl$_3$) δ: 0.96-1.25 (9.91H, m), 1.50-1.75 (0.09H, brs), 2.03 (0.27H, s), 2.15 (2.73H, s), 2.45-2.65 (1H, m), 2.80 (1H, m), 2.93 (0.27H, s), 2.95 (2.73H, s), 3.08-3.20 (4H, brs), 3.55-3.80 (4H, brs), 4.06-4.18 (0.91H, brs), 4.49-4.53 (0.09H, m), 4.80-4.98 (0.91H, m), 5.11-5.13 (0.09H, m), 6.30 (0.09H, s), 6.35 (0.91H, s), 6.60-6.64 (2H, m), 6.79-6.86 (2H, m), 7.00-7.13 (3H, m).

EXAMPLE 90

Production of cis-1-acetyl-4-[(4-benzylphenyl)amino]-2-methyl-1,2,3,4-tetrahydroquinoline (Compound 112)

Reactions and treatments were carried out in the same manner as in Example 2, and thus 10 mg (8%) of the title compound was obtained as a white solid.

$^1$H-NMR (400 MHz, CDCl$_3$) δ: 1.16 (3H, d, J=6.6 Hz), 1.65-1.68 (1H, m), 2.10 (3H, s), 2.22 (1H, ddd, J=5.6, 7.5, 13.5 Hz), 3.77 (2H, dd, J=15.6, 19.8 Hz), 4.49 (1H, brs), 4.82 (1H, brs), 6.73 (1H, t, J=6.8 Hz), 6.80 (1H, d, J=8.3 Hz), 7.06 (1H, d, J=7.3 Hz), 7.09-7.26 (9H, m).

EXAMPLE 91

Production of 1-acetyl-4-[(4-chlorophenyl)amino]-N,N,2-trimethyl-1,2,3,4-tetrahydroquinoline-6-carboxamide (Compound 113)

Compound 42 was hydrolyzed by a known method, and thus 74 mg (64%) of the title compound was obtained as a pale yellow solid (cis:trans=3:1).

$^1$H-NMR (400 MHz, CDCl$_3$) δ: 1.16 (2.25H, d, J=6.4 Hz), 1.21 (0.75H, d, J=6.6 Hz), 1.23-1.34 (0.75H, m), 1.80-1.90 (0.25H, m), 2.20 (0.75H, s), 2.22 (2.25H, s), 2.45 (0.25H, ddd, J=6.6, 6.6, 13.4 Hz), 2.66 (0.75H, ddd, J=4.0, 8.6, 12.4 Hz), 2.91 (2.25H, s), 3.00 (0.75H, s), 3.07 (2.25H, s), 3.11 (0.75H, s), 3.89 (1H, brs), 4.13-4.22 (0.75H, m), 4.54-4.60 (0.25H, m), 4.87 (1H, brs), 6.52-6.58 (2H, m), 7.08-7.16 (2H, m), 7.18-7.41 (2.75H, m), 7.49 (0.25H, d, J=1.7 Hz).

EXAMPLE 92

Production of 1-acetyl-4-[(4-chlorophenyl)amino]-N,2-dimethyl-1,2,3,4-tetrahydroquinoline-6-carboxamide (Compound 114)

Compound 41 was subjected to hydrolysis and amidation by know methods, and thus 71 mg (64%) of the title compound was obtained as a pale yellow amorphous substance (cis:trans=3:1).

$^1$H-NMR (400 MHz, CDCl$_3$) δ: 1.16 (2.25H, d, J=6.4 Hz), 1.21 (0.75H, d, J=6.6 Hz), 1.23-1.33 (0.75H, m), 1.83-1.92 (0.25H, m), 2.20 (0.75H, s), 2.20 (2.25H, s), 2.42 (0.25H, ddd, J=7.2, 7.2, 14.4 Hz), 2.67 (0.75H, ddd, J=4.0, 8.4, 12.3 Hz), 2.98 (2.25H, s), 3.02 (0.75H, d, J=4.9 Hz), 3.86 (1H, brs), 4.02-4.20 (0.75H, m), 4.59-4.64 (0.25H, m), 4.80-4.92 (1H, m), 6.01 (0.75H, brs), 6.09 (0.25H, brs), 6.54-6.60 (2H, m), 7.10-7.35 (3H, m), 7.63 (0.75H, s), 7.66 (0.25H, dd, J=2.3, 8.4 Hz), 7.74 (0.75H, dd, J=2.0, 8.1 Hz), 7.85 (0.25H, d, J=2.0 Hz).

EXAMPLE 93

Production of 1-acetyl-4-[(4-chlorophenyl)amino]-2-methyl-1,2,3,4-tetrahydroquinoline-6-carbohydrazide (Compound 115)

Compound 42 was amidated by a known method, and thus 136 mg (61%) of the title compound was obtained as a pale brown amorphous substance (cis:trans=3:1).

$^1$H-NMR (400 MHz, CDCl$_1$) δ: 1.17 (2.25H, d, J=6.3 Hz), 1.22 (0.75H, d, J=6.6 Hz), 1.24-1.34 (0.75H, m), 1.84-1.94 (0.25H, m), 2.21 (0.75H, s), 2.21 (2.25H, s), 2.42 (0.25H, ddd, J=6.7, 6.7, 13.7 Hz), 2.68 (0.75H, ddd, J=4.0, 8.3, 12.6 Hz), 3.87 (1H, d, J=7.1 Hz), 4.07 (2H, brs), 4.12-4.21 (0.75H; m), 4.58-4.66 (0.25H, m), 4.79-4.93 (1H, m), 6.53-6.59 (2H, m), 7.10-7.17 (2H, m), 7.23-7.39 (1H, m), 7.61-7.66 (1H, m), 7.72 (0.75H, dd, J=2.0, 8.1 Hz), 7.84 (0.25H, d, J=2.0 Hz).

EXAMPLE 94

Production of 1-acetyl-4-[(4-chlorophenyl)amino]-2-methyl-6-[1,3,4-oxadiazol-2(3H)-on-5-yl]-1,2,3,4-tetrahydroquinoline (Compound 116)

Triethylamine (744 μL, 534 μmol) was added to a THF (10 mL) solution of compound 115 (100 mg, 267 μmol) at room temperature, and 1,1'-carbodiimidazole (64.9 mg, 400 μmol) was further added thereto. The resulting mixture was stirred for 3 days at the same temperature. Water was added to the reaction liquid, and the mixture was extracted with chloroform. Subsequently, the organic layer was washed with saturated brine, dehydrated over anhydrous sodium sulfate, and then concentrated under reduced pressure. The resulting residue was purified by using silica gel chromatography (hexane:ethyl acetate=1:1→1:2), and thus 94.8 mg (89%) of the title compound was obtained as a pale yellow amorphous substance (cis:trans=3:1).

$^1$H-NMR (400 MHz, CDCl$_3$) δ: 1.19 (2.25H, d, J=6.4 Hz), 1.25 (0.75H, d, J=6.6 Hz), 1.27-1.37 (0.75H, m), 1.86-1.94 (0.25H, m), 2.24 (3H, s), 2.40-2.50 (0.25H, m), 2.69 (0.75H, ddd, J=3.9, 8.4, 12.3 Hz), 3.86 (0.75H, d, J=7.1 Hz), 3.98-4.10 (0.25H, m), 4.14-4.23 (0.75H, m), 4.57-4.65 (0.25H, m), 4.78-4.92 (1H, m), 6.54-6.61 (2H, m), 7.10-7.18 (2H, m).

EXAMPLE 95

Production of 1-acetyl-4-[(4-chlorophenyl)amino]-6-cyano-2-methyl-1,2,3,4-tetrahydroquinoline (Compound 117)

Compound 43 was subjected to reactions and treatments according to known methods, and the product was subjected to recrystallization from ethyl acetate and hexane. Thus, 40 mg (66%) of the title compound was obtained as a white solid.

Melting point: 211.5° C. to 212.8° C.

$^1$H-NMR (400 MHz, CDCl$_3$) δ: 1.20 (3H, d, J=6.4 Hz), 1.30-1.39 (1H, m), 2.05 (3H, s), 2.69 (1H, ddd, J=4.1, 9.9, 13.1 Hz), 3.84 (1H, d, J=6.4 Hz), 4.08-4.22 (1H, m), 4.78-4.85 (1H, m), 6.54 (2H, d, J=8.0 Hz), 7.14 (2H, d, J=8.0 Hz), 7.28 (2H, d, J=12.2 Hz), 7.57 (1H, s), 7.61 (1H, d, J=12.2 Hz).

EXAMPLE 96

Production of 1-acetyl-4-[(4-chlorophenyl)amino]-N-methoxy-2-methyl-1,2,3,4-tetrahydroquinoline-6-carboxamide (Compound 118)•hydrochloride Compound 42 was subjected to reactions and treatments according to known methods, and the hydrochloride was washed with diethyl ether and ethyl acetate. Thus, 73 mg (44%) of the title compound was obtained as a pale yellow solid (cis:trans=3:1).

Melting point: 120.8° C. to 123.0° C.

$^1$H-NMR (400 MHz, CD$_3$OD) δ: 1.10-1.40 (3.75H, m), 2.00-2.06 (0.25H, m), 2.20 (2.25H, s), 2.27 (0.75H, s), 2.54-2.70 (1H, m), 3.80 (2.25H, s), 3.87 (0.75H, s), 4.39 (0.75H, dd, J=4.1, 12.1 Hz), 4.74-4.89 (1H, m), 5.04-5.09 (0.25H, m), 6.91-6.96 (2H, m), 7.23-8.11 (5H, m).

EXAMPLE 97

Production of 1-acetyl-4-[(4-chlorophenyl)amino]-2-methyl-6-(1H-tetrazol-5-yl)-1,2,3,4-tetrahydroquinoline (Compound 119)

Compound 117 was subjected to reactions and treatments according to known methods, and thus 39 mg (70%) of the title compound was obtained as a yellow solid (cis:trans=10:1).

Melting point: 190.5° C. to 191.1° C.

$^1$H-NMR (400 MHz, CDCl$_3$) δ: 1.08-1.37 (3.91H, m), 1.27-1.50 (0.09H, m), 2.20-2.42 (3H, brs), 2.62-2.78 (1H, m), 4.16-4.32 (0.91H, brs), 4.50-4.54 (0.09H, m), 4.60-4.92 (1H, m), 6.56 (2H, d, J=8.8 Hz), 7.04 (2H, d, J=8.8 Hz), 7.32-7.38 (1H, brs), 8.00-8.24 (2H, m).

EXAMPLE 98

Production of 1-acetyl-4-[(4-chlorophenyl)amino]-2-methyl-6-[1,2,4-oxadiazol-5(2H)-on-3-yl]-1,2,3,4-tetrahydroquinoline (Compound 120)

Compound 117 was subjected to reactions and treatments according to known methods, and 40 mg (54%) of the title compound was obtained as a white solid (cis:trans=7:1).

Melting point: 163.2° C. to 164.0° C.

$^1$H-NMR (400 MHz, CDCl$_3$) δ: 1.15-1.36 (3.87H, m), 1.55-1.62 (0.13H, m), 2.04 (0.39H, s), 2.16 (2.61H, s), 2.61-2.75 (1H, m), 4.14-4.22 (0.87H, brs), 4.36-4.44 (0.13H, m), 4.67-4.91 (1H, m), 6.56-6.61 (2H, m), 7.13-7.17 (2H, m), 7.30-7.32 (1H, brs), 7.67 (1H, s), 7.75 (1H, d, J=8.5 Hz).

EXAMPLE 99

Production of cis-1-acetyl-4-[(4-chlorophenyl)amino]-6-hydroxymethyl-2-methyl-1,2,3,4-tetrahydroquinoline (Compound 121)

Compound 41 was subjected to a reduction treatment by a known method, and thus 11 mg (32%) of the title compound was obtained as a colorless transparent oily substance.

$^1$H-NMR (400 MHz, CDCl$_3$) δ: 1.15 (3H, d, J=6.4 Hz), 1.19-1.30 (1H, m), 1.82 (1H, brs), 2.64 (1H, ddd, J=4.0, 8.6, 12.3 Hz), 3.85 (1H, brs), 4.12-4.20 (1H, m), 4.65 (2H, s), 4.90 (1H, brs), 6.56 (2H, d, J=9.0 Hz), 7.12-7.17 (3H, m), 7.24-7.34 (2H, m).

EXAMPLE 100

Production of 1-acetyl-4-[(4-ethoxycarbonylmethylphenyl)amino]-6-fluoro-2-methyl-1,2,3,4-tetrahydroquinoline (Compound 122)

Reactions and treatments were carried out in the same manner as in Example 48, and thus 453 mg (39%) of the title compound was obtained as a colorless transparent oily substance (cis:trans=3:1).

$^1$H-NMR (400 MHz, CDCl$_3$) δ: 1.14 (2.25H, d, J=6.3 Hz), 1.19 (0.75H, d, J=6.6 Hz), 1.25 (0.75H, t, J=7.3 Hz), 1.25 (2.25H, t, J=7.1 Hz), 1.22-1.29 (0.75H, m), 1.72-1.87 (0.25H, m), 2.15 (0.75H, s), 2.17 (2.25H, s), 2.40-2.51 (0.25H, m), 2.65 (0.75H, ddd, J=4.2, 8.6, 12.5 Hz), 3.49 (0.5H, s), 3.51 (1.5H, s), 3.72-3.88 (1H, m), 4.10-4.18 (2.75H, m), 4.52-4.59 (0.25H, m), 4.80-4.98 (1H, m), 6.58 (1.5H, d, J=8.6 Hz), 6.60 (0.5H, d, J=8.1 Hz), 6.93-7.15 (5H, m).

EXAMPLE 101

Production of 1-acetyl-4-[(4-carboxymethylphenyl)amino]-6-fluoro-2-methyl-1,2,3,4-tetrahydroquinoline (Compound 123)

Compound 122 was subjected to reactions and treatments in the same manner as in Example 49, and thus 342 mg (100%) of the title compound was obtained as a pale green amorphous substance (cis:trans=3:1).

$^1$H-NMR (400 MHz, CDCl$_3$) δ: 1.14 (2.25H, d, J=6.4 Hz), 1.18 (0.75H, d, J=6.6 Hz), 1.20-1.30 (0.75H, m), 1.68-1.84 (0.25H, m), 2.14 (0.75H, s), 2.17 (2.25H, s), 2.42-2.50 (0.25H, m), 2.64 (0.75H, ddd, J=4.0, 8.4, 12.3 Hz), 3.53 (0.5H, s), 3.56 (1.5H, s), 4.14 (0.75H, dd, J=4.0, 12.1 Hz), 4.53-4.57 (0.25H, m), 4.80-5.00 (1H, m), 6.60 (1.5H, d, J=8.6 Hz), 6.60 (0.5H, d, J=8.8 Hz), 6.94-7.30 (5H, m).

EXAMPLE 102

Production of 1-acetyl-4-[(4-carbamoylmethylphenyl)amino]-6-fluoro-2-methyl-1,2,3,4-tetrahydroquinoline (Compound 124)

Compound 123 was subjected to reactions and treatments by known methods, and thus 64 mg (80%) of the title compound was obtained as a pale yellow amorphous substance (cis:trans=3:1).

$^1$H-NMR (400 MHz, CDCl$_3$) δ: 1.15 (2.25H, d, J=6.4 Hz), 1.19 (0.75H, d, J=6.6 Hz), 1.21-1.32 (0.75H, m), 1.80-1.94 (0.25H, m), 2.15 (0.75H, s), 2.17 (2.25H, s), 2.41-2.53 (0.25H, m), 2.66 (0.75H, ddd, J=4.1, 8.5, 12.4 Hz), 3.46 (0.5H, s), 3.49 (1.5H, s), 3.82-3.96 (1H, m), 4.10-4.21 (0.75H, m), 4.43-4.62 (0.25H, m), 4.82-5.02 (1H, m), 5.45 (2H, brs), 6.59-6.66 (2H, m), 6.96-7.17 (5H, m).

EXAMPLE 103

Production of 1-acetyl-4-[4-(N,N-dimethylaminocarbonylmethyl)phenylamino]-6-fluoro-2-methyl-1,2,3,4-tetrahydroquinoline (Compound 125)

Reactions and treatments were carried out in the same manner as in Example 102 using compound 123, and thus 45 mg (53%) of the title compound was obtained as a pale yellow amorphous substance (cis:trans=5:1).

$^1$H-NMR (400 MHz, CDCl$_3$) δ: 1.14 (2.52H, d, J=6.4 Hz), 1.18 (0.48H, d, J=6.4 Hz), 1.20-1.30 (0.84H, m), 1.70-1.84 (0.16H, m), 2.15 (0.48H, s), 2.17 (2.52H, s), 2.40-2.50 (0.16H, m), 2.64 (0.84H, ddd, J=4.0, 8.4, 12.3 Hz), 2.95 (0.48H, s), 2.96 (2.52H, s), 3.00 (0.48H, s), 3.01 (2.52H, s), 3.59 (0.32H, s), 3.62 (1.68H, s), 3.70-3.86 (1H, m), 4.09-4.18 (0.84H, m), 4.52-4.58 (0.16H, m), 4.80-4.95 (1H, m), 6.56-6.61 (2H, m), 6.94-7.02 (1H, m), 7.03-7.15 (4H, m).

EXAMPLE 104

Production of 1-acetyl-4-[(4-chlorophenyl)amino] (2-hydroxyethyl)-2-methyl-1,2,3,4-tetrahydroquinoline-6-carboxamide (Compound 126)

Compound 42 was amidated by a known method, and thus 82 mg (73%) of the title compound was obtained as a white amorphous substance (cis:trans=3:1).

$^1$H-NMR (900 MHz, CDCl$_3$) δ: 1.17 (2.251-1, d, J=6.4 Hz), 1.21 (0.75H, d, J=6.6 Hz), 1.24-1.33 (0.75H, m), 1.84-1.92 (0.25H, m), 2.20 (3H, s), 2.38-2.47 (0.25H, m), 2.68 (0.75H, ddd, J=12.3, 8.4, 4.0 Hz), 3.52-3.66 (2H, m), 3.76-3.91 (2H, m), 4.13-4.23 (0.75H, m), 4.57-4.65 (0.25H, m), 4.79-4.91 (1H, m), 6.48-6.61 (2H, m), 7.12 (0.5H, d, J=8.8 Hz), 7.15 (1.5H, d, J=8.8 Hz), 7.20-7.37 (1H, m), 7.66-7.77 (1.75H, m), 7.87 (0.25H, s).

EXAMPLE 105

Production of 4-[(1-acetyl-4-[(4-chlorophenyl)amino]-2-methyl-1,2,3,4-tetrahydroquinolin-6-yl]-2-methyl-1H-imidazole (Compound 127)

[Step 1] 44 mg (cis:trans=3:1) of 1-acetyl-6-bromo-4-[(4-chlorophenyl)amino]-2-methyl-1,2,3,4-tetrahydroquinoline (compound 74) and 56 mg of 2-methyl-5-(tributylstannyl)-1-[[2-(trimethylsilyl)ethoxy]methyl]-1H-imidazole were dissolved in 1 mL of DMF, and 6 mg of tetrakis(triphenylphosphine)palladium was added to the solution. The mixture was stirred in a sealed tube for 12 hours at 120° C. After completion of the reaction, DMF was distilled off under reduced pressure. The resulting residue was dissolved in ethyl acetate, and then the solution was filtered through Celite to remove any insoluble materials. The ethyl acetate solution was washed with water, dehydrated over anhydrous sodium sulfate, and then concentrated under reduced pressure. The resulting residue was purified by using silica gel chromatography (ethyl acetate:aqueous ammonia=1:0.01). Thus, 31 mg (cis:trans=3:1, yield 53%) of 1-acetyl-6-{2-methyl-1-[[2-(trimethylsilyl)ethoxy]methyl]-1 H-imidazol-5-yl}-4-[(4-chlorophenyl)amino]-2-methyl-1,2,3,4-tetrahydroquinoline was obtained as a brown oily substance.

[Step 2] 12 mg (cis:trans=3:1) of 1-acetyl-6-[2-methyl-1-[[2-(trimethylsilyl)ethoxy]methyl]-1H-imidazol-5-yl]-4-[(4-chlorophenyl)amino]-2-methyl-1,2,3,4-tetrahydroquinoline was dissolved in 1 mL of dichloromethane, and 0.5 mL of trifluoroacetic acid was added to the solution. The mixture was stirred for 3 hours at room temperature. After completion of the reaction, trifluoroacetic acid and dichloromethane were distilled off under reduced pressure. The resulting residue was neutralized with a saturated aqueous solution of sodium hydrogen carbonate, and then was extracted three times with chloroform. The extraction product was dehydrated over anhydrous sodium sulfate, and then was concentrated under reduced pressure. The resulting residue was purified by using silica gel chromatography (methanol:chloroform=1:10), and thus 9 mg (cis:trans=3:1, 100%) of the title compound was obtained as a yellow solid.

$^1$H-NMR (400 MHz, CDCl$_3$) δ: 1.12-1.30 (3.75H, m), 1.72-1.84 (0.25H, m), 2.18 (0.75H, s), 2.20 (2.25H, s), 2.42-2.48 (3.25H, m), 2.63 (0.75H, ddd, J=4.1, 8.4, 12.8 Hz), 3.80-3.92 (1H, m), 4.12-4.24 (0.75H, m), 4.80-3.96 (0.25H, m), 4.52-4.60 (1H, m), 6.52-6.60 (2H, m), 7.05-7.17 (3H, m), 7.52-7.75 (2H, m).

EXAMPLE 106

Production of 1-acetyl-4-[(4-chlorophenyl)amino]-N-cyano-2-methyl-1,2,3,4-tetrahydroquinoline-6-carboxamide (Compound 128)

Compound 42 was amidated by a known method, and thus 75 mg (56%) of the title compound was obtained as a pale yellow amorphous substance (cis:trans=4:1).

$^1$H-NMR (400 MHz, CDCl$_3$) δ: 1.15 (2.4H, d, J=6.3 Hz), 1.18 (0.6H, d, J=6.6 Hz), 1.22-1.32 (0.8H, m), 1.29 (9H, t, J=7.3 Hz), 1.70-1.86 (0.2H, m), 2.17 (0.6H, s), 2.18 (2.4H, s), 2.40-2.50 (0.2H, m), 2.65 (0.8H, ddd, J=12.3, 8.5, 4.0 Hz), 3.17 (6H, q, J=7.3 Hz), 3.98-4.06 (0.8H, m), 4.12-4.23 (1H, m), 4.55-4.64 (0.2H, m), 4.82-4.94 (1H, m), 6.54-6.60 (3H, m), 7.06-7.19 (3H, m), 7.91 (1H, s), 7.97-8.06 (1H, m), 8.09 (0.2H, s).

EXAMPLE 107

Production of 1-acetyl-4-[(4-chlorophenyl)amino]-N-hydroxy-2-methyl-1,2,3,4-tetrahydroquinoline-6-carboxamide (Compound 129)

Compound 42 was amidated by a known method, and thus 33 mg (31%) of the title compound was obtained as a pale yellow oily substance (cis:trans=3:1).

$^1$H-NMR (400 MHz, CDCl$_3$) δ: 1.19 (2.25H, d, J=6.4 Hz), 1.23 (0.75H, d, J=6.6 Hz), 1.25-1.36 (0.75H, m), 1.83-1.92 (0.25H, m), 2.22 (0.75H, s), 2.24 (2.25H, s), 2.41-2.51 (0.25H, m), 2.69 (0.75H, ddd, J=12.3, 8.3, 4.2 Hz), 4.20 (0.75H, dd, J=12.0, 3.9 Hz), 4.63 (0.25H, dd, J=5.0, 5.0 Hz), 4.81-4.93 (1H, m), 6.58 (1.5H, d, J=8.8 Hz), 6.59 (0.5H, d, J=8.8 Hz), 7.11 (0.5H, d, J=9.0 Hz), 7.15 (1.5H, d, J=9.0 Hz), 7.24-7.28 (0.75H, m), 7.37 (0.25H, d, J=8.3 Hz), 7.99-8.07 (1.75H, m), 8.13 (0.25H, s).

EXAMPLE 108

Production of 1-acetyl-4-[(4-chlorophenyl)amino]-2-methyl-N-phenyl-1,2,3,4-tetrahydroquinoline-6-carboxamide (Compound 130)

Compound 42 was amidated by a known method, and thus 90 mg (86%) of the title compound was obtained as a light yellow amorphous substance (cis:trans=3:1).

$^1$H-NMR (400 MHz, CDCl$_3$) δ: 1.16-1.36 (3.75H, m), 1.87-1.96 (0.25H, m), 2.23 (3H, s), 2.38-2.46 (0.25H, m), 2.69 (0.75H, ddd, J=4.4, 8.8, 12.6 Hz), 3.80-3.95 (1H, m), 4.15-4.27 (0.75H, m), 4.63-4.69 (0.25H, m), 4.80-4.92 (1H, m), 6.54-6.64 (2H, m), 7.10-7.22 (3H, m), 7.22-7.46 (3H, m), 7.54-7.98 (4H, m).

EXAMPLE 109

Production of 1-acetyl-4-[(4-chlorophenyl)amino]-2-methyl-N-(3-pyridyl)-1,2,3,4-tetrahydroquinoline-6-carboxamide (Compound 131)

Compound 42 was amidated by a known method, and thus 65 mg (62%) of the title compound was obtained as a light yellow amorphous substance (cis:trans=3:1).

$^1$H-NMR (400 MHz, CDCl$_3$) δ: 1.19 (2.25H, d, J=6.4 Hz), 1.25 (0.75H, d, J=7.2 Hz), 1.28-1.36 (0.75H, m), 1.92-2.00 (0.25H, m), 2.23 (3H, s), 2.33-2.42 (0.25H, m), 2.70 (0.75H, ddd, J=4.4, 8.8, 12.8 Hz), 3.93 (1H, d, J=7.2 Hz), 4.18-4.26 (0.75H, m), 4.62-4.70 (0.25H, m), 4.76-4.92 (1H, m), 6.54-6.60 (2H, m), 7.10-7.18 (2H, m), 7.28-7.34 (1.5H, m), 7.45 (0.5H, d, J=8.4 Hz), 7.76-7.88 (2H, m), 7.95-8.05 (1H, m), 8.10-8.29 (1H, m), 8.35-8.40 (1H, m), 8.60 (0.75H, d, J=2.4 Hz), 8.66 (0.25H, d, J=2.4 Hz).

EXAMPLE 110

Production of 1-acetyl-4-[(4-morpholinophenyl)amino]-N,2-dimethyl-1,2,3,4-tetrahydroquinoline-6-carboxamide (compound 132)

72 mg of 1-acetyl-4-[(4-morpholinophenyl)amino]-2-methyl-1,2,3,4-tetrahydroquinoline-6-carboxylic acid (compound of Step 3 of Example 111), 51 mg of WSCD.HCl, and 36 mg of HOBt.H$_2$O were dissolved in 2 mL of dichloromethane, and 0.4 mL of a 2 M methylamine/tetrahydrofuran solution was added to the solution. The resulting mixture was stirred overnight at room temperature. After completion of the reaction, a saturated aqueous solution of sodium hydrogen carbonate was added to the mixture, and the mixture was extracted three times with chloroform. The extraction product was washed with saturated brine, dehydrated over anhydrous sodium sulfate, and then concentrated under reduced pressure. The resulting residue was purified by using silica gel chromatography (methanol:chloroform=1:10), and thus 52 mg (cis:trans=4:1, 70%) of the title compound was obtained as a yellow solid.

$^1$H-NMR (400 MHz, CDCl$_3$) δ: 1.14-1.26 (3.8H, m), 1.80-1.90 (0.2H, m), 2.14-2.20 (3H, m), 2.36-2.46 (0.2H, m), 2.56-2.75 (0.8H, m), 2.96-3.01 (7H, m), 3.50-3.62 (0.8H, m), 3.80-3.86 (4H, m), 4.05-4.25 (1H, m), 4.54-4.62 (0.2H, m), 4.78-4.86 (1H, m), 6.02-6.14 (1H, m), 6.56-6.95 (4H, m), 7.20-7.27 (1H, m), 7.64-7.84 (2H, m).

EXAMPLE 111

Production of 1-acetyl-4-[(4-morpholinophenyl)amino]-2-methyl-1,2,3,4-tetrahydroquinoline-6-carbohydrazide (Compound 133)

[Step 1] 500 mg of ethyl 1-acetyl-4-oxo-2-methyl-1,2,3,4-tetrahydroquinoline-6-carboxylate and 809 mg of 4-morpholinoaniline were dissolved in 20 mL of toluene, and 1.8 mL of titanium tetrachloride (1.0 M dichloromethane solution) was added to the solution under ice cooling. The mixture was heated to reflux for 8.5 hours. After completion of the reaction, the reaction liquid was filtered through Celite, and was concentrated under reduced pressure. Thus, 720 mg of a crude product was obtained.

[Step 2] 720 mg of the crude product and 799 mg of sodium cyanoborohydride were dissolved in 20 mL of methanol, and one droplet of acetic acid was added to the solution. The mixture was stirred for 12 hours at room temperature. After completion of the reaction, methanol was distilled off under reduced pressure. The resulting residue was neutralized with a saturated aqueous solution of sodium hydrogen carbonate, and then was extracted three times with chloroform. The extraction product was washed with saturated brine, dehydrated over anhydrous sodium sulfate, and then concentrated under reduced pressure. The resulting residue was purified by using silica gel chromatography (ethyl acetate:hexane=2:1), and thus 415 mg (52%, 2 steps) of 1-acetyl-4-[(4-morpholinophenyl)amino]-2-methyl-1,2,3,4-tetrahydroquinoline-ethyl 6-carboxylate was obtained as a white amorphous substance.

[Step 3] 415 mg of ethyl 1-acetyl-4-[(4-morpholinophenyl)amino]-2-methyl-1,2,3,4-tetrahydroquinoline-6-carboxylate was dissolved in 9 mL of ethanol, and 3 mL of 4 N sodium hydroxide was added to the solution. The mixture was stirred for 3 hours at 50° C. After completion of the reaction, the reaction liquid was washed with ether. The reaction liquid was adjusted to pH 6 with 1N hydrochloric acid, and then was extracted three times with chloroform. The extraction product was washed with saturated brine, dehydrated over anhydrous sodium sulfate, and then concentrated under reduced pressure. Thus, 388 mg (cis:trans=3:1) of a crude product was obtained.

[Step 4] 102 mg of 1-acetyl-4-[(4-morpholinophenyl)amino]-2-methyl-1,2,3,4-tetrahydroquinoline-6-carboxylic acid, 125 mg of WSCD.HCl, and 72 mg of HOBt.H$_2$O were dissolved in 1 mL of dichloromethane, and 0.12 mL of hydrazine monohydrate was added to the solution. The mixture was stirred overnight at room temperature. After completion of the reaction, a saturated aqueous solution of sodium hydrogen carbonate was added to the mixture, and the mixture was extracted three times with chloroform. The extraction product was washed with saturated brine, dehydrated over anhydrous sodium sulfate, and then concentrated under reduced pressure. The resulting residue was purified by using silica gel chromatography (methanol:chloroform=1:10), and thus 83 mg (cis:trans=3:1, 79%) of the title compound was obtained as a brown oily substance.

$^1$H-NMR (400 MHz, CDCl$_3$) δ: 1.14-1.26 (3.75H, m), 1.78-1.95 (0.25H, m), 2.18-2.20 (3H, m), 2.34-2.44 (0.25H, m), 2.60-2.72 (0.75H, m), 3.00-3.10 (4H, m), 3.60-3.76 (0.75H, m), 3.83-3.91 (4H, m), 3.96-4.22 (3H, m), 4.54-4.62 (0.25H, m), 4.74-4.92 (1H, m), 6.59-6.64 (2H, m), 6.79-6.85 (2H, m), 7.23-7.29 (1H, m), 7.71-7.85 (2H, m).

EXAMPLE 112

Production of 1-acetyl-4-[(4-morpholinophenyl)amino]-2-methyl-6-[1,3,4-oxadiazol-2(3H)-on-5-yl]-1,2,3,4-tetrahydroquinoline (Compound 134)

72 mg of 1-acetyl-4-[(4-morpholinophenyl)amino]-2-methyl-1,2,3,4-tetrahydroquinoline-6-carbohydrazide (compound 133) was dissolved in 4 mL of tetrahydrofuran, and 55 mg of N,N'-carbonyldiimidazole and 47 μL of triethylamine were added to the solution. The mixture was stirred overnight at room temperature. After completion of the reaction, water was added to the mixture, and the mixture was extracted three times with chloroform. The extraction product was washed with saturated brine, dehydrated over anhydrous sodium sulfate, and then concentrated under reduced pressure. The resulting residue was purified by using silica gel chromatography (ethyl acetate:hexane=5:1), and thus 57 mg (cis:trans=4:1, 75%) of the title compound was obtained as a pale green powder.

$^1$H-NMR (400 MHz, CDCl$_3$) δ: 1.17-1.32 (3.8H, m), 1.80-1.90 (0.2H, m), 2.42-2.52 (0.2H, m), 2.62-2.74 (0.8H, m), 3.56-3.61 (4H, m), 3.50-3.65 (0.8H, m), 3.83-3.89 (4H, m), 4.12-4.22 (1H, m), 4.55-4.61 (0.2H, m), 4.76-4.90 (1H, m), 6.61-6.67 (2H, m), 6.81-6.87 (2H, m), 7.26-7.28 (1H, m), 7.74-7.79 (1H, m), 7.87-7.91 (1H, m), 9.30-9.38 (1H, m).

EXAMPLE 113

Production of 1-acetyl-4-[(4-morpholinophenyl)amino]-N-methoxy-2-methyl-1,2,3,4-tetrahydroquinoline-6-carboxamide (Compound 135)

74 mg of 1-acetyl-4-[(4-morpholinophenyl)amino]-2-methyl-1,2,3,4-tetrahydroquinoline-6-carboxylic acid (compound of Step 3 of Example 111), 52 mg of WSCD.HCl, 37 mg of HOBt.H$_2$O, and 45 mg of methoxyamine hydrochloride were dissolved in 2 mL of dichloromethane, and 76 μL of triethylamine was added to the solution. The mixture was stirred overnight at room temperature. After completion of the reaction, a saturated aqueous solution of sodium hydrogen carbonate was added to the mixture, and the mixture was extracted three times with chloroform. The extraction product was washed with saturated brine, dehydrated over anhydrous sodium sulfate, and then concentrated under reduced pressure. The resulting residue was purified by using silica gel chromatography (methanol:chloroform=1:10), and thus 57 mg (cis:trans=4:1, 72%) of the title compound was obtained as a yellow solid.

$^1$H-NMR (400 MHz, CDCl$_3$) δ: 1.16-1.27 (3.8H, m), 1.82-1.92 (0.2H, m), 2.19-2.22 (3H, m), 2.32-2.48 (0.2H, m), 2.60-2.75 (0.8H, m), 3.50-3.62 (0.8H, m), 3.85-3.89 (7H, m), 4.08-4.24 (1H, m), 4.56-4.64 (0.2H, m), 4.76-4.92 (1H, m), 6.60-6.66 (2H, m), 6.82-6.87 (2H, m), 7.26-7.28 (1H, m), 7.64-7.81 (2H, m).

EXAMPLE 114

Production of 1-acetyl-4-[(benzoxazol-5-yl)amino]-2-methyl-1,2,3,4-tetrahydroquinoline (Compound 136)

[Step 1] 177 mg of 1-acetyl-4-oxo-2-methyl-1,2,3,4-tetrahydroquinoline and 77 mg of 5-aminobenzoxazole were dissolved in 2 mL of methylene chloride, and 0.32 mL of triethylamine and 0.57 mL of titanium tetrachloride (1.0 M dichloromethane solution) were added to the solution under ice cooling. The mixture was stirred for 16 hours at room temperature. After completion of the reaction, the reaction liquid was filtered through Celite, and was concentrated under reduced pressure. Thus, a crude product of 1-acetyl-4-[(benzoxazol-5-yl)imino]-2-methyl-1,2,3,4-tetrahydroquinoline was obtained as a pale brown solid.

[Step 2] The crude product of 1-acetyl-4-[(benzoxazol-5-yl)imino]-2-methyl-1,2,3,4-tetrahydroquinoline thus obtained was dissolved in methanol, and 216 mg of sodium cyanoborohydride and 69 mg of acetic acid were added to the solution under ice cooling. The mixture was stirred for one hour at the same temperature. The mixture was neutralized with a saturated aqueous solution of sodium hydrogen carbonate, and then was extracted with chloroform. The organic layer was washed with a saturated solution sodium hydrogen carbonate and saturated brine, dehydrated over anhydrous sodium sulfate, and then concentrated under reduced pressure. The resulting residue was purified by using silica gel chromatography (chloroform to chloroform:methanol=40:1), and thus 66 mg (cis:trans=3:1, 36%) of the title compound was obtained as a pale yellow amorphous substance.

$^1$H-NMR (400 MHz, CDCl$_3$) δ: 1.16 (2.25H, d, J=6.4 Hz), 1.20 (0.75H, d, J=6.4 Hz), 1.23-1.36 (1H, m), 2.16 (0.75H, s), 2.21 (2.25H, s), 2.57 (0.25H, ddd, J=4.6, 7.3, 13.9 Hz), 2.69 (0.75H, ddd, J=4.2, 8.8, 12.2 Hz), 3.95 (1H, br), 4.14-4.26 (0.75H, m), 4.58-4.62 (0.25H, m), 4.88-5.01 (1H, m), 6.66 (0.25H, dd, J=2.4, 8.8), 6.76 (0.75H, dd, J=2.4, 8.8 Hz), 6.93 (0.75H, d, J=2.4 Hz), 7.05 (0.25H, J=2.4 Hz), 7.14-7.22 (2H, m), 7.26-7.35 (2H, m), 7.38-7.44 (1H, m), 7.92 (0.25H, s), 7.99 (0.75H, s).

EXAMPLE 115

Production of 1-acetyl-6-fluoro-4-[(4-carboxyphenyl)amino]-2-methyl-1,2,3,4-tetrahydroquinoline (Compound 137)

[Step 1] 300 mg of 1-acetyl-6-fluoro-4-oxo-2-methyl-1,2,3,4-tetrahydroquinoline and 672 mg of ethyl 4-aminobenzoate were dissolved in 10 mL of toluene and 3 mL of dichloromethane, and 1.4 mL of titanium tetrachloride (1.0 M dichloromethane solution) was added to the solution under ice cooling. The mixture was stirred for 2.5 hours while the mixture was heated to reflux. After completion of the reaction, magnesium sulfate and diethyl ether were added to the reaction mixture, and the reaction mixture was stirred for 10 minutes. The reaction liquid was filtered through Celite, and then was concentrated under reduced pressure. Thus, 500 mg of a crude product of 1-acetyl-4-[(4-ethoxycarbonylphenyl)amino]-6-fluoro-2-methyl-1,2,3,4-tetrahydroquinoline was obtained.

[Step 2] 500 mg of the crude product of 1-acetyl-4-[(4-ethoxycarbonylphenyl)amino]-6-fluoro-2-methyl-1,2,3,4-tetrahydroquinoline was dissolved in 1.5 mL of ethanol, and 0.5 mL of a 4 N aqueous solution of sodium hydroxide was added to the solution under ice cooling. The mixture was stirred for 6 hours at room temperature, and then was stirred for 6.5 hours at 60° C. After completion of the reaction, the reaction liquid was washed with diethyl ether, and was adjusted to pH 6 with a 1 N aqueous solution of hydrochloric acid. Subsequently, the reaction liquid was extracted three times with chloroform. The extraction product was dehydrated over anhydrous sodium sulfate, and then was concentrated under reduced pressure. Thus, 160 mg (cis:trans=3:1, 87%) of 1-acetyl-4-[(4-carboxyphenyl)amino]-6-fluoro-2-methyl-1,2,3,4-tetrahydroquinoline was obtained as a yellow solid.

$^1$H-NMR (400 MHz, CD$_3$OD) δ: 1.13-1.25 (3H, m), 1.26-1.40 (0.75H, m), 1.75-1.88 (0.25H, m), 2.10-2.25 (3H, m), 2.42-2.54 (0.25H, m), 2.62-2.72 (0.75H, m), 4.28-4.34 (0.75H, m), 4.68-4.76 (0.25H, m), 4.80-4.93 (1H, m), 6.61-6.70 (2H, m), 6.88-6.92 (1H, m), 7.02-7.10 (1H, m), 7.25-7.31 (1H, m), 7.77-7.83 (2H, m).

EXAMPLE 116

Production of 1-acetyl-4-[(4-chlorophenyl)amino]-2-methyl-1,2,3,4-tetrahydroquinolin-6-ylboronic acid (Compound 138)

[Step 1] 150 mg (cis:trans=11:1) of 1-acetyl-6-bromo-4-[(4-chlorophenyl)amino]-2-methyl-1,2,3,4-tetrahydroquinoline and 116 mg of bis(pinacolato)diborane were dissolved in 2.5 mL of 1,4-dioxane. 27 mg of dichlorobis(triphenylphosphine)palladium and 112 mg of potassium acetate were added to the solution, and the mixture was stirred in a sealed tube for 3 hours at 90° C. After completion of the reaction, water was added to the reaction mixture, and the mixture was extracted three times with ethyl acetate. The extraction product was washed with saturated brine, dehydrated over anhydrous sodium sulfate, and then concentrated under reduced pressure. The resulting residue was purified by using silica gel chromatography (ethyl acetate:hexane=1:2), and 132 mg (yield 79%) of 1-acetyl-4-[(4-chlorophenyl)amino]-2-methyl-6-(4,4,5,5-tetramethyl-1,3,2-dioxaboran-2-yl)-1,2,3,4-tetrahydroquinoline was obtained as a pale brown oily substance.

[Step 2] 132 mg of 1-acetyl-4-[(4-chlorophenyl)amino]-2-methyl-6-(4,4,5,5-tetramethyl-1,3,2-dioxaboran-2-yl)-1,2,3,4-tetrahydroquinoline was dissolved in 6 mL of acetone and 3 mL of water, and ammonium acetate and sodium periodate were added to the solution. The mixture was stirred overnight at room temperature. After completion of the reaction, water was added to the reaction mixture, and the mixture was extracted three times with ethyl acetate. The extraction product was washed with sodium thiosulfate and saturated brine, dehydrated over anhydrous sodium sulfate, and then concentrated under reduced pressure. The resulting residue was purified by using silica gel chromatography (ethyl acetate:hexane=1:2), and then was recrystallized from ethyl acetate-hexane. Thus, 23 mg (cis:trans=20:1, yield 21%) of the title compound was obtained as a white crystalline powder.

$^1$H-NMR (400 MHz, CDCl$_3$) δ: 1.15-1.35 (3.95H, m), 1.60-1.75 (0.05H, m), 2.18-2.25 (3H, m), 2.45-2.55 (0.05H, m), 2.60-2.78 (0.95H, m), 3.80-4.05 (1H, m), 4.12-4.32 (0.95H, m), 4.65-4.75 (0.05H, m), 4.83-4.91 (1H, m), 6.57-6.68 (2H, m), 7.09-7.32 (4H, m), 7.61-7.80 (1H, m).

EXAMPLE 117

Production of 1-acetyl-2-methyl-4-(4-morpholinophenoxy)-1,2,3,4-tetrahydroquinoline-6-carboxylic acid (Compound 139)

[Step 1] 2.75 g of ethyl (S)-1-acetyl-2-methyl-4-oxo-1,2,3,4-tetrahydroquinoline-6-carboxylate was dissolved in 50 mL of tetrahydrofuran, and 4.10 g of cerium(III) chloride heptahydrate and 416 mg of sodium borohydride were slowly added to the solution at 0° C. The mixture was stirred for 3 hours at room temperature. After completion of the reaction, an aqueous solution of ammonium chloride was added to the reaction mixture, and the mixture was extracted three times with ethyl acetate. The extraction product was washed with saturated brine, dehydrated over anhydrous sodium sulfate, and then concentrated under reduced pressure. The resulting residue was purified by using silica gel chromatography (hexane:ethyl acetate=3:1→1:1), and thus 1.70 g (61.3%, cis-form only) of ethyl (2S,4R)-1-acetyl-4-hydroxy-2-methyl-1,2,3,4-tetrahydroquino line-6-carboxylate was obtained as a pale yellow oily substance.

[Step 2] 906.1 mg of ethyl (2S,4R)-1-acetyl-4-hydroxyl-2-methyl-1,2,3,4-tetrahydroquinoline-6-carboxylate, 798.1 mg of benzoic acid, and 1.13 g of 1,1'-azobis(N,N-dimethylformamide) were purged with argon, and then were dissolved in 10 mL of toluene in an argon atmosphere. 1.61 mL of tributylphosphine was added dropwise to the solution. The mixture was stirred for 6 hours at 60° C., and then water was added to the reaction liquid. The mixture was extracted three times with ethyl acetate. The extraction product was washed with saturated brine, dehydrated over anhydrous sodium sulfate, and then concentrated under reduced pressure. The resulting residue was purified by using silica gel chromatography (hexane:ethyl acetate=4:1→2:1), and thus 1.02 g of ethyl (2S,4S)-1-acetyl-4-benzoyloxy-2-methyl-1,2,3,4-tetrahydroquinoline-6-carboxylate (including 21% of ethyl (S)-1-acetyl-2-methyl-1,2-dihydroquinoline-6-carboxylate) was obtained as a pale yellow oily substance.

[Step 3] 1.02 g of ethyl (2S,4S)-1-acetyl-4-benzoyloxy-2-methyl-1,2,3,4-tetrahydroquinoline-6-carboxylate was dissolved in 10 mL of ethanol, and 1.11 g of potassium carbonate was slowly added to the solution. The mixture was stirred for 18 hours at 50° C., subsequently solids were filtered off, and the filtrate was washed two times with chloroform. The filtrate was concentrated under reduced pressure, and the resulting residue was purified by using silica gel chromatography (hexane:ethyl acetate=2:1→1:2). Thus, 346 mg (38.2%, 2 steps) of ethyl (2S,4S)-1-acetyl-4-hydroxyl-2-methyl-1,2,3,4-tetrahydroquinoline-6-carboxylate was obtained as a pale yellow oily substance.

[Step 4] Reactions and treatments were carried out in the same manner as in Step 2 of Example 117, using 89.3 mg of ethyl (2S,4S)-1-acetyl-4-hydroxyl-2-methyl-1,2,3,4-tetrahydroquinoline-6-carboxylate instead of ethyl (2S,4R)-1-acetyl-4-hydroxyl-2-methyl-1,2,3,4-tetrahydroquinoline-6-carboxylate, and 4-nitrophenol was used instead of benzoic acid. Thus, 73.6 mg (57.4%) of ethyl (2S,4R)-1-acetyl-2-methyl-4-(4-nitrophenoxy)-1,2,3,4-tetrahydroquinoline-6-carboxylate was obtained as a white solid.

[Step 5] 73.6 mg of ethyl (2S,4R)-1-acetyl-2-methyl-4-(4-nitrophenoxy)-1,2,3,4-tetrahydroquinoline-6-carboxylate was dissolved in 2 mL of methanol, and 18.4 mg of palladium-carbon was added to the solution. The mixture was purged with hydrogen, and then was stirred for 3 hours at room temperature. After completion of the reaction, the reaction mixture was filtered through Celite, and the filtrate was concentrated under reduced pressure. The resulting residue was purified by using silica gel chromatography (hexane:ethyl acetate=1:1), and thus 66.1 mg (96.9%) of ethyl (2S,4S)-1-acetyl 4-(4-aminophenoxy)-2-methyl-1,2,3,4-tetrahydroquinoline-6-carboxylate was obtained as a pale yellow oily substance.

(Step 6) 66.1 mg of ethyl (2S,4S)-1-acetyl-4-(4-aminophenoxy)-2-methyl-1,2,3,4-tetrahydroquinoline-6-carboxylate was dissolved in 2 mL of toluene, and 312 μL of N,N-diisopropylethylamine and 113 μL of 2-bromoethyl ether were added to the solution at 0° C. The mixture was heated to reflux for 14 hours. After completion of the reaction, the reaction liquid was cooled, water was added thereto, and the mixture was extracted three times with chloroform. The extraction product was washed with saturated brine, dehydrated over anhydrous sodium sulfate, and then concentrated under reduced pressure. The resulting residue was purified by using silica gel chromatography (hexane:ethyl acetate=1:1), and thus 59.4 mg (75.7%) of ethyl (2S,4S)-1-acetyl-2-methyl-4-(4-morpholinophenoxy)-1,2,3,4-tetrahydroquinoline-6-carboxylate was obtained as a pale yellow oily substance.

[Step 7] 59.4 mg of ethyl (2S,4S)-1-acetyl-2-methyl-4-(4-morpholinophenoxy)-1,2,3,4-tetrahydroquinoline-6-carboxylate was dissolved in 1 mL of ethanol, and 163 μL of 4 N sodium hydroxide was added to the solution. The mixture was stirred for 4 hours at room temperature. After completion of the reaction, the reaction liquid was adjusted to pH 7 with 1 N hydrochloric acid, and then was extracted three times with chloroform-methanol. The extraction product was dehydrated over anhydrous sodium sulfate, and then was concentrated under reduced pressure. The resulting residue was purified by using silica gel chromatography (chloroform:methanol=10:1), and thus 51.7 mg (93.3%, cis:trans=14:1) of the title compound was obtained as a pale peach-colored amorphous substance.

$^1$H-NMR (400 MHz, CDCl$_3$) δ: 1.21 (3H, d, J=6.4 Hz), 1.54-1.62 (1H, m), 2.24 (3H, s), 2.73 (1H, ddd, J=4.9, 7.8, 12.9 Hz), 3.06 (0.28H, t, J=4.8 Hz), 3.11 (3.72H, t, J=4.8 Hz), 3.83-3.90 (4H, m), 4.81-84 (0.93H, m), 4.91-4.96 (0.07H, m), 5.03 (0.93H, dd, J=4.5, 9.9 Hz), 5.28-5.29 (0.07H, m), 6.95 (4H, dd, J=9.3, 19.0 Hz), 7.29-7.31 (1H, m), 8.04-8.10 (1H, m), 8.28 (1H, s).

EXAMPLE 118

Production of 1-acetyl-N,2-dimethyl-4-(4-morpholinophenoxy)-1,2,3,4-tetra hydroquinoline-6-carboxamide (Compound 140)

48.6 my of (2S,4R)-1-acetyl-2-methyl-4-(4-morpholinophenoxy)-1,2,3,4-tetrahydroquinoline-6-carboxylic acid, 27.2 mg of WSCD.HCl, and 24.6 mg of HOBt.H$_2$O were dissolved in 1 mL of dichloromethane, and the solution was stirred for 1.5 hours at room temperature. 178 μL of monomethylamine (2.0M tetrahydrofuran solution) was added to the reaction liquid, and the mixture was stirred for another 1.5 hours at room temperature. After completion of the reaction, water was added to the reaction mixture, and the mixture was extracted three times with chloroform. The extraction product was washed with saturated brine, dehydrated over anhydrous sodium sulfate, and then concentrated under reduced pressure. The resulting residue was purified by using silica gel chromatography (chloroform:methanol=10:1), and then was recrystallized from chloroform-hexane. Thus, 27.2 mg (53.3%, cis:trans=15:1) of the title compound was obtained as a white crystalline powder.

$^1$H-NMR (400 MHz, CDCl$_3$) δ: 1.18 (3H, d, J=6.4 Hz), 1.50-1.52 (0.92H, m), 1.60-1.66 (0.08H, m), 2.15 (0.24H, s), 2.19 (2.76H, s), 2.72 (0.92H, ddd, J=4.9, 8.2, 12.8 Hz), 2.79-2.83 (0.08H, m), 3.00 (3H, d, J=4.9 Hz), 3.09 (4H, t, J=4.6 Hz), 3.82-3.88 (4H, t, m), 4.79-4.81 (0.92H, m), 4.88-4.92 (0.08H, m), 4.99 (0.92H, dd, J=4.6, 10.2 Hz), 5.25 (0.08H, t, J=3.8 Hz), 6.26-6.27 (1H, m), 6.81-6.85 (0.32H, m), 6.89-6.96 (3.68H, m), 7.25-7.30 (1H, m), 7.69 (0.08H, dd, J=2.0, 8.3 Hz), 7.76 (0.08H, d, J=2.0 Hz), 7.76-7.82 (0.92H, m), 7.85-7.86 (0.92H, m).

EXAMPLE 119

Production of 1-acetyl-4-(4-chlorophenoxy)-2-methyl-1,2,3,4-tetrahydroquinoline-6-carboxylic acid (Compound 141)

[Step 1] Reactions and treatments were carried out in the same manner as in Step 2 of Example 117, using 104.9 mg of 4-chlorophenol instead of benzoic acid. Thus, 106.5 mg (72.6%) of ethyl (2S,4R)-1-acetyl-4-(4-chlorophenoxy)-2-methyl-1,2,3,9-tetrahydroquinoline-6-carboxylate was obtained as a white solid.

[Step 2] Reactions and treatments were carried out in the same manner as in Step 7 of Example 117, using 111.9 mg of ethyl (2S,4R)-1-acetyl-4-(4-chlorophenoxy)-2-methyl-1,2,3,4-tetra hydroquinoline-6-carboxylate instead of ethyl (2S,4S)-1-acetyl-2-methyl-4-(4-morpholinophenoxy)-1,2,3,4-tetrahydroquinoline-6-carboxylate. The product was recrystallized from ethanol-hexane, and thus 58.5 mg (72.6%, cis:trans=14:1) of the title compound was obtained as a white crystalline powder.

$^1$H-NMR (400 MHz, CDCl$_3$) δ: 1.22 (3H, d, J=6.3 Hz), 1.58-1.65 (1H, m), 2.25 (3H, s), 2.74 (1H, ddd, J=4.9, 7.9, 12.8 Hz), 4.84-4.86 (1H, m), 5.08 (1H, dd, J=4.8, 9.9 Hz), 6.79 (0.16H, d, J=8.5 Hz), 6.95 (1.84H, d, J=8.8 Hz), 7.18 (0.16H, d, J=8.8 Hz), 7.27-7.34 (2.92H, m), 8.09 (1H, d, J=8.1 Hz), 8.20 (1H, s).

EXAMPLE 120

Production of (2S,4R)-1-acetyl-4-(4-chlorophenoxy)-2-methyl-1,2,3,4-tetra hydroquinoline-6-carboxamide (Compound 142)

Reactions and treatments were carried out in the same manner as in Example 118, using 41.1 mg of (2S,4R)-1-acetyl-4-(4-chlorophenoxy)-2-methyl-1,2,3,4-tetra hydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 58.5 mg (95.6%, cis-form only) of the title compound was obtained as a white crystalline powder.

$^1$H-NMR, (400 MHz, CDCl$_3$) δ: 1.20 (3H, d, J=6.3 Hz), 1.57-1.66 (1H, m), 2.22 (3H, s), 2.73 (1H, ddd, J=4.9, 8.1, 12.8 Hz), 4.82-4.84 (1H, m), 5.06 (1H, dd, J=4.8, 10.1 Hz), 5.92 (2H, d, J=116 Hz), 6.92-6.95 (2H, m) 7.26-7.30 (3H, m), 7.83 (1H, dd, J=2.1, 8.2 Hz), 7.87 (1H, s).

EXAMPLE 121

Production of N-{4-[(2S,4R)-(1-acetyl-2-methyl-1,2,3,4-tetrahydroquinolin-4-yl)oxy]phenyl}methanesulfonamide (Compound 143)

[Step 1] Reactions and treatments were carried out in the same manner as in Step 2 of Example 117, using 102.6 g of (2S,4R)-1-acetyl-4-hydroxyl-2-methyl-1,2,3,4-tetrahydroquinoline instead of ethyl (2S,4R)-1-acetyl-4-hydroxyl-2-methyl-1,2,3,4-tetrahydroquinoline-6-carboxylate, and using 4-nitrophenol instead of benzoic acid. Thus, 118.2 mg (72.4%) of (2S,4R)-1-acetyl-2-methyl-4-(4-nitrophenoxy)-1,2,3,4-tetrahydroquinoline was obtained as a pale yellow amorphous substance.

[Step 2] Reactions and treatments were carried out in the same manner as in Step 5 of Example 117, using 118.2 mg of (2S,4S)-1-acetyl-4-hydroxyl-2-methyl-1,2,3,4-tetrahydroquinoline instead of ethyl (2S,4R)-1-acetyl-2-methyl-4-(4-nitrophenoxy)-1,2,3,4-tetrahydroquinoline-6-carboxylate.

Thus, 69.6 mg (64.9%) of (2S,4R)-1-acetyl-4-(4-aminophenoxy)-2-methyl-1,2,3,4-tetrahydroquinoline was obtained as a pale yellow amorphous substance.

[Step 3] (2S,4R)-1-acetyl-4-(4-aminophenoxy)-2-methyl-1,2,3,4-tetrahydroquinoline was dissolved in 2 mL of dichloromethane, and 28.4 μL of pyridine and 19.1 μL of methanesulfonyl chloride were added to the solution at 0° C. The mixture was stirred for 2 hours at 0° C. After completion of the reaction, the reaction mixture was diluted with chloroform, and then was washed with 1 N hydrochloric acid, a saturated aqueous solution of sodium hydrogen carbonate, and saturated brine. Subsequently, the resultant was dehydrated over anhydrous sodium sulfate, and then was concentrated under reduced pressure. The resulting residue was purified by using silica gel chromatography (hexane:acetone=2:1), and then was recrystallized from chloroform-hexane. Thus, 28.2 mg (32.0%, cis-form only) of the title compound was obtained as a pale peach-colored amorphous compound.

$^1$H-NMR (400 MHz, CDCl$_3$) δ: 1.19 (3H, d, J=6.4 Hz), 1.52-1.55 (1H, m), 2.20 (3H, s), 2.75 (1H, ddd, J=4.8, 8.2, 12.8 Hz), 2.98 (3H, s), 4.89 (1H, brs), 4.99 (1H, dd, J=4.5, 10.5 Hz), 6.87 (1H, brs), 6.97-7.00 (2H, m), 7.16-7.19 (1H, m), 7.23-7.26 (3H, m), 7.29-7.35 (1H, m), 7.42 (1H, d, J=7.6 Hz).

EXAMPLE 122

Production of ethyl 1-acetyl-4-[(4-cyclohexylphenyl)amino]-2-methyl-1,2,3,4-tetrahydroquinoline-6-carboxylate (Compound 144)

[Step 1] 275.3 mg of ethyl (S)-1-acetyl-2-methyl-4-oxo-1,2,3,4-tetrahydroquinoline-6-carboxylate and 525.8 mg of 4-cyclohexylaniline were dissolved in 15 mL of toluene, and 1.0 mL of titanium tetrachloride (1.0 M dichloromethane solution) was added to the solution under ice cooling. The mixture was heated to reflux for 6 hours. After completion of the reaction, ethyl acetate and 360 mg of magnesium sulfate were added to the reaction mixture, and the mixture was stirred for 10 minutes. Subsequently, the reaction liquid was filtered through Celite and concentrated under reduced pressure. Thus, 454.7 mg of a crude product was obtained.

[Step 2] 454.7 mg of the crude product was dissolved in 5 mL of acetic acid, and 635.8 mg of sodium cyanoborohydride was added to the solution. The mixture was stirred for one hour at room temperature. After completion of the reaction, water was added to the mixture, and the mixture was extracted three times with ethyl acetate. The extraction product was washed with a saturated aqueous solution of sodium hydrogen carbonate and saturated brine, dehydrated over anhydrous sodium sulfate, and then concentrated under reduced pressure. The resulting residue was purified by using silica gel chromatography (ethyl acetate:hexane=2:1→1:2), and thus 350.5 mg (80.7%, 2 steps, cis:trans=10:1) of the title compound was obtained as a pale yellow amorphous substance.

$^1$H-NMR (400 MHz, CDCl$_3$) δ: 1.17 (3H, d, J=6.4 Hz), 1.20-1.30 (8.9H, m), 1.81-1.89 (5.1H, m), 2.20 (3H, s), 2.36-2.48 (1.1H, m), 2.68 (0.9H, ddd, J=4.3, 8.4, 12.6 Hz), 3.68 (1H, d, J=7.6 Hz), 4.22-4.25 (0.9H, m), 4.34 (2H, q, J=6.0 Hz), 4.63-4.66 (0.1H, m), 4.81-4.87 (1H, m), 6.60-6.63 (2H, m), 7.01-7.07 (2H, m), 7.21 (0.9H, d, J=7.1 Hz), 7.31 (0.1H, d, J=8.0 Hz), 7.94-7.99 (1H, m), 8.08 (0.9H, s) 8.11 (0.1H, d, J=1.7 Hz).

EXAMPLE 123

Production of 1-acetyl-4-[(4-cyclohexylphenyl)amino]-2-methyl-1,2,3,4-tetrahydroquinoline-6-carboxylic acid (Compound 145)

Reactions and treatments were carried out in the same manner as in Step 7 of Example 117, using 307.7 mg of ethyl (2S,4R)-1-acetyl-4-[(4-cyclohexylphenyl)amino]-2-methyl-1,2,3,4-tetrahydroquinoline-6-carboxylate instead of ethyl (2S,4S)-1-acetyl-2-methyl-4-(4-morpholinophenoxy)-1,2,3,4-tetrahydroquinoline-6-carboxylate, and the product was recrystallized from ethyl acetate-hexane. Thus, 233.8 mg (81.2%, cis:trans=10:1) of the title compound was obtained as a pale orange-colored crystalline powder.

$^1$H-NMR (400 MHz, CDCl$_3$) δ: 1.18 (3H, d, J=6.4 Hz), 1.21-1.42 (5.9H, m), 1.78-1.43 (5.1H, m), 2.22 (3H, s), 2.36-2.48 (1.1H, m), 2.69 (0.9H, ddd, J=4.4, 8.5, 12.6 Hz), 4.22 (0.9H, dd, J=3.9, 11.7 Hz), 4.63-4.67 (0.1H, m), 4.78-4.90 (1H, m), 6.61 (2H, d, J=8.5 Hz), 6.69-7.06 (2H, m), 7.24-7.30 (1H, m), 8.00-8.05 (1H, m), 8.12 (0.9H, s), 8.16 (0.1H, s).

EXAMPLE 124

Production of 1-acetyl-4-[(4-cyclohexylphenyl)amino]-N,2-dimethyl-1,2,3,4-tetrahydroquinoline-6-carboxamide (Compound 146)

Reactions and treatments were carried out in the same manner as in Example 118, using 112.0 mg of (2S,4R)-1-acetyl-4-[(4-cyclohexylphenyl)amino]-2-methyl-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid. Thus, 94.4 mg (72.9%, cis:trans=10:1) of the title compound was obtained as a white crystalline powder.

$^1$H-NMR (400 MHz, CDCl$_3$) δ: 1.15 (3H, d, J=6.4 Hz), 1.19-1.41 (5.9H, m), 1.81-1.85 (5.1H, m), 2.19 (2.7H, s), 2.21 (0.3H, s), 2.33-2.41 (1.1H, m), 2.66 (0.9H, ddd, J=4.1, 8.5, 12.4 Hz), 2.96 (2.7H, d, J=4.6 Hz), 2.99 (0.3H, d, J=4.9 Hz), 3.64-3.74 (1H, m), 4.17 (0.9H, dd, J=3.9, 12.0 Hz), 4.63 (0.1H, t, J=5.6 Hz), 4.82-4.85 (1H, m), 6.14 (1H, m), 6.59 (2H, d, J=8.5 Hz), 7.01-7.06 (2H, m), 7.21 (0.9H, d, J=8.1 Hz), 7.32 (0.1H, d, J=8.6 Hz), 7.67-7.71 (1H, m), 7.78 (0.9H, dd, J=2.1, 8.2 Hz) 7.85 (0.1H, d, J=1.7 Hz).

EXAMPLE 125

Production of 1-acetyl-4-[(4-cyclohexylphenyl)amino]-2-methyl-1,2,3,4-tetrahydroquinoline-6-carboxamide (Compound 147)

Reactions and treatments were carried out in the same manner as in Example 118, using 129.6 mg of (2S,4R)-1-acetyl-4-[(4-cyclohexylphenyl)amino]-2-methyl-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 94.4 mg (72.9%, cis:trans=10:1) of the title compound was obtained as a white crystalline powder.

$^1$H-NMR (400 MHz, CDCl$_3$) δ: 1.16 (3H, d, J=6.1 Hz), 1.21-1.42 (5.9H, m), 1.81-1.88 (5.1H, m), 2.20 (2.7H, s), 2.22 (0.3H, s), 2.37-2.41 (1.1H, m), 2.67 (0.9H, ddd, J=4.4, 8.6, 12.6 Hz), 3.70-3.80 (1H, m), 4.28-4.20 (0.9H, m), 4.64 (0.1H, t, J=5.4 Hz), 4.83-4.85 (1H, m), 5.99 (2H, d, J=91.2 Hz), 6.60 (2H, d, J=8.6 Hz), 7.01-7.06 (2H, m), 7.24 (0.9H, d, J=7.8 Hz), 7.34 (0.1H, d, J=8.3 Hz), 7.72-7.91 (2H, m).

EXAMPLE 126

Production of tert-butyl 12-{(2S,4R)-1-acetyl-4-[(4-chlorophenyl)amino]-2-methyl-1,2,3,4-tetrahydroquinoline-6-carboxamido}-4,7,10-trioxadodecanoate (Compound 148)

Reactions and treatments were carried out in the same manner as in Example 110, using 29 mg of (2S)-1-acetyl-4-[(4-chlorophenyl)amino]-2-methyl-1,2,3,4-tetrahydroquinoline-6-carboxylic acid and 44 mg of tert-butyl 12-amino-4,7,10-trioxadodecanoate. Thus, 51 mg (100%) of the title compound was obtained as a colorless oily substance.

$^1$H-NMR (400 MHz, CDCl$_3$) δ: 1.16 (3H, d, J=6.4 Hz), 1.20-1.31 (1H, m), 1.42 (9H, s), 2.20 (3H, s), 2.46 (2H, t, J=6.5 Hz), 2.68 (1H, ddd, J=4.1, 8.5, 12.4 Hz), 3.55-3.69 (14H, m), 4.10-4.15 (1H, m), 4.16-4.24 (1H, m), 4.80-4.90 (1H, m), 6.59 (2H, d, J=8.8 Hz), 7.00 (1H, brs), 7.11-7.16 (2H, m), 7.21 (1H, d, J=8.0 Hz), 7.75 (1H, s), 7.78 (1H, dd, J=1.7, 8.1 Hz).

EXAMPLE 127

Production of tert-butyl 12-{(2S,4R)-1-acetyl-2-methyl-4-[(4-morpholinophenyl)amino]-1,2,3,4-tetrahydroquinoline-6-carboxamido}-4,7,10-trioxadodecanoate (Compound 149)

Reactions and treatments were carried out in the same manner as in Example 110; using 29 mg of (2S)-1-acetyl-2-methyl-4-[(4-morpholinophenyl)amino]-1,2,3,4-tetrahydroquinoline-6-carboxylic acid and 40 mg of tert-butyl 12-amino-4,7,10-trioxadodecanoate. Thus, 33 mg (69%) of the title compound was obtained as a colorless oily substance.

$^1$H-NMR (400 MHz, CDCl$_3$) δ: 1.15 (3H, d, J=6.4 Hz), 1.18-1.27 (1H, m), 1.42 (9H, s), 2.19 (3H, s), 2.46 (2H, t, J=6.5 Hz), 2.68 (1H, ddd, J=4.3, 8.6, 12.4 Hz), 2.99-3.07 (4H, m), 3.55-3.70 (14H, m), 3.86 (4H, t, J=4.8 Hz), 4.14-4.22 (1H, m), 4.79-4.88 (1H, m), 6.65 (2H, d, J=8.5 Hz), 6.84 (2H, d, J=8.5 Hz), 6.97 (1H, brs), 7.21 (1H, d, J=8.1 Hz), 7.77 (1H, dd, J=1.7, 8.1 Hz), 7.84 (1H, s).

EXAMPLE 128

Production of 4-{4-{(2S,4R)-1-acetyl-4-[(4-chlorophenyl)amino]-2-methyl-1,2,3,4-tetrahydroquinoline-6-carboxamido}phenyl}methyl butanoate (Compound 150)

Reactions are treatments were carried out in the same manner as in Example 110, using 24 mg of (2S)-1-acetyl-4-[(4-chlorophenyl)amino]-2-methyl-1,2,3,4-tetrahydroquinoline-6-carboxylic acid and 17 mg of 4-aminophenyl-4-methyl butanoate. Thus, 24 mg (66%) of the title compound was obtained as a colorless oily substance.

$^1$H-NMR (400 MHz, CDCl$_3$) δ: 1.18 (3H, d, J=6.3 Hz), 1.21-1.35 (1H, m), 1.89-1.97 (2H, m), 2.22 (3H, s), 2.32 (2H, t, J=7.4 Hz), 2.59-2.72 (3H, m), 3.66 (3H, s), 3.92 (1H, d, J=7.6 Hz), 4.15-4.25 (1H, m), 4.80-4.92 (1H, m), 6.57 (2H, d, J=8.6 Hz), 7.15 (2H, dd, J=6.6, 8.6 Hz), 7.23-7.28 (1H, m), 7.48 (1H, d, J=8.3 Hz), 7.77 (1H, s), 7.78-7.83 (1H, m).

EXAMPLE 129

Production of 4-(4-{(2S,4R)-1-acetyl-2-methyl-4-[(4-morpholinophenyl)amino]-1,2,3,4-tetrahydroquinoline-6-carboxamido}phenyl)methyl butanoate (Compound 151)

Reactions and treatments were carried out in the same manner as in Example 110, using 28 mg of (2S)-1-acetyl-2-methyl-4-[(4-morpholinophenyl)amino]-1,2,3,4-tetrahydroquinoline-6-carboxylic acid and 17 mg of 4-aminophenyl-4-methyl butanoate. Thus, 27 mg (68%) of the title compound was obtained as a colorless oilyl substance.

$^1$H-NMR (400 MHz, CDCl$_3$) δ: 1.18 (3H, d, J=6.4 Hz), 1.20-1.33 (1H, m), 1.89-1.98 (2H, m), 2.21 (3H, s), 2.32 (2H, t, J=7.5 Hz), 2.60-2.75 (3H, m), 2.95-3.15 (4H, brs), 3.67 (3H, s), 3.82-3.88 (4H, m), 4.20 (1H, brs), 4.80-4.90 (1H, m), 6.65 (1H, brs), 6.85 (1H, brs), 7.16 (2H, d, J=8.3 Hz), 7.23-7.28 (2H, m), 7.49 (1H, d, J=8.3 Hz), 7.74-7.77 (1H, m), 7.80-7.85 (2H, m).

EXAMPLE 130

Production of (2S,4R)-1-acetyl-4-(4-chlorophenoxy)-2-methyl-6-morpholino-1,2,3,4-tetrahydroquinoline (Compound 152)

[Step 1] Reactions are treatments were carried out in the same manner as in Step 2 of Example 117, using 145.2 mg of (2S,4R)-1-acetyl-4-hydroxyl-2-methyl-6-morpholino-1,2,3,4-tetrahydroquinoline instead of ethyl (2S,4R)-1-acetyl-4-hydroxyl-2-methyl-1,2,3,4-tetrahydroquinoline-6-carboxylate. Thus, 180.6 mg of (2S,4S)-1-acetyl-2-methyl-6-morpholino-1,2,3,4-tetrahydroquinolin-4-yl benzoate (including 14% of (S)-1-acetyl-2-methyl-6-morpholinoquinoline) was obtained as a white solid.

[Step 2] 180.6 mg of (2S,4S)-1-acetyl-2-methyl-6-morpholino-1,2,3,4-tetrahydroquinolin-4-yl benzoate was dissolved in 2 mL of ethanol, and 30.7 mg of sodium ethoxide was added to the solution. The mixture was stirred for 2 hours at room temperature. After completion of the reaction, the reaction mixture was concentrated under reduced pressure, water was added thereto, and the mixture was extracted three times with ethyl acetate. The extraction product was washed with saturated brine, dehydrated over anhydrous sodium sulfate, and then concentrated under reduced pressure. The resulting residue was purified by using silica gel chromatography (ethyl acetate:hexane=1:2). Thus, 97.8 mg (67.4%) of (2S,4S)-1-acetyl-4-hydroxyl-2-methyl-6-morpholino-1,2,3,4-tetrahydroquinoline was obtained as a white solid.

[Step 3] Reactions and treatments were carried out in the same manner as in Step 2 of Example 117, using 97.8 mg of (2S,4S)-1-acetyl-4-hydroxyl-2-methyl-6-morpholino-1,2,3,4-tetrahydroquinoline instead of ethyl (2S,4R)-1-acetyl-4-hydroxyl-2-methyl-1,2,3,4-tetrahydroquinoline-6-carboxylate, and 86.6 mg of 4-chlorophenol instead of benzoic acid. Thus, 73.6 mg (54.4%) of the title compound was obtained as a white amorphous substance.

$^1$H-NMR (400 MHz, CDCl$_3$) δ: 1.16 (3H, d, J=6.3 Hz), 1.40-1.52 (1H, m), 2.16 (3H, s), 2.73 (1H, ddd, J=4.6, 8.3., 12.6 Hz), 3.08-3.19 (4H, m), 3.84 (4H, t, J=4.8 Hz), 4.88 (1H, brs), 4.97 (1H, dd, J=3.9, 10.5 Hz), 6.83 (1H, dd, J=2.6, 8.7 Hz), 6.92-6.95 (3H, m), 7.04 (1H, brs), 7.25-7.29 (2H, m).

EXAMPLE 131

Production of ethyl 1-acetyl-2-methyl-4-{[4-(tetrahydro-2H-pyran-4-yl)phenyl]amino}-1,2,3,4-tetrahydroquinoline-6-carboxylate (Compound 153)

Reactions and treatments were carried out in the same manner as in Example 122, using 319.0 mg of 4-tetrahydro-2H-pyran-4-yl)aniline instead of 4-cyclohexylaniline. Thus, 218.1 mg (83.3%, 2 steps, cis:trans=9:1) of the title compound was obtained as a pale yellow amorphous substance.

$^1$H-NMR (400 MHz, CDCl$_3$) δ: 1.17 (3H, d, J=6.4 Hz), 1.21-1.28 (0.9H, m), 1.34 (3H, t, J=7.1 Hz), 1.74-1.88 (4.1H, m), 2.20 (2.7H, s), 2.22 (0.3H, s), 2.39-2.49 (0.1H, m), 2.62-2.72 (1.9H, m), 3.48-3.55 (2H, m), 3.76 (1H, brs), 4.04-4.09 (2H, m), 4.23-4.25 (0.9H, m), 4.34 (2H, q, J=5.9 Hz), 4.65 (0.1H, t, J=5.3 Hz), 4.82-4.89 (1H, m), 6.62-6.65 (2H, m), 7.04-7.08 (2H, m), 7.22 (0.9H, d, J=8.1 Hz), 7.32 (0.1H, d, J=8.3 Hz), 7.95-8.00 (1H, m), 8.06 (0.9H, s) 8.11 (0.1H, d, J=2.0 Hz).

EXAMPLE 132

Production of 1-acetyl-2-methyl-4-{[4-(tetrahydro-2H-pyran-4-yl)phenyl]amino}-1,2,3,4-tetrahydroquinoline-6-carboxylic acid (Compound 154)

Reactions and treatments were carried out in the same manner as in Step 7 of Example 117, using 178.4 mg of ethyl (2S,4R)-1-acetyl-2-methyl-4-{[4-(tetrahydro-2H-pyran-4-yl)phenyl]amino}-1,2,3,4-tetrahydroquinoline-6-carboxylate instead of ethyl (2S,4S)-1-acetyl-2-methyl-4-(4-morpholinophenoxy)-1,2,3,4-tetrahydroquinoline-6-carboxylate, and the product was recrystallized from ethyl acetate-hexane. Thus, 120.4 mg (71.9%, cis:trans=9:1) of the title compound was obtained as a white crystalline powder.

$^1$H-NMR (400 MHz, CDCl$_3$) δ: 1.19 (3H, d, J=6.1 Hz), 1.23-1.28 (0.9H, m), 1.75-1.84 (4.1H, m), 2.23 (3H, s), 2.45-2.49 (0.1H, m), 2.64-2.72 (1.9H, m), 3.49-3.56 (2H, m), 4.07-4.10 (2H, m), 4.21-4.25 (0.9H, m), 4.64-4.68 (0.1H, m), 4.85-4.87 (1H, m), 6.63 (2H, d, J=8.0 Hz), 7.03-7.08 (2H, m), 7.25-7.26 (0.9H, m), 7.36 (0.1H, d, J=8.8 Hz), 8.01-8.06 (1H, m), 8.11 (0.9H, s) 8.17 (0.1H, s).

EXAMPLE 133

Production of 1-acetyl-N,2-dimethyl-4-{[4-(tetrahydro-2H-pyran-4-yl)phenyl]amino}-1,2,3,4-tetrahydroquinoline-6-carboxamide (Compound 155)

Reactions and treatments were carried out in the same manner as in Example 118, using 51.5 mg of (2S,4R)-1-acetyl-2-methyl-4-{[4-(tetrahydro-2H-pyran-4-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid. Thus, 40.5 mg (76.3%, cis:trans=9:1) of the title compound was obtained as a white crystalline powder.

$^1$H-NMR (400 MHz, CDCl$_3$) δ: 1.16 (2.7H, d, J=6.3 Hz), 1.21 (0.3H, d, J=6.6 Hz), 1.23-1.31 (0.9H, m), 1.71-1.87 (4.1H, m), 2.19 (2.7H, s), 2.21 (0.3H, s), 2.35-2.44 (0.1H, m), 2.62-2.70 (1.9H, m), 2.96 (2.7H, d, J=4.9 Hz), 2.99 (0.3H, d, J=4.9 Hz), 3.47-3.54 (2H, m), 3.81 (1H, brs), 4.05-4.09 (2H, m), 4.16-4.20 (0.9H, m), 4.64 (0.1H, t, J=5.5 Hz), 4.83-4.85 (1H, m), 6.17-6.24 (1H, m), 6.62 (2H, d, J=8.5 Hz), 7.03-7.08 (2H, m), 7.22 (0.9H, d, J=8.0 Hz), 7.33 (0.1H, d, J=8.6 Hz), 7.66-7.76 (1.9H, m), 7.87 (0.1H, d, J=2.2 Hz).

EXAMPLE 134

Production of 1-acetyl-2-methyl-4-{[4-(tetrahydro-2H-pyran-4-yl)phenyl]amino}-1,2,3,4-tetrahydroquinoline-6-carboxamide (compound 156)

Reactions and treatments were carried out in the same manner as in Example 118, using 104.8 mg of (2S,4R)-1-acetyl-2-methyl-4-{[4-(tetrahydro-2H-pyran-4-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 70.5 mg (67.3%, cis:trans=9:1) of the title compound was obtained as a white crystalline powder.

$^1$H-NMR (400 MHz, CDCl$_3$) δ: 1.17 (3H, d, J=6.3 Hz), 1.20-1.33 (0.9H, m), 1.73-1.92 (4.1H, m), 2.21 (2.7H, s), 2.22 (0.3H, s), 2.34-2.44 (0.1H, m), 2.62-2.70 (1.9H, m), 3.47-3.54 (2H, m), 3.84 (1H, brs), 4.05-4.08 (2H, m), 4.18-4.22 (0.9H, m), 4.66 (0.1H, t, J=5.4 Hz), 4.83-4.85 (1H, m), 6.03 (2H, d, J=89.0 Hz), 6.62 (2H, d. J=8.6 Hz), 7.03-7.07 (2H, m), 7.24 (0.9H, d, J=8.1 Hz), 7.36 (0.1H, d, J=8.0 Hz), 7.72-7.74 (0.1H, m), 7.79-7.82 (1.8H, m), 7.92-7.93 (0.1H, m).

EXAMPLE 135

Production of methyl 6-{(2S,4R)-1-acetyl-2-methyl-4-[(4-morpholinophenyl)amino]-1,2,3,4-tetrahydroquinoline-6-carboxamido}hexanoate (Compound 157)

81.9 mg of (2S,4R)-1-acetyl-2-methyl-4-[(4-morpholinophenyl)amino]-1,2,3,4-tetrahydroquinoline-6-carboxamide was dissolved in 2 mL of dichloromethane, and 174.2 μL of N,N-diisopropylethylamine and 124.9 mg of hexafluorophosphate (benzotriazol-1-yloxy)tripyrrolidinophosphonium were added to the solution. The mixture was stirred for one hour at room temperature. Subsequently, 108.9 mg of 6-aminohexanoate methyl-monohydrochloride was added thereto, and the mixture was stirred for one hour at room temperature. After completion of the reaction, water was added to the reaction mixture, and then the mixture was extracted three times with chloroform. The extraction product was washed with saturated brine, dehydrated over anhydrous sodium sulfate, and then concentrated under reduced pressure. The resulting residue was purified by using silica gel chromatography (chloroform:methanol=10:1), and thus 54.0 mg (50.3%, cis-form only) of the title compound was obtained as a pale yellow crystalline powder.

$^1$H-NMR (400 MHz, CDCl$_3$) δ: 1.15 (3H, d, J=6.4 Hz), 1.19-1.28 (1H, m), 1.34-1.42 (2H, m), 1.56-1.69 (4H, m), 2.15 (3H, s), 2.33 (2H, t, J=7.3 Hz), 2.67 (1H, brs), 3.02 (4H, brs), 3.35-3.48 (2H, m), 3.65 (3H, s), 3.86 (4H, t, J=2.3 Hz), 4.14 (1H, brs), 9.83-4.85 (1H, m), 6.18-6.20 (1H, m), 6.64-6.68 (4H, m), 7.21 (1'-1, d, J=8.1 Hz), 7.73-7.76 (2H, m).

EXAMPLE 136

Production of methyl 6-{(2S,4R)-1-acetyl-4-[(4-chlorophenyl)amino]-2-methyl-1,2,3,4-tetrahydroquinoline-6-carboxamido}hexanoate (compound 158)

Reactions and treatments were carried out in the same manner as in Example 135, using 35.9 mg of (2S,4R)-1-acetyl-4-[(4-chlorophenyl)amino]-2-methyl-1,2,3,4-tetrahydroquinoline-6-carboxamide instead of (2S,4R)-1-acetyl-2-methyl-4-[(4-morpholinophenyl)amino]-1,2,3,4-tetrahydroquinoline-6-carboxamide. Thus, 30.1 mg (61.9%, cis-form only) of the title compound was obtained as a pale yellow crystalline powder.

$^1$H-NMR (400 MHz, CDCl$_3$) δ: 1.16 (3H, d, J=6.4 Hz), 1.20-1.28 (1H, m), 1.33-1.41 (2H, m), 1.56-1.69 (4H, m), 2.19 (3H, s), 2.32 (2H, t, J=7.3 Hz), 2.67 (1H, ddd, J=4.3, 8.7, 12.6 Hz), 3.38-3.44 (2H, m), 3.65 (3H, s), 3.98 (1H, d, 7.1 Hz), 4.16-4.20 (1H, m), 4.85-4.87 (1H, m), 6.17 (1H, t, J=5.5 Hz), 6.55-6.59 (2H, m), 7.12-7.16 (2H, m), 7.22 (1H, d, J=8.1 Hz), 7.68 (1H, s), 7.73 (1H, dd, 2.0, 8.0 Hz).

EXAMPLE 137

Production of 1-acetyl-6-(4-isopropylpiperazin-1-yl)-2-methyl-4-[(4-morpholinophenyl)amino]-1,2,3,4-tetrahydroquinoline (Compound 159)

88.9 mg of (2S,4R)-1-acetyl-6-bromo-2-methyl-4-[(4-morpholinophenyl)amino]-1,2,3,4-tetrahydroquinoline was dissolved in 4 mL of toluene, and 142.5 μL of 1-isopropylpiperazine, 9.2 mg of tris(dibenzylideneacetone)dipalladium(0), 6.0 mg of (2-biphenyl)-di-tert-butylphosphine, and 38.4 mg of tert-butoxy sodium were sequentially added to the solution. The mixture was heated to reflux for 12 hours. The reaction liquid was cooled, and then was filtered through Celite. The filtrate was washed with chloroform, water was added to the filtrate, and the mixture was extracted three times with chloroform. The extraction product was washed with saturated brine, dehydrated over anhydrous sodium sulfate, and then concentrated under reduced pressure. The resulting residue was purified by using silica gel chromatography (chloroform:methanol=10:1), and then was recrystallized from ethyl acetate-hexane. Thus, 22.0 mg (22.4%, cis: trans=9:1) of the title compound was obtained as a pale yellow crystalline powder.

$^1$H-NMR (400 MHz, CDCl$_3$) δ: 1.08-1.27 (10H, m), 2.14 (3H, s), 2.57-2.74 (6H, m), 3.03 (4H, t, J=4.6 Hz), 3.12-3.20 (4H, m), 3.50 (1H, brs), 3.86 (4H, t, J=4.8 Hz), 4.09-4.13 (1H, m), 4.86 (1H, brs), 6.64 (2H, d, J=8.8 Hz), 6.77-6.85 (3H, m), 6.91-7.01 (2H, m).

EXAMPLE 138

Production of 1-acetyl-2-methyl-6-[4-(methylsulfonyl) piperazin-1-yl]-4-[(4-morpholinophenyl)amino]-1,2,3,4-tetrahydroquinoline (Compound 160)

[Step 1] Reactions and treatments were carried out in the same manner as in Example 137, using 84.2 mg of piperazine instead of 1-isopropylpiperazine. Thus, 54.2 mg (60.3%, cis: trans=9:1) of (2S,4R)-1-acetyl-2-methyl-4-[(4-morpholinophenyl)amino]-6-(piperazin-1-yl)-1,2,4-tetrahydroquinoline was obtained as a pale yellow amorphous substance.

[Step 2] Reactions and treatments were carried out in the same manner as in Step 3 of Example 121, using 54.2 mg of (2S,4R)-1-acetyl-2-methyl-4-[(4-morpholinophenyl) amino]-6-(piperazin-1-yl)-1,2,3,4-tetrahydroquinoline instead of (2S,4R)-1-acetyl-4-(4-aminophenoxy)-2-methyl-1,2,3,4-tetrahydroquinoline. Thus, 42.7 mg (66.9%, cis: trans=9:1) of the title compound was obtained as a pale yellow crystalline powder.

$^1$H-NMR (400 MHz, CDCl$_3$) δ: 1.13 (3H, d, J=6.4 Hz), 1.17-1.26 (1H, m), 2.15 (3H, s), 1.58-2.64 (1H, m), 2.81 (3H, s), 3.01-3.11 (4H, m), 3.16-3.26 (4H, m), 3.33-3.39 (4H, m), 3.48-3.52 (1H, m), 3.79-3.87 (4H, m), 4.09-4.11 (1H, m), 4.25 (1H, brs), 6.64 (2H, d, J=7.8 Hz), 6.79-6.92 (3H, m), 6.96 (1H, s), 7.00-7.04 (1H, m).

EXAMPLE 139

Production of 1-acetyl-2-methyl-6-morpholino-4-[(4-morpholinophenyl)amino]-1,2,3,4-tetrahydroquinoline (Compound 161)

Reactions and treatments were carried out in the same manner as in Example 137, using 87.1 µL of morpholine instead of 1-isopropylpiperazine. Thus, 36.5 mg (40.5%, cis: trans=9:1) of the title compound was obtained as a pale yellow crystalline powder.

$^1$H-NMR (400 MHz, CDCl$_3$) δ: 1.13 (3H, d, J=6.3 Hz), 1.21-1.27 (1H, m), 2.15 (3H, s), 2.61 (1H, ddd, J=4.0, 8.6, 12.3 Hz), 3.02-3.15 (8H, m), 3.52 (1H, brs), 3.80-3.87 (8H, m), 4.11 (1H, dd, J=3.4, 11.7 Hz), 4.87 (1H, s), 6.64 (2H, d, J=8.8 Hz), 6.78 (1H, dd, J=2.7, 8.6 Hz), 6.84 (2H, d, J=8.5 Hz), 6.94-6.95 (1H, m), 7.01-7.03 (1H, m).

EXAMPLE 140

Production of ethyl 1-acetyl-2-methyl-4-{[4-(2-methylthiazol-4-yl)phenyl]amino}-1,2,3,4-tetrahydroquinoline-6-carboxylate (Compound 162)

Reactions and treatments were carried out in the same manner as in Example 122, using 862.3 mg of 4-(2-methylthiazol-4-yl)aniline instead of 4-cyclohexylaniline. Thus, 549.6 mg (81.0%, 2 steps, cis:trans=10:1) of the title compound was obtained as a pale orange-colored amorphous substance.

$^1$H-NMR (400 MHz, CDCl$_3$) δ: 1.18 (3H, d, J=6.1 Hz), 1.21-1.28 (0.9H, m), 1.33 (3H, t, J=7.1 Hz), 1.84-1.91 (0.1H, m), 2.20 (0.3H, s), 2.22 (2.7H, s), 2.49-2.52 (0.1H, m), 2.68-2.75 (3.9H, m), 3.94 (1H, d, J=7.8 Hz), 4.29-4.41 (2.9H, m), 4.70-4.75 (0.1H, m), 4.87-4.90 (1H, m), 6.67-6.71 (2H, m), 7.08 (0.1H, s), 7.11 (0.9H, s), 7.23 (0.9H, d, J=8.0 Hz), 7.32 (0.1H, d, J=8.0 Hz), 7.68-7.74 (2H, m), 7.96-8.02 (1.9H, m), 8.13 (0.1H, d, J=2.0 Hz).

EXAMPLE 141

Production of 1-acetyl-2-methyl-4-{[4-(2-methylthiazol-4-yl)phenyl]amino}-1,2,3,4-tetrahydroquinoline-6-carboxylic acid (Compound 163)

Reactions and treatments were carried out in the same manner as in Step 7 of Example 117, using 500.6 mg of ethyl (2S,4R)-1-acetyl-2-methyl-4-([4-(2-methylthiazol-4-yl) phenyl]amino)-1,2,3,4-tetrahydroquinoline-6-carboxylate instead of ethyl (2S,4S)-1-acetyl-2-methyl-4-(4-morpholinophenoxy)-1,2,3,4-tetrahydroquinoline-6-carboxylate, and the product was recrystallized from ethyl acetate-hexane. Thus, 312.7 mg (66.8%, cis:trans=10:1) of the title compound was obtained as a pale yellow crystalline powder.

$^1$H-NMR (400 MHz, CDCl$_1$) δ: 1.18 (3H, d, J=6.4 Hz), 1.21-1.36 (0.9H, m), 1.84-1.90 (0.1H, m), 2.21 (0.3H, s), 2.24 (2.7H, s), 2.47-2.52 (0.1H, m), 2.66-2.79 (3.9H, m), 4.29 (0.9H, dd, J=3.8, 11.8 Hz), 4.68-4.72 (0.1H, m), 4.86-4.88 (1H, m), 6.69-6.70 (2H, m), 7.06 (0.1H, s), 7.09 (0.9H, s), 7.25 (0.9H, d, J=8.1 Hz), 7.34 (0.1H, d, J=8.3 Hz), 7.65-7.71 (2H, m), 8.00-8.5 (1.9H, m), 8.16-8.17 (0.1H, m).

EXAMPLE 142

Production of 1-acetyl-2-methyl-4-{[4-(2-methylthiazol-4-yl)phenyl]amino}-1,2,3,4-tetrahydroquinoline-6-carboxamide (Compound 164)

Reactions and treatments were carried out in the same manner as in Example 118, using 105.4 mg of (2S,4R)-1-acetyl-2-methyl-4-{[4-(2-methylthiazol-4-yl)phenyl] amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 74.9 mg (75.5%, cis:trans=10:1) of the title compound was obtained as a pale yellow crystalline powder.

$^1$H-NMR (400 MHz, CDCl$_3$) δ: 1.18 (3H, d, J=6.4 Hz), 1.22-1.34 (0.9H, m), 1.89-1.95 (0.1H, m), 2.21 (0.3H, s), 2.22 (2.7H, s), 2.40-2.47 (0.1H, m), 2.66-2.75 (3.9H, m), 4.06 (1H, brs), 4.26-4.29 (0.9H, m), 4.69-4.72 (0.1H, m), 4.86-4.87 (1H, m), 5.96 (2H, d, J=134 Hz), 6.66-6.68 (2H, m), 7.08 (0.1H, s), 7.10 (0.9H, s), 7.25 (0.9H, d, J=8.6 Hz), 7.36 (0.1H, d, J=8.3 Hz), 7.67-7.73 (3H, m), 7.82 (0.9H, dd, J=1.8, 8.2 Hz), 7.93 (0.1H, d, J=2.0 Hz).

EXAMPLE 143

Production of 1-acetyl-N,2-dimethyl-4-{[4-(2-methylthiazol-4-yl)phenyl]amino}-1,2,3,4-tetrahydroquinoline-6-carboxamide (Compound 165)

Reactions and treatments were carried out in the same manner as in Example 118, using 105.4 mg of (2S,4R)-1-acetyl-2-methyl-4-{[4-(2-methylthiazol-4-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid. Thus, 86.0 mg (79.2%, cis:trans=10:1) of the title compound was obtained as a pale yellow crystalline powder.

$^1$H-NMR (400 MHz, CDCl$_3$) δ: 1.16 (3H, d, J=6.4 Hz), 1.20-1.32 (0.9H, m), 1.84-1.91 (0.1H, m), 2.19 (0.3H, s), 2.21 (2.7H, s), 2.39-2.46 (0.1H, m), 2.68 (0.9H, ddd, J=3.6, 8.6, 12.5 Hz), 2.73 (0.3H, s), 2.74 (2.7H, s), 2.93 (2.7H, d, J=4.9 Hz), 2.97 (0.3H, d, J=4.9 Hz), 4.07 (1H, brs), 4.23-4.27 (0.9H, m), 4.67-4.71 (0.1H, m), 4.84-4.87 (1H, m), 6.27 (0.9H, d, J=4.6 Hz), 6.38-6.40 (0.1H, m), 6.64-6.66 (2H, m), 7.07 (0.1H, s), 7.10 (0.9H, s), 7.22 (0.9H, d, J=8.0 Hz), 7.31-7.33 (0.1H; m), 7.66-7.71 (3H, m), 7.78 (0.9H, dd, J=2.0, 8.3 Hz), 7.87 (0.1H, d, J=2.2 Hz).

EXAMPLE 144

Production of 1-acetyl-N-benzoyl-2-methyl-4-[(4-morpholinophenyl)amino]-1,2,3,4-tetrahydroquinoline-6-carboxamide (Compound 166)

[Step 1] Reactions and treatments were carried out in the same manner as in Example 118, using 122.8 mg of (2S,4R)-1-acetyl-2-methyl-4-[(4-morpholinophenyl)amino]-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 140.4 mg (100%) of (2S,4R)-1-acetyl-2-methyl-4-[(4-morpholinophenyl)amino]-1,2,3,4-tetrahydroquinoline-6-carboxamide was obtained as a pale yellow solid.

[Step 2] 33.2 mg of (2S,4R)-1-acetyl-2-methyl-4-[(4-morpholinophenyl)amino]-1,2,3,4-tetrahydroquinoline-6-carboxamide was dissolved in 1 mL of tetrahydrofuran, and 10.3 mg of sodium hydride was added to the solution at 0° C. The mixture was stirred for 30 minutes at room temperature. Subsequently, 10.3 µL of benzoyl chloride was added dropwise to the mixture, and the mixture was stirred for 12 hours at room temperature. After completion of the reaction, water was added to the reaction mixture, and the mixture was extracted three times with chloroform. The extraction product was washed with saturated brine, dehydrated over anhydrous sodium sulfate, and then concentrated under reduced pressure. The resulting residue was purified by using silica gel chromatography (chloroform:methanol=10:1), and then was recrystallized from ethyl acetate-hexane. Thus, 23.6 mg (56.8%, cis:trans=20:1) of the title compound was obtained as a pale yellow crystalline powder.

$^1$H-NMR (400 MHz, CDCl$_3$) δ: 1.20 (3H, d, J=6.1 Hz), 1.22-1.36 (0.95H, m), 1.88-1.95 (0.05H, m), 2.23 (3H, s), 2.36-2.40 (0.05H, m), 2.69 (0.95H, ddd, J=4.3, 8.5, 12.6 Hz), 3.00-3.02 (4H, m), 3.79-3.86 (5H, m), 4.17-4.21 (0.95H, m), 4.62-4.64 (0.05H, m), 4.83-4.85 (1H, m), 6.63 (2H, d, J=8.8 Hz), 6.79-6.85 (2H, m), 7.28 (1H, d, J=8.3 Hz), 7.43-7.52 (2H, m), 7.56-7.61 (1H, m), 7.70-7.72 (2H, m), 7.83-7.86 (2H, m), 8.93 (1H, s).

EXAMPLE 145

Production of ethyl 1-acetyl-2-methyl-4-{[4-(oxazol-2-yl)phenyl]amino}-1,2,3,4-tetrahydroquinoline-6-carboxylate (Compound 167)

Reactions and treatments were carried out in the same manner as in Example 122, using 336.4 mg of 4-(oxazol-2-yl)aniline instead of 4-cyclohexylaniline. Thus, 221.5 mg (75.4%, 2 steps, cis:trans=8:1) of the title compound was obtained as a pale yellow amorphous substance.

$^1$H-NMR (400 MHz, CDCl$_3$) δ: 1.19 (3H, d, J=6.4 Hz), 1.23-1.29 (0.89H, m), 1.33 (3H, t, J=7.11 Hz), 1.86-1.90 (0.11H, m), 2.23 (3H, s), 2.46-2.53 (0.11H, m), 2.72 (0.89H, ddd, J=4.3, 8.5, 12.6 Hz), 4.24-4.37 (3.89H, m), 4.76 (0.11H, t, J=4.9 Hz), 4.88-4.92 (1H, m), 6.69-6.72 (2H, m), 7.15 (0.11H, s), 7.17 (0.89H, s), 7.24 (0.89H, d, J=8.3 Hz), 7.35 (0.11H, d, J=8.2 Hz), 7.62 (0.11H, s), 7.63 (0.89H, s), 7.85-7.90 (2H, m), 7.98-8.01 (1.89H, m), 8.12 (0.11H, d, J=1.7 Hz).

EXAMPLE 146

Production of 1-acetyl-2-methyl-4-{[4-(oxazol-2-yl)phenyl]amino}-1,2,3,4-tetrahydroquinoline-6-carboxylic acid (Compound 168)

Reactions and treatments were carried out in the same manner as in Step 7 of Example 117, using 188.0 mg of ethyl (2S,4R)-1-acetyl-2-methyl-4-{[4-(oxazol-2-yl)phenyl]amino}-1,2,3,4-tetrahydroquinoline-6-carboxylate instead of ethyl (2S,4S)-1-acetyl-2-methyl-4-(4-morpholinophenoxy)-1,2,3,4-tetrahydroquinoline-6-carboxylate, and the product was recrystallized from ethyl acetate-hexane. Thus, 140.0 mg (79.5%, cis:trans=9:1) of the title compound was obtained as a white crystalline powder.

$^1$H-NMR (400 MHz, CDCl$_3$) δ: 1.19 (2.7H, d, J=6.4 Hz), 1.24 (0.3H, d, J=6.6 Hz), 1.31-1.40 (0.9H, m), 1.88-1.94 (0.1H, m), 2.23 (0.3H, s), 2.24 (2.7H, s), 2.46-2.53 (0.1H, m), 2.66-2.75 (0.9H, m), 4.31-4.34 (0.9H, m), 4.73-4.75 (0.1H, m), 4.90-4.92 (1H, m), 6.68 (2H, d, J=8.8 Hz), 7.21 (1H, s), 7.25-7.26 (0.9H, m), 7.35-7.37 (0.1H, m), 7.62 (1H, s), 7.83-7.88 (2H, m), 7.99-8.06 (1.9H, m), 8.16 (0.1H, s).

EXAMPLE 147

Production of 1-acetyl-2-methyl-4-{[4-(oxazol-2-yl)phenyl]amino}-1,2,3,4-tetrahydroquinoline-6-carboxamide (Compound 169)

Reactions and treatments were carried out in the same manner as in Example 118, using 78.3 mg of (2S,4R)-1-acetyl-2-methyl-4-{[4-(oxazol-2-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 60.4 mg (77.4%, cis:trans=9:1) of the title compound was obtained as a white crystalline powder.

$^1$H-NMR (400 MHz, CDCl$_3$) δ: 1.17 (3H, d, J=6.3 Hz), 1.29-1.37 (0.9H, m), 1.93-1.97 (0.1H, m), 2.21 (0.3H, s), 2.22 (2.7H, s), 2.38-2.46 (0.1H, m), 2.69 (0.9H, ddd, J=4.1, 8.6, 12.4 Hz), 4.27-4.36 (1.9H, m), 4.72-4.74 (0.1H, m), 4.86-4.88 (1H, m), 6.07 (2H, d, J=144 Hz), 6.64-6.68 (2H, m), 7.14 (0.1H, s), 7.15 (0.9H, s), 7.25 (0.9H, d, J=8.5 Hz), 7.38 (0.1H, d, J=7.6 Hz), 7.61 (0.1H, s), 7.63 (0.9H, s), 7.73 (1H, s), 7.79-7.86 (2.9H, m), 7.94 (0.1H, d, J=2.0 Hz).

EXAMPLE 148

Production of 1-acetyl-N,2-dimethyl-4-{[4-(oxazol-2-yl)phenyl]amino}-1,2,3,4-tetrahydroquinoline-6-carboxamide (Compound 170)

Reactions and treatments were carried out in the same manner as in Example 118, using 78.3 mg of (2S,4R)-1-acetyl-2-methyl-4-{[4-(oxazol-2-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid. Thus, 66.3 mg (82.0%, cis:trans=9:1) of the title compound was obtained as a white crystalline powder.

$^1$H-NMR (400 MHz, CDCl$_3$) δ: 1.15 (3H, d, J=6.3 Hz), 1.25-1.35 (0.9H, m), 1.91-1.96 (0.1H, m), 2.19 (0.3H, s), 2.20 (2.7H, s), 2.36-2.44 (0.1H, m), 2.67 (0.9H, ddd, J=4.3, 8.7, 12.6 Hz), 2.90 (2.7H, d, J=4.9 Hz), 2:96 (0.3 Hz, d, J=4.9 Hz), 4.22-4.28 (0.9H, m), 4.28-4.45 (1H, m), 4.69-4.71 (0.1H, m), 4.85-4.86 (1H, m), 6.60-6.71 (3H, m), 7.13 (1H, s), 7.22 (0.9H, d, J=8.0 Hz), 7.34 (0.1H, d, J=8.0 Hz), 7.61 (0.1H, s), 7.63 (0.9H, s), 7.71 (1H, s), 7.77-7.81 (2.9H, m), 7.90 (0.1H, d, J=2.0 Hz).

EXAMPLE 149

Production of ethyl 1-acetyl-2-methyl-4-{[4-(1,2,3-thiadiazol-5-yl)phenyl]amino}-1,2,3,4-tetrahydroquinoline-6-carboxylate (Compound 171)

Reactions and treatments were carried out in the same manner as in Example 122, using 531.7 mg of 4-(1,2,3-thiadiazol-5-yl)aniline instead of 4-cyclohexylaniline. Thus, 302.0 mg (69.2%, 2 steps, cis:trans=15:1) of the title compound was obtained as a pale yellow amorphous substance.

$^1$H-NMR (400 MHz, CDCl$_3$) δ: 1.20 (3H, d, J=6.4 Hz), 1.33 (3H, t, J=7.1 Hz), 1.37-1.43 (0.94H, m), 1.89-1.95 (0.06H, m), 2.23 (3H, s), 2.50-2.56 (0.06, m), 2.74 (0.94H, ddd, J=4.1, 8.5, 12.4 Hz), 4.09-4.13 (1H, m), 4.30-4.39 (3H, m), 4.89-4.91 (1H, m), 6.78 (1.88H, d, J=8.6 Hz), 6.91 (0.12H, d, J=8.5 Hz), 7.24-7.26 (0.94H, m), 7.33-7.36 (0.06H, m), 7.86-7.92 (2H, m), 7.99-8.01 (1.94H, m), 8.13-8.15 (0.06H, m), 8.45 (1H, s).

EXAMPLE 150

Production of 1-acetyl-2-methyl-4-{[4-(1,2,3-thiadiazol-5-yl)phenyl]amino}-1,2,3,4-tetrahydroquinoline-6-carboxylic acid (Compound 172)

Reactions and treatments were carried out in the same manner as in Step 7 of Example 117, using 270.6 mg of ethyl (2S,4R)-1-acetyl-2-methyl-4-{[4-(1,2,3-thiadiazol-5-yl)phenyl]amino}-1,2,3,4-tetrahydroquinoline-6-carboxylate instead of ethyl (2S,4S)-1-acetyl-2-methyl-4-(4-morpholinophenoxy)-1,2,3,4-tetrahydroquinoline-6-carboxylate, and the product was recrystallized from chloroform-hexane. Thus, 252.4 mg (99.6%, cis:trans=20:1) of the title compound was obtained as a pale yellow amorphous substance.

$_1$H-NMR (400 MHz, CDCl$_3$) δ: 1.20 (3H, d, J=6.3 Hz), 1.21-1.40 (0.95H, m), 1.90-1.96 (0.05H, m), 2.25 (3H, s), 2.49-2.55 (0.05, m), 2.73 (0.95H, ddd, J=4.2, 8.6, 12.5 Hz), 4.33 (0.95H, dd, J=3.8, 11.8 Hz), 4.73-4.75 (0.05H, m), 4.89-4.91 (1H, m), 6.75 (2H, d, J=8.6 Hz), 7.26-7.28 (0.95H, m), 7.37-7.39 (0.05H, m), 7.84-7.89 (2H, m), 8.04 (2H, s), 8.42 (0.05H, s), 8.45 (0.95H, s).

EXAMPLE 151

Production of 1-acetyl-2-methyl-4-{[4-(1,2,3-thiadiazol-5-yl)phenyl]amino}-1,2,3,4-tetrahydroquinoline-6-carboxamide (Compound 173)

Reactions and treatments were carried out in the same manner as in Example 118, using 61.2 mg of (2S,4R)-1-acetyl-2-methyl-4-{[4-(1,2,3-thiadiazol-5-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 44.9 mg (73.5%, cis:trans=20:1) of the title compound was obtained as a pale yellow amorphous substance.

$^1$H-NMR (400 MHz, CDCl$_3$) δ: 1.20 (3H, d, J=6.4 Hz), 1.32-1.40 (0.95H, m), 1.90-1.94 (0.05H, m), 2.24 (3H, s), 2.44-2.51 (0.05, m), 2.73 (0.95H, ddd, J=4.3, 8.7, 12.6 Hz), 3.71-3.73 (0.05H, m), 4.17 (0.95H, d, J=7.3 Hz), 4.29-4.35 (1H, m), 4.89-4.90 (1H, m), 5.86 (2H, d, 139 Hz), 6.74-6.76 (2H, m), 7.26-7.28 (0.95H, m), 7.35-7.39 (0.05H, m), 7.76 (1H, s), 7.81 (1H, dd, J=2.0, 8.0 Hz), 7.87-7.91 (2H, m), 8.43 (0.05H, s), 8.45 (0.95H, s).

EXAMPLE 152

Production of 1-acetyl-N,2-dimethyl-4-([4-(1,2,3-thiadiazol-5-yl)phenyl]amino)-1,2,3,4-tetrahydroquinoline-6-carboxamide (Compound 174)

Reactions and treatments were carried out in the same manner as in Example 118, using 61.2 mg of (2S,4R)-1-acetyl-2-methyl-4-{[4-(1,2,3-thiadiazol-5-yl)phenyl]amino}-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid. Thus, 76.0 mg (100%, cis:trans=20:1) of the title compound was obtained as a pale yellow amorphous substance.

$^1$H-NMR (400 MHz, CDCl$_3$) δ: 1.18 (3H, d, J=6.3 Hz), 1.30-1.38 (0.95H, m), 1.92-1.95 (0.05H, m), 2.22 (3H, s), 2.44-2.50 (0.05, m), 2.72 (0.95H, ddd, J=3.8, 8.6, 12.5 Hz), 2.95 (2.85H, d, J=4.9 Hz), 3.00 (0.15H, d, J=4.9 Hz), 3.69-3.74 (0.05H, m), 4.20 (0.95H, d, J=7.3 Hz), 4.27-4.33 (0.95H, m), 4.73-4.75 (0.05H, m), 4.88-4.90 (1H, m), 6.18 (0.95H, d, J=4.6 Hz), 6.28-6.31 (0.05H, m), 6.74 (2H, d, J=8.5 Hz), 7.24 (0.95H, d, J=8.0 Hz), 7.30-7.33 (0.05H, m), 7.70 (1H, s), 7.75 (1H, dd, J=2.0, 8.3 Hz), 7.83-7.88 (2H, m), 8.43 (0.05H, s), 8.45 (0.95H, s).

EXAMPLE 153

Production of (2S,4R)—N, 1-diacetyl-2-methyl-4-[(4-morpholinophenyl)amino]-1,2,3,4-tetrahydroquinoline-6-carboxamide (Compound 175)

[Step 1] Reactions and treatments were carried out in the same manner as in Example 118, using 122.8 mg of (2S,4R)-1-acetyl-2-methyl-4-[(4-morpholinophenyl)amino]-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using 155.3 µL of benzyl alcohol instead of monomethylamine. Thus, 133.4 mg (89.0%) of (2S,4R)-1-acetyl-2-methyl-4-[(4-morpholinophenyl)amino]-1,2,3,4-tetrahydroquinoline-6-carboxylic acid benzyl ester was obtained as a pale yellow amorphous substance.

[Step 2] 133.4 mg of (2S,4R)-1-acetyl-2-methyl-4-[(4-morpholinophenyl)amino]-1,2,3,4-tetrahydroquinoline-6-carboxylic acid benzyl ester was dissolved in 5 mL of dichloromethane, and 107.4 µL of pyridine, 3.3 mg of 4-dimethylaminopyridine, and 55.7 μL of trifluoroacetic anhydride were added to the solution at 0° C. The mixture was stirred for 4 hours at room temperature. After completion of the reaction, water was added to the reaction mixture, and the mixture was extracted three times with chloroform. The extraction product was washed with saturated brine, dehydrated over anhydrous sodium sulfate, and then concentrated under reduced pressure. The resulting residue was purified by using silica gel chromatography (hexane:ethyl acetate=1:2). Thus, 111.1 mg (69.9%) of (2S,4R)-1-acetyl-2-methyl-4-[2,2,2-trifluoro-N-(4-morpholinophenyl)acetamido]-1,2,3,4-tetrahydroquinoline-6-carboxylic acid benzyl ester was obtained as a pale yellow amorphous substance.

[Step 3] Reactions and treatments were carried out in the same manner as in Step 5 of Example 117, using 111.1 mg of (2S,4R)-1-acetyl-2-methyl-4-[2,2,2-trifluoro-N-(4-morpholinophenyl)acetamido]-1,2,3,4-tetrahydroquinoline-6-carboxylic acid benzyl ester instead of ethyl (2S,4R)-1-acetyl-2-methyl-4-(4-nitrophenoxy)-1,2,3,4-tetrahydroquinoline-6-carboxylate, and using ethanol instead of methanol. Thus, 83.5 mg (88.3%) of (2S,4R)-1-acetyl-2-methyl-4-[2,2,2-trifluoro-N-(4-morpholinophenyl)acetamido]-1,2,3,4-tetrahydroquinoline-6-carboxylic acid was obtained as a pale yellow amorphous substance.

[Step 4] Reactions and treatments were carried out in the same manner as in Example 118, using 83.5 mg of (2S,4R)-1-acetyl-2-methyl-4-[2,2,2-trifluoro-N-(4-morpholinophenyl)acetamido]-1,2,3,4-tetrahydroquinoline-6-carboxylic acid instead of (2S,4R)-1-acetyl-2-methyl-4-(4-morpholinophenoxy)-1,2,3,4-tetrahydroquinoline-6-carboxylic acid, and using aqueous ammonia instead of monomethylamine. Thus, 86.9 mg (100%) of (2S,4R)-1-acetyl-2-methyl-4-[2,2,2-trifluoro-N-(4-morpholinophenyl)acetamido]-1,2,3,4-tetrahydroquinoline-6-carboxamide was obtained as a pale yellow amorphous substance.

[Step 5] Reactions and treatments were carried out in the same manner as in Step 2 of Example 144, using 86.9 mg of (2S,4R)-1-acetyl-2-methyl-4-{2,2,2-trifluoro-N-(4-morpholinophenyl)acetamido}-1,2,3,4-tetrahydroquinoline-6-carboxamide instead of (2S,4R)-1-acetyl-2-methyl-4-{(4-morpholinophenyl)amino}-1,2,3,4-tetrahydroquinoline-6-carboxamide. Thus, 12.7 mg (16.3%, cis-form only) of the title compound was obtained as a pale yellow crystalline powder.

$^1$H-NMR (400 MHz, CDCl$_3$) δ: 1.18 (3H, d, J=6.3 Hz), 1.23-1.32 (1H, m), 2.25 (3H, s), 2.58 (3H, s), 2.70 (1H, ddd, J=4.1, 8.5, 12.4 Hz), 3.04 (4H, t, J=4.5 Hz), 3.65 (1H, brs), 3.86 (4H, t, J=4.6 Hz), 4.16-4.19 (1H, m), 4.82-4.84 (1H, m), 6.63 (2H, d, J=8.5 Hz), 6.85 (2H, d, J=4.6 Hz), 7.30 (1H, d, J=8.1 Hz), 7.80-7.85 (2H, m), 8.59 (1H, s).

EXAMPLE 154

Production of (2S,4R)-1-acetyl-N-isopropyl-2-methyl-4-[(4-morpholinophenyl)amino]-1,2,3,4-tetrahydroquinoline-6-carboxamide (Compound 176)

Reactions and treatments were carried out in the same manner as in Example 110, using 82 mg of (2S,4R)-1-acetyl-2-methyl-4-[(4-morpholinophenyl)amino]-1,2,3,4-tetrahydroquinoline-6-carboxylic acid and 36 mg of isopropylamine. Thus, 78 mg (86%) of the title compound was obtained as a pale yellow amorphous substance.

$^1$H-NMR (400 MHz, CDCl$_3$) δ: 1.15 (3H, d, J=6.4 Hz), 1.18-1.29 (1H, m), 1.23 (6H, d, J=6.6 Hz), 2.18 (3H, s), 2.60-2.75 (1H, m), 2.90-3.15 (4H, m), 3.80-3.90 (4H, m), 4.10-4.32 (2H, m), 4.77-4.93 (1H, m), 5.82 (1H, d, J=7.8 Hz), 6.50-7.00 (4H, m), 7.20 (1H, d, J=7.8 Hz), 7.71 (1H, dd, J=8.2, 1.8 Hz), 7.75 (1H, 5).

EXAMPLE 155

Production of (2S,4R)-1-acetyl-2-methyl-4-[(4-morpholinophenyl)amino]-N-(pyridin-2-yl)-1,2,3,4-tetrahydroquinoline-6-carboxamide (Compound 177)

Reactions and treatments were carried out in the same manner as in Example 110, using 82 mg of (2S,4R)-1-acetyl-2-methyl-4-[(4-morpholinophenyl)amino]-1,2,3,4-tetrahydroquinoline-6-carboxylic acid and 28 mg of 2-aminopyridine. Thus, 20 mg (21%) of the title compound was obtained as a yellow amorphous substance.

$^1$H-NMR (400 MHz, CDCl$_3$) δ: 1.19 (3H, d, J=6.3 Hz), 1.22-1.32 (1H, m), 2.20 (3H, s), 2.70 (1H, ddd, J=12.3, 8.4, 4.0 Hz), 2.96-3.08 (4H, m), 3.48-3.64 (1H, m), 3.80-3.87 (4H, m), 4.12-4.26 (1H, m), 4.78-4.92 (1H, m), 6.64 (2H, d, J=8.8 Hz), 6.85 (2H, d, J=8.6 Hz), 7.05-7.08 (1H, m), 7.29 (1H, d, J=8.0 Hz), 7.73-7.77 (1H, m), 7.79 (1H, dd, J=8.3, 2.0 Hz), 7.94 (1H, s), 8.26 (1H, d, J=4.9 Hz), 8.63 (1H, brs).

EXAMPLE 156

Production of (2S,4R)-1-acetyl-N-cyclohexyl-2-methyl-4-[(4-morpholinophenyl)amino]-1,2,3,4-tetrahydroquinoline-6-carboxamide (Compound 178)

Reactions and treatments were carried out in the same manner as in Example 110, using 82 mg of (2S,4R)-1-acetyl-2-methyl-4-[(4-morpholinophenyl)amino]-1,2,3,4-tetrahydroquinoline-6-carboxylic acid and 60 mg of cyclohexylamine. Thus, 86 mg (87%) of the title compound was obtained as a yellow amorphous substance.

$^1$H-NMR (400 MHz, CDCl$_3$) δ: 1.05-1.27 (8H, m), 1.33-1.47 (2H, m), 1.55-1.77 (2H, m), 1.90-2.03 (2H, m), 2.20 (3H, s), 2.60-2.77 (1H, m), 2.90-3.13 (4H, m), 3.40-3.66 (1H, m), 3.77-4.00 (5H, m), 4.10-4.28 (1H, m), 4.77-4.92 (1H, m), 5.85 (1H, d, J=8.0 Hz), 6.50-6.75 (2H, m), 6.75-7.00 (2H, m), 7.20 (1H, d, J=8.0 Hz), 7.71 (1H, d, J=8.0 Hz), 7.73 (1H, s).

EXAMPLE 157

Production of (2S,4R)-1-acetyl-2-methyl-4-[(3-morpholinophenyl)amino]-1,2,3,4-tetrahydroquinoline-6-carboxylic acid (Compound 179)

Reactions and treatments were carried out in the same manner as in Example 2, using ethyl (2S)-1-acetyl-4-oxo-2-methyl-1,2,3,4-tetrahydroquinoline-6-carboxylate and 3-morpholinoaniline, and subsequently, hydrolysis of the ester was carried out by a known method. Thus, 70 mg (32%) of the title compound was obtained as a light orange-colored powder.

$^1$H-NMR (400 MHz, CDCl$_3$) δ: 1.18 (3H, d, J=6.1 Hz), 1.18-1.32 (1H, m), 2.25 (3H, s), 2.70 (1H, ddd, J=12.3, 8.4, 4.0 Hz), 3.08-3.22 (4H, m), 3.80-3.90 (4H, m), 4.23-4.30 (1H, m), 4.80-4.92 (1H, m), 6.23 (1H, d, J=8.0 Hz), 6.28 (1H, s), 6.39 (1H, dd, J=1.9, 10.2 Hz), 7.11 (1H, t, J=8.2 Hz), 7.25 (1H, d, J=10.2 Hz), 7.99 (1H, dd, J=1.8, 8.2 Hz), 8.08 (1H, s).

EXAMPLE 158

Production of (2S,4R)-1-acetyl-N,2-dimethyl-4-[(3-morpholinophenyl)amino]-1,2,3,4-tetrahydroquinoline-6-carboxamide (Compound 180)

Reactions and treatments were carried out in the same manner as in Example 110, using 31 mg of (2S,4R)-1-acetyl- 2-methyl-4-[(3-morpholinophenyl)amino]-1,2,3,4-tetrahydroquinoline-6-carboxylicacid (compound 179) and monomethylamine. Thus, 23 mg (73%) of the title compound was obtained as a light yellow oily substance.

$^1$H-NMR (400 MHz, CDCl$_3$) δ: 1.17 (3H, d, J=6.3 Hz), 1.20-1.32 (1H, m), 2.20 (3H, s), 2.68 (1H, ddd, J=12.6, 8.6, 4.3 Hz), 2.98 (3H, d, J=4.9 Hz), 3.14 (4H, t, J=4.9 Hz), 3.76 (18, d, J=7.0 Hz), 4.18-4.28 (1H, m), 4.78-4.90 (1H, m), 6.00-6.10 (1H, m), 6.18 (1H, d, J=7.8 Hz), 6.23 (1H, s), 6.38 (1H, dd, J=1.9, 8.1 Hz), 7.11 (1H, t, J=8.0 Hz), 7.20-7.24 (1H, m), 7.71 (1H, s), 7.77 (1H, dd, J=2.0, 8.0 Hz).

EXAMPLE 159

Production of (2S,4R)-1-acetyl-2-methyl-4-[(3-morpholinophenyl)amino]-1,2,3,4-tetrahydroquinoline-6-carboxamide (Compound 181)

Reactions and treatments were carried out in the same manner as in Example 110, using 25 mg of (2S,4R)-1-acetyl-2-methyl-4-[(3-morpholinophenyl)amino]-1,2,3,4-tetrahydroquinoline-6-carboxylic acid (compound 179) and aqueous ammonia. Thus, 20 mg (80%) of the title compound was obtained as a light yellow oily substance.

$^1$H-NMR (400 MHz, CDCl$_3$) δ: 1.18 (3H, d, J=6.4 Hz), 1.20-1.30 (1H, m), 2.21 (3H, s), 2.69 (1H, ddd, J=12.6, 8.6, 4.3 Hz), 3.11-3.16 (4H, m), 3.74-3.80 (1H, m), 3.82-3.87 (4H, m), 4.20-4.29 (1H, m), 4.79-4.90 (1H, m), 5.54 (1H, brs), 5.99 (1H, brs), 6.19 (1H, dd, J=1.8, 7.7 Hz), 6.23 (1H, t, J=2:2 Hz), 6.38 (1H, dd, J=1.8, 7.9 Hz), 7.11 (1H, t, J=8.1 Hz), 7.23-7.28 (1H, m), 7.78 (1H, s), 7.82 (1H, dd, J=1.7, 8.3 Hz).

TEST EXAMPLES

Compounds 1, 2, and 3 used in the Test Examples were products available from ChemBridge Corp., and compound 47 was a product available from Princeton Biomolecular Research, Inc. Furthermore, compounds 13 and 75 were products produced according to the method described in WO 2002/79165, and compounds 5, 8, 9, 10, 11, 12, 15, 16, 17, 21, 46, 48, 49, 50, 51, and 52 used herein were products produced according to the method described in JP-A No. 2002-053557. In addition to these, products produced by the methods described in the Examples were used.

Test Example 1

<Materials and Methods>

HepG2 cells derived from human liver cancer were inoculated in an amount of $5 \times 10^4$ cells per well on a 48-well plate, using minimum essential medium (MEM, Sigma-Aldrich Company) containing 10% bovine fetal serum. On the next day, the medium was exchanged with Dulbecco's modified eagle medium (DMEM (Sigma-Aldrich Company)) containing 10% bovine fetal serum without Phenol Red. Then, a test compound dissolved in DMSO was added thereto to obtain a final concentration of 3 µM or 10 µM, and the amount of medium was adjusted to 400 µL per well. The cells were incubated for 48 hrs in a CO$_2$ incubator in which the oxygen concentration was adjusted to 4%, and then the culture supernatant was collected. The EPO concentration in the culture supernatant was immediately measured using an EPO ELISA kit (Roche Diagnostics GmbH). The method was carried out according to the operation manual.

The amount of EPO production in a non-stimulated state where no compounds were added, was designated as 100%, and the amount of EPO production (% of control) induced by each of the compounds was determined. The results are presented in Tables 25 to 27.

TABLE 25

| Compound No. | % of control (3 µM) |
|---|---|
| 1 | 235 |
| 2 | 167 |
| 3 | 187 |
| 4 | 163 |
| 5 | 205 |
| 6 | 225 |
| 7 | 261 |
| 8 | 248 |
| 9 | 405 |
| 10 | 172 |
| 11 | 163 |
| 12 | 197 |
| 13 | 229 |
| 14 | 257 |
| 15 | 348 |
| 16 | 288 |
| 17 | 172 |
| 18 | 178 |
| 19 | 191 |
| 20 | 174 |
| 21 | 231 |
| 22 | 150 |
| 23 | 135 |
| 24 | 117 |
| 25 | 242 |
| 26 | 214 |
| 27 | 292 |
| 28 | 167 |
| 29 | 305 |
| 30 | 339 |
| 31 | 302 |
| 34 | 288 |
| 36 | 114 |
| 38 | 201 |
| 39 | 131 |
| 40 | 144 |
| 41 | 119 |
| 42 | 102 |
| 43 | 452 |
| 44 | 301 |
| 45 | 286 |
| 46 | 391 |
| 47 | 292 |

TABLE 26

| Compound No. | % of control (3 µM) |
|---|---|
| 49 | 271 |
| 50 | 289 |
| 51 | 239 |
| 52 | 314 |
| 53 | 134 |
| 54 | 148 |
| 55 | 134 |
| 56 | 213 |
| 57 | 251 |
| 62 | 193 |
| 65 | 414 |
| 69 | 150 |
| 70 | 165 |
| 71 | 149 |
| 72 | 243 |
| 74 | 398 |
| 75 | 346 |
| 76 | 227 |
| 77 | 221 |
| 78 | 217 |
| 79 | 476 |
| 80 | 219 |
| 81 | 234 |

TABLE 26-continued

| Compound No. | % of control (3 μM) |
|---|---|
| 85 | 147 |
| 92 | 192 |
| 95 | 213 |
| 97 | 264 |
| 103 | 108 |
| 104 | 204 |
| 105 | 245 |
| 107 | 130 |
| 110 | 207 |
| 111 | 126 |
| 113 | 112 |
| 114 | 198 |
| 117 | 204 |
| 118 | 138 |
| 119 | 125 |
| 121 | 222 |
| 122 | 139 |
| 123 | 142 |
| 124 | 147 |
| 125 | 148 |

TABLE 27

| Compound No. | % of control (3 μM) |
|---|---|
| 126 | 161 |
| 127 | 96 |
| 128 | 176 |
| 129 | 125 |
| 130 | 133 |
| 131 | 153 |
| 132 | 208 |
| 133 | 113 |
| 134 | 157 |
| 135 | 124 |
| 136 | 141 |
| 137 | 110 |
| 140 | 124 |
| 142 | 129 |
| 143 | 130 |
| 144 | 180 |
| 146 | 152 |
| 149 | 190 |
| 151 | 110 |
| 152 | 186 |
| 154 | 116 |
| 159 | 292 |
| 160 | 190 |
| 161 | 351 |
| 162 | 284 |
| 163 | 128 |
| 164 | 336 |
| 166 | 185 |
| 168 | 144 |
| 170 | 128 |
| 171 | 333 |
| 172 | 152 |
| 173 | 323 |
| 174 | 218 |
| 175 | 270 |
| 176 | 325 |
| 177 | 265 |
| 178 | 370 |
| 179 | 138 |
| 181 | 162 |

<Results>

When the test compounds were added to a final concentration of 3 μM, enhancement of EPO production by as much as 976% (compound 79) was shown (see Tables 25 to 27). Furthermore, compounds 42, 127, 145, 147, 157, 158, 165, 167, and 169, by which enhancement of EPO production was not shown at a concentration of 3 μM, also exhibited enhancement of EPO production by 138%, 130%, 157%, 130%, 237%, 248%, 159%, 142%, and 120%, respectively, when the final concentration was adjusted to 10 μM. Therefore, it was clearly known that these compounds have an EPO production enhancing activity, and it was found that these compounds are useful as therapeutic agents for anemia.

Test Example 2

<Materials and Methods>

K562 cells (obtained from ATCC), which is a human pro-erythroblast cell line, were inoculated at a concentration of $1 \times 10^5$ cells/1 mL in each well of a 24-well plate, using complete medium (RPMI-1640 medium containing 10% bovine fetal serum), and 1 μL of a test compound at a 1000-fold concentration was added to each well. Subsequently, the cells were incubated for 3 days in a $CO_2$ incubator (37° C., 5% $CO_2$). The medium was exchanged, and the cells were further incubated for 3 days. The cells were collected and counted. Subsequently, the amount of hemoglobin produced in the cells was determined by adjusting the number of cells to $3 \times 10^5$ cells, and measuring the fluorescence of the porphyrin ring. That is, the cells collected by centrifugation were suspended in 500 μL of 2 M oxalic acid, and were heated to boil for 30 minutes. The cells were cooled, and then the fluorescence intensity was measured by using a fluorescence microplate reader (Spectra MAX GeminiEM; Molecular Devices Corp.) (Em: 400 nm, Ex: 603 nm). The amount of hemoglobin in a non-stimulated state where no compound was added was designated as 100%, and the amount of hemoglobin (% of control) produced as induced by each of the compounds was determined. The results are presented in Tables 28 to 31.

TABLE 28

| Compound No. | % of control (6 μM) |
|---|---|
| 1 | 575 |
| 3 | 912 |
| 4 | 92 |
| 5 | 245 |
| 6 | 326 |
| 7 | 260 |
| 8 | 412 |
| 9 | 406 |
| 10 | 409 |
| 11 | 361 |
| 12 | 398 |
| 13 | 365 |
| 14 | 440 |
| 15 | 409 |
| 16 | 416 |
| 17 | 517 |
| 18 | 374 |
| 19 | 284 |
| 20 | 117 |
| 21 | 301 |
| 22 | 383 |
| 23 | 544 |
| 26 | 188 |
| 27 | 281 |
| 28 | 216 |
| 29 | 201 |
| 30 | 136 |
| 31 | 156 |
| 32 | 145 |
| 33 | 115 |
| 34 | 257 |
| 35 | 287 |
| 36 | 83 |
| 37 | 494 |
| 38 | 190 |
| 39 | 327 |
| 40 | 256 |
| 41 | 529 |

TABLE 28-continued

| Compound No. | % of control (6 μM) |
|---|---|
| 42 | 303 |
| 44 | 162 |

TABLE 29

| Compound No. | % of control (6 μM) |
|---|---|
| 45 | 387 |
| 46 | 326 |
| 47 | 701 |
| 48 | 139 |
| 53 | 307 |
| 54 | 186 |
| 56 | 119 |
| 57 | 221 |
| 58 | 107 |
| 59 | 108 |
| 60 | 113 |
| 61 | 132 |
| 62 | 168 |
| 63 | 98 |
| 64 | 113 |
| 65 | 461 |
| 66 | 151 |
| 67 | 119 |
| 68 | 154 |
| 69 | 407 |
| 71 | 150 |
| 72 | 577 |
| 74 | 375 |
| 75 | 282 |
| 76 | 185 |
| 77 | 120 |
| 78 | 210 |
| 79 | 186 |
| 82 | 325 |
| 83 | 282 |
| 84 | 286 |
| 85 | 189 |
| 86 | 237 |
| 87 | 262 |
| 88 | 112 |
| 89 | 154 |
| 90 | 241 |
| 91 | 130 |
| 92 | 128 |
| 93 | 245 |

TABLE 30

| Compound No. | % of control (6 μM) |
|---|---|
| 94 | 199 |
| 95 | 158 |
| 96 | 530 |
| 97 | 553 |
| 98 | 56 |
| 99 | 69 |
| 100 | 105 |
| 101 | 508 |
| 102 | 91 |
| 103 | 485 |
| 104 | 536 |
| 105 | 358 |
| 106 | 227 |
| 107 | 139 |
| 108 | 399 |
| 109 | 229 |
| 110 | 211 |
| 111 | 46 |
| 112 | 139 |
| 113 | 163 |
| 114 | 152 |

TABLE 30-continued

| Compound No. | % of control (6 μM) |
|---|---|
| 115 | 163 |
| 119 | 124 |
| 120 | 188 |
| 121 | 149 |
| 122 | 213 |
| 124 | 119 |
| 125 | 118 |
| 126 | 124 |
| 128 | 120 |
| 129 | 136 |
| 130 | 172 |
| 131 | 263 |
| 132 | 198 |
| 133 | 136 |
| 134 | 298 |
| 135 | 178 |
| 136 | 136 |
| 137 | 190 |

TABLE 31

| Compound No. | % of control (6 μM) |
|---|---|
| 139 | 193 |
| 140 | 231 |
| 141 | 209 |
| 142 | 478 |
| 143 | 396 |
| 144 | 338 |
| 145 | 414 |
| 146 | 208 |
| 147 | 160 |
| 148 | 506 |
| 149 | 367 |
| 150 | 534 |
| 151 | 341 |
| 152 | 337 |
| 153 | 294 |
| 154 | 320 |
| 155 | 387 |
| 156 | 371 |
| 157 | 396 |
| 158 | 411 |
| 160 | 259 |
| 161 | 308 |
| 162 | 316 |
| 163 | 172 |
| 164 | 367 |
| 165 | 304 |
| 166 | 282 |
| 167 | 227 |
| 168 | 204 |
| 169 | 243 |
| 171 | 243 |
| 172 | 168 |
| 173 | 158 |
| 174 | 163 |
| 175 | 275 |
| 176 | 355 |
| 177 | 353 |
| 178 | 388 |
| 179 | 124 |
| 180 | 150 |
| 181 | 382 |

<Results>

When the test compound was added at a concentration of 6 μM, enhancement of hemoglobin production by as much as 912% (compound 3) was shown (see Tables 28 to 31). Furthermore, compounds 4, 36, 63, 98, 99, 102, and 111 also exhibited enhancement of hemoglobin production by 162%, 143%, 260%, 142%, 306%, 115%, and 171%, respectively, when the drug concentration was adjusted to 20 μM. Therefore, it was found that these compounds have an effect of enhancing maturation of proerythroblast cells to red blood cells and thereby enhancing the production of hemoglobin.

From the results shown above, it was demonstrated that the 1-acyl-4-(substituted oxy, substituted amino, or substituted thio)-1,2,3,4-tetrahydroquinoline derivative of the present invention, more particularly, the tetrahydroquinoline compound represented by the formula (1), salts thereof, and solvates of the compound and the salts, have an EPO production enhancing activity and a hemoglobin production enhancing activity, and are useful as a therapeutic agent for anemia.

Industrial Applicability

The present invention discovered for the first time that a 1-acyl-4-(substituted oxy, substituted amino, or substituted thio)-1,2,3,4-tetrahydroquinoline derivative, more particularly, a tetrahydroquinoline compound represented by the formula (1), salts thereof, and solvates of the compound and the salts have an excellent EPO production enhancing activity and/or a hemoglobin production enhancing activity. Thus, the present invention provides an orally administrable, low molecular weight prophylactic and/or therapeutic agent for anemia having an excellent EPO production enhancing activity and/or hemoglobin production enhancing activity. The present invention provides a new low molecular weight prophylactic and/or therapeutic agent for anemia, which is useful in the pharmaceutical industry and has industrial applicability.

The invention claimed is:

1. A tetrahydroquinoline compound, a salt thereof, or a solvate of the compound or the salt, wherein the tetrahydroquinoline compound is selected from the group consisting of:
   1-acetyl-4-(4-fluorophenoxy)-2-methyl-1,2,3,4-tetrahydroquinoline [compound (27)];
   1-acetyl-4-(2-fluorophenoxy)-2-methyl-1,2,3,4-tetrahydroquinoline [compound (29)];
   1-acetyl-4-(2,4-difluorophenoxy)-2-methyl-1,2,3,4-tetrahydroquinoline [compound (30)];
   1-acetyl-4-(3,4-difluorophenoxy)-2-methyl-1,2,3,4-tetrahydroquinoline [compound (31)];
   1-acetyl-4-(4-fluorophenoxy)-6-fluoro-2-methyl-1,2,3,4-tetrahydroquinoline [compound (34)]; and
   1-acetyl-4-(4-hydroxyphenoxy)-2-methyl-1,2,3,4-tetrahydroquinoline [compound (57)].

2. A pharmaceutical composition comprising the tetrahydroquinoline compound according to claim 1, a salt thereof, or a solvate of the compound or the salt, and a pharmaceutically acceptable carrier.

3. The pharmaceutical composition according to claim 2, wherein the pharmaceutical composition is used for enhancing EPO production.

4. The pharmaceutical composition according to claim 2, wherein the pharmaceutical composition is used for enhancing hemoglobin production.

5. The pharmaceutical composition according to claim 2, wherein the pharmaceutical composition is used for the treatment of anemia.

* * * * *